(12) United States Patent
Harriman et al.

US006951848B2

(10) Patent No.: US 6,951,848 B2
(45) Date of Patent: Oct. 4, 2005

(54) FUNCTIONALIZED HETEROCYCLES AS MODULATORS OF CHEMOKINE RECEPTOR FUNCTION AND METHODS OF USE THEREFOR

(75) Inventors: Geraldine C. B. Harriman, Charlestown, RI (US); Kenneth G. Carson, Needham, MA (US); Daniel L. Flynn, Natick, MA (US); Michael E. Solomon, New York, NY (US); Yuntao Song, Ann Harbor, MI (US); Bharat K. Trivedi, Farmington Hills, MI (US); Bruce D. Roth, Plymouth, MI (US); Christine N. Kolz, Dexter, MI (US); Ly Pham, Ann Harbor, MI (US); Kuai-lin Sun, Canton, MI (US)

(73) Assignee: Millennium Pharmaceuticals, Inc.,, Cambridge, MA (US)

( * ) Notice: Subject to any disclaimer, the term of this patent is extended or adjusted under 35 U.S.C. 154(b) by 192 days.

(21) Appl. No.: 10/096,361

(22) Filed: Mar. 12, 2002

(65) Prior Publication Data

US 2003/0064991 A1 Apr. 3, 2003

Related U.S. Application Data
(60) Provisional application No. 60/275,248, filed on Mar. 12, 2001.

(51) Int. Cl.[7] .................. A61K 31/33; A61K 31/40; A61K 31/405; C07D 209/04
(52) U.S. Cl. .................. 514/183; 514/408; 514/412; 514/415; 514/424; 548/469; 548/485; 548/511; 548/452
(58) Field of Search .................. 514/183, 408, 514/412, 415, 424, 419; 548/469, 485, 511, 452, 490, 492

(56) References Cited

U.S. PATENT DOCUMENTS

| | | | | |
|---|---|---|---|---|
| 4,133,814 A | * | 1/1979 | Jones et al. | 548/525 |
| 4,810,801 A | * | 3/1989 | Mertens et al. | 548/411 |
| 5,414,088 A | * | 5/1995 | Von Der Saal et al. | 546/158 |
| 5,556,874 A | * | 9/1996 | Dobrusin et al. | 514/414 |
| 5,955,492 A | | 9/1999 | Thompson et al. | |
| 6,410,540 B1 | | 6/2002 | Goehring et al. | |
| 2002/0068752 A1 | | 6/2002 | Augelli-Szafran et al. | |

FOREIGN PATENT DOCUMENTS

| | | | |
|---|---|---|---|
| DE | 3445669 | * | 6/1986 |
| DE | 3932953 | * | 4/1991 |

(Continued)

OTHER PUBLICATIONS

DeGraw et al.,J. Medicinal Chem.,7/2,213–15(1964), also cited as Chemical Abstract DN 60:68112.*

(Continued)

*Primary Examiner*—Richard L. Raymond
*Assistant Examiner*—Sudhaker B. Patel
(74) *Attorney, Agent, or Firm*—Hamilton, Brook, Smith & Reynolds, P.C.

(57) ABSTRACT

Disclosed are novel compounds having the formula

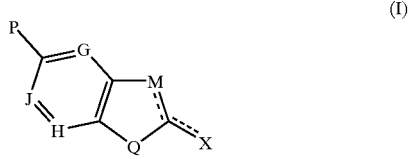

(I)

or a physiologically acceptable salt, amide, ester or prodrug thereof. The compounds can be used to modulate (antagonize, agonize) chemokine receptor function. Also disclosed is a method for treating a patient having an inflammatory disease and/or viral infection comprising administering an effective amount of a compound of Formula I. In particular embodiments, the invention is a method for treating a patient infected with HIV.

36 Claims, 22 Drawing Sheets

FOREIGN PATENT DOCUMENTS

| | | | |
|---|---|---|---|
| DE | 39335514 | * | 5/1991 |
| EP | 1 191 027 A1 | | 3/2002 |
| JP | 52053851 | * | 4/1977 |
| WO | WO 97/35572 | | 10/1997 |
| WO | 9819997 | * | 5/1998 |
| WO | WO 99/41239 | | 8/1999 |
| WO | WO 00/12074 | | 3/2000 |
| WO | WO 00/42045 | | 7/2000 |

OTHER PUBLICATIONS

Chemical Abstract DN 115:92265, also cited as DE 3935514.*

Chemical Abstract DN 115:92262, also cited as DE 3932953.*

Chemical Abstract DN 111:115180, also cited as 4810801.*

Chemical Abstract DN 52:72273, also cited as Zhurnal Obshschei Khimii, 28,78–87(1958).*

Chemical Abstract DN 105:152998, also cited as J. Med. Chem., 29/9,1637–43(*1986).*

Chemical Abstract DN: 90:151974, also cited as JP 52053851.*

Debnath et al, J. Med. Chem., 42,3202–9(1999).*

Verani et al, PuibMed Abstract 12462390, also cited as Curr. Mol. Med., 2/8, 691–702(2002).*

Agrawal et al(Expert Opinion Ther. Targetrs 5/3, 303–326(2001).*

Tagat et al,Bioorgic & Med. Chem. Letters, 11,2143–46(2001).*

Granata et al, PubMed. 12876405, also cited as Int. Arch Allergy Immunol., 13/3,153–63(2003).*

Scott et al, PubMed Abstract 12783578, also cited as Expert Opin. Ther. Targets,7/3,427–40(2003).*

Cecil Textbook of Medicine, Vool. 1, 20$^{th}$ Edn.,pp. 1004–1010(1996).*

F.M.Uckun t al,Current Cancer Drug Targets,1, 59–71(2001).*

Mikerova, N.I. et al., "Synthesis and Antiviral Activity of Derivatives of 2–Methyl–3– Ethoxycarbonyl–5–(5– Nitropyrimid–4–YL) Oxyindole," *Pharm. Chem. J.*, 25(6) :391–393 (1991).

Purohit, M.G. et al., "Synthesis and Antiserotonin Activity of Ethyl 5–0– (4–Methylpiperazin–1–ylacetyl) – 2–Methylindole–3–Carboxylates and 3–(4–Methyl–1–Piperazinyl–glyoxylyl)indoles," *Indian Journal of Chemistry*, 34B(9) :796–801 (1995).

Grinev, A.N. et al., *Chemical Abstracts*, 74(5), 22645u (1971).

Wrotek, J. et al., *Chemical Abstracts*, 75(25), 151627j (1971).

Gadaginamath, G.S. et al., *Chemical Abstracts*, 131(3), 31897a (1999).

Fadeeva, N.I. et al., *Chemical Abstracts*, 115(15), 158914d (1991).

Gadaginamath, G.S. et al., *Chemical Abstracts*, 124(11), 146011e (1996).

Mezentseva, M.V. et al., *Chemical Abstracts*, 115(13), 135866a (1991).

Zemskii, B.P. et al., *Chemical Abstracts*, 91(7), 56952h, (1979).

Shvedov, V.I. et al., *Chemical Abstracts*, 94(11), 76565z (1981).

Panisheva, E.K. et al., *Chemical Abstracts*, 115(5), 49345y (1991).

Zemskii, B.P. et al., "Synthesis and Neurotropic Activity of Heterocyclic Derivatives of 1–Piperazinylalkylindoles," *Pharm. Chem. J.*, 13(4) :378–381 (1979).

* cited by examiner

Example 185

FUNCTIONALIZED HETEROCYCLES AS MODULATORS OF CHEMOKINE RECEPTOR FUNCTION AND METHODS OF USE THEREFOR

RELATED APPLICATION

This application claims the benefit of U.S. Provisional Application No. 60/275,248, filed on Mar. 12, 2001. The entire teachings of the above application are incorporated herein by reference.

BACKGROUND OF THE INVENTION

Chemokines mediate a range of proinflammatory effects on cells (e.g., leukocytes), such as chemotaxis, degranulation, and integrin activation (Baggiolini et al., *Adv. Immunol.*, 1994;55:97–179; Oppenheim et al., *Annu. Rev. Immunol.*, 1991;9:617–648; Miller et al., *Crit. Rev. Immunol.*, 1992;12:17–46). These effects are mediated by binding to the seven-transmembrane-spanning G-protein coupled receptors (Baggiolini et al., *Adv. Immunol.*, 1994;55:97–179; Murphy, *Annu. Rev. Immunol.*, 1994;12:593–633; Schall et al., *Curr. Opin. Immunol.*, 1994;6:865–873; Gerard et al., *Curr. Opin. Immunol.*, 1994;6:140–145; Mackay, *Curr. Bio.*, In press). Chemokine receptors also serve as coreceptors for Human Immunodeficiency Virus (HIV) entry into cells. This came from observations that RANTES, MIP-1α, and MIP-1β suppressed infection of susceptible cells in vitro by macrophage-tropic primary HIV-1 isolates (Cocchi et al., *Science* (Wash. D.C.), 1995;270:1811–1815). The chemokine receptor CXCR-4 was found to support infection and cell fusion of $CD4^+$ cells by laboratory-adapted, T-tropic HIV-1 strains (Feng et al., *Science* (Wash. D.C.), 1996;272:872–877). CCR-5, which is a RANTES, MIP-1α, and MIP1β receptor, was subsequently identified as the principal coreceptor for primary macrophage-tropic strains (Choe et al., *Cell*, 1996;85:1135–1148; Alkhatib et al., *Science* (Wash. D.C.), 1996;272:1955–1958; Doranz et al., *Cell*, 1996;85:1149–1158; Deng et al., *Nature* (Lond.) 1996;381:661–666; Dragic et al., *Nature* (Lond.), 1996;381:667–673). The importance of CCR-5 for HIV-1 transmission was underscored by the observation that certain individuals who had been repeatedly exposed to HIV-1 but remained uninfected had a defect in CCR-5 expression (Liu et al., *Cell*, 1996; 86:367–377; Samson et al., *Nature* (Lond.), 1996;382:722–725; Dean et al., *Science* (Wash. D.C.), 1996;273:1856–1862; Huang et al., *Nature Med.*, 1996;2:1240–1243). These noninfectable individuals were found to be homozygous for a defective CCR-5 allele that contains an internal 32-base pair deletion (CCR-5 Δ32). The truncated protein encoded by this gene is apparently not expressed at the cell surface. CCR-5 Δ32 homozygous individuals comprise ~1% of the Caucasian population and heterozygous individuals comprise ~20%. In studies of about 2700 HIV-1 infected individuals, no Δ32 homozygotes were found. Individuals who are heterozygous for Δ32 CCR-5 allele have been shown to progress more slowly to AIDS than wild-type homozygous individuals (Samson et al., *Nature* (Lond.), 1996;382:722–725; Dean et al., *Science* (Wash. D.C.), 1996;273:1856–1862; Huang et al., *Nature Med.*, 1996;2:1240–1243). Thus, the identity of CCR-5 as the principal coreceptor for primary HIV isolates provides an opportunity to understand pathogenesis HIV infection and to identify new avenues for the treatment of HIV (e.g., HIV-1) infection. Prior studies of CCR5 also provide a basis for further studies into the pathogenesis of inflammatory diseases and for developing novel treatments for inflammatory diseases.

SUMMARY OF THE INVENTION

The invention relates to functionalized heteocyclic compounds (e.g., functionalized indoles (e.g., indole amines), functionalized benzimidazolones (e.g., benzimidazolone amines)) of Formula I, and to physiologically acceptable salts, amides, esters or prodrugs thereof. In one aspect, the compound is a functionalized benzimidazolone of Formula V. In another aspect, the compound is a functionalized indole of Formula VI. In particular embodiments, functionalized indole is an indole amine of Formula VII or Formula VIII. In certain embodiments, the compounds having the formulae

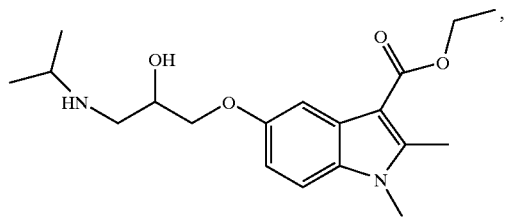

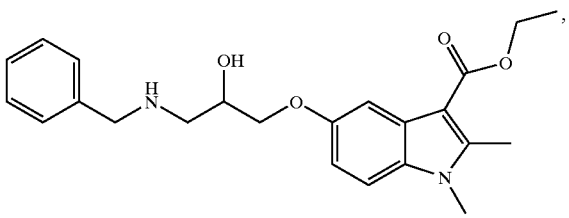

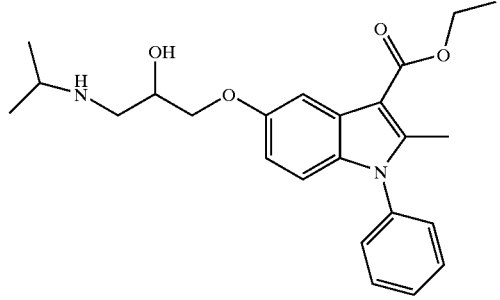

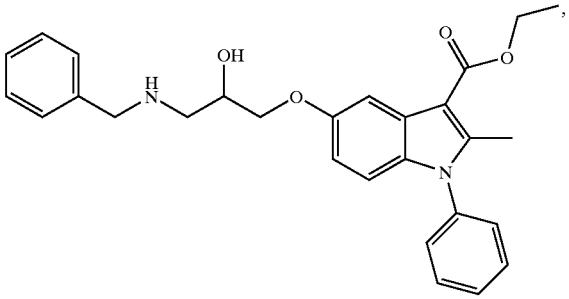

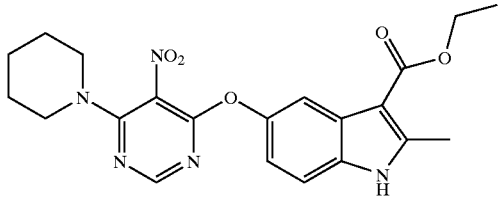

-continued

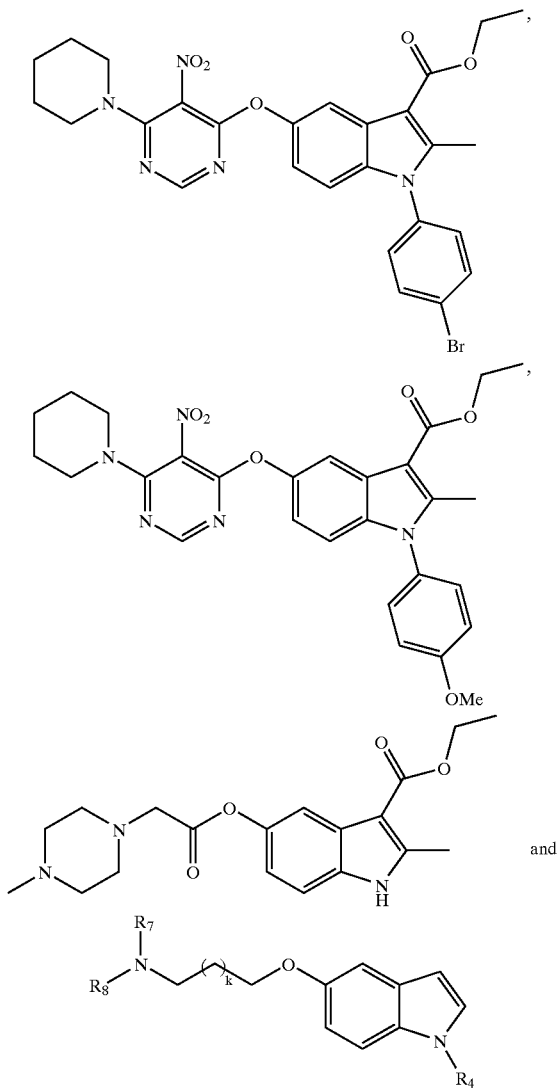

wherein R$_7$ and R$_8$ are independently hydrogen, methyl, ethyl or isopropyl; k is zero or one; and R$_4$ is hydrogen, methyl, ethyl, n-propyl, n-butyl, pentyl, phenyl or substituted phenyl, are excluded from the invention.

The compounds disclosed herein can modulate chemokine receptor and can be used to inhibit the binding of a ligand, such as a chemokine ligand (e.g., RANTES, MIP-1α, MIP-1β) or a virus to a chemokine receptor (e.g., CCR5). Accordingly, processes and cellular responses mediated by chemokine receptors can be inhibited using the compounds described herein.

The invention also relates to a pharmaceutical composition comprising a compound described herein and a physiologically acceptable vehicle, excipient, carrier or adjuvant.

The invention further relates to a method for treating a patient having a disease associated with aberrant or pathogenic leukocyte recruitment and/or activation, such a an acute or chronic inflammatory disorder, and to a method for treating a patient having a viral infection. The method comprises administering to a patient in need thereof an effective amount of a compound described herein. In particular embodiments, the invention is a method for treating a patient infected with HIV. In other embodiments, the invention is a method for inhibiting progression to AIDS or ARC in a patient infected with HIV.

The invention further relates to a functionalized heteocyclic compound (e.g., functionalized indoles (e.g., indole amines), functionalized benzimidazolones (e.g., benzimidazolone amines)), as described herein, for use in therapy (including prophylaxis) or diagnosis, and to the use of such a functionalized heteocyclic compound for the manufacture of a medicament for the treatment of a particular disease or condition as described herein (e.g., an inflammatory disease, HIV infection, AIDS).

DETAILED DESCRIPTION OF THE INVENTION

Figure 1:
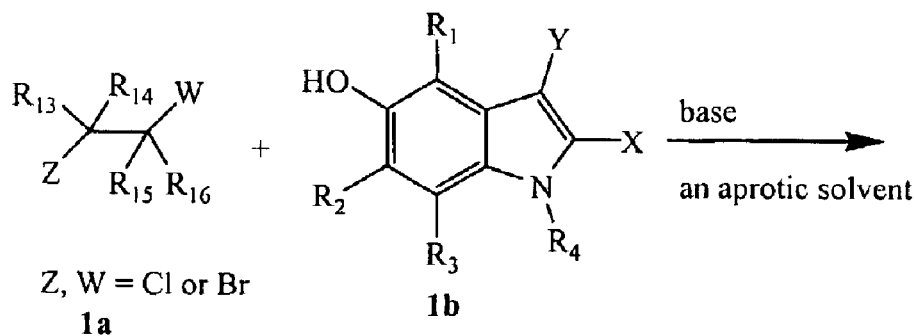
FIG. 1 is a schematic diagram showing the preparation of indole amines of Formula 1d.
Figure 1:
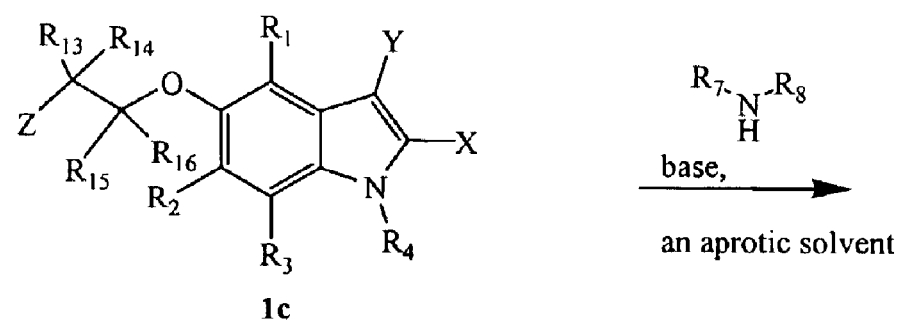
Figure 1:
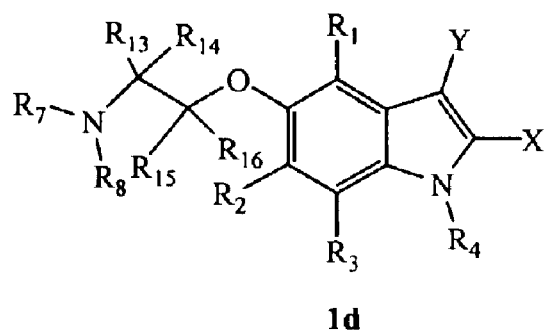

The present invention relates to functionalized heterocycles which are useful as modulators (agonists, antagonists) of a chemokine receptor (e.g., CCR1, CCR2, CCR2A, CCR2B, CCR3, CCR4, CCR5, CCR6, CCR7, CCR8, CCR9, CXCR1, CXCR2, CXCR3, CXCR4), to pharmaceutical compositions which include these compounds and a pharmaceutically acceptable carrier and to therapeutic and diagnostic methods which include administering a compound as described herein to a patient in need thereof. In one aspect, the functionalized heterocycles of the invention are chemokine receptor antagonists, which bind receptor and inhibit a function of the receptor, such as binding of a chemokine ligand or other ligand (e.g., virus) to receptor. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, granule release of proinflammatory mediators and/or infection by a virus (e.g., HIV). In particular embodiments, the functionalized heterocycles (e.g, functionalized indoles, functionalized benzimidazolones) described herein can inhibit the interaction of CD-4/human immunodeficiency virus glycoprotein 120 (HIV GP-120) with the C—C chemokine receptor 5 (CCR-5), and thus are useful in the treatment of HIV infection and AIDS.

The functionalized heterocyclic compounds of the invention have the formula

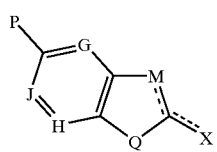

(I)

wherein:

G is $CR_1$ or N;

J is $CR_2$ or N;

H is $CR_3$ or N;

M is C—Y, CH—Y, N—Y or N;

Q is $NR_4$, $SR_4$, O, SO or $SO_2$;

X is hydrogen, halogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, oxygen, $NR_5$, S, $SR_5$ or $NR_5 R_6$;

Y is

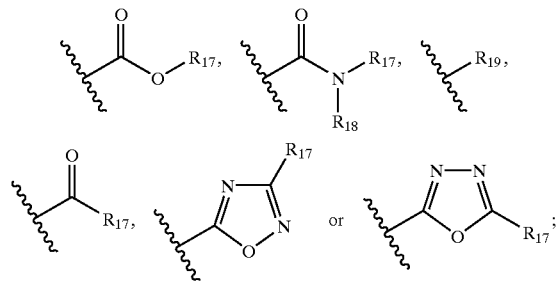

P is —A—L-nitrogen-containing heteroaryl, —A—L-substituted nitrogen-containing heteroaryl,

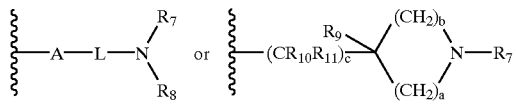

wherein a, b and c are each, independently, an integer from 0 to about 4. In particular embodiments, P is

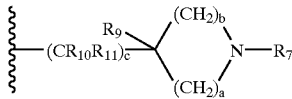

with the proviso that when a is 0, c is not 1 and when b is 0, c is not 1;

A is O, N(—$R_{12}$), a bond or is absent;

L is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, a bond, or

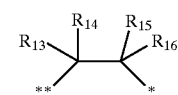

wherein * is the point of attachment to A; and

** is the point of attachment to N;

$R_1$, $R_2$, $R_3$, $R_{11}$, $R_{13}$, $R_{14}$, $R_{15}$, $R_{16}$ and $R_{19}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, halogen, $C_1$–$C_8$ alkoxy,

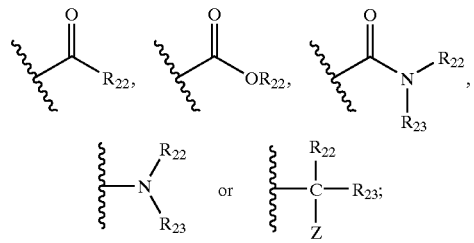

$R_{22}$ and $R_{23}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl; or $R_{22}$ and $R_{23}$ taken together with the atoms to which they are bonded can form a three to about eight membered cyclic ring which can contain zero to about three heteroatoms selected from the group consisting of oxygen, nitrogen and sulfur;

Z is aryl, substituted aryl, heteroaryl or substituted heteroaryl;

$R_4$, $R_5$, $R_6$, $R_7$, $R_8$, $R_9$, $R_{12}$, $R_{17}$ and $R_{18}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl,

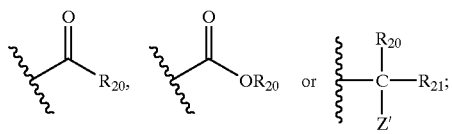

$R_{20}$ and $R_{21}$ are independently hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl or alkylheteroaryl; or $R_{20}$ and $R_{21}$ taken together with the atoms to which they are bonded can form a three to about eight membered cyclic ring which can contain zero to about three heteroatoms selected from the group consisting of oxygen, nitrogen and sulfur;

Z' is aryl, substituted aryl, heteroaryl or substituted heteroaryl; or $R_1$ taken together with any one of $R_7$, $R_8$, $R_9$, $R_{10}$, $R_{11}$, $R_{12}$, $R_{13}$, $R_{14}$, $R_{15}$ or $R_{16}$ and the atoms to which they are bonded can form a substituted or unsubstituted three to about eight membered cyclic ring which can contain zero to about three heteroatoms selected from the group consisting of oxygen, nitrogen and sulfur;

$R_2$ taken together with any one of $R_3$, $R_7$, $R_8$, $R_9$, $R_{10}$, $R_{11}$, $R_{12}$, $R_{13}$, $R_{14}$, $R_{15}$ or $R_{16}$ and the atoms to which they are bonded can form a substituted or unsubstituted three to about eight membered cyclic ring which can contain zero to about three heteroatoms selected from the group consisting of oxygen, nitrogen and sulfur;

P taken together with either $R_1$ or $R_2$ and the atoms to which they are bonded can form a five to about eight membered substituted nonaromatic ring that can contain a heteroatom selected from the group consisting of oxygen, nitrogen and sulfur; and any two of $R_7$, $R_8$, $R_9$, $R_{10}$, $R_{11}$, $R_{12}$, $R_{13}$, $R_{14}$, $R_{15}$, $R_{16}$ and $R_{17}$, taken together with the atoms to which they are bonded can form a substituted or unsubstituted three to about eight membered cyclic ring which can contain zero to about three heteroatoms selected from the group consisting of oxygen, nitrogen and sulfur.

The invention includes pharmaceutically or physiologically acceptable salts, esters, amides, and prodrugs of the compounds described herein.

In certain embodiments, the compound does not have a formula selected from the group consisting of:

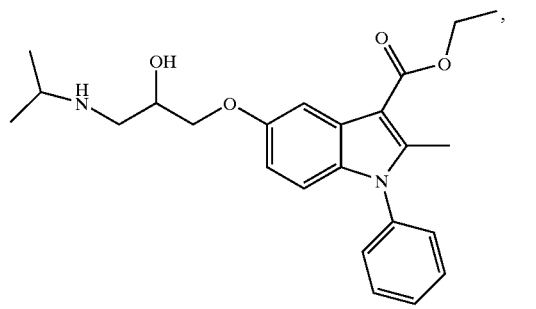

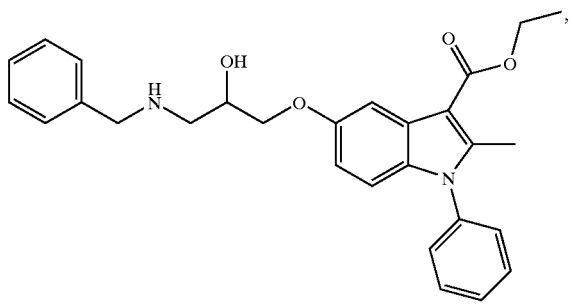

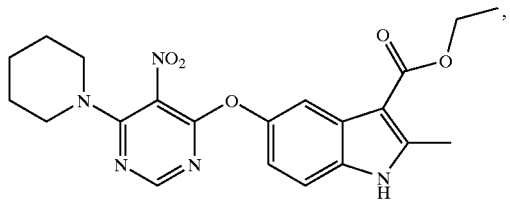

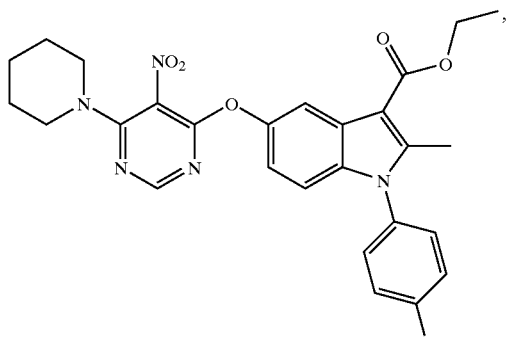

-continued

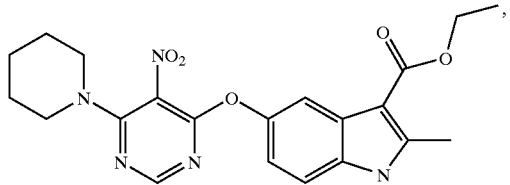

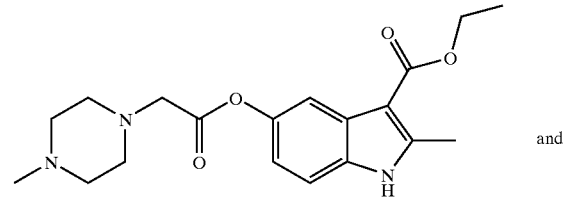

and

-continued

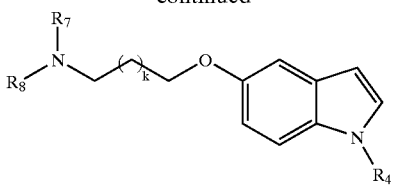

wherein $R_7$ and $R_8$ are independently hydrogen, methyl, ethyl or isopropyl; k is zero or one; and $R_4$ is hydrogen, methyl, ethyl, n-propyl, n-butyl, pentyl, phenyl or substituted phenyl.

Preferably, Q in Formula I is $NR_4$, and the compound has the Formula

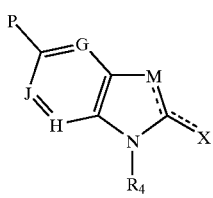

(II)

wherein G, J, H, M, $R_4$, P and X are as described in Formula I. Also preferred are compounds of Formula II wherein G is $CR_1$, J is $CR_2$ and H is $CR_3$.

Also preferred are compounds of Formula III or Formula IV.

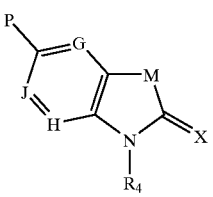

(III)

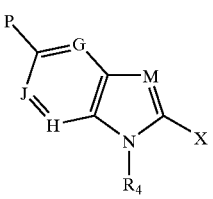

(IV)

In Formula III, G, J, H, P and $R_4$ are as described in Formula I;
M is N—Y or CH—Y; and
X is oxygen, S or $SR_5$.

Also preferred are compounds of Formula III wherein G is $CR_1$, J is $CR_2$ and H is $CR_3$ and X is oxygen.

In Formula IV, G, J, H, P and $R_4$ are as described in Formula I;
M is C—Y or N; and
X is hydrogen, halogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, $SR_5$ or $NR_5 R_6$.

Also preferred are compounds of Formula III wherein G is $CR_1$, J is $CR_2$ and H is $CR_3$.

In one aspect, the functionalized heterocycle is a functionalized benzimidazole of Formula V:

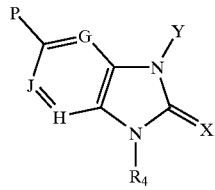

(V)

wherein G, J, H, Y, P and $R_4$ are as described in Formula I, and X is O, S or $NR_5$. In particular embodiments, the compound has the structure of Formula V wherein G is $CR_1$, J is $CR_2$ and H is $CR_3$.

Preferred compound of Formula V are those where $R_4$ is hydrogen. Additional preferred compounds of Formula V are those where X is oxygen. For example, the functionalized heterocycle can be an aza-benzimidazolone amine having a formula selected from Formulas Va, Vb, Vc, Vd, Ve and Vd, or a benzimidazolone amine of Formula Vf.

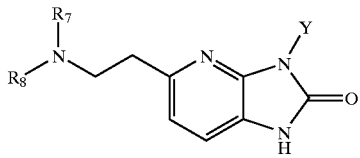

(Va)

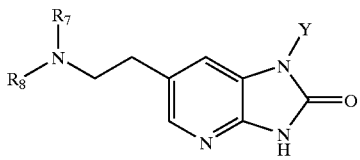

(Vb)

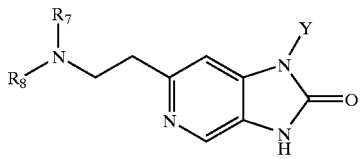

(Vc)

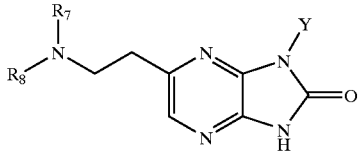

(Vd)

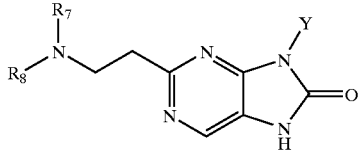

(Ve)

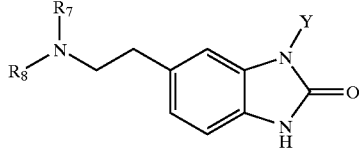

(Vf)

In Formulas Va–Vf, $R_7$, $R_8$, $R_{11}$ and Y are as defined above for Formula I.

In another aspect, the functionalized heterocycle of Formula III is a functionalized indole of Formula VI:

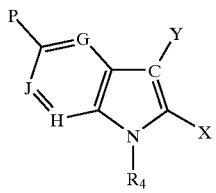

(VI)

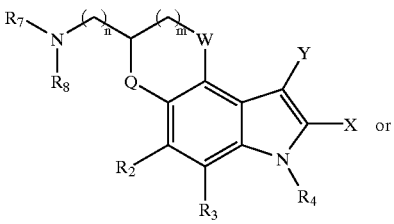

(VII)

wherein G, J, H, P, X, Y and $R_4$ are as described in Formula I. In particular embodiments, the compound has the structure of Formula VI wherein G is $CR_1$, J is $CR_2$ and H is $CR_3$. For example, the functionalized heterocycle can be an aza-indole-amine having a formula selected from Formulas VIa, VIb, VIc, VId and VIe, or an indole-amine of Formula VIf.

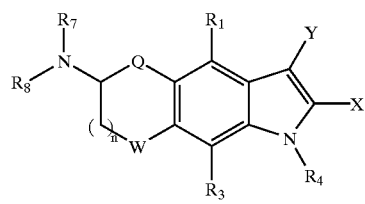

(VIII)

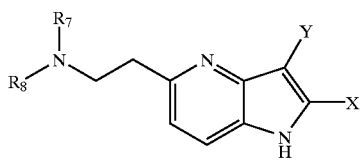

(VIa)

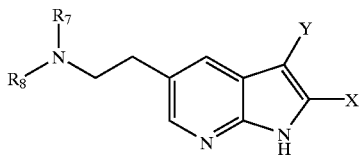

(VIb)

In Formulas VII and VIII, n is an integer from zero to about three;

m is zero or one;

W is $CH_2$ or $C(\!=\!O)$;

Q is $CH_2$, $NR_{18}$, O or S; and $R_1$, $R_2$, $R_3$, $R_4$, $R_7$, $R_8$, X and Y are as described in Formula I.

In particular embodiments, the compound is a compound of Formulas I–III or V wherein X is oxygen.

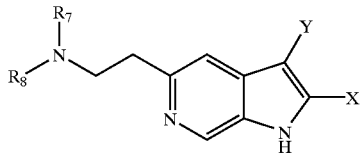

(VIc)

In other embodiments, the compound is a compound of Formulas I–V, VI, VII or VIII wherein J is $CR_2$, H is $CR_3$, and $R_2$ and $R_3$ are independently hydrogen, a halogen, $—CH_3$, $—CF_3$ or $—OCH_3$.

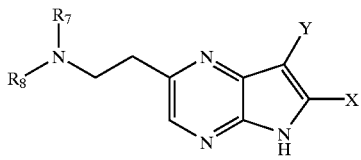

(VId)

In additional embodiments, the compound is of Formulas I–V, VI, VII or VIII wherein Y is

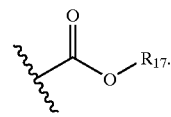

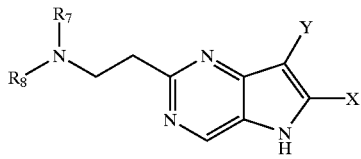

(VIe)

In more specific embodiments, the compound is a compound of Formulas I–V, VI, VII or VIII wherein Y is

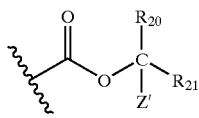

(VIf)

In Formulas VIa–VIf, $R_7$, $R_8$, $R_{11}$ and Y are as defined above for Formula I.

In certain embodiments, the compound has the structure of Formula VI or VIa–VIf where X is phenyl, substituted phenyl, pyridyl or substituted pyridyl. Preferably, X is phenyl.

In further aspects, the functionalized heterocycle can have the formula:

wherein $R_{20}$ and $R_{21}$ are independently hydrogen, $C_1$–$C_8$ alkyl, substituted $C_1$–$C_8$ alkyl or $R_{20}$ and $R_{21}$ taken together with the carbon atom to which they are bonded form a three to about eight membered ring which can contain one to about three heteroatoms selected from the group consisting of oxygen, nitrogen and sulfur; and Z' is selected from the group consisting of aryl, substituted aryl, heteroaryl and substituted heteroaryl.

In further embodiments, the compound is a compound of Formulas I–V, VI, VII or VIII wherein Y is

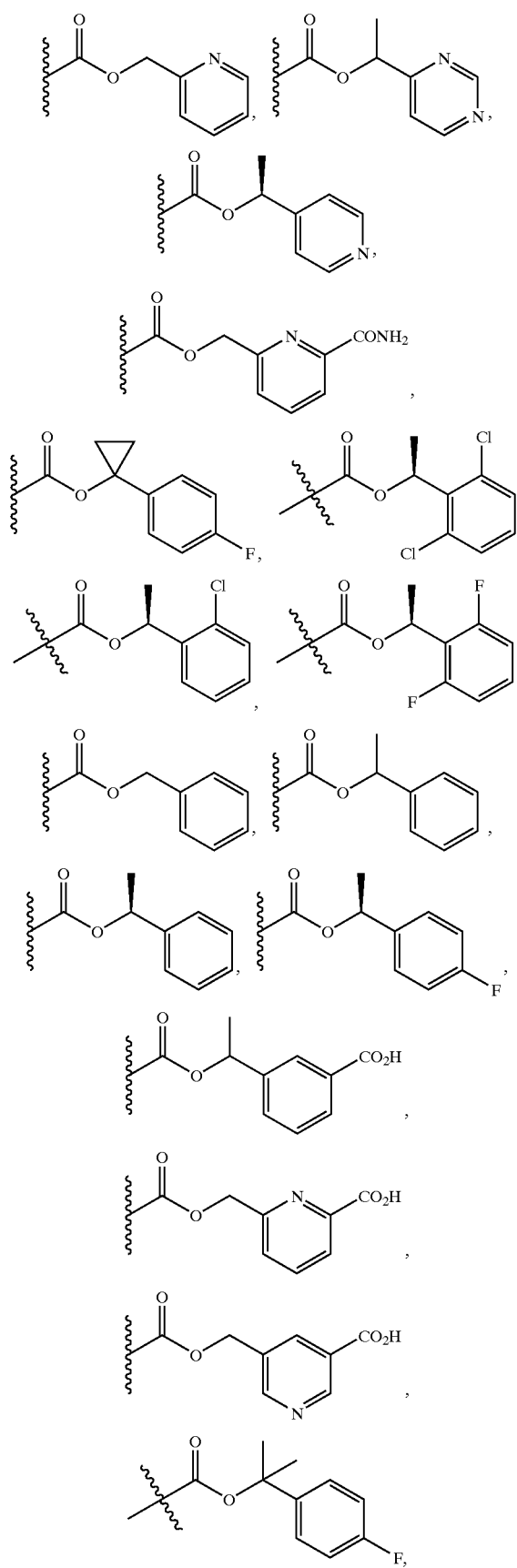

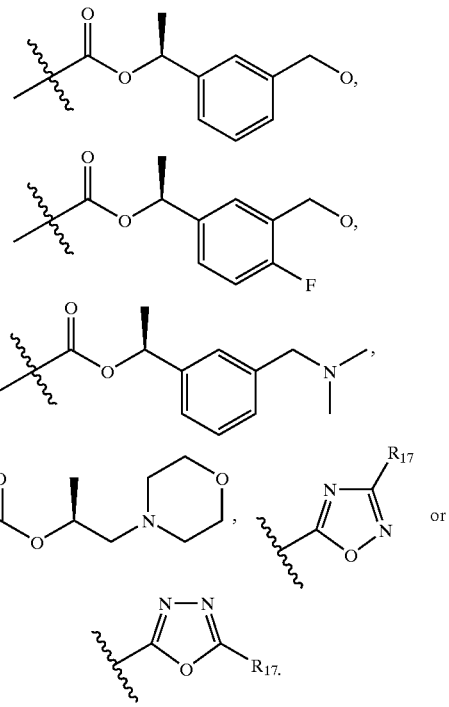

In more particular embodiments, the compound is of formulas I–V, VI, VII or VIII wherein Y is

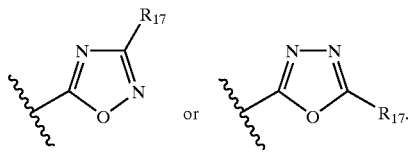

In other embodiments, the compound is a compound of Formulas I–V, VI, VII or VIII wherein $R_{17}$ and $R_{19}$ are independently selected from the group consisting of $C_1$–$C_8$ alkyl, substituted $C_1$–$C_8$ alkyl, phenyl, substituted phenyl and pyridyl. In particular embodiments, $R_{17}$ and $R_{19}$ are phenyl.

In certain embodiments, the compound is a compound of Formulas I–V or VI wherein L is

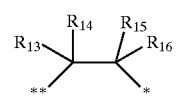

wherein * is the point of attachment to A, ** is the point of attachment to N, and A is a bond.

In more particular embodiments, the compound is a compound of Formulas I–V or VI wherein P is

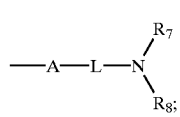

$R_7$ and $R_8$ are ethyl, and L is

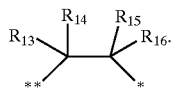

In addition particular embodiments, the compound is a compound of Formulas I–V or VI wherein P is

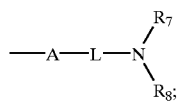

$R_7$ and $R_8$ are ethyl, L is

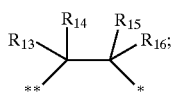

and Y is

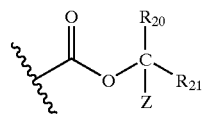

wherein $R_{20}$ and $R_{21}$ are independently hydrogen, $C_1$–$C_8$ alkyl, substituted $C_1$–$C_8$ alkyl, or $R_{20}$ and $R_{21}$ taken together with the carbon atom to which they are bonded form a three to about eight membered ring which can contain one to about three heteroatoms selected from the group consisting of oxygen, nitrogen and sulfur; and Z is selected from the group consisting of aryl, substituted aryl, heteroaryl and substituted heteroaryl.

In further particular embodiments, the compound is a compound of Formulas I–V or VI wherein P is

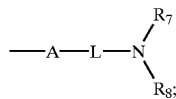

$R_7$ and $R_8$ taken together with the nitrogen atom to which they are bonded form a three to about eight membered cyclic ring which can contain one or two additional heteroatoms selected from the group consisting of oxygen, nitrogen and sulfur;

L is

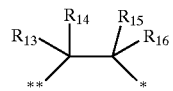

and Y is

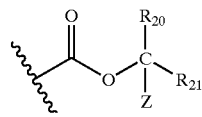

wherein $R_{20}$ and $R_{21}$ are independently hydrogen, $C_1$–$C_8$ alkyl, substituted $C_1$–$C_8$ alkyl, or $R_{20}$ and $R_{21}$ taken together with the carbon atom to which they are bonded form a three to about eight membered ring which can contain one to about three heteroatoms selected from the group consisting of oxygen, nitrogen and sulfur; and Z is selected from the group consisting of aryl, substituted aryl, heteroaryl and substituted heteroaryl.

Preferred compounds of Formulas I, II, IV or VI include those wherein X is methyl or trifluoromethyl, A is a bond, $R_4$ is hydrogen and Y is

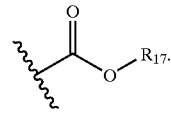

Preferred compounds of Formulas I–V, VII or VIII include those wherein X is oxygen, $R_4$ is hydrogen and Y is

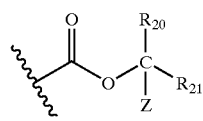

$R_{20}$ and $R_{21}$ are independently hydrogen, $C_1$–$C_8$ alkyl, substituted $C_1$–$C_8$ alkyl, or $R_{20}$ and $R_{21}$ taken together with the carbon atom to which they are bonded form a three to about eight membered ring which can contain one to about three heteroatoms selected from the group consisting of oxygen, nitrogen and sulfur; and Z is selected from the group consisting of aryl, substituted aryl, heteroaryl and substituted heteroaryl.

Further preferred compounds of Formulas I–V, VI, VII or VIII are those wherein X is oxygen, $R_4$ is hydrogen and Y is

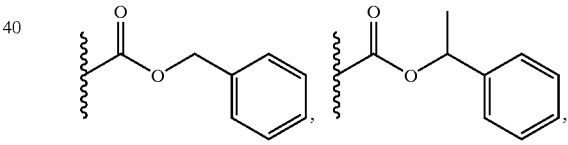

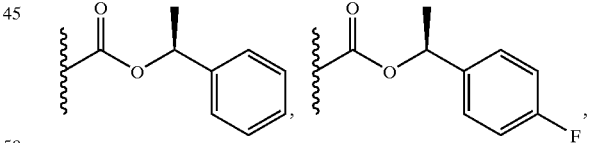

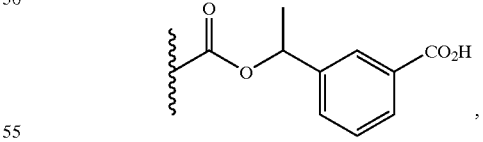

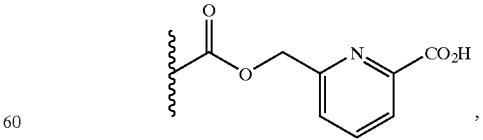

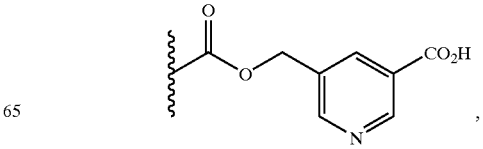

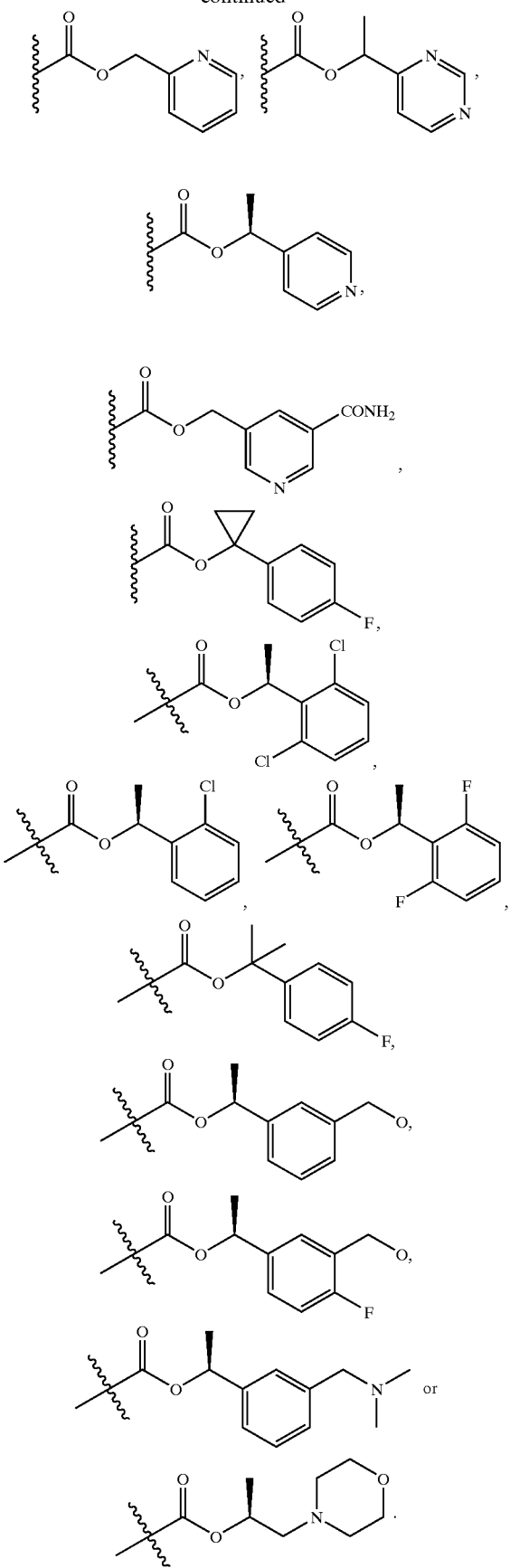

In more particular embodiments, the compound is selected from:

5-[2-(4-tert-Butoxycarbonyl-piperazin-1-yl)-ethoxy]-2-methyl-1H-indole-3-carboxylic acid benzyl ester;
1-[2-(3-Benzyloxycarbonyl-2-methyl-1H-indole-5-yloxy)-ethyl]-piperazin-1-ium; chloride;
2-Methyl-5-[2-(4-methyl-piperazin-1-yl)-ethoxy]-1H-indole-3-carboxylic acid benzyl ester;
2-Methyl-5-[2-(3-methyl-pyrrolidin-1-yl)-ethoxy]-1H-indole-3-carboxylic acid benzyl ester;
1-[2-(3-Benzyloxycarbonyl-2-methyl-1H-indole-5-yloxy)-ethyl]-3-phenyl-pyrrolidinium; chloride;
5-(2-Diisopropylamino-ethoxy)-2-methyl-1H-indole-3-carboxylic acid benzyl ester;
1-Benzyl-5-(2-diethylamino-ethoxy)-2-methyl-1H-indole-3-carboxylic acid benzyl ester;
1-Methyl-5-(2-diethylamino-ethoxy)-2-methyl-1H-indole-3-carboxylic acid benzyl ester;
5-(1-Diethylcarbamoyl-propoxy)-2-methyl-1H-indole-3-carboxylic acid benzyl ester;
2-Methyl-5-(4-pyrrolidin-1-yl-butoxy)-1H-indole-3-carboxylic acid benzyl ester;
2-Methyl-5-(4-pyrrolidin-1-yl-butoxy)-1H-indole-3-carboxylic acid benzyl ester;
2-Methyl-5-(2-piperidin-1-yl-ethoxy)-1H-indole-3-carboxylic acid benzyl ester;
5-(2-Diethylamino-ethoxy)-2-methyl-1H-indole-3-carboxylic acid benzyl ester;
5-(2-Diethylamino-ethyl)-2-phenyl-1H-indole-3-carboxylic acid benzyl ester;
2-Methyl-5-[2-(3,3,4,4-tetramethyl-pyrrolidin-1-yl)-ethoxy]-1H-indole-3-carboxylic acid benzyl ester;
2-Methyl-5-[2-(2-phenyl-pyrrolidin-1-yl)-ethoxy]-1H-indole-3-carboxylic acid benzyl ester;
5-[2-((R)-3-Hydroxymethyl-pyrrolidin-1-yl)-ethoxy]-2-methyl-1H -indole-3-carboxylic acid benzyl ester;
2-Methyl-5-[2-(2-pyridin-3-yl-pyrrolidin-1-yl)-ethoxy]-1H-indole-3-carboxylic acid benzyl ester;
5-(2-Dipropylamino-ethoxy)-2-methyl-1H-indole-3-carboxylic acid benzyl ester;
5-(2-Diethylamino-ethyl)-2-trifluoromethyl-1H-indole-3-carboxylic acid benzyl ester;
2-Methyl-5-(2-pyrrolidine-1-yl-ethylamino)-1H-indole-3-carboxylic acid benzyl ester;
5-Amino-2-methyl-1H-indole-3-carboxylic acid benzyl ester;
5-[Bis-(2-pyrrolidine-1-yl-ethyl)-amino]-2-methyl-1H-indole-3-carboxylic acid benzyl ester;
5-[Acetyl-(2-pyrrolidine-1-yl-ethyl)-amino]-2-methyl-1H-indole-3-carboxylic acid benzyl ester;
2-Methyl-5-(4-phenyl-piperazin-1-yl)-1H-indole-3-carboxylic acid benzyl ester;
5-[2-(4-Hydroxy-piperidine-1-yl)-ethoxy]-2-methyl-1H-indole-3-carboxylic acid benzyl ester;
2-Methyl-5-[2-(2-methyl-pyrrolidin-1-yl)-ethoxy]-1H-indole-3-carboxylic acid benzyl ester;
2-Methyl-5-[2-(2-oxa-6-aza-bicyclo[2.2.1]hept-6-yl)-ethoxy]-1H-indole-3-carboxylic acid benzyl ester;
5-{2-[3-(Acetyl-methyl-amino)-pyrrolidin-1-yl)-ethoxy}-2-methyl-1H-indole-3-carboxylic acid benzyl ester;
5-[2-(2,5-Dimethyl-pyrrolidin-1-yl)-ethoxy]-2-methyl-1H-indole-3-carboxylic acid benzyl ester;
5-[2-(3-Dimethylamino-pyrrolidin-1-yl)-ethoxy]-2-methyl-1H-indole-3-carboxylic acid benzyl ester, dihydrochloride;
2-Methyl-5-[2-(1,3,3-trimethyl-6-aza-bicyclo[3.2.1]oct-6-yl)-ethoxy]-1H-indole-3-carboxylic acid benzyl ester;

2-Methyl-5-[2-(1,3,3-trimethyl-6-aza-bicyclo[3.2.1]oct-6-yl)-ethyl]-1H-indole-3-carboxylic acid benzyl ester;

5-[2-((R)-2-Methoxymethyl-pyrrolidin-1-yl)-ethyl]-2-methyl-1H-indole-3-carboxylic acid benzyl ester;

2-Methyl-5-[2-(2-methyl-pyrrolidin-1-yl)-ethyl]-1H-indole-3-carboxylic acid benzyl ester;

5-[2-((R)-2-Hydroxymethyl-pyrrolidin-1-yl)-ethyl]-2-methyl-1H-indole-3-carboxylic acid benzyl ester;

5-[2-((S)-2-Methoxymethyl-pyrrolidin-1-yl)-ethyl]-2-methyl-1H-indole-3-carboxylic acid benzyl ester;

5-(2-Azetidin-1-yl-ethyl]-2-methyl-1H-indole-3-carboxylic acid benzyl ester;

2-Methyl-5-[2-(2-oxa-5-aza-bicyclo[2.2.1]hept-5-yl)-ethyl]-1H-indole-3-carboxylic acid benzyl ester;

5-{2-[3-(Acetyl-methyl-amino)-pyrrolidin-1-yl]-ethyl}-2-methyl-1 H-indole-3-carboxylic acid benzyl ester;

5-[2-(4-Hydroxy-piperidine-1-yl)-ethyl]-2-methyl-1H-indole-3-carboxylic acid benzyl ester;

2-Methyl-5-(3-pyrrolidin-1-yl-propoxy)-1H-indole-3-carboxylic acid benzyl ester;

2-Methyl-S-(1-methyl-piperidin-2-yl-methoxy)-1H-indole-3-carboxylic acid benzyl ester;

5-(1-Diethylcarbamoyl-1-methyl-ethoxy)-2-methyl-1H-indole-3-carboxylic acid benzyl ester;

2-Methyl-7-pyrrolidin-1-yl-methyl-3,7,8,9-tetrahydro-pyrano[3,2-e]indole-1-carboxylic acid benzyl ester;

2-Methyl-5-(2-methyl-2-pyrrolidin-1-yl-propoxy)-1H-indole-3-carboxylic acid benzyl ester;

2-Methyl-5-(1-methyl-piperidin-3-ylmethoxy)-1H-indole-3-carboxylic acid benzyl ester;

5-(1-benzyl-pyrrolidin-3-yloxy)-2-methyl-1H-indole-3-carboxylic acid benzyl ester;

5-(1-Ethyl-pyrrolidin-3-yloxy)-2-methyl-1H-indole-3-carboxylic acid benzyl ester;

2-Methyl-5-(pyrrolidin-3-yloxy)-1H-indole-3-carboxylic acid benzyl ester, hydrochloride;

5-(1-Isopropyl-pyrrolidin-3-yloxy)-2-methyl-1H-indole-3-carboxylic acid benzyl ester;

5-Carbamimidoylmethoxy-2-methyl-1H-indole-3-carboxylic acid benzyl ester;

5-(2-Imino-2-pyrrolidin-1-yl-ethoxy)-2-methyl-1H-indole-3-carboxylic acid benzyl ester;

2-Methyl-5-pyridin-3-yl-1H-indole-3-carboxylic acid benzyl ester;

2-Methyl-5-pyridin-3-yl-indole-1,3-dicarboxylic acid 3-benzyl ester 1-tert-butyl ester;

5-(3-Diethylamino-propyl)-2-methyl-1H-indole-3-carboxylic acid benzyl ester;

5-(3-Dimethylamino-prop-1-ynyl)-2-methyl-1H-indole-3-carboxylic acid benzyl ester;

5-((Z)-3-Dimethylamino-propenyl)-2-methyl-1H-indole-3-carboxylic acid benzyl ester;

5-(1-Ethyl-pyrrolidin-3-yl)-2-methyl-1H-indole-3-carboxylic acid benzyl ester;

2-Methyl-5-(2-pyrrolidin-1-yl-ethyl)-1H-indole-3-carboxylic acid benzyl ester hydrochloride;

2-Methyl-5-(2-pyrrolidin-1-yl-ethyl)-1H-indole-3-carboxylic acid benzyl ester;

2-Methyl-5-[2-(4-methyl-piperazin-1-yl)-ethyl]-1H-indole-3-carboxylic acid benzyl ester;

5-[2-(Cyclohexyl-methyl-amino)-ethyl]-2-methyl-1H-indole-3-carboxylic acid benzyl ester;

2-Methyl-5-(2-piperidin-1-yl-ethyl)-1H-indole-3-carboxylic acid benzyl ester;

5-(2-Diisobutylamino-ethyl)-2-methyl-1H-indole-3-carboxylic acid benzyl ester;

2-Methyl-5-(2-methylamino-ethyl)-1H-indole-3-carboxylic acid benzyl ester;

2-Methyl-5-{2-[methyl-(tetrahydro-pyran-4-yl)-amino]-ethyl}-1H-indole-3-carboxylic acid benzyl ester;

5-Aminomethyl-2-methyl-1H-indole-3-carboxylic acid benzyl ester, hydrochloride;

5-(tert-Butoxycarbonylamino-methyl)-2-methyl-1H-indole-3-carboxylic acid benzyl ester;

5-Diethylaminomethyl-2-methyl-1H-indole-3-carboxylic acid benzyl ester;

5-(2-Diethylamino-ethyl)-2-methyl-1H-indole-3-carboxylic acid (S)-1-phenyl-ethyl ester, hydrochloride;

5-(2-Diethylamino-ethyl)-2-methyl-1H-indole-3-carboxylic acid (S)-1-phenyl-ethyl ester;

5-(2-Dimethylamino-ethoxy)-2-methyl-1H-indole-3-carboxylic acid (S)-1-phenyl-ethyl ester;

2-Methyl-5-(2-morpholin-4-yl-ethoxy)-1H-indole-3-carboxylic acid 1-phenyl ethyl ester hydrochloride;

2-Methyl-5-(2-pyrrolidin-1-yl-ethoxy)-1H-indole-3-carboxylic acid-1-phenyl ethyl ester hydrochloride;

2-Methyl-5-(pyrrolidin-1-yl-ethoxy)-1H-indole-3-carboxylic acid benzyl ester;

2-Methyl-5-(1-methyl-2-pyrrolidin-1-yl-propoxy)-1H-indole-3-carboxylic acid benzyl ester;

5-(2-Cyclohexylamino-ethyl)-2-methyl-1H-indole-3-carboxylic acid benzyl ester;

5-(2-tert-Butoxycarbonylamino ethyl)-2-methyl-1H-indole-3-carboxylic acid benzyl ester;

5-(2-Diethylamino-ethyl)-2-methyl-1H-indole-3-carboxylic acid benzyl exter hydrochloride;

5-(2-Diethylamino-ethyl)-2-methyl-1H-indole-3-carboxylic acid-1-(4-bromophenyl)-ethyl ester;

5-(2-Diethylamino-ethyl)-2-methyl-1H-indole-3-carboxylic acid-1-(4-(2-methyl-2-propyl)phenyl)-ethyl ester;

5-(2-Diethylamino-ethyl)-2-methyl-1H-indole-3-carboxylic acid-1-(2-chlorophenyl)-ethyl ester;

5-(2-Diethylamino-ethyl)-2-methyl-1H-indole-3-carboxylic acid-1-(2,6-dichlorophenyl)-ethyl ester;

5-(2-Diethylamino-ethyl)-2-methyl-1H-indole-3-carboxylic acid 3,5-dichlorobenzyl ester;

5-(2-N-Cyclohexyl-N-methyl-amino-ethyl)-2-methyl-1H-indole-3-carboxylic acid-1-(4-bromophenyl)-ethyl ester;

5-(2-N-Cyclohexyl-N-methyl-amino-ethyl)-2-methyl-1H-indole-3-carboxylic acid-1-(3-fluorophenyl)-ethyl ester;

5-(2-Diethylamino-ethyl)-2-methyl-1H-indole-3-carboxylic acid-1-(3-fluorophenyl)-ethyl ester;

5-(2-N-Cyclohexyl-N-methyl-amino-ethyl)-2-methyl-1H-indole-3-carboxylic acid-1-(2-chlorophenyl)-ethyl ester;

5-(2-N-Cyclohexyl-N-methyl-amino-ethyl)-2-methyl-1H-indole-3-carboxylic acid-1-(2,6-dichlorophenyl)-ethyl ester;

5-(2-Pyrrolidino-ethyl)-2-methyl-1H-indole-3-carboxylic acid-1-(3-fluorophenyl)-ethyl ester;

5-(2-Pyrrolidino-ethyl)-2-methyl-1H-indole-3-carboxylic acid-1-(2-chlorophenyl)-ethyl ester;

5-(2-Pyrrolidino-ethyl)-2-methyl-1H-indole-3-carboxylic acid-1-(2,6-dichlorophenyl)-ethyl ester;

5-(2-Pyrrolidino-ethyl)-2-methyl-1H-indole-3-carboxylic acid-(S)-1-phenyl-ethyl ester;

5-(2-Pyrrolidino-ethyl)-2-methyl-1H-indole-3-carboxylic acid 3,5-dichloro-benzyl ester;

5-(2-Piperidino-ethyl)-2-methyl-1H-indole-3-carboxylic acid-1-(3-fluorophenyl)-ethyl ester;

5-(2-Piperidino-ethyl)-2-methyl-1H-indole-3-carboxylic acid-1-(2-chlorophenyl)-ethyl ester;

5-(2-Piperidino-ethyl)-2-methyl-1H-indole-3-carboxylic acid-1-(2,6-dichlorophenyl)-ethyl ester;

5-(2-Piperidino-ethyl)-2-methyl-1H-indole-3-carboxylic acid 3,5-dichloro-benzyl ester;

5-(2-Piperidino-ethyl)-2-methyl-1H-indole-3-carboxylic acid-(S)-1-phenyl-ethyl ester;

5-(2-(4-Hydroxy-piperidino)-ethyl)-2-methyl-1H-indole-3-carboxylic acid-1-(3-fluorophenyl)-ethyl ester;

5-(2-(4-Hydroxy-piperidino)-ethyl)-2-methyl-1H-indole-3-carboxylic acid-1-(2-chlorophenyl)-ethyl ester;

5-(2-(4-Hydroxy-piperidino)-ethyl)-2-methyl-1H-indole-3-carboxylic acid-1-(2,6-dichlorophenyl)-ethyl ester;

5-(2-(4-Hydroxy-piperidino)-ethyl)-2-methyl-1H-indole-3-carboxylic acid 3,5-dichloro-benzyl ester;

5-(2-(4-Hydroxy-piperidino)-ethyl)-2-methyl-1H-indole-3-carboxylic acid-(S)-1-phenyl-ethyl ester;

5-(2-Piperidino-ethyl)-2-methyl-1H-indole-3-carboxylic acid 3-nitro-4-methyl-benzyl ester;

5-(2-Diethylamino-ethyl)-2-methyl-1H-indole-3-carboxylic acid 3-nitro-4-methyl-benzyl ester;

5-(2-Pyrrolidino-ethyl)-2-methyl-1H-indole-3-carboxylic acid 3-nitro-4-methyl-benzyl ester;

5-(2-N-Cyclohexyl-N-methyl-amino-ethyl)-2-methyl-1H-indole-3-carboxylic acid 3-nitro-4-methyl-benzyl ester;

5-(2-Piperidino-ethyl)-2-methyl-1H-indole-3-carboxylic acid-1-(4-fluorophenyl)-ethyl ester;

5-(2-Pyrrolidino-ethyl)-2-methyl-1H-indole-3-carboxylic acid-1-(4-fluorophenyl)-ethyl ester;

5-(2-N-Cyclohexyl-N-methyl-amino-ethyl)-2-methyl-1H-indole-3-carboxylic acid-1-(4-fluorophenyl)-ethyl ester;

5-(2-Diethylamino-ethyl)-2-methyl-1H-indole-3-carboxylic acid 2-biphenyl methyl ester;

5-(2-Piperidino-ethyl)-2-methyl-1H-indole-3-carboxylic acid 2-biphenyl methyl ester;

5-(2-Pyrrolidino-ethyl)-2-methyl-1H-indole-3-carboxylic acid 2-biphenyl methyl ester;

5-(2-N-Cyclohexyl-N-methyl-amino-ethyl)-2-methyl-1H-indole-3-carboxylic acid 2-biphenyl methyl ester;

5-(2-Diethylamino-ethyl)-2-methyl-1H-indole-3-carboxylic acid-1-(3-chlorophenyl)-ethyl ester;

5-(2-Diethylamino-ethyl)-2-methyl-1H-indole-3-carboxylic acid-1-(2-trifluoromethyl-phenyl)-ethyl ester;

5-(2-Diethylamino-ethyl)-2-methyl-1H-indole-3-carboxylic acid-1-(2-bromophenyl)-ethyl ester;

5-(2-Diethylamino-ethyl)-2-methyl-1H-indole-3-carboxylic acid-1-(2,4-dichlorophenyl)-ethyl ester;

5-(2-Diethylamino-ethyl)-2-methyl-1–1-indole-3-carboxylic acid-1-(4-chlorophenyl)-ethyl ester;

5-(2-Diethylamino-ethyl)-2-methyl-1H-indole-3-carboxylic acid 5,6,7,8-tetrahydronaphth-5-yl ester;

5-(2-Diethylamino-ethyl)-2-methyl-1H-indole-3-carboxylic acid indan-1-yl ester, 5-(2-Diethylamino-ethyl)-2-methyl-1H-indole-3-carboxylic acid 1-methyl-1-cyclopentyl ester;

5-(2-Diethylamino-ethyl)-2-methyl-1H-indole-3-carboxylic acid 1-methyl-1-cyclohexyl ester;

5-(2-Piperidino-ethyl)-2-methyl-1H-indole-3-carboxylic acid-1-(2-bromophenyl)-ethyl ester;

5-(2-Piperidino-ethyl)-2-methyl-1H-indole-3-carboxylic acid-1-(4-bromophenyl)-ethyl ester;

5-(2-Piperidino-ethyl)-2-methyl-1H-indole-3-carboxylic acid-1-(4-(2-methyl-2-propyl)phenyl)-ethyl ester;

5-(2-Piperidino-ethyl)-2-methyl-1H-indole-3-carboxylic acid-1-(2,4-dichlorophenyl)-ethyl ester;

5-(2-Piperidino-ethyl)-2-methyl-1H-indole-3-carboxylic acid-1-(4-chlorophenyl)-ethyl ester;

5-(2-Piperidino-ethyl)-2-methyl-1H-indole-3-carboxylic acid 1,2,3,4-tetrahydronaphth-1-yl ester;

5-(2-Piperidino-ethyl)-2-methyl-1H-indole-3-carboxylic indan-1-yl ester;

5-(2-Piperidino-ethyl)-2-methyl-1H-indole-3-carboxylic acid 1-methyl-1-cyclopentyl ester;

5-(2-Piperidino-ethyl)-2-methyl-1H-indole-3-carboxylic acid 1-methyl-1-cyclohexyl ester;

5-(2-(4-Hydroxy-piperidino)-ethyl)-2-methyl-1H-indole-3-carboxylic acid-1-(2-bromophenyl)-ethyl ester;

5-(2-(4-Hydroxy-piperidino)-ethyl)-2-methyl-1H-indole-3-carboxylic acid-1-(4-bromophenyl)-ethyl ester;

5-(2-(4-Hydroxy-piperidino)-ethyl)-2-methyl-1H-indole-3-carboxylic acid-1-(4-(2-methyl-2-propyl)phenyl)-ethyl ester;

5-(2-(4-Hydroxy-piperidino)-ethyl)-2-methyl-1H-indole-3-carboxylic acid-1-(2,4-dichlorophenyl)-ethyl ester;

5-(2-(4-Hydroxy-piperidino)-ethyl)-2-methyl-1H-indole-3-carboxylic acid-1-(4-chlorophenyl)-ethyl ester;

5-(2-(4-Hydroxy-piperidino)-ethyl)-2-methyl-1H-indole-3-carboxylic acid (1,2,3,4-tetrahydronaphthyl-1-yl) ester;

5-(2-(4-Hydroxy-piperidino)-ethyl)-2-methyl-1H-indole-3-carboxylic acid (1-indanyl) ester;

5-(2-Pyrrolidino-ethyl)-2-methyl-1H-indole-3-carboxylic acid 1-(2-bromophenyl)-ethyl ester;

5-(2-Pyrrolidino-ethyl)-2-methyl-1H-indole-3-carboxylic acid 1-(4-bromophenyl)-ethyl ester;

5-(2-Pyrrolidino-ethyl)-2-methyl-1H-indole-3-carboxylic acid 1-(4-t-butylphenyl)-ethyl ester;

5-(2-Pyrrolidino-ethyl)-2-methyl-1H-indole-3-carboxylic acid 1-(2,4-dichlorophenyl)-ethyl ester;

5-(2-Pyrrolidino-ethyl)-2-methyl-1H-indole-3-carboxylic acid 1-(4-chlorophenyl)-ethyl ester;

5-(2-(2-Pyrrolidino-ethyl)-2-methyl-1H-indole-3-carboxylic acid (1,2,3,4-tetrahydronaphthyl-1-yl) ester;

5-(2-(2-Pyrrolidino-ethyl)-2-methyl-1H-indole-3-carboxylic acid (1-indanyl) ester;

5-(2-(2-Pyrrolidino-ethyl)-2-methyl-1H-indole-3-carboxylic acid (1-methylcyclopetan-1-yl) ester;

5-(2-(2-Pyrrolidino-ethyl)-2-methyl-1H-indole-3-carboxylic acid (1-methylcyclohex-1-yl) ester;

5-(2-N-Cyclohexyl-N-methyl-amino-ethyl)-2-methyl-1H-indole-3-carboxylic acid 1-(4-bromophenyl)-ethyl ester;

5-(2-N-Cyclohexyl-N-methyl-amino-ethyl)-2-methyl-1H-indole-3-carboxylic acid 1-(2-bromophenyl)-ethyl ester;

5-(2-N-Cyclohexyl-N-methyl-amino-ethyl)-2-methyl-1H-indole-3-carboxylic acid 1-(4-t-butylphenyl)-ethyl ester;

5-(2-N-Cyclohexyl-N-methyl-amino-ethyl)-2-methyl-1H-indole-3-carboxylic acid 1-(2,4-dichlorophenyl)-ethyl ester;

5-(2-N-Cyclohexyl-N-methyl-amino-ethyl)-2-methyl-1H-indole-3-carboxylic acid 1-(4-chlorophenyl)-ethyl ester;

5-(2-N-Cyclohexyl-N-methyl-amino-ethyl)-2-methyl-1H-indole-3-carboxylic acid (1,2,3,4-tetrahydronaphthyl-1-yl) ester;

5-(2-N-Cyclohexyl-N-methyl-amino-ethyl)-2-methyl-1H-indole-3-carboxylic acid (1-indanyl) ester;

5-(2-N-Cyclohexyl-N-methyl-amino-ethyl)-2-methyl-1H-indole-3-carboxylic acid (1-methylcyclopetan-1-yl) ester;

5-(2-N-Cyclohexyl-N-methyl-amino-ethyl)-2-methyl-1H-indole-3-carboxylic acid (1-methylcyclohex-1-yl) ester;

5-(2-Diethylamino-ethyl)-2-methyl-1H-indole-3-carboxylic acid 1-(3-methoxyphenyl)-ethyl ester;

5-(2-Piperidino-ethyl)-2-methyl-1H-indole-3-carboxylic acid 1-(3-methoxyphenyl)-ethyl ester;

5-(2-(4-Hydroxy-piperidino)-ethyl)-2-methyl-1H-indole-3-carboxylic acid 1-(3-methoxyphenyl)-ethyl ester;

5-(2-Pyrrolidino-ethyl)-2-methyl-1H-indole-3-carboxylic acid 1-(3-methoxyphenyl)-ethyl ester;

5-(2-N-Cyclohexyl-N-methyl-amino-ethyl)-2-methyl-1H-indole-3-carboxylic acid 1-(3-methoxyphenyl)-ethyl ester;

5-(2-Diethylamino-ethyl)-2-methyl-1H-indole-3-carboxylic acid 1-(2,5-dimethylphenyl)-ethyl ester;

5-(2-Piperidinyl-ethyl)-2-methyl-1H-indole-3-carboxylic 1-(2,5-dimethylphenyl)-ethyl ester;

5-(2-(4-Hydroxy-piperidino)-ethyl)-2-methyl-1H-indole-3-carboxylic acid 1-(2,5-dimethylphenyl)-ethyl ester;

5-(2-Pyrrolidino-ethyl)-2-methyl-1H-indole-3-carboxylic acid 1-(2,5-dimethylphenyl)-ethyl ester;

5-(2-N-Cyclohexyl-N-methyl-amino-ethyl)-2-methyl-1H-indole-3-carboxylic acid 1-(2,5-dimethylphenyl)-ethyl ester;

5-(2-Diethylamino-ethyl)-2-methyl-1H-indole-3-carboxylic acid 1-(2,4-dimethylphenyl)-ethyl ester;

5-(2-Piperidinyl-ethyl)-2-methyl-1H-indole-3-carboxylic 1-(2,4-dimethylphenyl)-ethyl ester;

5-(2-(4-Hydroxy-piperidino)-ethyl)-2-methyl-1H-indole-3-carboxylic acid 1-(2,4-dimethylphenyl)-ethyl ester;

5-(2-Pyrrolidino-ethyl)-2-methyl-1H-indole-3-carboxylic acid 1-(2,4-dimethylphenyl)-ethyl ester;

5-(2-N-Cyclohexyl-N-methyl-amino-ethyl)-2-methyl-1H-indole-3-carboxylic acid 1-(2,4-dimethylphenyl)-ethyl ester;

5-(2-Diethylamino-ethyl)-2-methyl-1H-indole-3-carboxylic acid 1-(3,4-dichlorophenyl)-ethyl ester;

5-(2-Pyrrolidino-ethyl)-2-methyl-1H-indole-3-carboxylic acid 1-(3,4-dichlorophenyl)-ethyl ester;

5-(2-Piperidinyl-ethyl)-2-methyl-1H-indole-3-carboxylic 1-(3,4-dichlorophenyl)-ethyl ester;

5-(2-N-Cyclohexyl-N-methyl-amino-ethyl)-2-methyl-1H-indole-3-carboxylic acid 1-(3,4-dichlorophenyl)-ethyl ester;

5-(2-Diethylamino-ethyl)-2-methyl-1H-indole-3-carboxylic acid 1-(2-methylphenyl)-ethyl ester;

5-(2-Pyrrolidino-ethyl)-2-methyl-1H-indole-3-carboxylic acid 1-(2-methylphenyl)-ethyl ester;

5-(2-Piperidinyl-ethyl)-2-methyl-1H-indole-3-carboxylic 1-(2-methylphenyl)-ethyl ester;

5-(2-N-Cyclohexyl-N-methyl-amino-ethyl)-2-methyl-1H-indole-3-carboxylic acid 1-(2-methylphenyl)-ethyl ester;

5-(2-Diethylamino-ethyl)-2-methyl-1H-indole-3-carboxylic acid 1-(2,3,4,5-tetrafluorophenyl)-ethyl ester;

5-(2-Pyrrolidino-ethyl)-2-methyl-1H-indole-3-carboxylic acid 1-(2,3,4,5-tetrafluorophenyl)-ethyl ester;

5-(2-Piperidinyl-ethyl)-2-methyl-1H-indole-3-carboxylic acid 1-(2,3,4,5-tetrafluorophenyl)-ethyl ester;

5-(2-N-Cyclohexyl-N-methyl-amino-ethyl)-2-methyl-1H-indole-3-carboxylic acid 1-(2,3,4,5-tetrafluorophenyl)-ethyl ester;

5-(2-Diethylamino-ethyl)-2-methyl-1H-indole-3-carboxylic acid 1-(2,6-dimethylphenyl)-ethyl ester;

5-(2-Pyrrolidino-ethyl)-2-methyl-1H-indole-3-carboxylic acid 1-(2,6-dimethylphenyl)-ethyl ester;

5-(2-Piperidinyl-ethyl)-2-methyl-1H-indole-3-carboxylic 1-(2,6-dimethylphenyl)-ethyl ester;

5-(2-N-Cyclohexyl-N-methyl-amino-ethyl)-2-methyl-1H-indole-3-carboxylic acid 1-(2,6-dimethylphenyl)-ethyl ester;

5-(2-Diethylamino-ethyl)-2-methyl-1H-indole-3-carboxylic acid 1-(S)-(4-fluorophenyl)-ethyl ester;

5-(2-Diethylamino-ethyl)-2-methyl-1H-indole-3-carboxylic acid (S)-1-(4-fluoro-phenyl)-ethyl ester;

5-(2-Diethylamino-ethyl)-2-methyl-1H-indole-3-carboxylic acid (S)-1-pyridin-4-yl-ethyl ester; and 2-Methyl-5-(2-pyrrolidin-1-yl-ethyl)-1H-indole-3-carboxylic acid (S)-1-(4-fluoro-phenyl)-ethyl ester.

In further embodiments, the compound is a functionalized indole selected from:

5-(2-Amino-ethyl)-2-methyl-1H-indole-3-carboxylic acid benzyl ester hydrochloride;

5-(2-Diethylamino-ethyl)-2-methyl-1H-indole-3-carboxylic acid benzyl ester hydrochloride;

2-Methyl-5-(2-pyrrolidin-1-yl-ethyl)-1H-indole-3-carboxylic acid (S)-1-pyridin-4-yl-ethyl ester;

2-Methyl-5-(2-piperidin-1-yl-ethyl)-1H-indole-3-carboxylic acid (S)-1-(4-fluoro-phenyl)-ethyl ester;

2-Methyl-5-(2-piperidin-1-yl-ethyl)-1H-indole-3-carboxylic acid (S)-1-pyridin-4-yl-ethyl ester;

5-[2-(4-Hydroxy-piperidin-1-yl)-ethyl]-2-methyl-1H-indole-3-carboxylic acid (S)-1-(4-fluoro-phenyl)-ethyl ester;

5-[2-(4-Hydroxy-piperidin-1-yl)-ethyl]-2-methyl-1H-indole-3-carboxylic acid (S)-1-pyridin-4-yl-ethyl ester;

5-[2-(Cyclohexyl-methyl-amino)-ethyl]-2-methyl-1H-indole-3-carboxylic acid (S)-1-(4-fluoro-phenyl)-ethyl ester;

5-[2-(Cyclohexyl-methyl-amino)-ethyl]-2-methyl-1H-indole-3-carboxylic acid (S)-1-pyridin-4-yl-ethyl ester;

5-(1-Ethyl-piperidin-4-yl)-2-methyl-1H-indole-3-carboxylic acid (S)-1-(4-fluoro-phenyl)-ethyl ester;

5-(1-Ethyl-piperidin-4-yl)-2-methyl-1H-indole-3-carboxylic acid (S)-1-pyridin-4-yl-ethyl ester;

5-[1-(-Ethyl-piperidin-4-yl)-1-methyl-ethyl]-2-methyl-1H-indole-3-carboxylic acid (S)-1-(4-fluoro-phenyl)-ethyl ester;

5-[1-(1-Ethyl-piperidin-4-yl)-1-methyl-ethyl]-2-methyl-1H-indole-3-carboxylic acid (S)-1-pyridin-4-yl-ethyl ester;

5-(1-Ethyl-4-methyl-piperidin-4-yl)-2-methyl-1H-indole-3-carboxylic acid (S)-1-(4-fluoro-phenyl)-ethyl ester;

5-(1-Ethyl-4-methyl-piperidin-4-yl)-2-methyl-1H-indole-3-carboxylic acid (S)-1-pyridin-4-yl-ethyl ester;

5-(1-Isopropyl-pyrrolidin-3-yl)-2-methyl-1H-indole-3-carboxylic acid (S)-1-(4-fluoro-phenyl)-ethyl ester;

5-(1-Isopropyl-pyrrolidin-3-yl)-2-methyl-1H-indole-3-carboxylic acid (S)-1-pyridin-4-yl-ethyl ester;

5-(1-Ethyl-1-aza-spiro[4.4]non-7-yl)-2-methyl-1H-indole-3-carboxylic acid (S)-1-(4-fluoro-phenyl)-ethyl ester;

5-(1-Ethyl-1-aza-spiro[4.4]non-7-yl)-2-methyl-1H-indole-3-carboxylic acid (S)-1-pyridin-4-yl-ethyl ester;

2-Methyl-7-(2-propyl)-1H-azepino[5,6-h]indole-3-carboxylic acid benzyl ester;

7-Isopropyl-2-methyl-1,5,6,7,8,9-hexahydro-azepino[4,5-f]indole-3-carboxylic acid (S)-1-(4-fluoro-phenyl)-ethyl ester; and 7-Isopropyl-2-methyl-1,5,6,7,8,9-hexahydro-azepino[4,5-f]indole-3-carboxylic acid (S)-1-pyridin-4-yl-ethyl ester.

In further embodiments, the compound is a functionalized benzimidazolone selected from:

6-(2-Diethylamino-ethyl)-2-oxo-2,3-dihydro-benzoimidazole-1-carboxylic acid benzylamide;

2-Oxo-6-(2-pyrrolidin-1-yl-ethyl)-2,3-dihydro-benzoimidazole-1-carboxylic acid benzylamide;

2-Oxo-6-(2-piperidin-1-yl-ethyl)-2,3-dihydro-benzoimidazole-1-carboxylic acid benzylamide;

6-[2-(Cyclohexyl-methyl-amino)-ethyl]-2-oxo-2,3-dihydro-benzoimidazole-1-carboxylic acid benzylamide;

6-{2-[4-(Furan-2-carbonyl)-piperazin-1-yl]-ethyl}-2-oxo-2,3-dihydro-benzoimidazole-1-carboxylic acid benzylamide;

{4-[2-(3-benzylcarbamoyl-2-oxo-2,3-dihydro-1H-benzoimidazol-5-yl)-ethyl]-piperazin-1-yl}-acetic acid ethyl ester;

6-{2-[4-(Isopropylcarbamoyl-methyl)-piperazin-1-yl]ethyl}-2-oxo-2,3-dihydro-benzoimidazole-1-carboxylic acid benzylamide;

2-Oxo-6-{2-[4-(3-phenyl-alkyl)-piperazin-1-yl]-ethyl}-2,3-dihydro-benzoimidazole-1-carboxylic acid benzylamide;

2-Oxo-6-[2-(4-pyridin-2-yl-piperazin-1-yl)-ethyl]-2,3-dihydro-benzoimidazole-1-carboxylic acid benzylamide;

6-{2-[4-(4-Acetyl-phenyl)-piperazin-1-yl]-ethyl}-2-oxo-2,3-dihydro-benzoimidazole-1-carboxylic acid benzylamide;

2-Oxo-6-[2-(4-phenethyl-piperazin-1-yl)-ethyl]-2,3-dihydro-benzoimidazole-1-carboxylic acid benzylamide;

6-{2-[4-(2-Cyclohexyl-ethyl)-piperazin-1-yl]-ethyl}-2-oxo-2,3-dihydro-benzoimidazole-1-carboxylic acid benzylamide;

6-[2-(4-benzyl-piperidin-1-yl)-ethyl]-2-oxo-2,3-dihydro-benzoimidazole-1-carboxylic acid benzylamide;

6-{2-[4-(2-Morpholin-4-yl-2-oxo-ethyl)-piperazin-1-yl]-ethyl}-2-oxo-2,3-dihydro-benzoimidazole-1-carboxylic acid benzylamide;

6-(2-Diethylamino-ethyl)-2-oxo-2,3-dihydro-benzoimidazole-1-carboxylic acid phenethyl-amide;

6-(2-Diethylamino-ethyl)-2-oxo-2,3-dihydro-benzoimidazole-1-carboxylic acid isopropylamide;

6-(2-Diethylamino-ethyl)-2-oxo-2,3-dihydro-benzoimidazole-1-carboxylic acid (3,4,5-trimethoxy-phenyl)-amide;

6-(2-Diethylamino-ethyl)-2-oxo-2,3-dihydro-benzoimidazole-1-carboxylic acid (2,4-dimethoxy-phenyl)-amide;

6-(2-Diethylamino-ethyl)-2-oxo-2,3-dihydro-benzoimidazole-1-carboxylic acid propylamide;

6-(2-Diethylamino-ethyl)-2-oxo-2,3-dihydro-benzoimidazole-1-carboxylic acid (4-isopropyl-phenyl)-amide;

6-(2-Diethylamino-ethyl)-2-oxo-2,3-dihydro-benzoimidazole-1-carboxylic acid naphthalen-1-ylamide;

6-(2-Diethylamino-ethyl)-2-oxo-2,3-dihydro-benzoimidazole-1-carboxylic acid (4-fluoro-phenyl)-amide;

6-(2-Diethylamino-ethyl)-2-oxo-2,3-dihydro-benzoimidazole-1-carboxylic acid 2-chloro-benzylamide;

6-(2-Diethylamino-ethyl)-2-oxo-2,3-dihydro-benzoimidazole-1-carboxylic acid (4-chloro-phenyl)-amide;

6-(2-Diethylamino-ethyl)-2-oxo-2,3-dihydro-benzoimidazole-1-carboxylic acid 2-methyl-benzylamide;

6-(2-Diethylamino-ethyl)-2-oxo-2,3-dihydro-benzoimidazole-1-carboxylic acid 4-methoxy-benzylamide;

6-(2-Diethylamino-ethyl)-2-oxo-2,3-dihydro-benzoimidazole-1-carboxylic acid (3-chloro-phenyl)-amide;

6-(2-Diethylamino-ethyl)-2-oxo-2,3-dihydro-benzoimidazole-1-carboxylic acid (2-ethoxy-phenyl)-amide;

6-(2-Diethylamino-ethyl)-2-oxo-2,3-dihydro-benzoimidazole-1-carboxylic acid (4-benzyloxy-phenyl)-amide;

4-[2-(3-benzylcarbamoyl-2-oxo-2,3-dihydro-1H-benzoimidazol-5-yl)-ethyl]-piperazine-1-carboxylic acid tert-butyl ester;

2-Oxo-6-(2-pyrrolidin-1-yl-ethyl)-2,3-dihydro-benzoimidazole-1-carboxylic acid (1-phenyl-ethyl)-amide;

6-(2-Diethylamino-ethyl)-2-oxo-2,3-dihydro-benzoimidazole-1-carboxylic acid (1S-phenyl-ethyl)-amide;

2-Oxo-6-{2-[4-(2-oxo-2,3-dihydro-benzoimidazole-1-yl)-piperidin-1-yl]-ethyl}-2,3-dihydro-benzoimidazole-1-carboxylic acid benzylamide; and 2-Oxo-6-(2-pyrrolidin-1-yl-ethyl)-2,3-dihydro-benzoimidazole-1-carboxylic acid tert-butylamide.

In additional embodiments, the compound is selected from:

2-Methyl-6-pyrrolidin-1-yl-5,6,7,8-tetrahydro-1H-benz[f]indole-3-carboxylic acid (S)-1-(4-fluoro-phenyl)-ethyl ester;

2-Methyl-6-pyrrolidin-1-yl-5,6,7,8-tetrahydro-1H-benz[f]indole-3-carboxylic acid (S)-1-pyridin-4-yl-ethyl ester;

6-Diethylamino-2-methyl-1,5,6,7-tetrahydro-1-aza-s-indacene-3-carboxylic acid (S)-1-(4-fluoro-phenyl)-ethyl ester;

6-Diethylamino-2-methyl-1,5,6,7-tetrahydro-1-aza-s-indacene-3-carboxylic acid (S)-1-pyridin-4-yl-ethyl ester; and 2-Methyl-6-pyrrolidino-5,6,7,8-tetrahydrobenzo[h]-1H-indole-3-carboxylic acid benzyl ester.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as mixtures including thereof. Further, certain of the compounds of the present invention can exist in unsolvated forms as well as solvated forms, including hydrated forms. All unsolvated and solvated forms, including hydrated forms, are encompassed within the scope of the present invention.

As used herein, the term "substituted" means substituents chosen from the group consisting of alkyl, alkenyl, alkynyl, heteroalkyl, alkoxy, carboxy, hydroxy, nitro, halogen, cyano, amino, alkyl amino, alkenyl amino, alkynyl amino, aryl amino, dialkyl amino, dialkenyl amino, diaryl amino, aryl, substituted aryl, heteroaryl, substituted heteroaryl, alkyl aryl, aryl alkyl, heteroaryl alkyl, keto (=O), =NR$^{60}$, wherein R$^{60}$ is —H, —OH, —NH$_2$, an aromatic group or a substituted aromatic group, —SO$_3$H, —CHO, —(CH$_2$)$_n$—NH$_2$, —(CH$_2$)$_n$—NH-alkyl, —(CH$_2$)$_n$—N(alkyl)$_2$, where n is an integer from one to about eight. When a ring (e.g., aryl, heteroaryl, heterocyclic, cycloalkyl, cycloalkenyl, cycloalkynyl) is substituted with another ring, the rings can be fused.

As used herein, the term "alkyl" refers to straight or branched hydrocarbon radicals having from one to about eight carbon atoms, and to cyclic hydrocarbon radicals having from three to about eight carbon atoms and includes, methyl, ethyl, n-propyl, isopropyl, n-butyl, sec-butyl, tert-butyl, pentyl, isopentyl, neopentyl, cyclopropyl, cyclobutyl, cyclopentyl, cyclohexyl, hexyl, heptyl, cycloheptyl, octyl, cyclooctyl and the like. An alkyl group can be substituted with one to about three substituents independently selected for each position. The term "alkenyl" refers to an alkyl group that contains one or more double bonds between carbon atoms (e.g., n-butenyl, cyclooctenyl and the like). The term "alkynyl" refers to an alkyl group that contains one or more triple bonds between carbon atoms (e.g., n-butynyl, cycolooctynyl and the like). An alkenyl or alkynyl group can be substituted as described herein. The term "alkoxy" refers to —O-alkyl.

As used herein, the terms "cyclic" and/or "cyclo" can refer to mono cyclic and multicyclic structures (e.g., bicyclic, tricyclic) that can optionally be substituted with one to about three substituents independently selected for each position.

"Heterocyclic" refers to a closed ring structure having from about five to about fifteen atoms in the ring where one or more of the atoms in the ring is an atom other than carbon, such as oxygen, nitrogen or sulfur. A heterocyclic group can be substituted with one to about three substituents independently selected for each position. Examples of suitable heterocyclic groups and substituted heterocyclic groups include, 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 1H-benzimidazol-2-one-3-yl, 1-alkyl-benzimidazol-2-one-3-yl, 1-methyl-benzimidazol-2-one-3-yl, 2-piperazinyl, 1-piperidinyl, 2-piperidinyl, 3-piperidinyl, 4-piperidinyl, 4-thiazolidinyl, diazolonyl, N-substituted diazolonyl and the like.

The term "aryl" refers to aromatic carbocyclic ring structure having from about five to about fifteen carbon atoms. An aryl group can be substituted with one to about five substituents independently selected for each position. Examples of suitable aryl groups include, phenyl, 1-naphthyl, 2-naphthyl, 1-anthracyl, 2-anthracyl and the like. The term "heteroaryl" refers to a closed aromatic ring structure having from about five to about fifteen atoms in the ring where one or more of the atoms in the ring is an atom other than carbon, such as oxygen, nitrogen or sulfur. A heteroaryl group can be substituted with one to about five substituents independently selected for each position. Examples of suitable heteroaryl groups and substituted heteroaryl groups include N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl, 5-oxazolyl, 2-indolyl, 3-indolyl, 4-indolyl, 5-indolyl, 6-indolyl, 7-indolyl, 3-chloropyridyl, 5-methylbenzimidazolyl, 6-acetylisothiazolyl, 5-iodobenzothianyl and the like.

The term "acyl" refers to —C(=O)-alkyl.

The terms "arylalkyl" and "aralkyl" refer to -alkyl-aryl. The term "heteroarylalkyl" refers to -alkyl-heteroaryl. The term "alkylaryl" refers to -aryl-alkyl. The term "alkylheteroaryl" refers to -heteroaryl-alkyl.

Halogens are fluorine, chlorine, bromine and iodine.

The symbol "—" can represent a chemical bond. The symbol "$\rlap{=}{\text{—}}$" represents a chemical bond that can be a single bond or optionally a double bond.

As used herein, the term "patient" refers to any animal (e.g., mammals, birds, fish) in need of therapy, such as humans, cows, dogs, cats, sheep, horses, chickens, pigs and the like.

The compounds described herein can be prepared and administered as neutral compounds, salts, esters, amides and/or prodrugs. As used herein, the phrase "pharmaceutically acceptable salts, esters, amides, and prodrugs" refers to those salts (e.g., carboxylate salts, amino acid addition salts), esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The compounds described herein can form pharmaceutically or physiologically acceptable acid addition and/or base salts. All of these forms are within the scope of the present invention.

Pharmaceutically acceptable acid addition salts of the compounds described herein include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, and the like. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate, gluconate, galacturonate and the like (see, for example, Berge S. M. et al., "Pharmaceutical Salts," *J. of Pharma. Sci.*, 1977;66:1).

Acid addition salts of compounds which contain a basic group (e.g., amine) can be prepared using suitable methods. For example, acid addition salts can be prepared by contacting the free base form of a compound with a sufficient amount of a desired acid to produce the salt in the conventional manner. The free base form can be regenerated by contacting the salt form with a base and isolating the free base in the conventional manner. The free base form of a compound can differ from a salt forms somewhat in certain physical properties such as solubility in polar solvents.

Pharmaceutically acceptable base addition salts can be formed with suitable metals or amines, such as alkali and alkaline earth metals or organic amines. Examples of metals which are suitable for use as cations in base addition salts include sodium, potassium, magnesium, calcium and the like. Amines suitable for use as cations in base addition salts include N,N'-dibenzylethylenediamine, chloroprocaine, choline, diethanolamine, dicyclohexylamine, ethylenediamine, N-methylglucamine, and procaine (see, for example, Berge, Supra., 1977).

Base addition salts of compounds which contain an acidic group (e.g., carboxylic acid) can be prepared using suitable methods. For example, the free acid form of a compound can be contacted with a sufficient amount of the desired base to produce a salt in the conventional manner. The free acid form can be regenerated by contacting the salt form with a suitable acid and isolating the free acid in the conventional manner. The free acid form of a compound can differ from the base addition salt form somewhat in certain physical properties such as solubility in polar solvents.

Examples of pharmaceutically acceptable, nontoxic esters of the compounds of this invention include $C_1$–$C_6$ alkyl esters. In certain embodiments, the alkyl group of the alkyl ester is a straight or branched chain $C_1$–$C_6$ alkyl group. Acceptable alkyl esters also include $C_5$–$C_7$ cycloalkyl esters as well as arylalkyl esters such as, but not limited to benzyl. $C_1$–$C_4$ esters are preferred. esters of the compounds of the present invention can be prepared using any suitable method.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared using any suitable method.

The term "prodrug" refers to compounds that can be transformed in vivo (e.g., following administration to an animal), by metabolic processes or other processes, to yield a compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

While not wishing to be bound by any particular theory or mechanism, it is believed that compounds of the invention are antagonists of the chemokine receptor CCR5, and that therapeutic benefits derived from the method of the invention are the result of antagonism of CCR5 function. Thus, the compounds, compositions and method of the invention can be used to treat a patient having a condition involving cells which express CCR5 on their surface and which respond to signals transduced through CCR5, as well as the specific conditions recited herein. For example, the functionalized heterocycles (e.g, functionalized indoles, functionalized benzimidazolones) described herein can block the interaction of CD-4/human immunodeficiency virus glycoprotein 120 (HIV GP-120) interaction with the CCR-5 receptor, and thus are useful in the treatment of HIV infection and AIDS.

Therapeutic Methods

The invention further relates to a method of modulating (inhibiting or promoting) chemokine receptor function (e.g., binding of a ligand (e.g. a chemokine such as RANTES, MIP-1α and/or MIP-1β), a virus (e.g., HIV), chemokine receptor transduced signalling) in a patient in need of such therapy. For example, a patient having a disease associated with aberrant or pathogenic leukocyte recruitment and/or activation or a disease mediated by chemokines or chemokine receptor function, including inflammatory disorders (e.g., acute inflammatory disorders, chronic inflammatory disorders) characterized by the presence of chemokine (e.g., RANTES, MIP-1α and/or MIP-1β) responsive leukocytes (e.g., T cells, monocytes, eosinophils) can be treated (e.g., prophylactic treatment, therapeutic treatments (e.g., palliative treatment)) in accordance with the method of the invention. In another example, a patient infected with a virus, such as a virus that uses a chemokine receptor as a cellular receptor or co-receptor (e.g., HIV) can be treated (e.g., prophylactic treatment, therapeutic treatments (e.g., palliative treatment)) in accordance with the method of the invention.

In one aspect, the invention is a method of antagonizing a chemokine receptor, such as CCR5, in a mammal comprising administering to the mammal an effective amount of a compound described herein. According to the method, chemokine-mediated chemotaxis and/or activation of pro-inflammatory cells bearing receptors for chemokines (e.g., CCR5) can be inhibited. As used herein, "pro-inflammatory cells" includes but leukocytes (e.g., lymphocytes, macrophages) and other cell types which express chemokine receptor. For example, chemokine receptors (e.g., CCR5) can be expressed on cell types, such as neurons and epithelial cells. Accordingly, the invention provides a method for treating a patient having an inflammatory disease, such as the inflammatory diseases recited herein, comprising administering to said patient an effective amount of a compound described herein that can antagonize a chemokine receptor (e.g., CCR5).

In particular embodiments, the invention is a method of agonizing a chemokine receptor, such as CCR5, in a mammal comprising administering to the mammal an effective amount of a compound described herein, that can antagonize a chemokine receptor. According to the method, chemokine-mediated chemotaxis and/or activation of pro-inflammatory cells bearing receptors for chemokines can be promoted. Accordingly, the invention provides a method for treating a patient having an inflammatory disease, such as the inflammatory diseases recited herein, comprising administering to said patient an effective amount of a compound described herein that can agonize a chemokine receptor (e.g., CCR5).

Diseases and conditions associated with inflammation, infection, and cancer can be treated using the method. In one embodiment, the disease or condition is one in which the actions of leukocytes are to be inhibited or promoted for therapeutic or prophylactic purposes.

Diseases or conditions, including chronic diseases, of humans or other species which can be treated with compound which are chemokine receptor antagonists (e.g., CCR5 antagonists) include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dennatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, autoimmune thyroiditis, Behcet's syndrome;

rejection of transplanted tissues or organs, including allograft rejection (e.g., acute allograft rejection, chronic allograft rejection) or graft-versus-host disease;

viral infection, e.g., infection by simian immunodeficiency virus (SIV) or human immunodeficiency virus (HIV-1, HIV-2, including M-trophic and/or T-trophic strains), papilloma virus (e.g., human papilloma virus 16); flaviviruses such as Hepatitis B and Hepatitis C; Herpes virus (e.g., Herpes simplex virus (HSV-1, HSV-2), cytomegalovirus, Epstein-Barr virus, varicella-zoster virus, human herpes virus (e.g., HHV6, HHV7, HHV8,) herpes viruses which infect livestock, such as horses, cattle, pigs, chickens, turkeys and fish (e.g., pseudorabies virus, porcine cytomegalovirus)); parvovirus (e.g., parvo virus B19), human influenza virus A, human influenza virus B, rhinovirus, coronaviruses, enterovirus, human parainfluenza virus, respiratory syncytial virus (RSV), adenovirus (e.g. adenovirus-8), togavirus (e.g., rubella virus), paramyxovirus (e.g., Measles virus, Mumps virus), rhabdoviruses (e.g., rabes virus, molola virus, vesicular stomatitis virus), rotavirus, enteric calicivirus (e.g., Norwalk virus), enterovirus (e.g., coxsackievirus, echovirus, poliovirus), reovirus, lymphocyte choriomeningitis virus, bunyamwera virus, group C virus, tahyna virus, toscana virus, punta toro virus, dengue virus, orbivirus (e.g., Orungo virus, Tribec virus, Kemerova virus, Lipovnik virus), encephalits viruses (e.g., California encephalitis virus, La Crosse encephalitis virus, St. Loius encephalitis virus, West Nile virus, eastern equine encephalitis virus, Japanese encephalitis virus), for example.

other diseases or conditions in which undesirable inflammatory responses are to be inhibited can be treated, including, but not limited to, arteriosclerosis, atherosclerosis (e.g., transplant accelerated atherosclerosis), restenosis, ischemia/reperfusion injury, cytokine-induced toxicity, myositis (including polymyositis, dermatomyositis). Diseases or conditions of humans or other species which can be treated with agents that can promote or augment one or more functions of CCR5, include, but are not limited to:

cancers, for example, solid tumors and/or those with leukocytic infiltration of the skin or organs such as cutaneous T cell lymphoma (e.g., mycosis fungoides);

infectious diseases, such as bacterial, fungal and nematode infections and tuberculoid leprosy;

immunosuppression, such as that in patients undergoing radiation therapy, chemotherapy, or other therapy which causes immunosuppression; immunosuppression due to congenital deficiency in receptor function or other causes.

In one aspect, the invention is a method of treating a patient having a viral infection or disease, comprising administering to said patient an effective amount of a compound described herein. In certain embodiments, the compound can inhibit adhesion of the virus to a host cell, thereby inhibiting infection.

The compounds described herein which are antagonists of the CCR-5 chemokine receptor can have efficacy in inhibiting HIV infection and are thus can be useful in the treatment of AIDS.

In a preferred embodiment, the invention is method for inhibiting infection of a human by HIV (e.g., HIV-1 and/or HIV-2 including M-trophic and/or T-trophic strains) comprising administering to said human an effective amount of a compound as described herein.

In another preferred embodiment, the invention is method for treating a human that is infected by HIV (e.g., HIV-1 and/or HIV-2 including M-trophic and/or T-trophic strains) comprising administering to said human an effective amount of a compound as described herein.

In another preferred embodiment, the invention is method for delaying the onset of acquired immunodeficiency syndrome in a human that is infected by HIV (e.g., HIV-1 and/or HIV-2 including M-trophic and/or T-trophic strains) comprising administering to said human an effective amount of a compound as described herein.

In another preferred embodiment, the invention is method for treating human having HIV infection comprising administering to said human an effective amount of a compound as described herein.

In another preferred embodiment, the invention is method for inhibiting the onset of AIDS related complex (ARC) in a human having HIV infection comprising administering to said human an effective amount of a compound as described herein.

An "effective amount" of an antagonist compound is an amount which results in the inhibition of one or more processes mediated by a chemokine receptor, such as binding of a ligand (e.g., a chemokine ligand, a virus) in a subject. Examples of such processes include leukocyte migration, integrin activation, transient increases in the concentration of intracellular free calcium $[Ca^{2+}]_i$, granule release of proinflammatory mediators, infection. Alternatively, an "effective amount" of a compound is a quantity sufficient to achieve a desired therapeutic and/or prophylactic effect, such as an amount which results in the prevention of or a decrease in the symptoms associated with a disease associated with viral infection, or aberrant or pathogenic leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 1000 mg per day for an adult. Preferably, the dosage ranges from about 1 mg per day to about 100 mg per day. An antagonist of chemokine receptor function can also be administered in combination with one or more additional therapeutic agents, e.g. immunomodulators, antivirals, anti-infectives and the like.

In therapeutic use as agents for the treatment of HIV infection, the compounds utilized in the method of the invention can be administered at the initial dosage of about 1 to about 100 mg per kilogram daily. A daily dose range of about 25 to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), transdermally, topically, by inhalation (e.g., intrabronchial, intranasal, oral inhalation or intranasal drops), intracistemally, intravaginally, intravesically, locally (e.g., in powders, ointments or drops), as a buccal or nasal spray or rectally, depending on the disease or condition to be treated. Oral or parenteral administration are preferred modes of administration.

The compound can be administered to the patient in conjunction with an acceptable pharmaceutical or physiological carrier as part of a pharmaceutical composition for treatment of HIV infection, inflammatory disease, or the other diseases discussed above. Formulation of a compound to be administered will vary according to the route of administration selected (e.g., solution, emulsion, capsule).

Compositions

The invention also relates to pharmaceutical and/or physiological compositions which contain the compounds described herein. Such compositions can contain adjuvants such as preserving, wetting, emulsifying, and dispensing agents. Prevention of the action of microorganisms can be controlled by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Solid dosage forms for oral administration include capsules, tablets, pills, powders, and granules. In such solid dosage forms, the active compound can be admixed with at least one inert customary excipient (or carrier) such as sodium citrate or dicalcium phosphate; or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffm; (f) absorption accelerators, as for example, quaternary ammonium compounds; (g) wetting agents, as for example, cetyl alcohol, and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Such solid compositions or solid compositions that are similar to those described can be employed as fillers in soft- and hard-filled gelatin capsules using excipients such as lactose or milk sugar as well as high molecular weight polyethyleneglycols, and the like.

Solid dosage forms such as tablets, dragées, capsules, pills, and granules can be prepared with coatings and shells, such as enteric coatings or other suitable coatings or shells. Several such coating and/or shells are well known in the art, and can contain opacifying agents, and can also be of such composition that they release the active compound or compounds in a certain part of the intestinal tract in a delayed manner. Examples of embedding compositions which can be used are polymeric substances and waxes. The active compounds can also be used in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. If desired, the composition can also include adjuvants, such as wetting agents, emulsifying and suspending agents, sweetening, flavoring and/or perfuming agents. Suspensions, in addition to the active compounds, can contain suspending agents, such as, ethoxylated isostearyl alcohols, polyoxyethylene sorbitol and sorbitan esters, microcrystalline cellulose, aluminum metahydroxide, bentonite, agar-agar, tragacanth, and the like. Mixtures of suspending agents can be employed if desired. Compositions for rectal administrations are preferably suppositories which can be prepared by mixing the compounds of the present invention with suitable nonirritating excipients or carriers such as cocoa butter, polyethyleneglycol, or a suppository wax which are solid at ordinary temperatures but liquid at body temperature and therefore, melt in the rectum or vaginal cavity and release the active component.

Dosage forms for topical administration of a compound of this invention include ointments, powders, sprays and inhalants. The active component is can be admixed under suitable conditions (e.g., sterile conditions) with a physiologically acceptable carrier and any preservatives, buffers, or propellants as may be required. Ophthalmic formulations, eye ointments, powders, and solutions are also contemplated as being within the scope of this invention.

The quantity of active component in a unit dose preparation may be varied or adjusted from 1 mg to about 1000 mg, preferably about 10 mg to about 100 mg according to the particular application and the potency of the active component. The composition can, if desired, also contain other compatible therapeutic agents. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The compounds described herein can be used in the form of pharmaceutical formulations, and the following examples illustrate typical compositions that are additional embodiments of the invention.

Table Formulation

The compounds described herein can be formulated in tablets. In one example, the compound of Example 1 can be mixed with lactose and cornstarch (for mix) and blended to uniformity to a powder. The cornstarch (for paste) can be suspended in 6 mL of water and heated with stirring to form a paste. The paste can be added to the mixed powder, and the mixture can be granulated. The wet granules can be passed through a No. 8 hard screen and dried at 50° C. The mixture can lubricated with 1% magnesium sterate and compressed into a tablet. The tablets can administered to a patient at the rate of 1 to 4 each day for treatment of AIDS.

| Tablet Formulation | |
|---|---|
| Ingredient | Amount |
| Compound of Example 1 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

Parental Solution

The compounds described herein can be formulated as a solution for parenteral administration. In one example, the compound of Example 26 can be added to a solution of 700 mL of propylene glycol and 200 mL of water for injection. The mixture can be stirred and the pH can be adjusted to 5.5 with hydrochloric acid. The volume can be adjusted to 1000 mL with water for injection. The solution can be sterilized, filled into 5.0 mL ampoules, each containing about 2.0 mL (40 mg of invention compound), and sealed under nitrogen. The solution can be administered by injection to a patient suffering from HIV infections and in need of treatment.

Patch Formulation

The compounds described herein can be formulated for transdermal administration. In one example, about ten milligrams of 2-methyl-5-(2-morpholin-4-yl-ethoxy)-1H-indole-3-carboxylic acid, 1-phenylethyl ester, hydrochloride can be mixed with about 1 mL of propylene glycol and about 2 mg of acrylic-based polymer adhesive containing a resinous cross-linking agent. The mixture can be applied to an impermeable backing (e.g., about 30 cm$^2$) and applied to the upper back of a patient for sustained release treatment of inflammatory disease.

The invention is further directed to compositions comprising one or more compound described herein and one or more additional agents useful in the prevention or treatment of viral infection or viral disease (e.g., AIDS), and to methods wherein one or more compound as described herein is administered to a patient in need thereof with one or more additional agents useful in the prevention or treatment of viral infection or viral disease (e.g., AIDS). For example, where the compounds of the invention are to administered to a patient having a viral infection or disease, they can be co-administered (administered before, following or concurrently with) another therapeutic agent, such as immunomodulators, anti-infectives (e.g, antiviral agents), or prophylactic or therapeutic vaccines known to those of ordinary skill in the art. For example, suitable agents for co-administration with the compounds described herein include, for example, amantadine, rimantadine, ribavirin, ganciclovir, foscarnet, acyclovir, vidarabine, famciclovir, valacyclovir, penciclovir, idoxuridine sorivudine, cidofovir, trifluridine, interferon (e.g., interferion α, interferion α2b, interferion β, interferion γ). In particular embodiments, the compounds of this invention can be administered to a patient exposed to HIV (e.g., administered pre-exposure and/or postexposure), in combination with effective amounts of the anti-HIV compounds, immunomodulators, anti-infectives, or prophylactic or therapeutic vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase [RT] inhibitor) |
| GW141 W94/ VX478 Amprenavir | Glaxo Wellcome | HIV infection, AIDS, ARC (protease inhibitor) |
| GW1592U89 Abacavir | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in Combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination |
| Alferon Interferon | Interferon Sciences | Kaposi's sarcoma, HIV in combination |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infections, AIDS, ARC |
| Beta-fluoro-ddA | Nat'l Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| (−)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Combivir AZT+3TC | Glaxo Wellcome | HIV infection, AIDS, ARC |
| Curdlan sulfate | AJI Pharma USA | HIV infection |
| Cytomegalovirus immune globin | MedImmune | CMV retinitis |
| Cytovene Ganciclovir | Syntex/Roche | Sight threatening CMV, peripheral CMV, retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| HIVID (ddc) Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | Triangle Pharmaceutical | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | Herpes zoster, herpes simplex |
| Foscavir/Foscarnet | Astra | CMV, HSV 1–2 |
| FTC | Triangle Pharmaceutical | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alpha-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |

-continued

| Drug Name | Manufacturer | Indication |
|---|---|---|
| JE 2147 (KNI-764) Protease inhibitor | Japan Energy/ Agouron PI | HIV infection, AIDS, ARC (reverse transcriptase inhibitor); also with AZT |
| KNI-272 | Nat'l Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection—HBV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| PNU-140690 | Pharmacia Upjohn | HIV infection, AIDS, ARC (protease inhibitor) |
| Probucol | Vyrex | HIV infection, AIDS |
| RBD-CD4 | Sheffield Med. Tech (Houston, TX) | HIV infection, AIDS, ARC |
| Ritonavir | Abbott | HIV infection, AIDS, ARC (protease inhibitor) |
| S-1153 | Agouron/Shionogi | NnRTI |
| Saquinavir | Hoffmann-La Roche | HIV infection, AIDS, ARC (protease inhibitor) |
| Stavudine; d4T Didehydrodeoxy- thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | Asymptomatic HIV positive, LAS, ARC |
| Zidovudine; AZT | Glaxo Wellcome | HIV infection, AIDS, ARC, Kaposi's sarcoma, in combination with other therapies |
| IMMUNO-MODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/ TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV core Particle Immunostimulant | Rorer | Seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine- Enkephalin | TNI Pharmaceutical (Chicago, IL) | AIDS, ARC |
| MTP-PE Muramyl- Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycen with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | Cryptosporidial diarrhea |
| Intraconazole- R51211 | Janssen Pharm. | Histoplasmosis; cryptococcal meningitis |
| Trimetrexate | Warner-Lambert | PCP |
| OTHER | | |
| Daunorubicin | NeXstar, Sequus | Kaposi's sarcoma |
| Recombinant Human Erythropoietin | Ortho Pharm. Corp. | Severe anemia associated with AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption related to AIDS |

It will be understood that the scope of combinations of the compounds of this invention with AIDS antivirals, immunomodulators, anti-infectives or vaccines is not limited to the list in the above table, but includes any combination with any pharmaceutical composition useful for the treatment of AIDS.

The compound or compositions described herein can be provided in multiple or unit dosage form within suitable containment means (e.g., bottle, box, envelope, tube). The compositions can be provided premixed or the component of the composition can be provided in separate containers for mixing by the user. When individually packaged components are provided, the individual packages can be contained within a single larger containment means (e.g., bottle, box, envelope, tube). Instructions for preparing and administering the compounds or compositions can be provided (e.g., printed on the container, printed on a package insert).

Synthesis of Compounds

The compounds described herein can be prepared using any suitable methods, such as, standard organic synthetic techniques, including combinatorial chemistry biological methods, such as through metabolism (e.g., fermentation) or any combination thereof. For example, the compounds of the invention can be prepared using the synthetic schemes diagramed in FIG. 1–FIG. 22.

As shown in FIG. 1, indole derivative 1b can be alkylated with 1a in the presence of a base, such as $Cs_2CO_3$, in an aprotic solvent, such as methyl ethyl ketone, to give indole derivative 1c. Compound 1c can be reacted with an amine in presence of a base, such as triethylamine, in an aprotic solvent, such as dioxane, to give the final product 1d.

Figure 2:
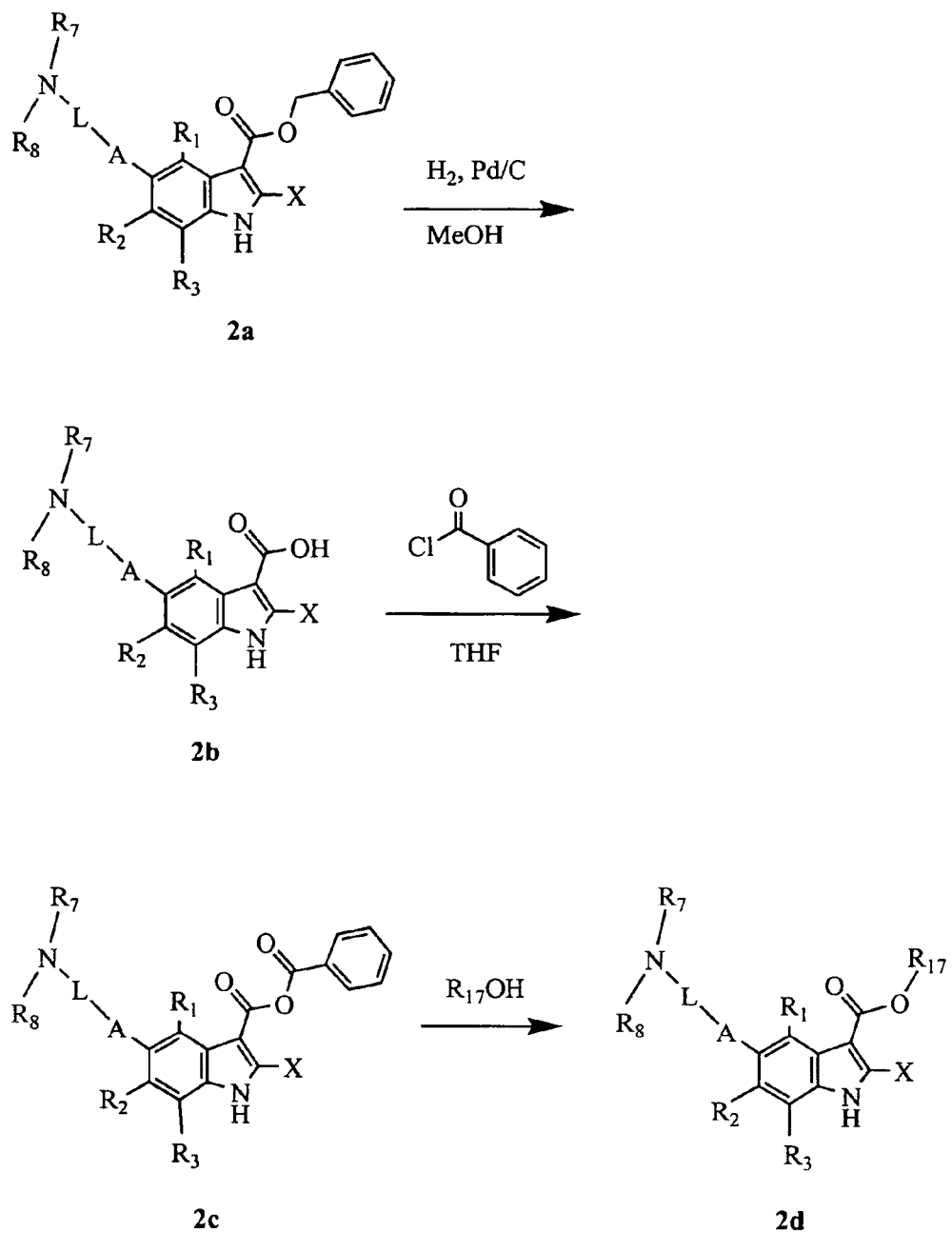
FIG. 2 is a schematic diagram showing the preparation of indole amines of Formula 2d.

As shown in FIG. 2, hydrogenolysis of 2a gives an acid 2b under standard hydrogenolysis conditions using palladium hydroxide on carbon as the catalyst. Treatment of compound 2b with benzoyl chloride in THF in presence of triethylamine gives 2c. Compound 2c can be reacted with an alcohol of choice to give the final product 2d.

Figure 3:
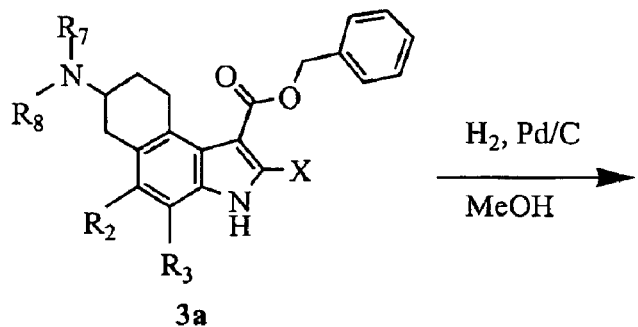
FIG. 3 is a schematic diagram showing the preparation of indole amines of Formula 3d.
Figure 3:
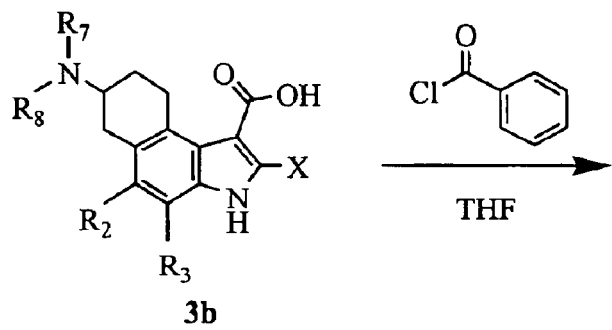
Figure 3:
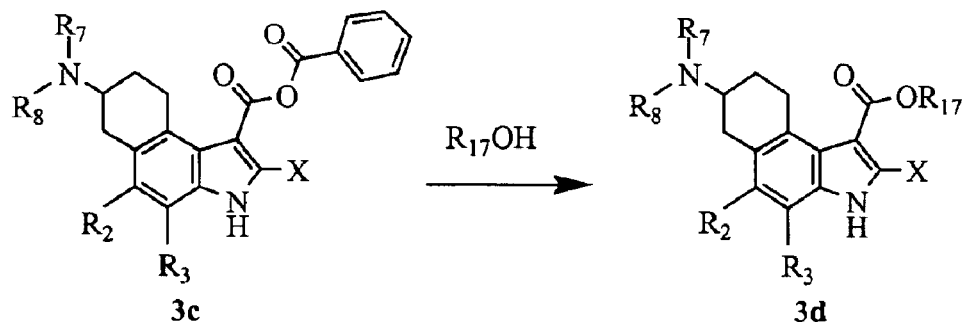

In FIG. 3, compound 3d can be derived from compound 3a in a transformation that is similar to the transformation shown in FIG. 2.

Figure 4:
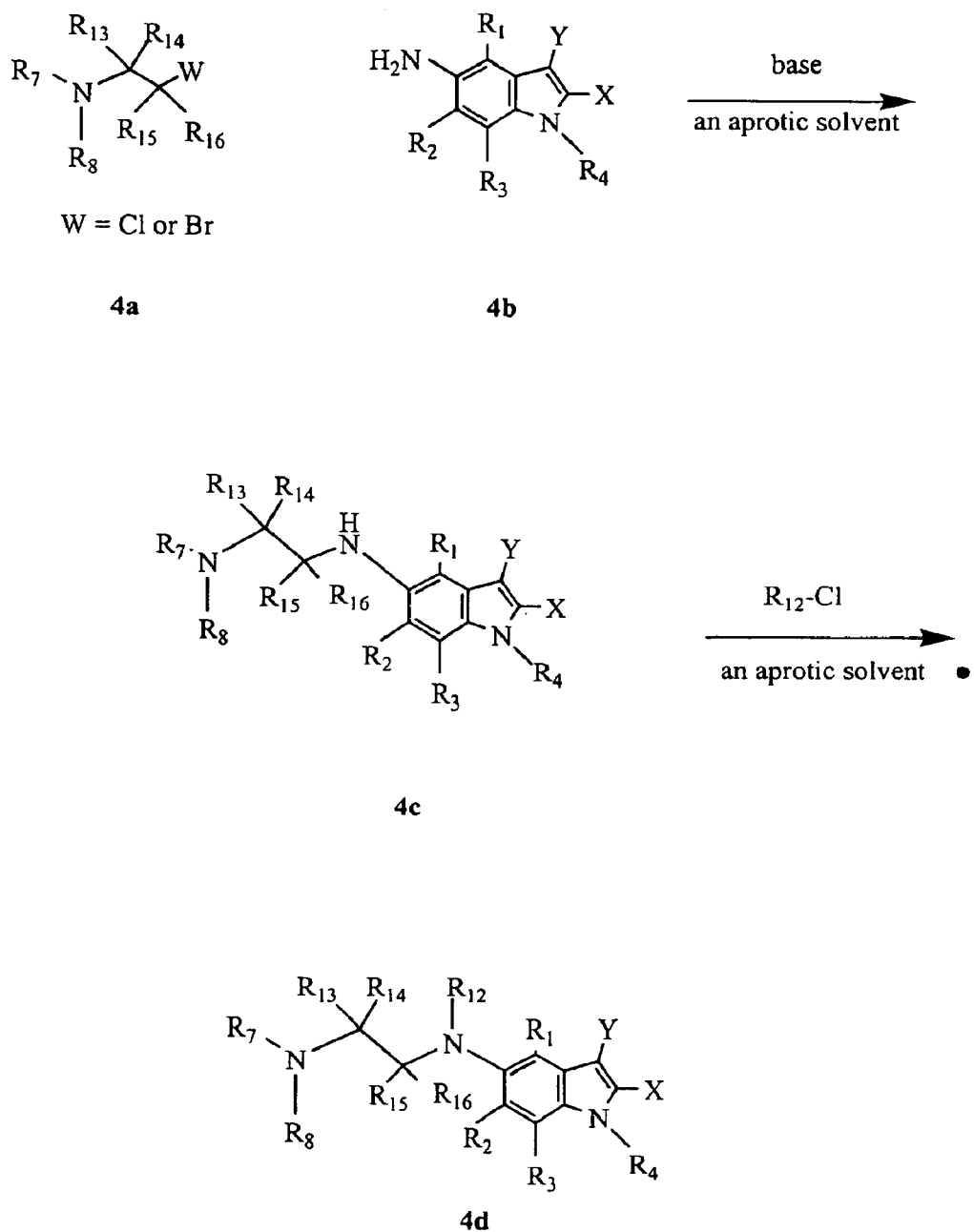
FIG. 4 is a schematic diagram showing the preparation of indole amines of Formula 4d.
Figure 5:
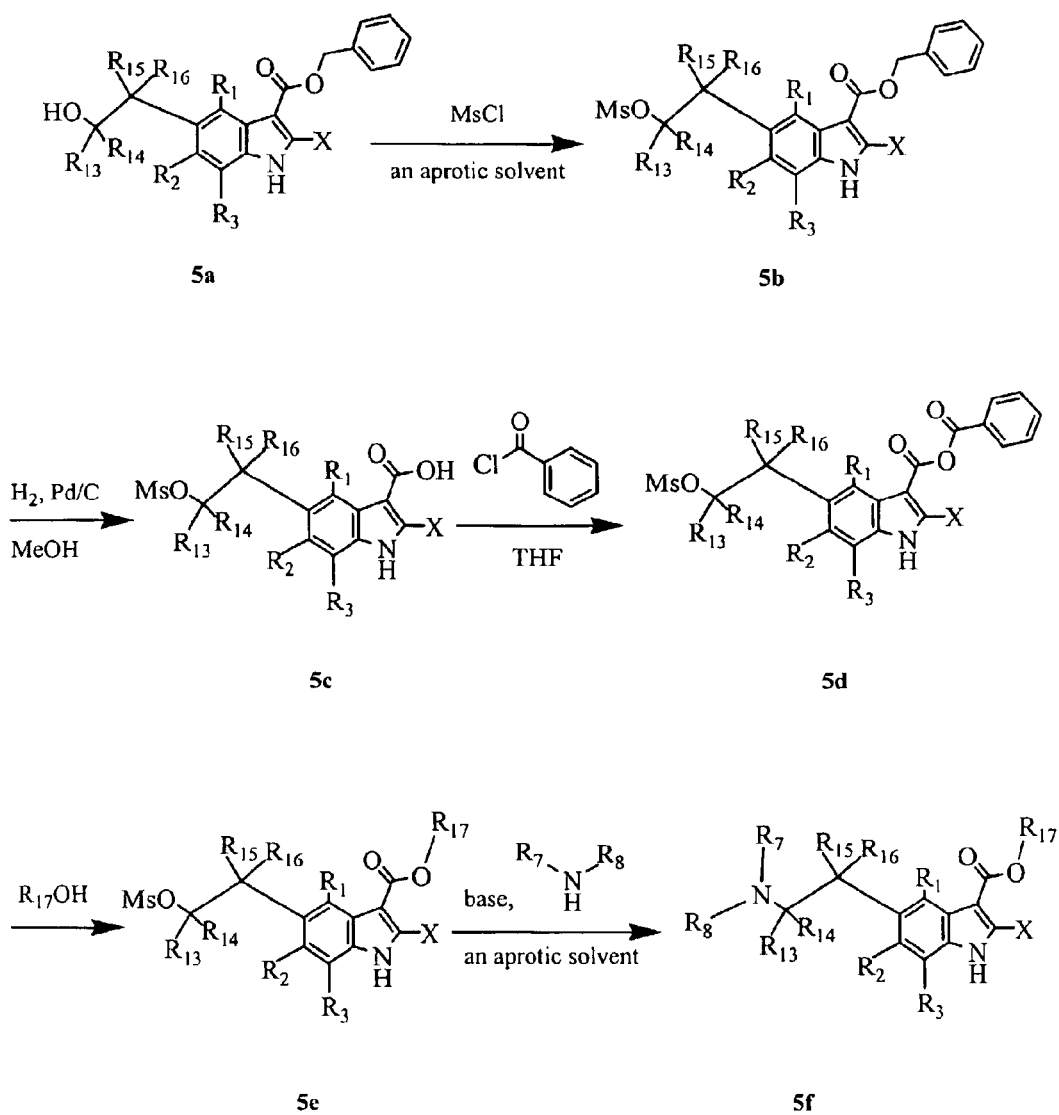
FIG. 5 is a schematic diagram showing the preparation of indole amines of Formula 5f.

As shown in FIG. 4, indole derivative 4b can be alkylated with 4a in the presence of a base, such as $K_2CO_3$, in a polar aprotic solvent, such as DMF, to give indole derivative 4c. Compound 4c can be further acylated or alkylated following standard procedures to give the final product 4d.

Mesylation of compound 5a (FIG. 5), which is obtained following known procedures, gives indole derivative 5b. Compound 5b can be converted to the mixed anhydride 5d in a similar manner as described for the synthesis of 2c. The mixed anhydride 5d can be reacted with an alcohol of choice to give ester 5e. Displacement of the mesylate group with an amine gives the final product 5f.

Figure 6:
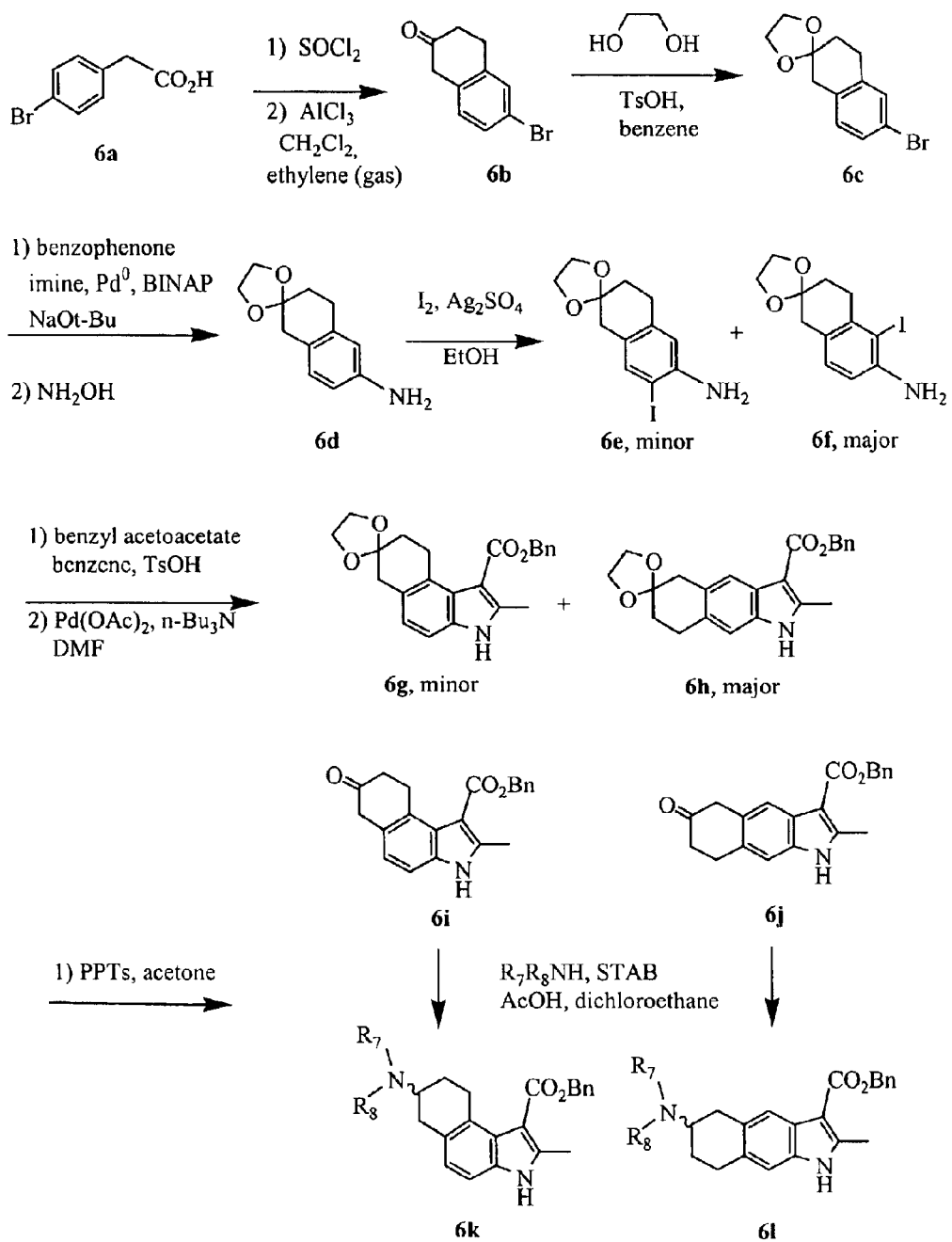
FIG. 6 is a schematic diagram showing the preparation of indole amines of Formulas 6k or 6l.

As shown in FIG. 6, commercially available bromophenylacetic acid 6a can was converted to the acid chloride, which underwent a Friedel-Crafts reaction with ethylene gas to provide a mixture of bromo-tetralone 6b. The ketone was protected as its ethylene ketal 6c, and the bromide was aminated using the procedure of Buchwald to give 6d. Compound 6d was iodinated using iodine/silver carbonate in reasonable yield, forming an inseparable ~3:1 mixture of regioisomers 6e and 6f. Formation of an aminocrotonate mixture was achieved using benzyl acetoacetate under dehydrating conditions, and the crude mixture of aminocrotonates was carried directly on to form the indole derivatives 6g and 6h via palladium-mediated closure, in low overall yield. Note that the linear isomer now predominated after the indole closure, a change in product ratio. The resulting mixture of ketal-protected indoles was deprotected, and the individual ketones 6i and 6j were separated. The ketones were then carried on to their respective indole-amine products 6k and 6l via reductive amination.

Figure 7:
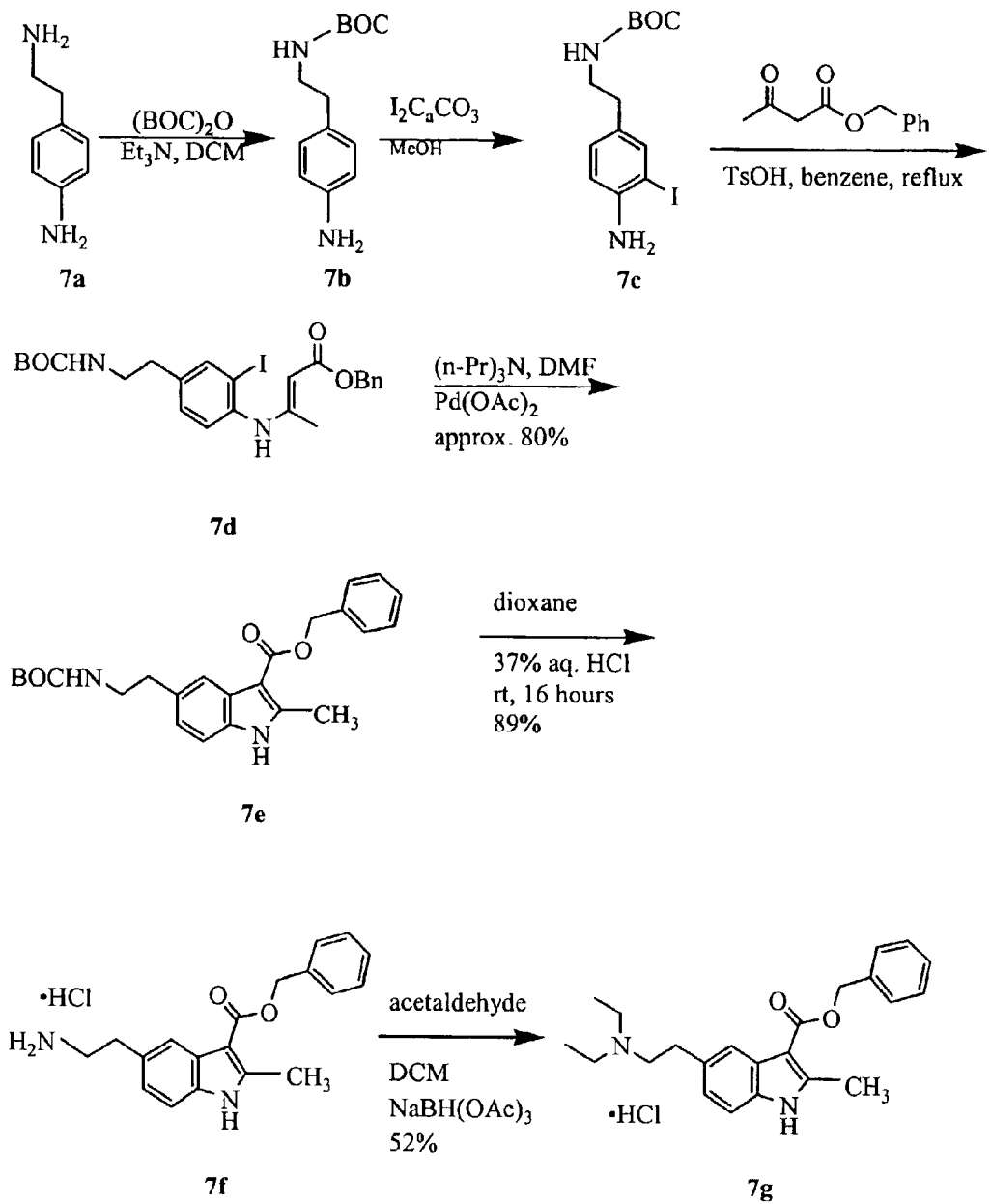
FIG. 7 is a schematic diagram showing the preparation of indole amines of Formula 7g.

One of the methods used to construct the indole nucleus was via the intra-molecular Heck reaction. One example is shown in FIG. 7. Boc protection of 7a gives 7b which can then be iodinated to afford 7c. Condensation of 7c with benzyl acetoacetate under dehydrating conditions can give 7d. Palladium catalyzed ring closure of 7d can afford 7e. Deprotection followed by reductive alkylation can give 7g.

Figure 9:
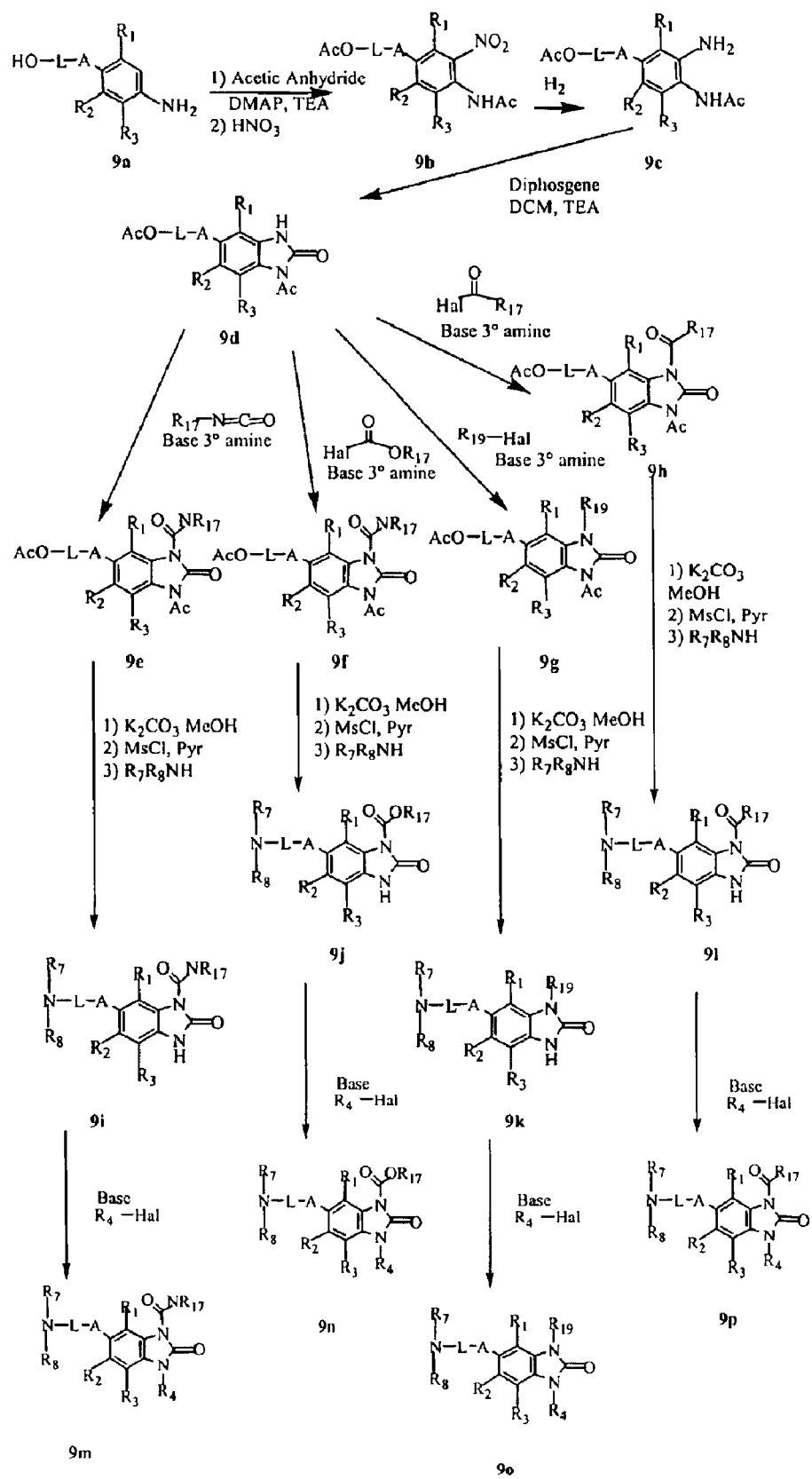
FIG. 9 is a schematic diagram showing the preparation of benzimidazolone amines of Formula 9m, 9n, 9o or 9p.

In the scheme diagramed in FIG. 9, a suitably substituted aniline 9a derivative can be first diacylated and nitrated to form 9b. 9b can then be hydrogenated to reduce the nitro groups to the aniline derivitive 9c. 9c can then be reacted with diphosgen to afford the benzimdazolone 9d. 9d can then be reacted with eather, a suitable isocyanate, haloformate, $R_{19}$-halide or acid chloride to functionalize the nitrogen of 9d and afford 9e, 9f, 9g or 9h, respectively. 9e, 9f, 9g or 9h can then be subjected to base catalyzed hydrolysis followed by mesylation and displacement by $R_7R_8NH$ to afford 9i, 9j, 9k or 9l, respectively. Functionalization of the remaining nitrogen can be accomplished by reacting 9i, 9j, 9k or 9l with a base and a suitable halide to afford 9m, 9n, 9o or 9p, respectively.

Figure 10:
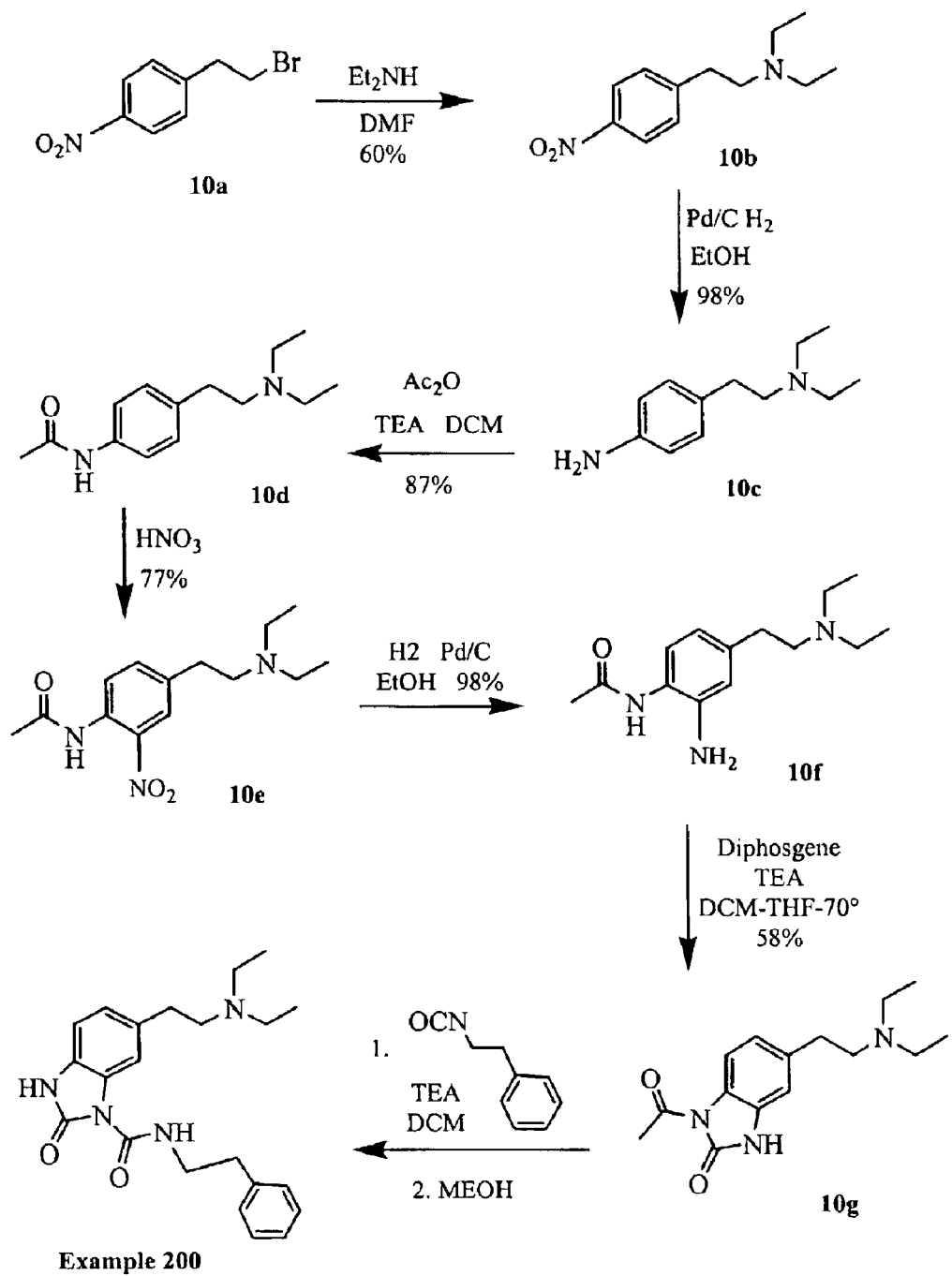
FIG. 10 is a schematic diagram showing the preparation of Example 200.

FIG. 10 shows another scheme suitable for preparing functionalized benzimidazolones. A suitable nitro benzene of the form 10a, for example, can be reacted with an amine of the form $NR_7R_8$ (diethyl amine in FIG. 10) to afford 10b. 10b can be hydrogenated to reduce the nitro group to the aniline derivative 10c, which can then be acylated to form 10d. 10d can be nitrated to afford 10e, which can subsequently be hydrogenated to reduce the nitro group to afford 10f. 10f can be treated with diphosgene to afford the benzimidazolone 10g. 10g can then be treated with triethylamine in dichloromethane followed by addition of a suitable isocyanate, followed by the addition of methanol to afford the desired benzimdazolone.

Figure 11:
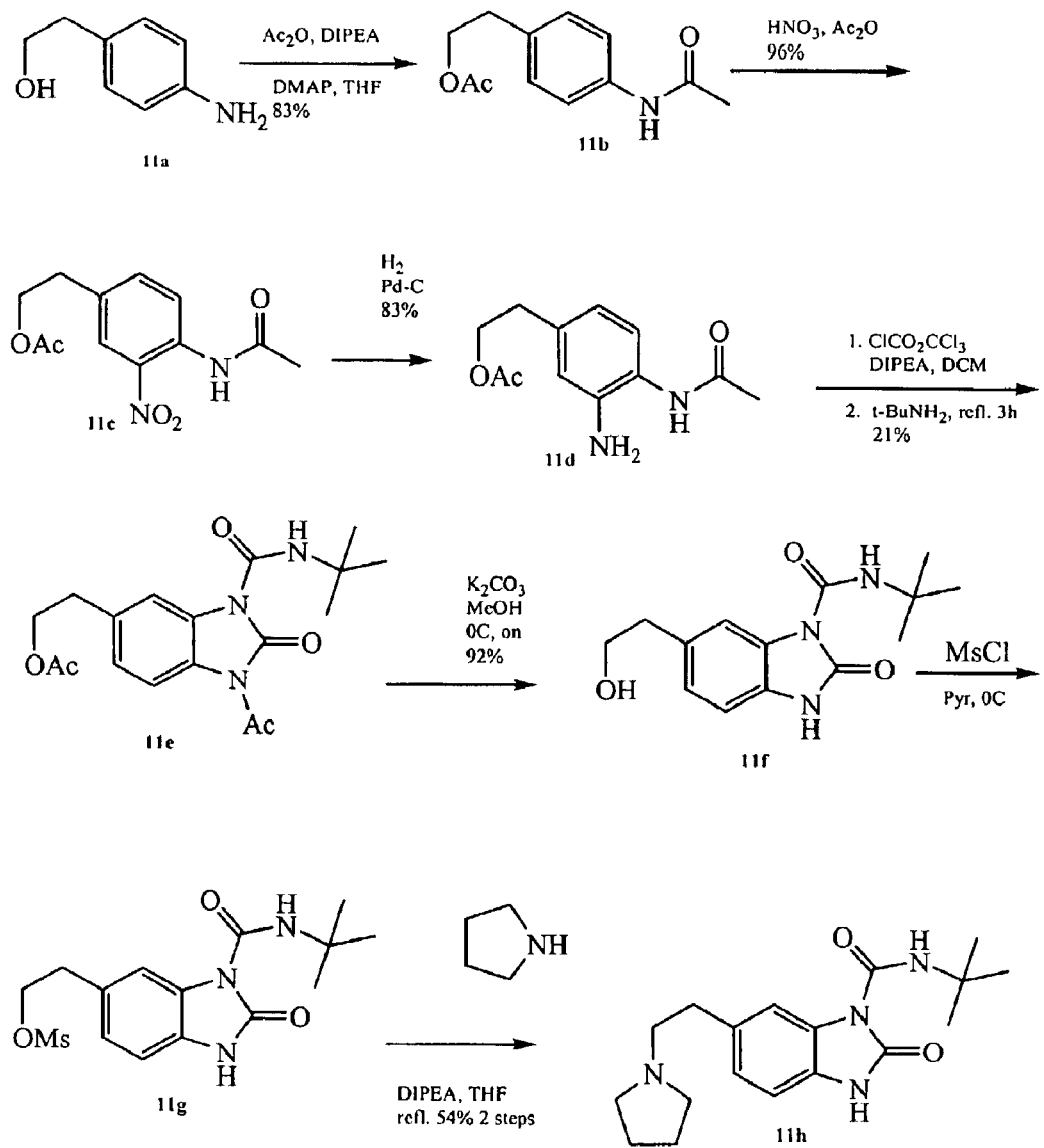
FIG. 11 is a schematic diagram showing the preparation of benzimidazolone amines of Formula 11h.

A further scheme suitable for preparing functionalized benzimidazolones is diagramed in FIG. 11. A suitable aniline derivative 11a can be acylated at both the nitrogen and oxygen positions by the action of acetic anhydride to afford 11b, which can be nitrated to afford 11c. 11c can be hydrogenated to reduce the nitro group and afford aniline 11d. 11d can be first reacted with diphosgene and then with tert-butylamine to afford 11 which can be subjected to base hydrolysis to afford 11f. 11f can be mesylated and reacted with an appropriate amine, such as pyrolidine, to afford 11h.

Aza-benzimidazolone compounds (e.g., 4-pyridoimidazolones, 7-pyridoimidazolones, 6-pyridobenzimidazolones, pyrazino-benzimidazolines, pyrimidinobenzimidazolones) can be prepared in accordance with the synthetic schemes diagramed in FIG. 12–FIG. 16.

Figure 12:
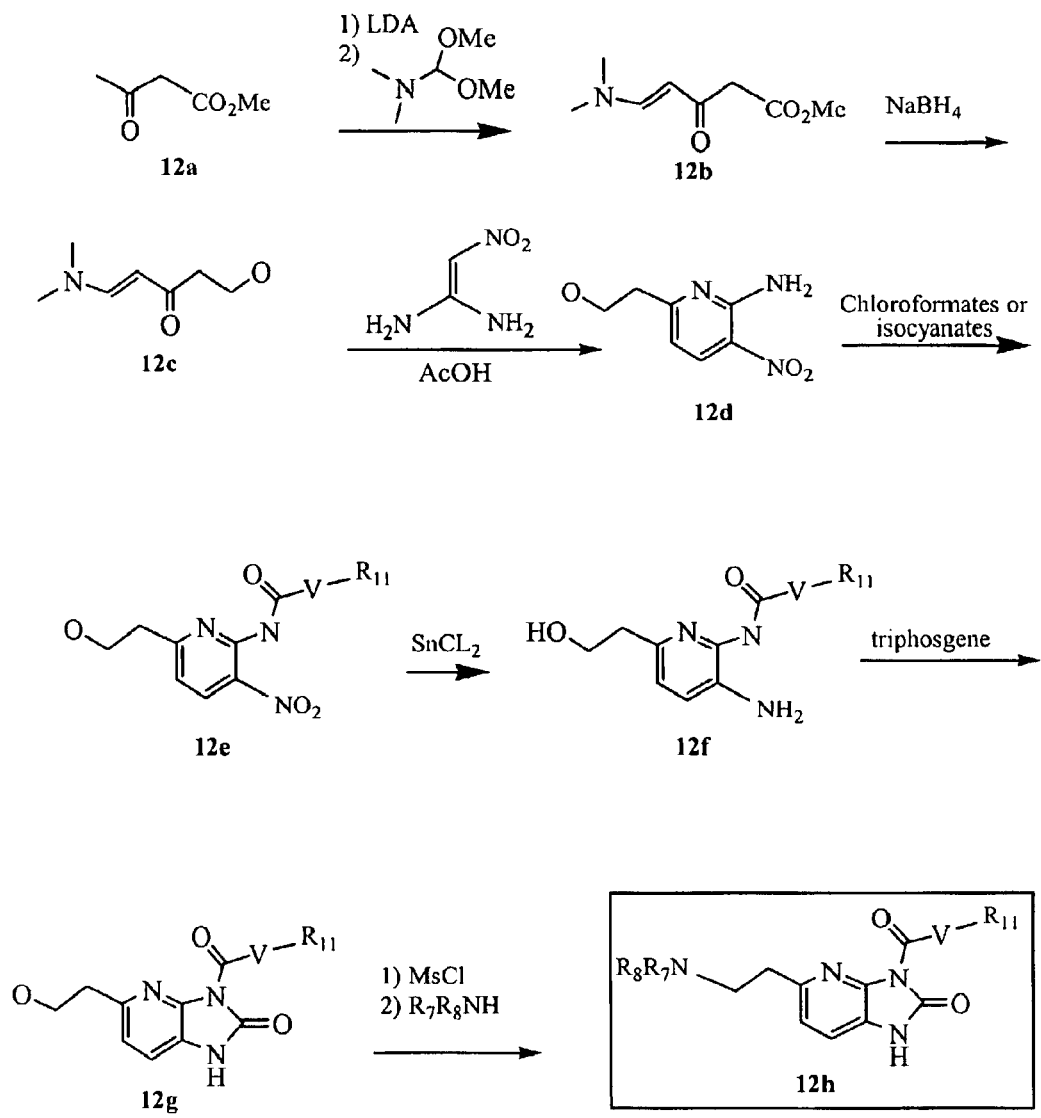
FIG. 12 is a schematic diagram showing the preparation of azabenzimidazolone amines of Formula 12h.

The synthesis of 4-pyridoimidazolones is shown in FIG. 12. In an adaptation of the method of Singh (*Indian J. Chem., Sect B.,* 1996;35(9):881–882), the dianion of methyl acetoacetate is condensed with a formamide equivalent, leading to unsaturated ketone 12b. Selective ester reduction is carried out using the method of Edafiogho (*J. Pharm. Sci.,* 1994;83(1);79–84). Mild acid condensation of hydroxyketone 12c with 2,2-diaminonitroethylene using the method of Troschuetz (*J. Heterocyclic Chem.,* 1996;33(6):1815–1821) leads to hydroxyethyl pyridine 12d. This aminopyridine can then reacted with chloroformates or isocyanates to produce carbamates/ureas as denoted by compound 12e. Subsequent nitro reduction followed by benzimidazolone closure (Kawamoto, *J. Med. Chem.,* 1999;42(25):5061–5063) leads to fully elaborated 4-pyrido derivatives 12g, which can then be subjected to mesylation/displacement to afford derivatives denoted by 12h (Formula Va).

Figure 13:
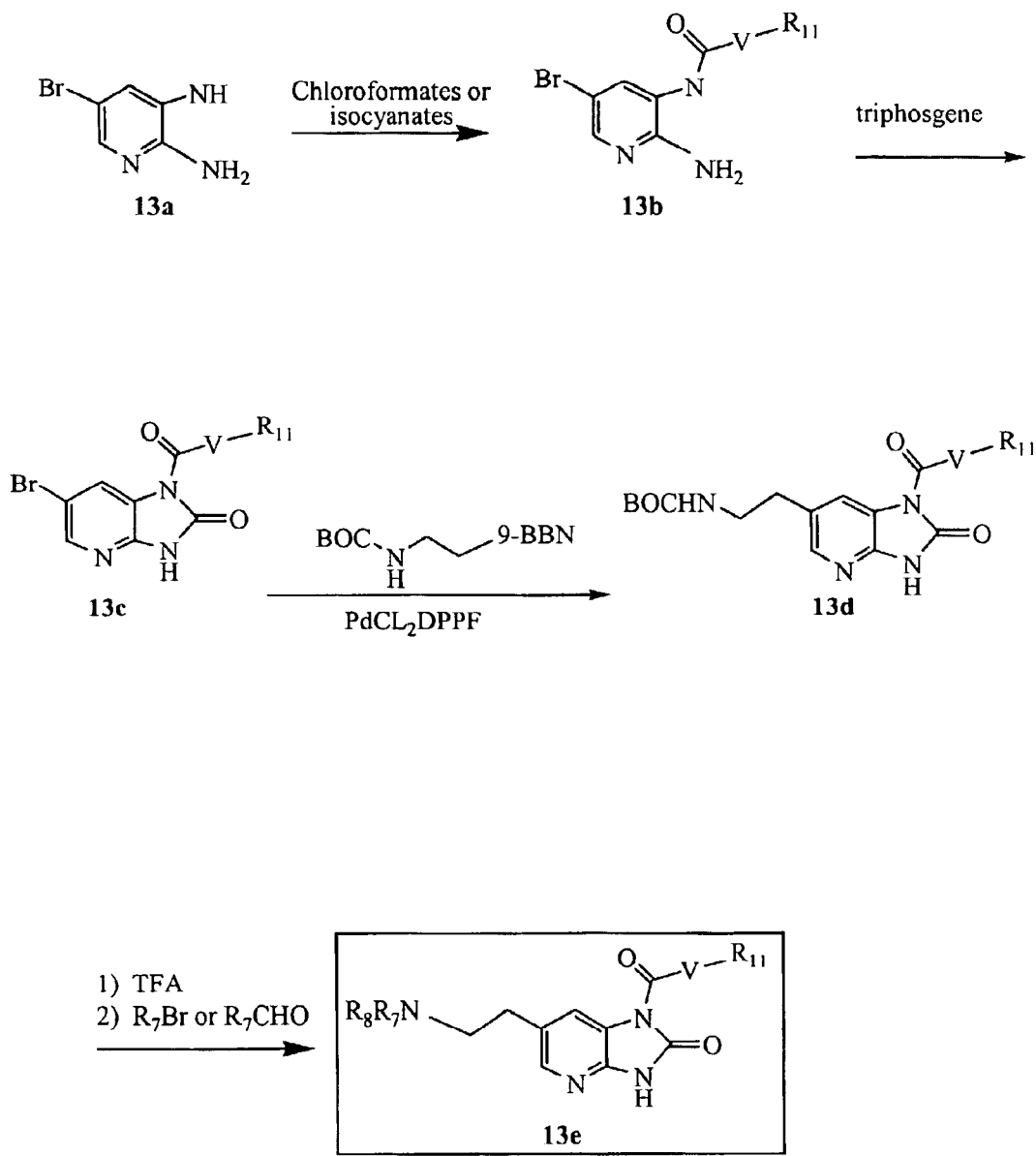
FIG. 13 is a schematic diagram showing the preparation of azabenzimidazolone amines of Formula 13e.

The synthesis of 7-pyridoimidazolones is shown in FIG. 13. Known diamine 13a (Seki T., *J. Heterocyclic Chem.,*

1995;32(3):1071–1073) can be condensed with chloroformates or isocyanates to provide carbarnates/ureas such as 13b. These can be cyclized to the corresponding bromobenzimidazolines 13c. Amino-ethyl homologation using the method of Overman (*J. Org. Chem.,* 1999;64:8743–8744) leads to BOC-protected compound 13d. These can then be deprotected and either alkylated or reductively aminated to provide compounds denoted by 13e (Formula Vb).

Figure 14:
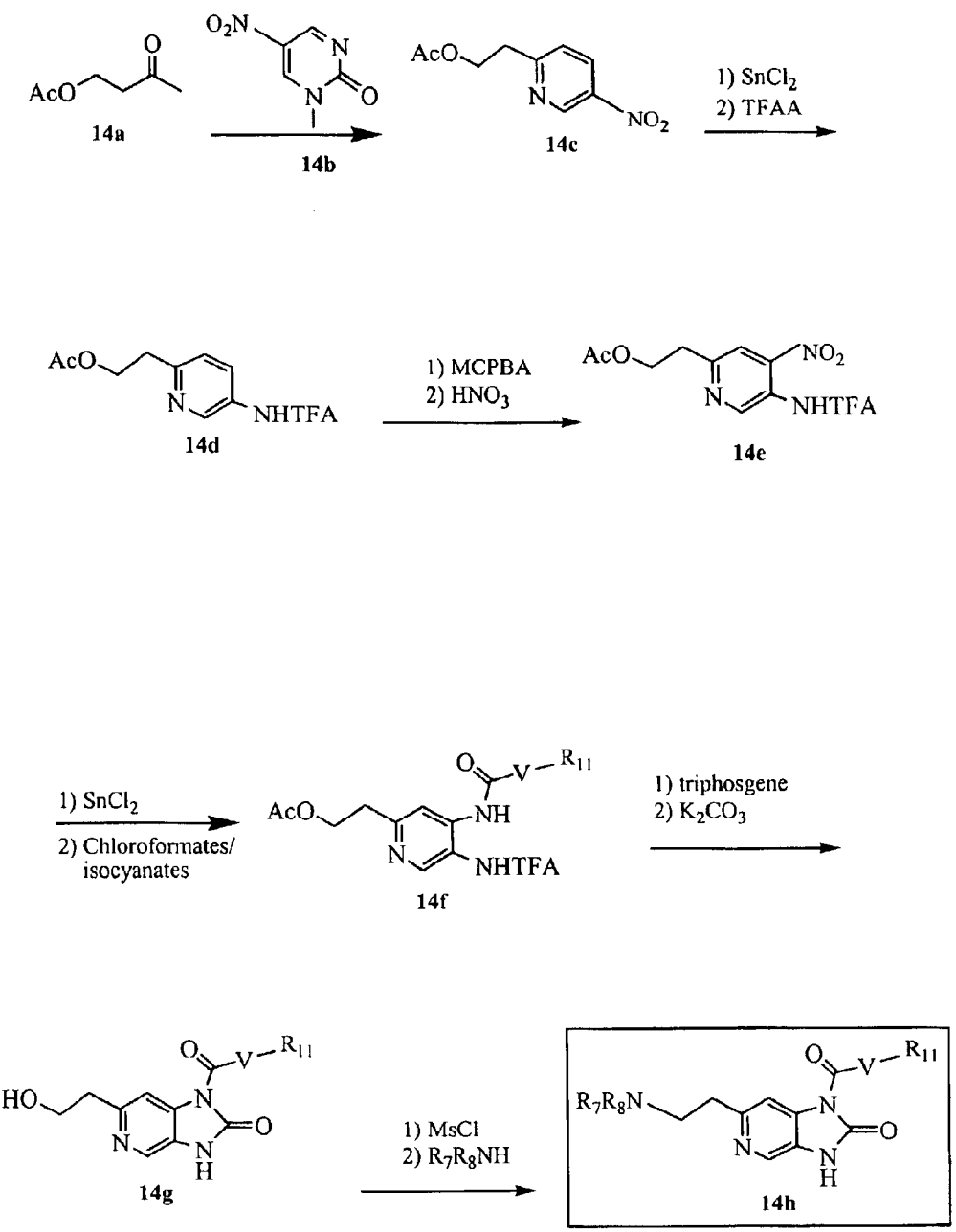
FIG. 14 is a schematic diagram showing the preparation of azabenzimidazolone amines of Formula 14h.

The synthesis of 6-pyridobenzimidazolones is shown in FIG. 14. Reaction of commercial 4-acetoxy-2-butanone 14a with 1-methyl-3,5-dinitro-2-pyridone 14b under the conditions of Nishiwaki (*Synthesis,* 1997;11: 1277–1280) leads to 3,6-disubstituted pyridine 14c. The nitro group can be reduced and protected as trifluoroacetate 14d. N-oxidation followed by nitration (Takada, *J. Med. Chem.,* 1996;39(14):2844–2851) leads to nitropyridine 14e. A second nitro reduction generates a mono-protected diamine derivative, which can then be condensed with chloroformates/isocyanates to afford 14f. Benzimidazolone closure and deprotection can be followed by mesylation and amine displacement to afford the 6-pyrido derivatives denoted by 14h (Formula Vc).

Figure 15:
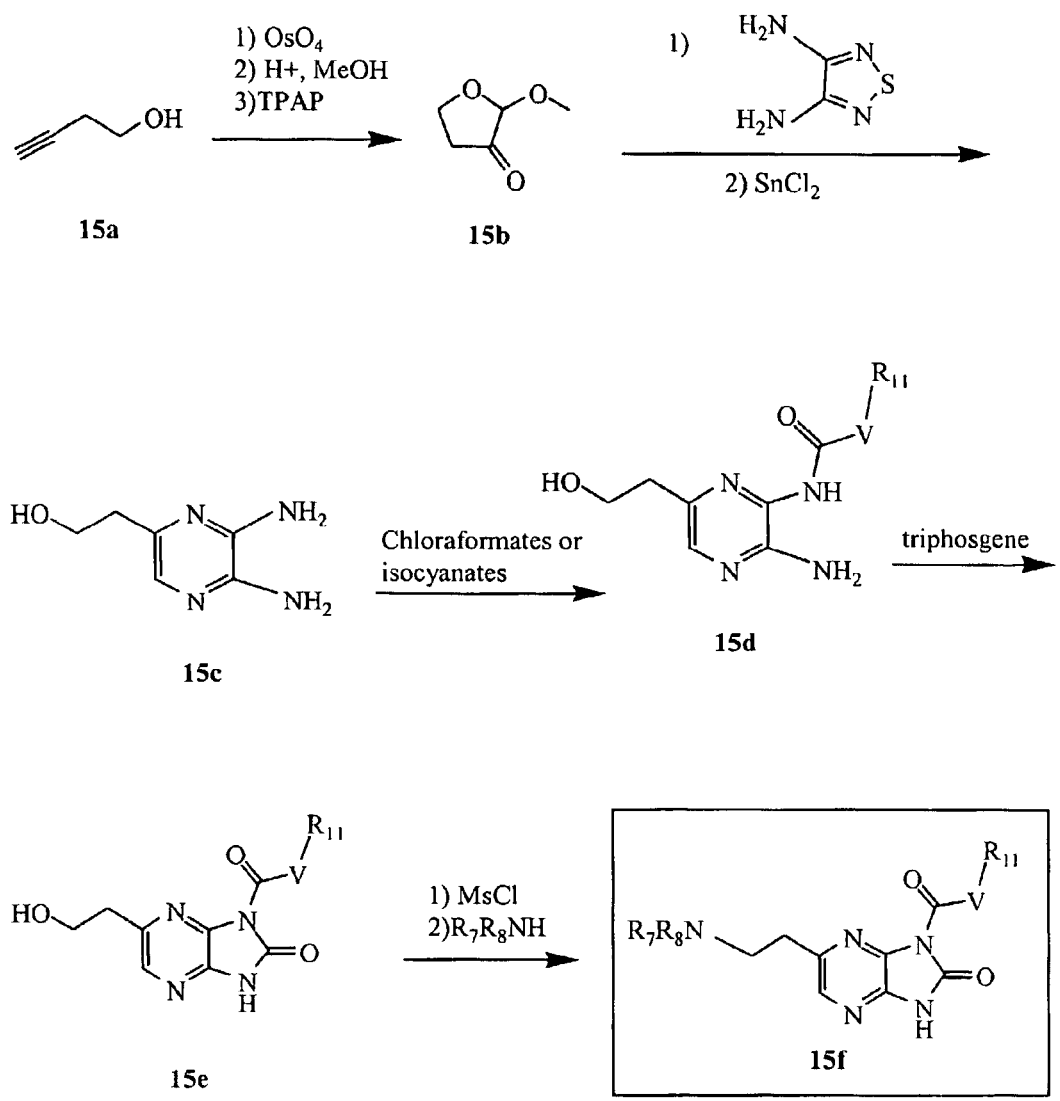
FIG. 15 is a schematic diagram showing the preparation of azabenzimidazolone amines of Formula 15f.

The synthesis of pyrazino-benzimidazolines is shown in FIG. 15. Following the precedent of Okada (*Heterocycles,* 1991;32(3):431–436), osmylation of homopropargyl alcohol, followed by protection as the methyl glycoside and subsequent per-ruthenate oxidation (Lee J., *Synlett,* 1994;3:206–208) affords masked keto-aldehyde 15b. Condensation with 3,4-diamino-1-thia-2,5-diazole followed by tin chloride reduction can lead to diamine 15c (Sato N., *J. Chem. Res., Synops.,* 1997;7:250–251). This diamine can then be condensed with chloroformates/isocyanates to afford 15d. Benzimidazolone closure can then be followed by mesylation and amine displacement to afford the 6-pyrido derivatives denoted by 15f (Formula Vd).

Figure 16:
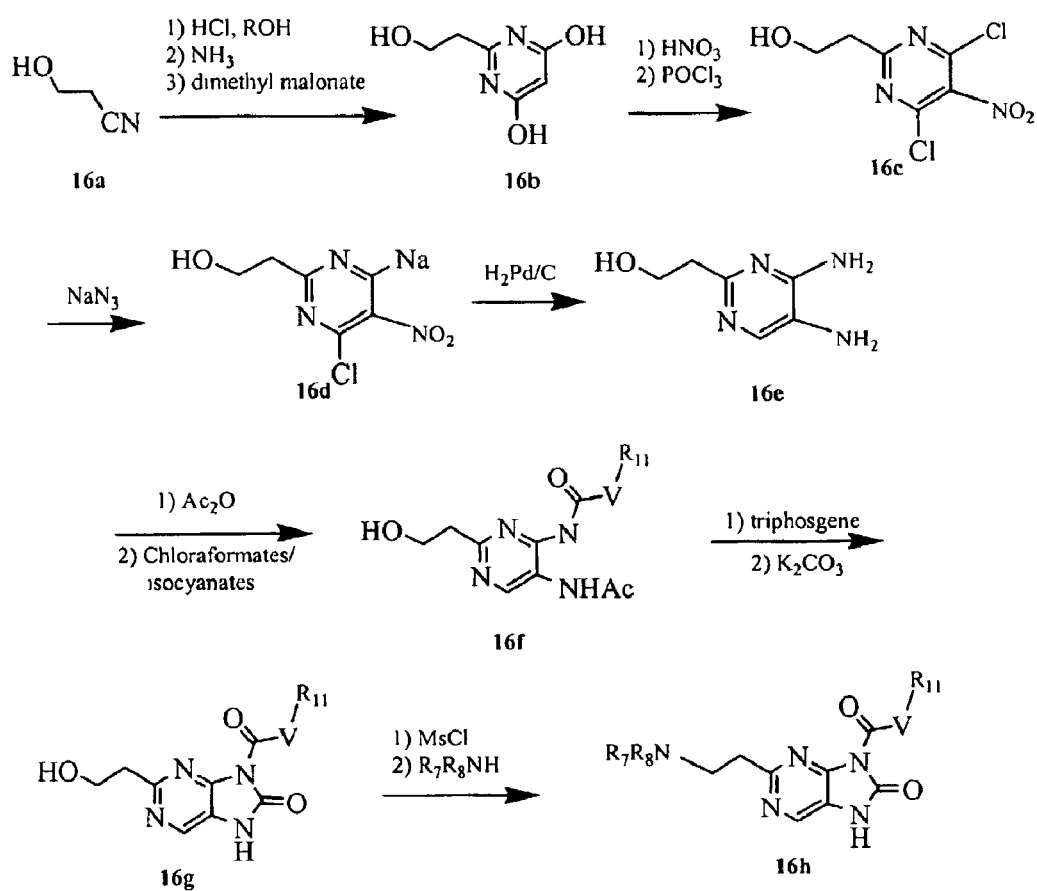
FIG. 16 is a schematic diagram showing the preparation of azabenzimidazolone amines of Formula 16h.

FIG. 16 shows the synthesis of pyrimidino-benzimidazolones as denoted by structure 16h (Formula Ve). Commercial 3-hydroxypropionitrile can be converted to its corresponding amidine, then condensed with dimethyl malonate to provide compound 16b. Following the precedent of Beck (*Bio-Org. & Med. Chem. Lett.,* 1999;9:967–972), this can be nitrated and chlorinated to provide compound 16c. Reaction with one equivalent of sodium azide can lead to chloro-azide 16d, which then provides diamine 16e after exhaustive catalytic reduction. Protection of the more reactive anilino-group as the acetate can then be followed by reaction with chloroformates/isocyanates to provide carbamates/ureas denoted by 16f. Subsequent benzimidazolone closure/deprotection lead to hydroxyethyl derivatives 16g, which can be elaborated to the final products by mesylation/displacement.

Aza-indole-amine compounds (e.g.,4-azaindole amines, 7-azaindole amines, 6-azaindol amines, pyrazinoindol amines, pyrimidinoindole amines) can be prepared in accordance with the synthetic schemes diagramed in FIG. 17–FIG. 21.

Figure 17:
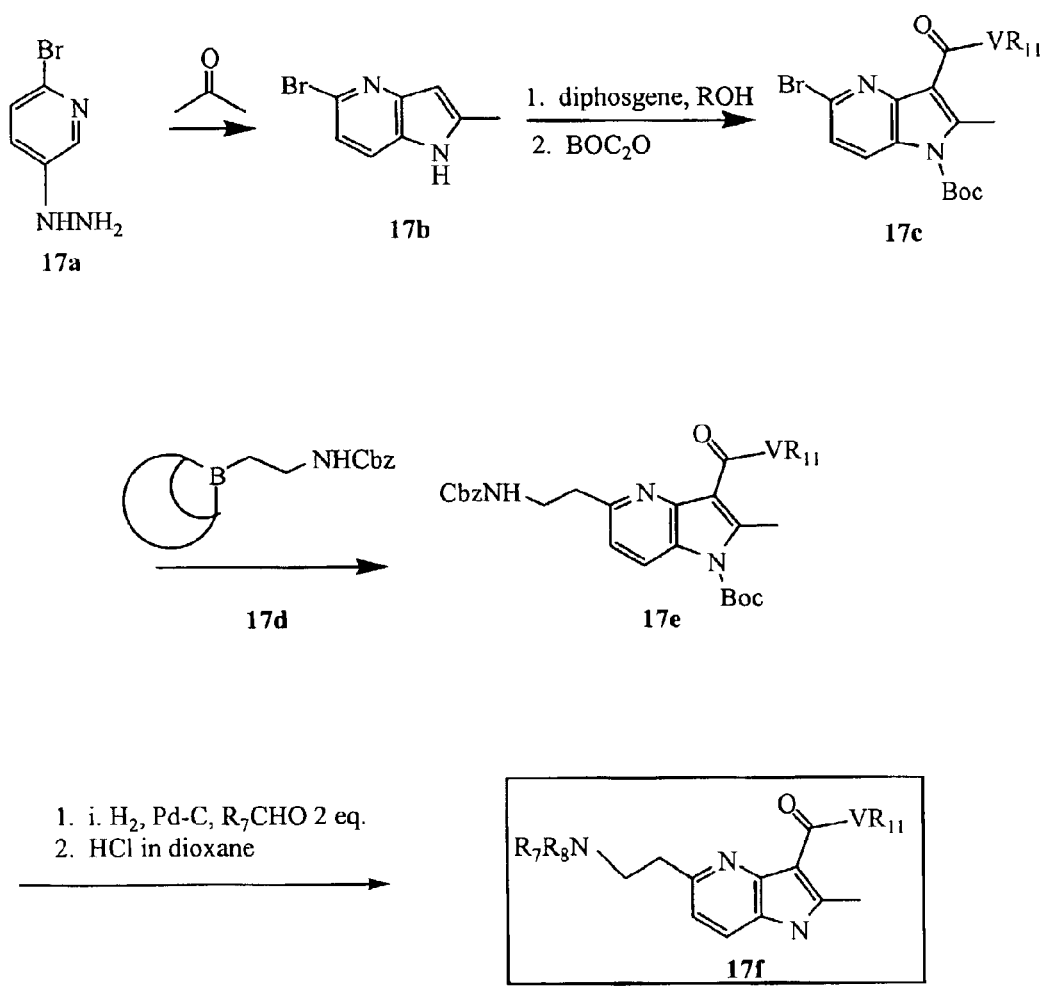
FIG. 17 is a schematic diagram showing the preparation of azaindole amines of Formula 17f.

The synthesis of 4-azaindoles is shown in FIG. 17. Following the procedure of Degussa (Patent No. GB 259982), Fischer-indole synthesis using hydrazone 17a and acetone provides bromo-azaindole 17b. Introduction of the 3-ester functional group can be accomplished by acylation at the 3-position with diphosgene and displacement of the resultant acyl chloride intermediate with an appropriate alcohol/amine. Protection of the indole nitrogen as the t-butyl carbamate provides ester 17c. Suzuki-Miyaura cross-coupling of 17c with amino-alkylborane 17d using the conditions described by Overman (*J. Org. Chem.,* 1999;64:8743–8744) leads to indole 17e. Removal of the protecting groups followed by either alkylation or reductive amination of the primary amine provide compounds denoted by structure 17f.

Figure 18:
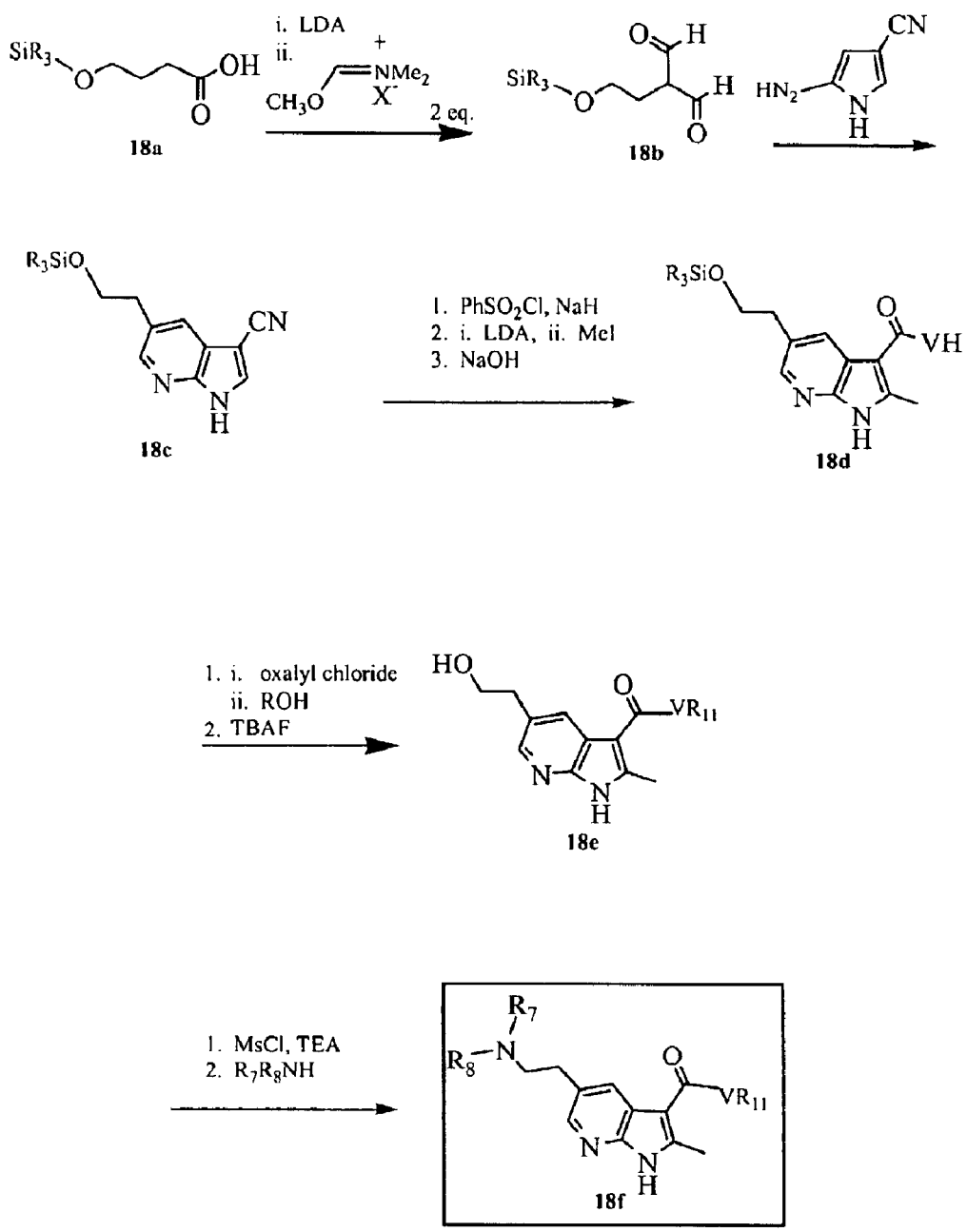
FIG. 18 is a schematic diagram showing the preparation of azaindole amines of Formula 18f.

The synthesis of 7-azaindoles is shown in FIG. 18. Acid 18a can be prepared following a procedure described by Labadie (*J. Org. Chem.,* 1983;48:4634–4642). Acid 18a can be converted to dialdehyde 18b following Knorr's method (*J. Org. Chem.,* 1984;49:1288–1290). Acid promoted condensation of dialdehyde 18b with 2-aminopyrrolidine using conditions described by Wibberley (Perkins I., *J. Chem. Soc.,* 1975:1910–1913) leads to the formation of azaindole 18c. Protection of the indole nitrogen with the phenyl sulfonyl group and subsequent directed alkylation can introduce a methyl group at the 2 position of the indole (Merour, *Tett. Lett.,* 1999;40:5853–5854). Hydrolysis of the cyano group to the acid under basic conditions also removes the phenyl sulfonyl group to provide acid-indole 18d. The carboxylic acid 18d can be converted to ester 18e by displacement of an acid chloride intermediate with an appropriate alcohol/amine. Deprotection of the protected primary alcohol followed by mesylation and displacement of the mesylate with an amine provides compounds denoted by structure 18f.

Figure 19:
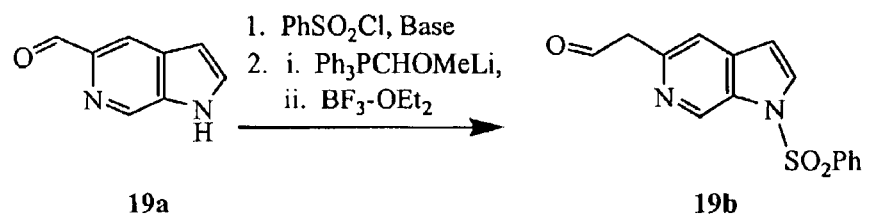
FIG. 19 is a schematic diagram showing the preparation of azaindole amines of Formula 19d.
Figure 19:
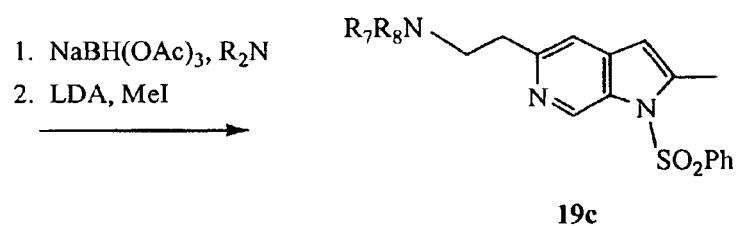
Figure 19:
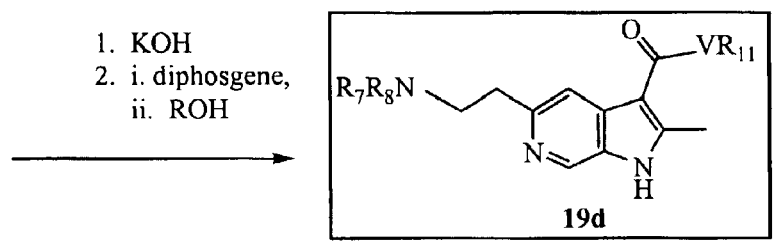

The synthesis of 6-azaindoles is shown in FIG. 19. Aldehyde 19a is prepared according to the method described by Dellouve-Courillon (*Tetrahedron,* 1990;46:3245–3266). Aza-indole 19a can be protected with the phenyl sulfonyl group and the formyl group can be homologated upon treatment with the anion of methoxymethyltriphenyl phosphonium chloride. Hydrolysis of the resultant enol ether under Lewis acid conditions leads to aldehyde 19b. Reductive amination using aldehyde 19b and a suitable amine provides amine 19c. Alkylation with methyl iodide at the 2 position of the indole is directed by the phenyl sulfonyl group. Removal of the sulfonyl group can be accomplished using potassium hydroxide. Introduction of the 3-ester functional group can be accomplished by acylation at the 3-position with diphosgene and displacement of the resultant acyl chloride intermediate with an appropriate alcohol/amine to provide compounds denoted by structure 19d.

Figure 20:
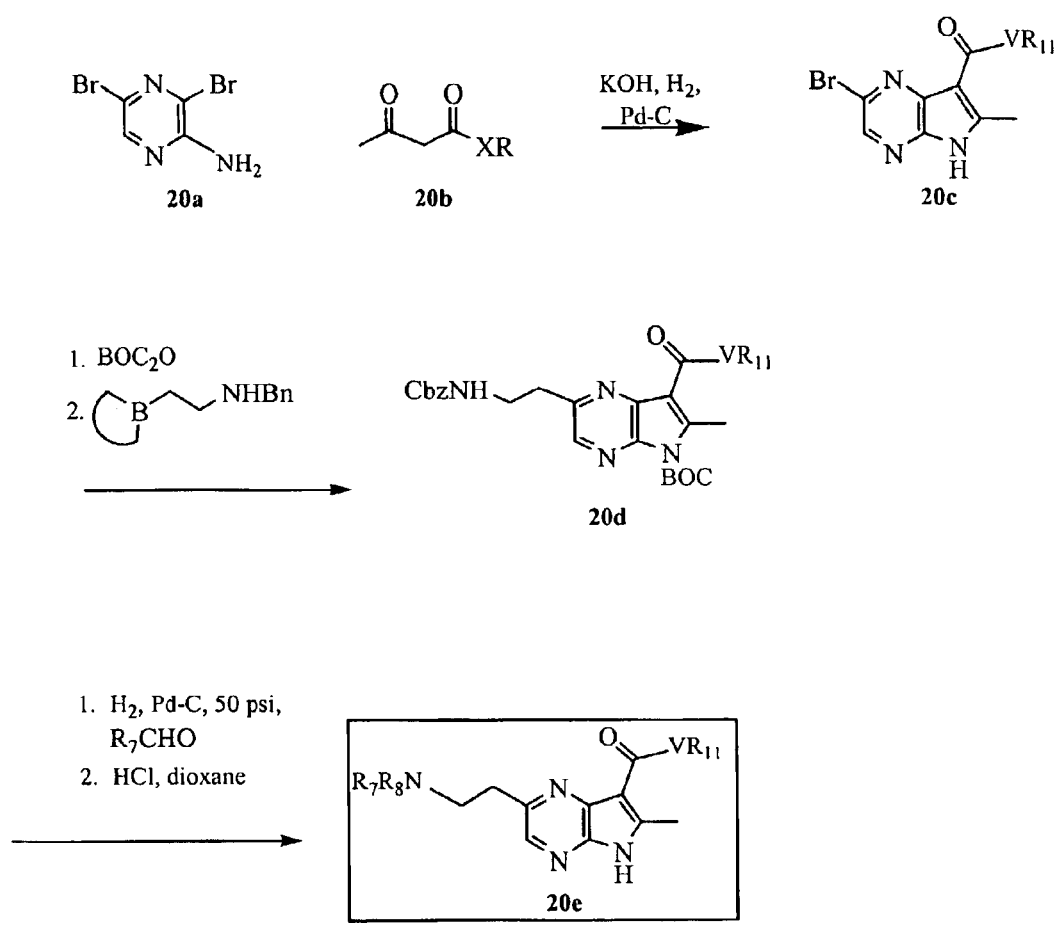
FIG. 20 is a schematic diagram showing the preparation of azaindole amines of Formula 20e.

The synthesis of pyrrolopyrazines is shown in FIG. 20. Commercially available pyrazine 20a can be condensed with an appropriate acetoacetate/acetoamide 20b under basic conditions to provide pyrrolopyrazine 20c (Constantin A., *Bull. Soc. Chim. Fr.,* 1989:467–471). Protection of the indole nitrogen of 20c as the t-butyl carbamate followed by Suzuki-Miyaura cross-coupling with amino-alkylborane using the conditions described by Overman (*J. Org. Chem.* 1999:64:8743–8744) leads to indole 20d. Removal of the protecting groups followed by either alkylation or reductive amination of the primary amine provides compounds denoted by structure 20e.

Figure 21:
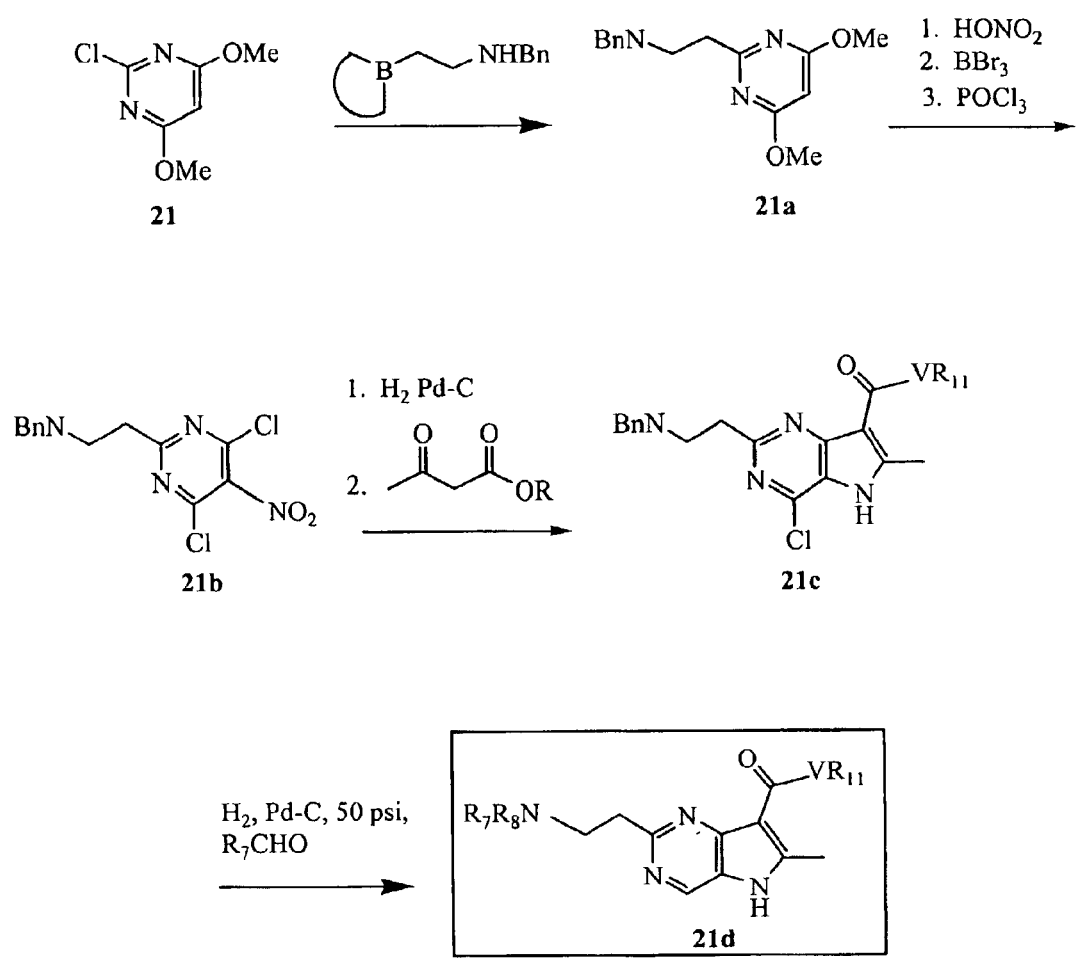
FIG. 21 is a schematic diagram showing the preparation of azaindole amines of Formula 21 d.

The synthesis of pyrrolopyrimidines is shown in FIG. 21. Commercially available pyrimidine 21a can be used in the Suzuki cross coupling reaction with and appropriate alkyl borane to provide 21b. Following the precedent of Beck, [Bio-Org. & Med. Chem. Lett., 1999, 9, 967–972] 21b nitrated, deprotected and chlorinated to provide compound 21c. Reduction of the nitro group followed by condensation of the resultant amine with an appropriate acetoacetate under basic conditions provide pyrrolopyrimidine 21d. Removal of the carbamate protecting group and the chlorine atom can be accomplished by hydrogenolysis under higher pressure. Reductive amination or alkylation of the primary amine provides compounds denoted by structure 21e.

The activity of compounds of the present invention can be assessed using any suitable assay, such as receptor binding assays and chemotaxis assays (see, for example, WO 99/37651; Hesselgesser et al., *J. Biol. Chem.* 273(25): 15687–15692 (1998) and WO 98/02151). For example, antagonists of chemokine (e.g., RANTES, MIP-1α and/or MIP-1β) binding to CCR5 can be identified utilizing suitable cells which express CCR5 (e.g., L1.2 cells transfected with a recombinant construct encoding CCR5) and undergo chemotaxis in response to binding of chemokine (e.g., RANTES, MIP-1α and/or MIP-1β) to receptor. Agonists of chemokine receptor (e.g., CCR5) function can be identified using suitable cells which express CCR5. For example, such a cell can be contacted with a test compound under conditions suitable for cellular chemotaxis upon binding of compound to chemokine receptor and chemotaxis can be monitored. The activity of the compounds described herein can be assessed in a high through-put receptor binding assay, which monitors the binding of ligand (e.g., $^{125}$I-RANTES, $^{125}$I-MIP-1α, 125I-MIP-1b, CD4/HIV GP120) to cells expressing chemokine receptor (e.g. CCR5) or membrane prepared from such cells. Compounds of the present invention can also be identified by virtue of their ability to inhibit the activation steps triggered by binding of a chemokine to its receptor, such as chemotaxis, integrin activation and granule mediator release.

CCR-5 Receptor Binding Assay

The compounds of the present invention were evaluated using the following CCR-5 receptor binding assay.

The $^{125}$I-gp120/sCD4/CCR-5 binding assay was carried out similarly as described in Wu et al., *Nature*, 1996;384:179–183. Briefly, the envelope gp120 protein derived from HIV-1 JR-FL (Trkola et al., *Nature*, 1996;384:184–186), an M-tropic strain, was iodinated using solid phase lactoperoxidase to a specific activity of 20 µCi/µg. For each binding reaction (in a final volume of 100 µL binding buffer [50 mM HEPES, pH 7.5, 1 mM CaCl$_2$, 5 mM MgCl$_2$, and 0.5% BSA]), 25 µL (2.5 µg) of membranes prepared from CCR-5/L 1.2 cells were mixed with 25 µL (3 nM) sCD4, followed by 25 µL (0.1 nM) radio-labeled gp120 in the presence or absence of 25 µL compound dissolved in DMSO (final concentration of DMSO 0.5%). The reactions were incubated at room temperature for 45 to 60 minutes and stopped by transferring the mixture to GFB filter plates, which were then washed 3 to 4 times with binding buffer containing 0.5 M NaCl. The plates were dried and MicroScint scintillation fluid was added before counting.

Particularly preferred compounds of the invention can inhibit the binding of sCD-4/GP-120 to CCR-5 by about fifty percent at a concentration of less than or equal to about 200 µM (IC50≦200 µM), in a suitable binding assay, such as the binding assay described herein. For example the IC$_{50}$ values for the compound of Example 5 and of the compound of Example 7 were 18.0 and 18.2 µM, respectively. Example 20 caused 50% inhibition at 17.5 µM. The compounds of Examples 56 and 66 had IC$_{50}$s of about 4.8 µm. The compound of Example 62 had an IC$_{50}$ of 13.9±1.6 µM. The compounds of Examples 69, 70, and 72 had IC$_{50}$s of 20.3±2.8 µM, 5.52±1.1 µM and 1.93±0.32 µM, respectively. Preferred compounds can inhibit the binding of sCD-4/GP-120 to CCR-5 with IC50s of about 10 µM to about 100 µM or about 1 nM to about 10 µM

EXAMPLES

Example 1

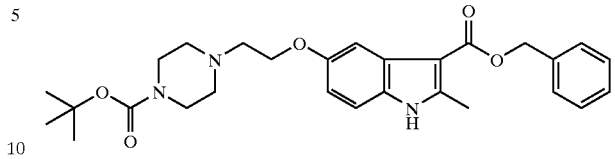

5-[2-(4-tert-Butoxycarbonyl-piperazin-1-yl)-ethoxy]-2-methyl-1H-indole-3-carboxylic acid benzyl ester Step A

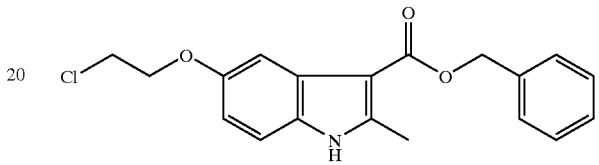

5-(2-Chloro-ethoxy)-2-methyl-1H-indole-3-carboxylic acid benzyl ester

A mixture of 5-hydroxy-2-methyl-1H-indole-3-carboxylic acid benzyl ester (88.9 mmol, 25.0 g, prepared according to Bell, M. R. U.S. Pat. No. 3,510,491, 1970), potassium carbonate (179 mmol, 24.6 g), potassium iodide (8.88 mmol, 1.47 g), and 1-bromo-2-chloroethane (267 mmol, 22.2 mL, Aldrich) in 444 mL of acetonitrile was heated at reflux under nitrogen for 16 hours, cooled to rt and concentrated under reduced pressure. The residue was partitioned between water (50 mL) and ethyl acetate (100 mL). The mixture was filtered through celite, the layers were separated and the aqueous phase was extracted with ethyl acetate (3×50 mL). The combined organic extracts were washed with saturated aqueous NaCl solution (30 mL), dried over MgSO$_4$ and concentrated to give a brown sticky solid (27.6 g, 90%). The product was purified by silica gel flash column chromatography (0–20% ethyl acetate/dichloromethane) to afford pure product as a white solid (8.06 g, 26%): mp 170–171° C.; IR (KBr) 3313, 1654, 1480, 1450, 1427, 1173, 774 cm$^{-1}$; $^1$HNMR (400 MHz, DMSO-d$_6$) δ 2.59 (s, 3H, ArCH$_3$), 3.87–3.89 (m, 2H, CH$_2$Cl), 4.11 (t, J=5.12 Hz, 2H, CH$_2$OAr), 5.28 (s, 2H, CO$_2$CH$_2$Ph), 6.73–6.76 (m, 1H, ArH), 7.23 (d, J=8.79 Hz, 1H, ArH), 7.29–7.32 (m, 1H, ArH), 7.36–7.39 (m, 3H, ArH), 7.46 (d, J=7.81 Hz, 2H, ArH), 11.75 (s, 1H, NH); MS(APCI$^-$): m/z 342.0 (M–1). Anal. Calcd for C$_{19}$H$_{18}$Cl$_1$N$_1$O$_3$: C, 66.38; H, 5.28; Cl, 10.31; N, 4.07. Found: C, 66.03; H, 5.20; Cl, 10.10; N, 4.40.

Step B

5-[2-(4-tert-Butoxycarbonyl-piperazin-1-yl)-ethoxy]-2-methyl-1H-indole-3-carboxylic acid benzyl ester To a mixture of 5-(2-chloro-ethoxy)-2-methyl-1H-indole-3-carboxylic acid benzyl ester (1.45 mmol, 0.500 g, Example 1, Step A) in 15.5 mL of acetonitrile was added potassium carbonate (1.45 mmol, 0.201 g), potassium iodide (0.145 mmol, 0.024 g), and piperazine-1-carboxylic acid tert-butyl ester (5.82 mmol, 1.08 g, Lancaster). The mixture was heated at reflux for 20 hours, another portion of piperazine-1-carboxylic acid tert-butyl ester (5.82 mmol, 1.08 g) and 2 mL of dimethylformamide were added and heating was continued for 24 hours. The reaction was cooled to rt and concentrated under reduced pressure. The residue was dissolved in ethyl acetate (30 mL), washed with water (4×10 mL), brine (1×10 mL), dried over $MgSO_4$, and concentrated to a yellow oil. The product was purified by silica gel flash column chromatography (50–100% ethyl acetate/hexane) to afford pure product as a white solid (0.550 g, 77%): mp 136–137° C.; IR (KBr) 3304, 2978, 2926, 1696, 1664, 1486, 1455, 1422, 1180, 1169, 1120 cm$^{-1}$; $^1$HNMR (400 MHz, $CDCl_3$) δ 1.44 (s, 9H, $(CH_3)_3C$), 2.43–2.58 (m, 4H, 2 $CH_2N$), 2.70 (s, 3H, $ArCH_3$), 2.73–2.81 (m, 2H, $CH_2N$), 3.40–3.48 (m, 4H, 2 $CH_2NBOC$), 4.01–4.09 (m, 2H, $CH_2OAr$), 5.36 (s, 2H, $CO_2CH_2Ph$), 6.79 (dd, J=8.79, 2.44 Hz, 1H, ArH), 7.14 (d, J=8.55 Hz, 1H, ArH), 7.31–7.39 (m, 3H, ArH), 7.47 (d, J=7.33 Hz, 2H, ArH), 7.55 (d, J=2.44 Hz, 1H, ArH), 8.34 (s, 1H, NH); MS(APCI$^+$): m/z 494.2 (M+1). Anal. Calcd for $C_{28}H_{35}N_3O_5$: C, 68.13; H, 7.15; N, 8.51. Found: C, 68.11; H, 7.43; N, 8.41.

Example 2

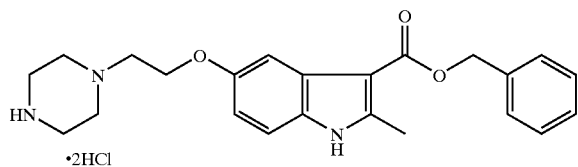

•2HCl

1-[2-(3-benzyloxycarbonyl-2-methyl-1H-indole-5-yloxy)-ethyl]-piperazin-1-ium; Chloride 5-[2-(4-tert-Butoxycarbonyl-piperazin-1-yl)-ethoxy]-2-methyl-1H-indole-3-carboxylic acid benzyl ester (0.885 mmol, 0.437 g, Example 1, Step B) was stirred in 10 mL of 4.0 M HCl in dioxane at room temperature under $N_2$ for 15 minutes. The precipitate was filtered off and dried at 60° C. under vacuum for 16 hours to give the bis hydrochloride salt as a white solid (0.362 g, 95%): mp 225–229° C. (dec); IR (KBr) 3267, 3008, 2917, 2435, 1653, 1183, 1089 cm$^{-1}$; $^1$HNMR(400 MHz, DMSO-$d_6$) δ 2.59 (s, 3H, $ArCH_3$), 3.34–3.50 (m, 8H, 4 $CH_2N$), 3.52–3.62 (m, 2H, $CH_2N$), 4.26–4.38 (m, 2H, $CH_2OAr$), 5.28 (s, 2H, $CO_2CH_2Ph$), 6.80–6.82 (m, 1H, ArH), 7.26 (d, J=8.79 Hz, 1H, ArH), 7.29–7.32 (m, 1H, ArH), 7.37–7.46 (m, 5H, ArH), 9.71 (s, 2H, 2 NH+), 11.88 (s, 1H, NH); MS(APCI$^+$): m/z 394.2 (M+1). Anal. Calcd for $C_{23}H_{27}N_3O_3$/2.0 HCl/0.70$H_2O$: C, 57.67; H, 6.40; N, 8.77; Cl$^-$, 14.80; $H_2O$, 2.63. Found: C, 57.30; H, 6.67; N, 8.50; Cl$^-$, 14.52; $H_2O$, 2.73.

Example 3

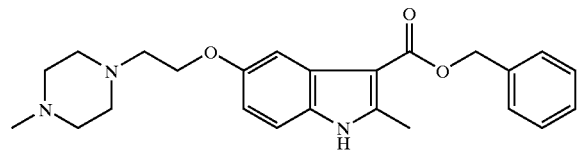

2-Methyl-5-[2-(4-methyl-piperazin-1-yl)-ethoxy]-1H-indole-3-carboxylic acid benzyl ester To a mixture of 5-(2-chloro-ethoxy)-2-methyl-1H-indole-3-carboxylic acid benzyl ester (1.45 mmol, 0.500 g, Example 1, Step A) in 7.27 mL of acetonitrile was added potassium carbonate (1.45 mmol, 0.201 g), potassium iodide (0.145 mmol, 0.024 g), and 1-methyl-piperazine (5.82 mmol, 0.645 mL, Aldrich). The mixture was heated at reflux for 22 hours, cooled to room temperature, and concentrated. The residue was partitioned between $CH_2Cl_2$ (50 mL) and water (50 mL), the layers were separated, and the aqueous phase was extracted with $CH_2Cl_2$ (3×20 mL). 1N HCl (30 mL) was added to the organic phase, the organic solvent was removed under reduced pressure, and the aqueous phase was washed with ethyl acetate (20 mL) to remove unreacted starting material. The aqueous phase was made basic by the addition of 50% aqueous NaOH and extracted with ethyl acetate (3×30 mL). These extracts were washed with saturated aqueous NaCl (20 mL), dried over $MgSO_4$, and concentrated to an off-white solid (0.462 g, 78%). A portion was recrystallized from acetone to afford the product as a white solid: mp 143–145° C.; IR (KBr) 3278, 2939, 2793, 1673, 1654, 1171 cm$^{-1}$; $^1$HNR (400 MHz, $CDCl_3$) δ 2.37 (s, 3H, $ArCH_3$), 2.49–2.68 (m, 8H, 4 $CH_2N$), 2.70 (s, 3H, $NCH_3$), 2.78–2.81 (m, 2H, $CH_2N$), 4.03–4.06 (m, 2H, $CH_2OAr$), 5.36 (s, 2H, $CO_2CH_2Ph$), 6.79 (d, J=8.55 Hz, 1H, ArH), 7.15 (d, J=8.79 Hz, 1H, ArH), 7.31 (d, J=6.59 Hz, 1H, ArH), 7.34–7.38 (m, 2H, ArH), 7.47 (d, J=7.33 Hz, 2H, ArH), 7.55 (s, 1H, ArH), 8.32 (s, 1H, NH); MS(APCI$^+$): m/z 408.2 (M+1). Anal. Calcd for $C_{24}H_{29}N_3O_3$/0.02$H_2O$: C, 70.67; H, 7.18; N, 10.30; $H_2O$, 0.09. Found: C, 70.48; H, 7.13; N, 10.18; $H_2O$, 0.46.

Example 4

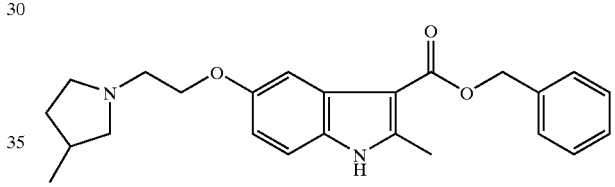

2-Methyl-5-[2-(3-methyl-pyrrolidin-1-yl)-ethoxy]-1H-indole-3-carboxylic acid benzyl ester To a mixture of 5-(2-chloro-ethoxy)-2-methyl-1H-indole-3-carboxylic acid benzyl ester (0.873 mmol, 0.300 g, Example 1, Step A) in 8.76 mL of acetonitrile was added potassium carbonate (0.873 mmol, 0.120 g), potassium iodide (0.0873 mmol, 0.015 g), and 3-methyl-pyrrolidine (11.74 mmol, 1.00 g, prepared from 3-methyl-pyrrolidin-2-one, Lancaster, according to Reder E.; et al. *Helv. Chim. Acta* 1995;78:73). The mixture was heated at reflux for 70 hours, cooled to room temperature, and concentrated. The residue was partitioned between ethyl acetate (30 mL) and water (30 mL), the layers were separated, and the aqueous phase was extracted with ethyl acetate (3×20 mL). These extracts were washed with saturated aqueous NaCl (20 mL), dried over $MgSO_4$, and concentrated to a dark brown oil (0.558 g). The product was purified by silica gel flash column chromatography (0–5% $Et_3N$/ethyl acetate) and triturated with ether to afford pure product as a cream colored solid (0.167 g, 49%): mp 121–122° C.; IR (KBr) 3305, 2954, 2923, 1663, 1485, 1453, 1179 cm$^{-1}$; $^1$HNMR (400 MHz, $CDCl_3$) δ 1.03 (d, J=6.59 Hz, 3H, $CHCH_3$), 1.34–1.43 (m, 1H, $CHCH_3$), 2.01–2.12 (m, 1H, aliphatic CH), 2.15–2.23 (m, 1H, aliphatic CH), 2.25–2.39 (m, 1H, CHN), 2.61–2.70 (m, 1H, CHN), 2.69 (s, 3H, $ArCH_3$), 2.83–3.00 (m, 3H, $CH_2N$), 3.01–3.11 (m, 1H, CHN), 4.05–4.12 (m, 2H, $CH_2OAr$), 5.36 (s, 2H, $CO_2CH_2Ph$), 6.75–6.77 (m, 1H, ArH), 7.12 (d, J=8.79 Hz, 1H, ArH), 7.31

(d,J=7.08 Hz, 1H, ArH), 7.34–7.38 (m, 2H, ArH), 7.47 (d, J=8.06 Hz, 2H, ArH), 7.54 (s, 1H, ArH), 8.47 (s, 1H, NH); MS(APCI$^+$): m/z 393.1 (M+1). Anal. Calcd for $C_{24}H_{28}N_2O_3$: C, 73.44; H, 7.19; N, 7.14. Found: C, 73.08; H, 7.13; N, 7.05.

Example 5

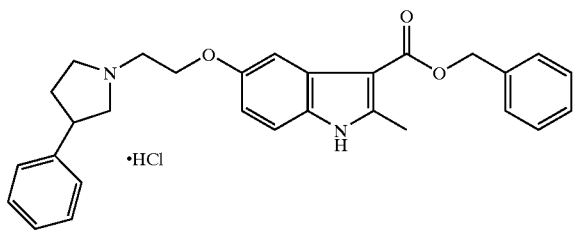

1-[2-(3-benzyloxycarbonyl-2-methyl-1H-indol-5-yloxy)-ethyl]-3-phenyl-pyrrolidinium; Chloride To a mixture of 5-(2-chloro-ethoxy)-2-methyl-1H-indole-3-carboxylic acid benzyl ester (0.873 mmol, 0.300 g, Example 1, Step A) in 8.76 mL of acetonitrile was added potassium carbonate (0.873 mmol, 0.120 g), potassium iodide (0.0873 mmol, 0.015 g), and 3-phenyl-pyrrolidine (10.54 mmol, 1.55 g, Array). The mixture was heated at reflux for 70 hours, cooled to room temperature, and concentrated. The residue was partitioned between ethyl acetate (30 mL) and water (30 mL), the layers were separated, and the aqueous phase was extracted with ethylacetate (3×20 mL). These washed with saturated aqueous NaCl (20 mL), dried over MgSO$_4$, and concentrated. The product was purified by silica gel flash column chromatography (0–5% Et$_3$N/ethyl acetate, then 10% MeOH/CH$_2$Cl$_2$), dissolved in ether, and treated with the dropwise addition of a saturated HCl/ether solution until a solid formed. Filtration of the precipitate and recrystallization from ethyl acetate afforded an off-white solid (0.053 g, 13%): mp 118–121° C.; IR (KBr) 3160, 2463, 1697, 1484, 1453, 1186, 1090 cm$^{-1}$; $^1$HNMR (400 MHz, DMSO-d$_6$) δ 2.59 (s, 3H, ArCH$_3$), 3.21–3.40 (m, 2H, aliphatic CH$_2$), 3.40–3.55 (m, 2H, CH$_2$N), 3.59–3.80 (m, 4H, 2 CH$_2$N), 3.82–3.98 (m, 1H, CHPh), 4.20–4.31 (m, 2H, CH$_2$OAr), 5.28 (s, 2H, CO$_2$CH$_2$Ph), 6.81 (d, J=8.30 Hz, 1H, ArH), 7.25–7.38 (m, 9H, ArH), 7.44–7.45 (m, 3H, ArH), 10.48–10.66 (m, 1H, NH+), 11.81 (s, 1H, NH); MS(APCI$^+$): m/z 455.2 (M+1). Anal. Calcd for $C_{29}H_{30}N_2O_3/1.00$ H$_1$Cl1/0.50H$_2$O: C, 69.66; H, 6.45; N, 5.60; Cl$^-$, 7.09; H$_2$O, 1.80. Found: C, 69.33; H, 6.31; N, 5.51; Cl$^-$, 6.97.

Example 6

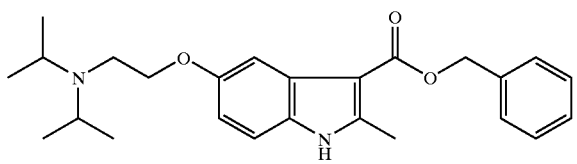

5-(2-Diisopropylamino-ethoxy)-2-methyl-1H-indole-3-carboxylic acid benzyl ester

To a solution of 5-(2-chloro-ethoxy)-2-methyl-1H-indole-3-carboxylic acid benzyl ester (0.873 mmol, 0.300 g, Example 1, Step A) in 10 mL of 2-butanone was added sodium iodide (8.73 mmol, 1.31 g). The solution was heated at reflux for 48 hours, cooled to room temperature, and concentrated to afford the crude product, 5-(2-iodo-ethoxy)-2-methyl-1H-indole-3-carboxylic acid benzyl ester: MS(APCI$^+$): m/z 436.0 (M+1).

To a mixture of the crude product in 8.73 mL of acetonitrile was added potassium carbonate (0.873 mmol, 0.121 g) and diisopropylamine (8.73 mmol, 1.22 mL, Aldrich). The mixture was heated at reflux for 70 hours, cooled to room temperature, and concentrated. The residue was partitioned between ethyl acetate (30 mL) and water (30 mL), the layers were separated, and the aqueous phase was extracted with ethyl acetate (3×20 mL). These extracts were washed with saturated aqueous NaCl (20 mL), dried over MgSO$_4$, and concentrated. The product was purified by silica gel flash column chromatography (0–10% MeOH/ethyl acetate) to give an off-white solid (0.100 g, 28%): mp 121–123° C.; IR (KBr) 3322, 3285, 2966, 1677, 1658, 1175 cm$^{-1}$; $^1$HNMR (400 MHz, CDCl$_3$) δ 0.98 (s, 12H, N[CH(CH$_3$)$_2$]$_2$), 2.65 (s, 3H, ArCH$_3$), 2.71–2.81 (m, 2H, CH$_2$N), 2.92–3.08 (m, 2H, N[CH(CH$_3$)$_2$]$_2$), 3.78–3.92 (m, 2H, CH$_2$OAr), 5.33 (s, 2H, CO$_2$CH$_2$Ph), 6.74 (d, J=8.55 Hz, 1H, ArH), 7.10 (d, J=8.55 Hz, 1H, ArH), 7.23–7.27 (m, 1H, Ar), 7.31–7.34 (m, 2H, ArH), 7.43 (d, J=8.30 Hz, 2H, ArH), 7.53 (s, 1H, ArH), 8.16 (s, 1H, NH); MS(APCI$^+$): m/z 409.2 (M+1). Anal. Calcd for $C_{25}H_{32}N_2O_3$: C, 73.50; H, 7.90; N, 6.86. Found: C, 73.18; H, 7.96; N, 6.71.

Example 7

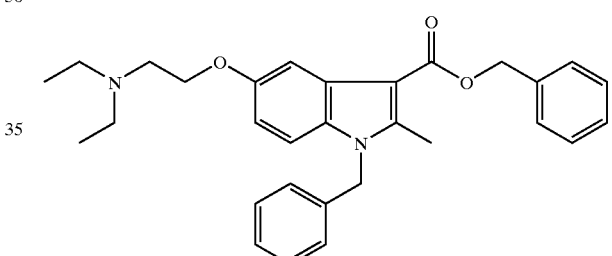

1-Benzyl-5-(2-diethylamino-ethoxy)-2-methyl-1H-indole-3-carboxylic acid benzyl ester Step A

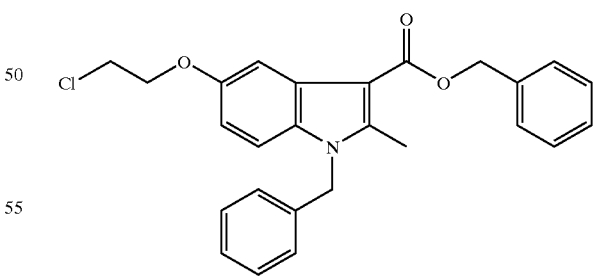

1-benzyl-5-(2-chloro-ethoxy)-2-methyl-1H-indole-3-carboxylic acid benzyl ester

To a suspension of NaH (0.959 mmol, 0.038 g, 60% in mineral oil, rinsed twice with hexanes) in 5 mL of DMF at 0° C. under N$_2$ was added a solution of 5-(2-chloro-ethoxy)-2-methyl-1H-indole-3-carboxylic acid benzyl ester (0.873 mmol, 0.300 g, Example 1, Step A) in 3.73 mL of DMF. The ice bath was removed and the solution was stirred for 2 hours at room temperature. Benzyl bromide (0.959 mmol, 0.114 mL, Aldrich) was added dropwise via syringe and the solution was stirred for 19 hours. Water (10 mL) was added and the mixture was stirred for 30 minutes. The resulting precipitate was filtered off, the filtrate was extracted with ethyl acetate (3×10 mL), and the extracts were washed with brine (1×10 mL), dried over $MgSO_4$, and concentrated. The residue was combined with the solid and purified by silica gel flash column chromatography (10–20% ethyl acetate/hexanes) to give an off-white solid (0.236 g, 62%): $^1$HNMR (400 MHz, DMSO-$d_6$) δ 2.64 (s, 3H, ArCH$_3$),3.86–3.89 (m, 2H, CH$_2$Cl), 4.09–4.12 (m, 2H, CH$_2$OAr), 5.30 (s, 2H, CO$_2$CH$_2$Ph), 5.46 (s, 2H, NCH$_2$Ph), 6.78 (dm, J=8.79 Hz, 1H, ArH), 6.96 (d, J=7.33 Hz, 2H, ArH), 7.18–7.30 (m, 3H, ArH), 7.32–7.40 (m, 4H, ArH), 7.44–7.49 (m, 3H, ArH); MS(APCI$^+$): m/z 434.1 (M+1).

Step B

1-Benzyl-5-(2-diethylamino-ethoxy)-2-methyl-1H-indole-3-carboxylic acid benzyl ester To a mixture of 1-benzyl-5-(2-chloro-ethoxy)-2-methyl-1H-indole-3-carboxylic acid benzyl ester (0.519 mmol, 0.225 g, Example 7, Step A) in 5.18 mL of DMF was added potassium carbonate (0.519 mmol, 0.072 g), potassium iodide (0.0519 mmol, 0.009 g), and diethylamine (2.07 mmol, 0.214 mL, Aldrich). The mixture was heated at 100° C. for 20 hours, an additional 2.07 mmol of diethylamine was added and heating was continued for 22 hours. The solution was cooled to room temperature, diluted with water (10 mL), and extracted with ethyl acetate (4×15 mL). The combined extracts were washed with water (10 mL), saturated aqueous NaCl (10 mL), dried over $MgSO_4$, and concentrated to an amber oil (0.248 g). The product was purified by silica gel flash column chromatography (5–10% MeOH/CH$_2$Cl$_2$) to give a tan waxy solid (0.130 g, 53%): mp 74–76° C.; IR (KBr) 2970, 2935, 1676, 1182, 1112 cm$^{-1}$; $^1$HNMR (400 MHz, DMSO-$d_6$) δ 0.92 (t, J=7.08 Hz, 6H, N(CH$_2$CH$_3$)$_2$), 2.46–2.55 (m, 4H, 2 NCH$_2$), 2.64 (s, 3H, ArCH$_3$), 2.69–2.71 (m, 2H, NCH$_2$), 3.83–3.86 (m, 2H, CH$_2$OAr), 5.29 (s, 2H, CO$_2$CH$_2$Ph), 5.44 (s, 2H, NCH$_2$Ph), 6.72 (dd, J=8.79, 2.20 Hz, 1H, ArH), 6.96 (d, J=7.33 Hz, 2H, ArH), 7.17–7.27 (m,3H, ArH), 7.29–7.39 (m, 4H, ArH), 7.42 (d, J=2.20 Hz, 1H, Arh), 7.48 (d, J=7.33 Hz, 2H, ArH); MS(APCI$^+$): m/z 471.2 (M+1). Anal. Calcd for $C_{30}H_{34}N_2O_3$: C, 76.57; H, 7.28; N, 5.95. Found: C, 76.23; H, 7.43; N, 5.86.

Example 8

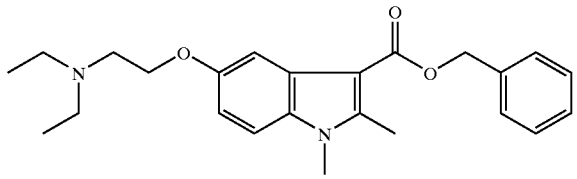

1-Methyl-5-(2-diethylamino-ethoxy)-2-methyl-1H-indole-3-carboxylic acid benzyl ester Step A

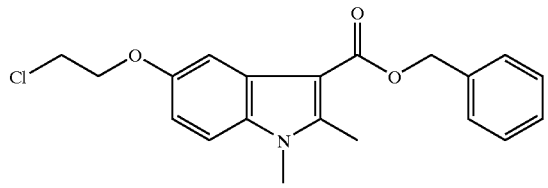

1-Methyl-5-(2-chloro-ethoxy)-2-methyl-1H-indole-3-carboxylic acid benzyl ester

To a suspension of NaH (0.959 mmol, 0.038 g, 60% in mineral oil, rinsed twice with hexanes) in 5 mL of DMF at 0° C. under $N_2$ was added a solution of 5-(2-chloro-ethoxy)-2-methyl-1H-indole-3-carboxylic acid benzyl ester (0.873 mmol, 0.300 g, Example 1, Step A) in 3.73 mL of DMF. The ice bath was removed and the solution was stirred for 2 hours at room temperature. Methyl iodide (0.959 mmol, 0.060 mL, Aldrich) was added dropwise via syringe and the solution was stirred for 20 hours. Water (10 mL) was added and the mixture was stirred for 30 minutes. The resulting precipitate was filtered off, the filtrate was extracted with ether (3×10 mL), and the extracts were washed with water (2×10 mL), brine (1×10 mL), dried over $MgSO_4$, and concentrated. The residue was combined with the solid and purified by silica gel flash column chromatography (30% ethyl acetate/hexanes) to give a white solid (0.216 g, 69%): $^1$HNMR (400 MHz, DMSO-$d_6$) δ 2.67 (s, 3H, ArCH$_3$), 3.66 (s, 3H, NCH$_3$), 3.87–3.89 (m, 2H, CH$_2$Cl), 4.09–4.12 (m, 2H, CH$_2$OAr), 5.29 (s, 2H, CO$_2$CH$_2$Ph), 6.80–6.83 (m, 1H, ArH), 7.21–7.50 (m, 7H, ArH); MS(APCI$^+$): m/z 358.0 (M+1).

Step B

1-Methyl-5-(2-diethylamino-ethoxy)-2-methyl-1H-indole-3-carboxylic acid benzyl ester To a mixture of 1-methyl-5-(2-chloro-ethoxy)-2-methyl-1H-indole-3-carboxylic acid benzyl ester (0.576 mmol, 0.206 g, Example 8, Step A) in 5.76 mL of DMF was added potassium carbonate (0.576 mmol, 0.080 g), potassium iodide (0.0576 mmol, 0.010 g), and diethylamine (2.30 mmol, 0.238 mL, Aldrich). The mixture was heated at 100° C. for 20 hours, an additional 2.30 mmol of diethylamine was added and heating was continued for 21 hours. The solution was cooled to room temperature, diluted with water (10 mL), and extracted with ethyl acetate (4×15 mL). The combined extracts were washed with water (10 mL), saturated aqueous NaCl (10 mL), dried over $MgSO_4$, and concentrated to a brown oil (0.234 g). The product was purified by silica gel flash column chromatography (5–10% MeOH/CH$_2$Cl$_2$) to give a tan solid (0.114 g, 50/o): mp 73–74° C.; IR (KBr) 2968, 2918, 1692, 1186, 1101 cm$^{-1}$; $^1$HNMR (400 MHz, DMSO-$d_6$) δ 0.92 (t, J=7.08 Hz, 6H, N(CH$_2$CH$_3$)$_2$), 2.46–2.51 (m, 4H, 2 NCH$_2$), 2.66 (s, 3H, ArCH$_3$), 2.68–2.73 (m, 2H, NCH$_2$), 3.65 (s, 3H, NCH$_3$), 3.85 (t, J=6.11 Hz, 2H, CH$_2$OAr), 5.28 (s, 2H, CO$_2$CH$_2$Ph), 6.75 (dd, J=8.79, 2.44 Hz, 1H, ArH), 7.28–7.32 (m, 1H, ArH), 7.35–7.39 (m, 4H, ArH), 7.46 (d, J=7.57 Hz, 2H, ArH); MS(APCI$^+$): m/z 395.1 (M+1). HPLC (ALLTECH/ ALLTIMA C-18,50:50–2:98H$_2$O/CH$_3$CN+0.05% TFA): retention time=3.617 min, 96.84% purity.

Example 9

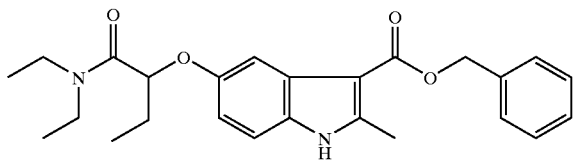

5-(1-Diethylcarbamoyl-propoxy)-2-methyl-1H-indole-3-carboxylic acid benzyl ester

Step A

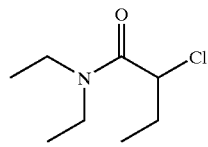

2-Chloro-N,N-diethyl-butyramide

Following the procedure of Kem K. M.; Nguyen N. V.; Cross D. J. *J. Org. Chem.* 1981;46:5188 for the preparation of chloroacetamides, a solution of 2-chlorobutyryl chloride (61.91 mmol, 8.73 g, Lancaster) in 28 mL of $CH_2Cl_2$ was added to diethylamine (56.28 mol, 4.12 g, Aldrich) in a mixture of $CH_2Cl_2$ (56 mL) and NaOH (56 mL, 20% aqueous) at −25° C. to furnish 2-chloro-N,N-diethyl-butyramide (7.23 g, 72%). $^1$HNMR (400 MHz, $CDCl_3$) δ 0.98 (t, J=7.33 Hz, 3H, $CH_2CH_3$), 1.12 (t, J=7.08 Hz, 3H, $CH_2CH_3$), 1.19–1.23 (m, 3H, $CH_2CH_3$), 1.89–2.00 (m, 1H, $CH_2CH_3$), 2.03–2.14 (m, 1H, $CH_2CH_3$), 3.22–3.38 (m, 2H, $NCH_2CH_3$), 3.41–3.52 (m, 2H, $NCH_2CH_3$), 4.26 (t, J=7.08 Hz, 1H, CHCl); MS(APCI$^+$): m/z 177.9 (M+1), 179.9 (M+3).

Step B

To a solution of 5-hydroxy-2-methyl-1H-indole-3-carboxylic acid benzyl ester (9.91 mmol, 2.78 g, prepared according to Bell M. R. U.S. Pat. No. 3,510,491, 1970) in 48 mL of 2-butanone was added cesium carbonate (9.91 mmol, 3.23 g) and a solution 2-chloro-N,N-diethyl-butyramide (9.91 mmol, 1.76 g, Example 9, Step A) in 2 mL of 2-butanone. The mixture was heated at reflux for 26 hours, cooled to room temperature, water (10 mL) was added, and the organic solvent was removed under reduced pressure. The residue was diluted with water (20 mL) and extracted with $CH_2Cl_2$ (3×10 mL). The combined extracts were washed with brine (10 mL), dried over $MgSO_4$ and concentrated to a thick, brown oil (4.51 g). The product was purified by silica gel flash column chromatography (30–50% ethyl acetate/hexanes, then 20–30% acetone/hexanes) to afford an off-white solid (1.76 g, 42%): mp 129–131° C.; IR(KBr) 3164, 2975, 2937, 1687, 1627, 1449, 1434, 1215, 1156, 1067 cm$^{-1}$; $^1$HNMR (400 MHz, $CDCl_3$) δ 1.03–1.10 (m, 9H, 3 $CH_2CH_3$), 1.86–1.99 (m, 2H, $CHCH_2CH_3$), 2.66 (s, 3H, $ArCH_3$), 3.30–3.35 (m, 2H, $NCH_2CH_3$), 3.38–3.45 (m, 2H, $NCH_2CH_3$), 4.69–4.72 (m, 1H, C(O)CHOAr), 5.33–5.40 (m, 2H, $CO_2CH_2Ph$), 6.62 (dd, J=8.79, 2.44 Hz, 1H, ArH), 6.85 (d, J=8.79 Hz, 1H, ArH), 7.27–7.30 (m, 1H, ArH), 7.33–7.37 (m, 2H, ArH), 7.46 (d, J=8.06 Hz, 2H, ArH), 7.52 (d, J=8.06 Hz, 1H, ArH), 9.18 (s, 1H, NH); MS(APCI$^+$): m/z 423.2 (M+1). Anal. Calcd for $C_{25}H_{30}N_2O_4$: C, 71.07; H, 7.16; N, 6.63;. Found: C, 71.13; H, 7.27; N, 6.51.

Example 10

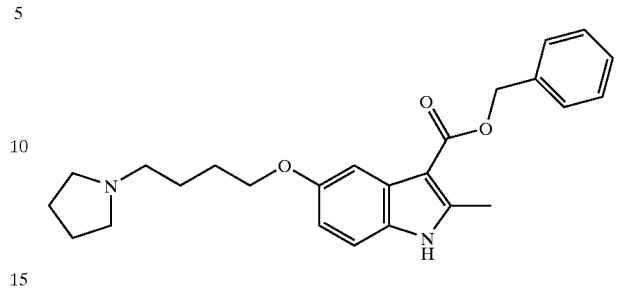

2-Methyl-5-(4-pyrrolidin-11-yl-butoxy)-1H-indole-3-carboxylic acid benzyl ester

Step A

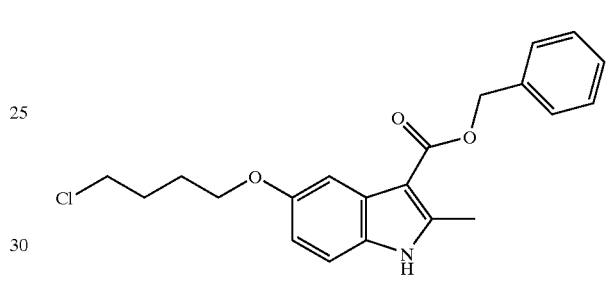

5-(4-Chloro-butoxy)-2-methyl-1H-indole-3-carboxylic acid benzyl ester

A mixture of 5-hydroxy-2-methyl-1H-indole-3-carboxylic acid benzyl ester (2.00 g, 7.11 mmol), 1-bromo-4-chlorobutane (1.64 mL, 14.22 mmol), and $Cs_2CO_3$ (4.63 g, 14.22 mmol) in 142 mL of 2-butanone was heated at reflux for 24 hours. The reaction mixture was cooled to room temperature, diluted with ethyl acetate (500 mL), washed with water (2×100 mL) and filtered through celite. The filtrate was dried over $MgSO_4$ and concentrated to give a brown oil. The product was purified by flash column chromatography on silica gel (20% ethyl acetate:hexanes) and triturated with diethyl ether to give 0.600 g (22.7%) of a white solid: mp 152–155° C.; IR (KBr) 2952, 2836, 1685, 1593, 1452, 1171, 1073 cm$^{-1}$; $^1$HNMR (400 MHz, DMSO-$d_6$) δ 1.78–1.83 (m, 4H, $OCH_2(CH_2)_2CH_2$), 2.45 (s, 3H, $CCH_3$), 3.67 (t, J=6.10 Hz, 2H, $OCH_2(CH_2)_2CH_2$), 3.85 (t, J=5.86 Hz, 2H, $OCH_2(CH_2)_2CH_2$), 5.27 (s, 2H, $OCH_2Ar$), 6.71 (dd, J=8.79, 2.44 Hz, 1H, ArH), 7.22 (d, J=8.55 Hz, 1H, ArH), 7.30–7.40 (m, 4H, ArH), 7.47 (d, J=7.81 Hz, 2H, ArH), 11.71 (s, 1H, NH); MS(APCI$^+$): m/z 372.1 (MH$^+$). Anal. Calcd for $C_{21}H_{22}N_1O_3Cl_1$: C, 67.83; H, 5.96; N, 3.77. Found: C, 67.44; H, 6.01; N, 3.85.

Step B

2-Methyl-5-(4-pyrrolidin-1-yl-butoxy)-1H-indole-3-carboxylic acid benzyl ester

A mixture of 5-(4-chloro-butoxy)-2-methyl-1H-indole-3-carboxylic acid benzyl ester (Example 10, Step A, 0.445 g, 1.20 mmol), pyrrolidine (0.120 mL, 4.79 mmol), $K_2CO_2$ (0.165 g, 1.20 mmol), and KI (0.020 g, 0.120 mmol) in 24 mL of acetonitrile was heated at reflux for 24 hours. The reaction mixture was cooled to room temperature, diluted with CH$_2$Cl$_2$ (50 mL) and washed with water (2×20 mL). The organic layer was dried over MgSO$_4$ and concentrated to give a yellow oil. Trituration of the residue with diethyl ether afforded 0.401 g (82.5%) of a light yellow solid: mp 152–155° C.; IR (KBr) 2952, 2836, 1685, 1452, 1171, 1073 cm$^{-1}$; $^1$HNMR (400 MHz, DMSO-d$_6$) δ 1.53 (m, 2H, OCH$_2$CH$_2$CH$_2$), 1.64–1.72 (m, 6H, OCH$_2$CH$_2$CH$_2$ & N(CH$_2$CH$_2$)$_2$), 2.45 (s, 3H, CCH$_3$), 2.47 (s, 6H, N(CH$_2$)$_3$), 3.82 (t, J=6.51 Hz, 2H, OCH$_2$CH$_2$CH$_2$), 5.28 (s, 2H, OCH$_2$Ar), 6.70 (dd, J=8.68, 1.93 Hz, 1H, ArH), 7.20 (d, J=8.92 Hz, 1H, ArH), 7.29–7.40 (m, 5H, ArH), 7.47 (d, J=7.96 Hz, 1H, ArH), 11.69 (s, 1H, NH); MS(APCI$^+$): m/z 407.2 (MH$^+$). Anal. Calcd for C$_{25}$H$_{30}$N$_2$O$_3$: C, 72.76; H, 7.34; N, 6.76. Found: C, 72.42; H, 7.48; N, 6.83.

Example 11

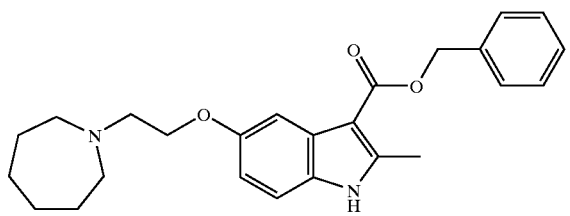

5-(2-Azepan-1-yl-ethoxy)-2-methyl-1H-indole-3-carboxylic acid benzyl ester

A mixture of 5-(2-chloro-ethoxy)-2-methyl-1H-indole-3-carboxylic acid benzyl ester (Example 1, Step A, 0.500 g, 1.45 mmol), hexamethyleneimine (0.656 mL, 5.80 mmol), K$_2$CO$_2$ (0.201 g, 1.45 mmol), and KI (0.024 g, 0.145 mmol) in 29 mL of acetonitrile was heated at reflux for 24 hours. The reaction mixture was cooled to room temperature, diluted with CH$_2$Cl$_2$ (50 mL) and washed with water (2×20 mL). The organic layer was dried over MgSO$_4$ and concentrated to give a brown oil. Trituration of the oil with diethyl ether afforded 0.295 g (49.9%) of a light yellow solid: mp 141–142° C.; IR (KBr) 3277, 2924, 1672, 1592, 1454, 1171, 1076 cm$^{-1}$; $^1$HNMR (400 MHz, DMSO-d$_6$) δ 1.50 (s, 8H, N(CH$_2$CH$_2$CH$_2$)$_2$), 2.45 (s, 3H, CCH$_3$), 2.62 (t, J=4.64 Hz, 4H, N(CH$_2$CH$_2$CH$_2$)$_2$), 2.78 (t, J=6.35 Hz, 2H, OCH$_2$CH$_2$), 3.87 (t, J=6.10 Hz, 2H, OCH$_2$CH$_2$), 5.27 (s, 2H, OCH$_2$Ar), 6.69 (dd, J=8.79, 2.44 Hz, 1H, ArH), 6.71 (d, J=8.79 Hz, 1H, ArH), 7.28–7.39 (m, 4H, ArH), 7.46 (d, J=7.32 Hz, 2H, ArH), 11.70 (s, 1H, NH); MS(APCI$^+$): m/z 407.2 (MH$^+$). Anal. Calcd for C$_{25}$H$_{30}$N$_2$O$_3$: C, 73.86; H, 7.44; N, 6.89. Found: C, 73.51; H, 7.42; N, 6.73.

Example 12

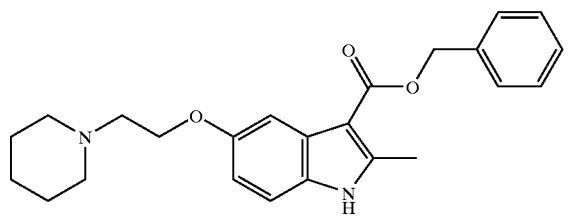

2-Methyl-5-(2-piperidin-1-yl-ethoxy)-1H-indole-3-carboxylic acid benzyl ester

A mixture of 5-(2-chloro-ethoxy)-2-methyl-1H-indole-3-carboxylic acid benzyl ester (0.500 g, 1.45 mmol, Example 1, Step A), piperidine (0.575 mL, 5.82 mmol), K$_2$CO$_2$ (0.201 g, 1.45 mmol), and KI (0.024 g, 0.145 mmol) in 29 mL of acetonitrile was heated at reflux for 24 hours. The reaction mixture was cooled to room temperature, diluted with CH$_2$Cl$_2$ (50 mL) and washed with water (2×20 mL). The organic layer was dried over MgSO$_4$ and concentrated to give 0.393 g (68.8%) of a white solid: mp 140–141° C.; IR (KBr) 3274, 2933, 1673, 1592, 1454, 1172, 1078 cm$^{-1}$; $^1$HNMR (400 MHz, DMSO-d$_6$) δ 1.33–1.43 (m, 2H, N(CH$_2$CH$_2$)$_2$CH$_2$), 1.44–1.48 (m, 4H, N(CH$_2$CH$_2$)$_2$CH$_2$), 2.42–2.43 (m, 4H, N(CH$_2$CH$_2$)$_2$CH$_2$), 2.45 (s, 3H, CCH$_3$), 2.56 (t, J=6.10 Hz, 2H, OCH$_2$CH$_2$), 3.89 (t, J=6.10 Hz, 2H, OCH$_2$CH$_2$), 5.26 (s, 2H, OCH$_2$Ar), 6.68 (dd, J=8.06, 6.35 Hz, 1H, ArH), 7.19 (d, J=8.79 Hz, 1H, ArH), 7.29–7.39 (m, 4H, ArH), 7.46 (d, J=7.32 Hz, 2H, ArH), 11.70 (s, 1H, NH); MS(APCI$^+$): m/z 393.1 (MH$^+$). Anal. Calcd for C$_{24}$H$_{28}$N$_2$O$_3$: C, 73.44; H, 7.19; N, 7.14. Found: C, 73.1 1; H, 7.16; N, 7.10.

Example 13

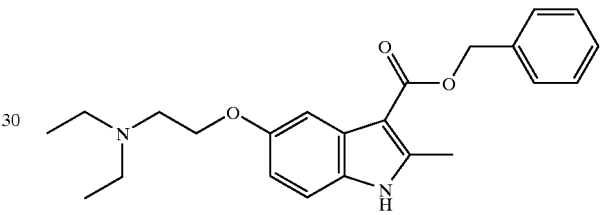

5-(2-Diethylamino-ethoxy)-2-methyl-1H-indole-3-carboxylic acid benzyl ester

A mixture of 5-(2-chloro-ethoxy)-2-methyl-1H-indole-3-carboxylic acid benzyl ester (Example 1, Step A, 0.500 g, 1.45 mmol), diethylamine (0.610 mL, 5.82 mmol), K$_2$CO$_2$ (0.201 g, 1.45 mmol), and KI (0.024 g, 0.145 mmol) in 29 mL of acetonitrile was heated at reflux for 96 hours. The reaction mixture was cooled to room temperature, diluted with CH$_2$Cl$_2$ (50 mL) and washed with water (2×20 mL). The organic layer was dried over MgSO$_4$ and concentrated to give a yellow oil. The product was purified by flash column chromatography on silica gel (2:3:95 Et$_3$N:acetone:CH$_2$Cl$_2$) to give 0.100 g (18.2%) of a light yellow solid: mp 125–126° C.; IR (KBr) 3275, 2969, 1673, 1654, 1454, 1172, 1079 cm$^{-1}$; $^1$HNMR (400 MHz, DMSO-d$_6$) δ 0.928 (t, J=6.11 Hz, 6H, NCH$_2$CH$_3$), 2.42–2.45 (m, 4H, NCH$_2$CH$_3$), 2.46 (s, 3H, CCH$_3$), 2.58 (t, J=6.12 Hz, 2H, OCH$_2$CH$_2$),3.82 (t, J=6.15 Hz, 2H, OCH$_2$CH$_2$), 5.26 (s, 2H, OCH$_2$Ar), 6.68 (dd, J=8.52, 2.10 Hz, 1H, ArH), 7.19 (d, J=8.55 Hz, 1H, ArH), 7.35–7.39 (m, 4H, ArH), 7.46 (d, J=7.81 Hz, 2H, ArH), 11.70 (s, 1H, NH); MS(APCI$^+$): m/z 381.1 (MH$^+$). HPLC (ALLTECH/ALLTIMA C-18 1:1–2:98H$_2$O/CH$_3$CN+0.05% TFA): retention time=2.95 min, 100% purity.

Example 14

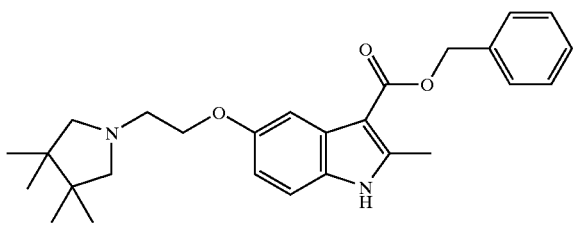

2-Methyl-5-[2-(3,3,4,4-tetramethyl-pyrrolidin-1-yl)-ethoxy]-1H-indole-3-carboxylic acid benzyl ester A mixture of 5-(2-chloro-ethoxy)-2-methyl-1H-indole-3-carboxylic acid benzyl ester (Example 1, Step A, 0.300 g, 0.873 mmol), 3,3,4,4-tetramethyl-pyrrolidine; hydrochloride (0.571 g, 3.49 mmol), $K_2CO_3$ (0.724 g, 5.234 mmol), and KI (0.014 g, 0.087 mmol) in 17.5 mL of acetonitrile was heated at reflux for 24 hours. The reaction mixture was cooled to room temperature, diluted with $CH_2Cl_2$ (50 mL) and washed with water (2×20 mL). The organic layer was dried over $MgSO_4$ and concentrated to give 0.379 g (42.0%) of a white solid: mp 181–182° C.;IR(KBr)3283, 2961, 1671, 1652, 1457, 1171, 1074 $cm^{-1}$; $^1$HNMR (400 MHz, DMSO-$d_6$) δ 0.85 (s, 12H, $NCH_2C(CH_3)_2$), 2.46 (s, 3H, $CCH_3$), 2.60 (s, 4H, $NCH_2C(CH_3)_2$), 2.81–2.84 (m, 2H, $OCH_2CH_2$), 3.83 (t, J=6.12 Hz, 2H, $OCH_2CH_2$), 5.27 (s, 2H, $OCH_2Ar$), 6.67 (dd, J=8.31, 3.20 Hz, 1H, ArH), 7.20 (d, J=8.40 Hz, 1H, ArH), 7.23–7.40 (m, 4H, ArH), 7.46 (d, J=7.89 Hz, 2H, ArH), 11.70 (s, 1H, NH); MS($APCI^+$): m/z 435.3 ($MH^+$). Anal. Calcd for $C_{27}H_{34}N_2O_3$: C, 74.62; H, 7.89; N, 6.45. Found: C, 74.31; H, 7.98; N, 6.19.

Example 15

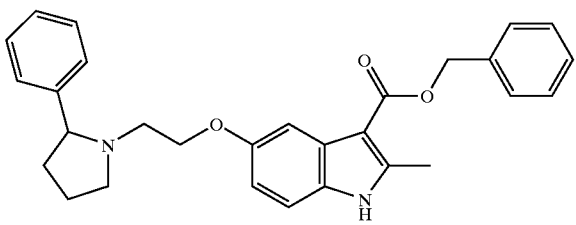

2-Methyl-5-[2-(2-phenyl-pyrrolidin-1-yl)-ethoxy]-1H-indole-3-carboxylic acid benzyl ester A mixture of 5-(2-chloro-ethoxy)-2-methyl-1H-indole-3-carboxylic acid benzyl ester (Example 1, Step A, 0.300 g, 0.873 mmol), 2-phenyl-pyrrolidine; hydrobromide (0.796 mL, 3.49 mmol), $K_2CO_3$ (0.724 g, 5.24 mmol), and KI (0.015 g, 0.087 mmol) in 17.5 mL of acetonitrile was heated at reflux for 24 hours. The reaction mixture was cooled to room temperature, diluted with $CH_2Cl_2$ (50 mL) and washed with water (2×20 mL). The organic layer was dried over $MgSO_4$ and concentrated to give a brown oil. The product was purified by flash column chromatography on silica gel (3% methanol:$CH_2Cl_2$) to give 0.110 g (27.5%) of a white solid: mp 141–142° C.; IR (KBr) 3272, 2949, 2815, 1674, 1592, 1454, 1173, 1079 $cm^{-1}$; $^1$HNMR (400 MHz, DMSO-$d_6$) δ 1.46–1.51 (m, 1H, $NCHCH_2CH_2CH_2$), 1.72–1.78 (m, 2H, $NCHCH_2CH_2CH_2$ & $NCHCH_2CH_2CH_2$), 2.05–2.09 (m, 1H, $NCHCH_2CH_2CH_2$), 2.25–2.29 (m, 1H, $NCHCH_2CH_2CH_2$), 2.31–2.39 (m, 1H, $NCHCH_2CH_2CH_2$), 2.46 (s, 3H, $CCH_3$), 2.70–2.76 (m, 2H, $OCH_2CH_2$), 3.25–3.30 (m, 1H, $NCHCH_2CH_2CH_2$),3.80–3.83 (m, 2H, $OCH_2CH_2$),5.26 (s, 2H, $OCH_2Ar$), 6.63 (dd, J=8.79, 2.44 Hz, 1H, ArH), 7.16–7.20 (m, 2H, ArH), 7.24–7.37 (m, 8H, ArH), 7.46 (d, J=7.08 Hz, 2H, ArH), 11.70 (s, 1H, NH); MS($APCI^+$): m/z 455.2 ($MH^+$). Anal. Calcd for $C_{29}H_{30}N_2O_3$: C, 76.63; H, 6.65; N, 6.16. Found: C, 76.43; H, 6.74; N, 6.07.

Example 16

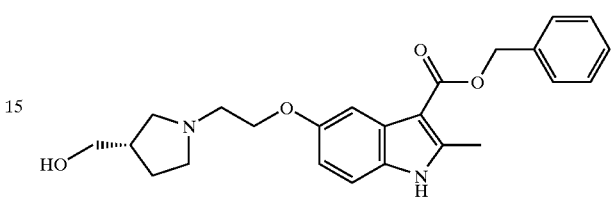

5-[2-((S)-3-Hydroxymethyl-pyrrolidin-1-yl)-ethoxy]-2-methyl-1H-indole-3-carboxylic acid benzyl ester A mixture of 5-(2-chloro-ethoxy)-2-methyl-1H-indole-3-carboxylic acid benzyl ester (Example 1, Step A, 0.300 g, 0.873 mmol), (S)-1-pyrrolidin-2-yl-methanol (0.353 g, 3.49 mmol), $K_2CO_3$ (0.241 g, 1.75 mmol), and KI (0.015 g, 0.087 mmol) in 17.5 mL of acetonitrile was heated at reflux for 24 hour. The reaction mixture was cooled to room temperature, diluted with $CH_2Cl_2$ (50 mL) and washed with water (2×20 mL). The organic layer was dried over $MgSO_4$ and concentrated to give a yellow oil. Trituration of the oil with diethyl ether afforded 0.091 g (25.3%) of a white solid: mp 126–127° C.; IR (KBr) 3312, 2923, 2822, 1663, 1586, 1451, 1177, 1063 $cm^{-1}$; $^1$HNMR (400 MHz, DMSO-$d_6$) δ 1.29–1.34 (m, 1H, $NCH_2CHCH_2CH_2$), 1.72–1.79 (m, 1H, $NCH_2CHCH_2CH_2$), 2.15–2.25 (m, 1H, $NCH_2CHCH_2CH_2$), 2.27–2.29 (m, 1H, $NCH_2CHCH_2CH_2$), 2.40–2.47 (m 3H, $CHCH_2OH$ & $NCH_2CHCH_2CH_2$), 2.46 (s, 3H, $CCH_3$), 2.68 (t, J=6.11 Hz, 2H, $OCH_2CH_2$),3.21–3.26 (m, 2H, $CHCH_2OH$), 3.88 (t, J=6.11 Hz, 2H, $OCH_2CH_2$), 4.52 (t, J=2.10 Hz, 1H, $CH_2OH$), 5.27 (s, 2H, $OCH_2Ar$), 6.68–6.71 (dd, J=8.55, 2.20 Hz, 1H, ArH), 7.19 (d, J=8.79 Hz, 1H, ArH), 7.29–7.39 (m, 4H, ArH), 7.46 (d, J=6.84 Hz, 2H, ArH), 11.70 (s, 1H, NH); MS($APCI^+$): m/z 409.2 ($MH^+$). Anal. Calcd for $C_{24}H_{28}N_2O_4$: C, 70.35; H, 6.92; N, 6.84. Found: C, 70.07; H, 6.84; N, 6.70.

Example 17

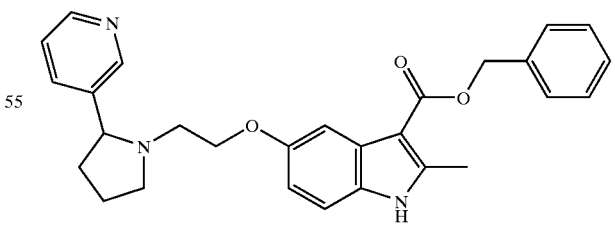

2-Methyl-5-[2-(2-pyridin-3-yl-pyrrolidin-1-yl)-ethoxy]-1H-indole-3-carboxylic acid benzyl ester A mixture of 5-(2-chloro-ethoxy)-2-methyl-1H-indole-3-carboxylic acid benzyl ester (Example 1, Step A, 0.400 g, 1.16 mmol), 3-pyrrolidin-2-yl-pyridine (0.345 mL, 2.33 mmol), K₂CO₂ (0.322 g, 2.33 mmol), and KI (0.019 g, 0.116 mmol) in 23 mL of acetonitrile was heated at reflux for 24 hours. The reaction mixture was cooled to room temperature, diluted with CH₂Cl₂ (50 mL) and washed with water (2×20 mL). The organic layer was dried over MgSO₄ and concentrated to give a brown oil. The product was purified by flash column chromatography on silica gel (3% methanol:CH₂Cl₂) and triturated with diethyl ether/hexanes/CH₂Cl₂ to give 0.120 g (23.0%) of a light yellow solid: mp 126–127° C.; IR (KBr)3036, 2962, 2793, 1693, 1594, 1454, 1168, 1077 cm⁻¹; ¹HNMR (400 MHz, DMSO-d₆) δ 1.40–1.52 (m, 1H, NCHCH₂CH₂CH₂), 1.70–1.85 (m, 2H, NCHCH₂CH₂CH₂ & NCHCH₂CH₂CH₂), 2.10–2.18 (m, 1H, NCHCH₂CH₂CH₂), 2.29–2.31 (m, 1H, NCHCH₂CH₂CH₂),2.34–2.42 (m, 1H, NCHCH₂CH₂CH₂), 2.46 (s, 3H, CCH₃), 2.71 (t, J=6.35 Hz, 2H, OCH₂CH₂), 3.38–3.42 (m, 1H, NCHCH₂CH₂CH₂), 3.82 (t, J=5.62 Hz, 2H, OCH₂CH₂), 5.26 (s, 2H, OCH₂Ar), 6.64 (dd, J=8.79, 2.44 Hz, 1H, ArH), 7.17 (t, J=8.55 Hz, 1H, ArH), 7.28 (t, J=7.08 Hz, 3H, ArH), 7.35 (t, J=7.33 Hz, 2H, ArH), 7.46 (d, J=7.81 Hz, 2H, ArH), 7.73 (d, J=7.81 Hz, 1H, ArH), 8.39–8.40 (m, 1H, ArH), 8.51 (s, 1H, ArH), 11.70 (s, 1H, NH); MS(APCI⁺): m/z 456.2 (MH⁺). Anal. Calcd for C₂₈H₂₉N₃O₃: C, 73.79; H, 6.42; N, 9.22. Found: C, 73.42; H, 6.45; N, 9.11.

Example 18

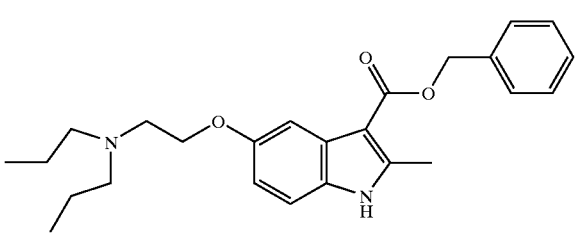

5-(2-Dipropylamino-ethoxy)-2-methyl-1H-indole-3-carboxylic acid benzyl ester

A mixture of 5-(2-chloro-ethoxy)-2-methyl-1H-indole-3-carboxylic acid benzyl ester (Example 1, Step A, 0.479 g, 3.49 mmol), dipropylamine (0.479 mL, 3.49 mmol), K₂CO₂ (0.241 g, 1.75 mmol), and KI (0.015 g, 0.087 mmol) in 17.5 mL of acetonitrile was heated at reflux for 48 hours. The reaction mixture was cooled to room temperature, diluted with CH₂Cl₂ (50 mL) and washed with water (2×20 mL). The organic layer was dried over MgSO₄ and concentrated to give a brown oil. The product was purified by flash column chromatography on silica gel (5% methanol:CH₂Cl₂) to give 0.043 g (12%) of a white solid: mp 123–125° C.; IR (KBr) 3272, 2961, 2871, 1672, 1591, 1454, 1172, 1078 cm⁻¹; ¹HNMR (400 MHz, DMSO-d₆) δ 0.81 (t, J=7.08 Hz, 6H, NCH₂CH₂CH₃), 1.35–1.40 (m, 4H, NCH₂CH₂CH₃), 2.39 (t, J=7.08 Hz, 4H, NCH₂CH₂CH₃), 2.48 (s, 3H, CCH₃), 2.73 (t, J=6.10 Hz, 2H, OCH₂CH₂), 3.87 (t, J=6.10 Hz, 2H, OCH₂CH₂), 5.29 (s, 2H, OCH₂Ar), 6.70 (d, J=8.55 Hz, 1H, ArH), 7.21 (d, J=8.79 Hz, 1H, ArH), 7.32–7.40 (m, 4H, ArH), 7.48 (d, J=7.08 Hz, 2H, Arh), 11.70 (s, 1H, NH); MS(APCI⁺): m/z 409.2 (MH⁺). Anal. Calcd for C₂₅H₃₂N₂O₃: C, 73.50; H, 7.90; N, 6.86. Found: C, 73.26; H, 7.90; N, 6.56.

Example 19

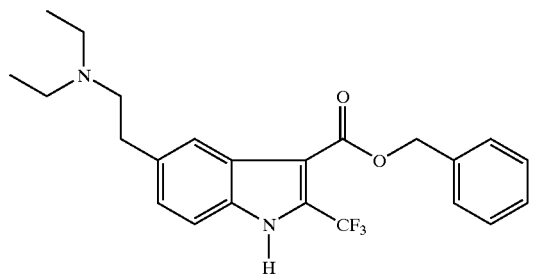

5-(2-Diethylamino-ethyl)-2-trifluoromethyl-1H-indole-3-carboxylic acid benzyl ester Step A

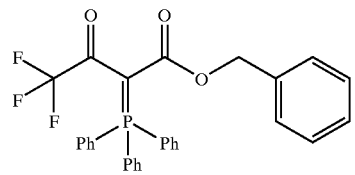

Trifluoro-oxo-(triphenyl-l⁵-phosphanylidene)-butyric acid benzyl ester

Benzyl(triphenylphosphoranylidene) acetate (20.50 g, 50 mmol, 1.0 eq) was placed in a 250-mL round bottom flask, and anhydrous THF (100 mL) was added. The solution was cooled to 0° C. Triethylamine (7.62 mL, 55 mmol, 1.1 eq) was added to the reaction flask slowly, and then trifluoroacetic anhydride was added dropwise, at this time, smoke was formed. The reaction mixture was stirred for 1.5 hours. After THF was removed in vacuo, the residue was dissolved in methanol, and then poured into water (200 mL). Precipitate was recrystallized from the methanol-water solution. The precipitate was filtered to give 21.16 g of the desired phosphorane as white, crystallized solid (84% yield).

Step B

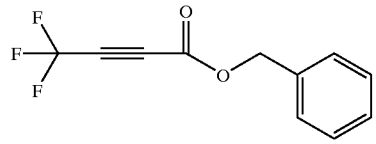

4,4,4-Trifluoro-but-2-ynoic acid benzyl ester

Trifluoro-oxo-triphenyl-l⁵-phosphanylidene)-butyric acid benzyl ester obtained in the previous step (21.16 g, 42 mmol) was placed in a vacuum distillation apparatus equipped with a dry ice-acetone trap, and thermolyzed under reduce pressure (7–9 torr). Once the distillation pot reached 220° C., the solid melted and evolution of alkyne began. The alkyne was collected in the dry ice-acetone trap and total 8.35 g of the desired trifluoro methyl alkyne as a clear liquid was afforded (87% yield).

Step C

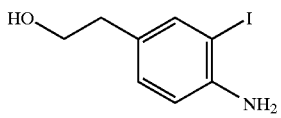

2-(4-Amino-3-iodo-phenyl)-ethanol

4-Aminophenethyl alcohol (9.60 g, 70 mmol, 1.0 eq) was added to a mixture of iodine (17.78 g, 70 mmol, 1.0 eq) and silver sulfate (21.83 g, 70 mmol, 1.0 eq) in anhydrous ethanol (200 mL) at room temperature. The reaction mixture was stirred under nitrogen for 1.5 hours. After stirring was stopped, the solid was removed by filtration. The filtrate was concentrated, and the residue was dissolved in dichloromethane (200 mL), and then washed with aqueous 5% NaOH solution (2×150 mL) and water (150 mL). The organic layer was dried over MgSO$_4$, filtered and concentrated in vacuo to give a crude oil which was purified by flash chromatography (SiO$_2$, hexanes-ethyl acetate) to yield 6.0 g of the desired ortho-iodo aniline as orange gel-like solid (32.4% yield).

Step D

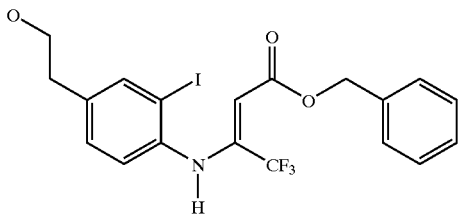

(E)-4,4,4-Trifluoro-3-[4-(2-hydroxy-ethyl)-2-iodo-phenylamino]-but-2-enoic acid benzyl ester 2-(4-Amino-3-iodo-phenyl)-ethanol (6.0 g, 23 mmol, 1.0 eq) was added to the solution of the 4,4,4-trifluoro-but-2-ynoic acid benzyl ester (5.7 g, 25 mmol, 1.1 eq) obtained from previous step in methanol (20 mL) at room temperature. The reaction mixture was stirred for 1 hour. After the solvent was removed, the residue was purified by flash chromatography (SiO$_2$, hexanes-ethyl acetate) to yield 9.5 g of the desired enamine as pale yellow liquid (84.0% yield).

Step E

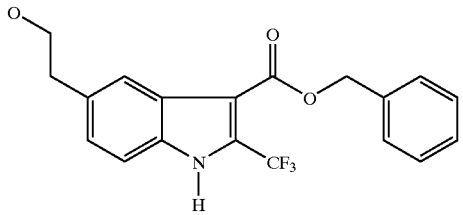

5-(2-hydroxy-ethyl)-2-trifluoromethyl-1H-indole-3-carboxylic acid benzyl ester A mixture of (E)-4,4,4-Trifluoro-3-[4-(2-hydroxy-ethyl)-2-iodo-phenylamino]-but-2-enoic acid benzyl ester (9.5 g, 19.3 mmol, 1.0 eq), Pd(OAc)$_2$ (433 mg, 1.93 mmol, 0.1 eq), triethylamine (3.1 mL, 23.2 mmol, 1.2 eq), triphenyphosphine (1.52 g, 5.79 mmol, 0.3 eq) and DMF (20 mL) was heated under refluxing in a 100-mL round bottom flask under nitrogen. The reaction mixture was stirred overnight. After the stirring was stopped, the mixture was partitioned between dichloromethane (100 mL) and water (100 mL) filtered through celite. The organic layer was washed with water (3×100 mL), dried over MgSO$_4$, and concentrated. The crude residue was purified by flash chromatography (SiO$_2$, hexanes-ethyl acetate) to yield 420 mg of the desired indole as pale yellow gel (6.0% yield).

Step F

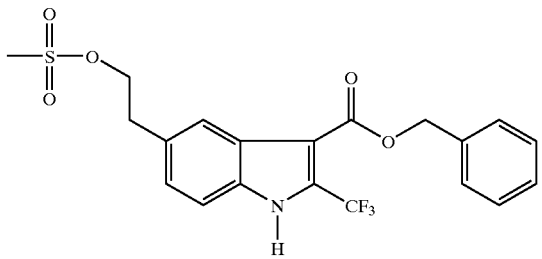

5-(2-Methanesulfonyloxy-ethyl)-2-trifluoromethyl-1H-indole-3-carboxylic acid benzyl ester Methanesulfonyl chloride (0.1 mL, 1.15 mmol, 1 eq) and triethylamine (0.32 mL, 2.30 mmol, 2 eq) were added to 5-(2-hydroxy-ethyl)-2-trifluoromethyl-1H-indole-3-carboxylic acid benzyl ester (420 mg, 1.15 mmol, 1 eq) obtained from previous step in THF (50 mL) solution in 100-mL round bottom flask at room temperature. The reaction mixture was stirred at room temperature for 3 hours (followed by TLC). After the solvent was removed, the residue was dissolved in ethyl acetate (100 mL), and then washed with sat NaHCO$_4$ and brine respectively. The organic layer was dried over MgSO$_4$, and concentrated to give a pale brown solid. The crude was carried over to the next step.

Step G

Diethylamine (0.48 mL, 4.63 mmol, 3 eq) was added into the crude 5-(2-Methanesulfonyloxy-ethyl)-2-trifluoromethyl-1H-indole-3-carboxylic acid benzyl ester in dioxanes (20 mL) solution. The reaction mixture was heated to reflux overnight. After the solvent was removed, the residue was purified by gravity chromatography (SiO$_2$, ethyl acetate-methanol-NH$_4$OH) to yield the desire indole amine as pale yellow gel (20.0% yield). Elemental Analysis: C$_{23}$H$_{25}$F$_3$N$_2$O$_2$.HCl: Calcd: C: 60.73; H: 5.76; N: 6.16. Found: C: 60.40; H: 5.83; N: 6.06. ESI-MS: m/z 419.73 (M+H)$^+$.

Example 20

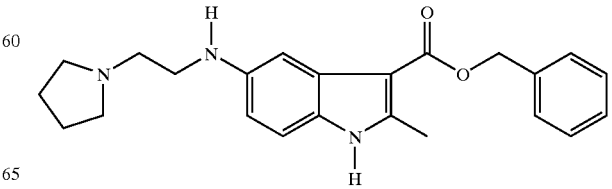

2-Methyl-5-(2-pyrrolidine-1-yl-ethylamino)-1H-indole-3-carboxylic acid benzyl ester

Step A

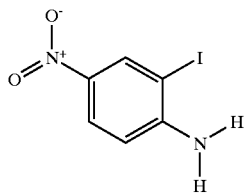

2-Iodo-4-nitro-phenylamine

2-Iodo-4-nitro-phenylamine was made according to the procedure described in *Synthetic Communications,* 1992;22 (22):3215.

Step B

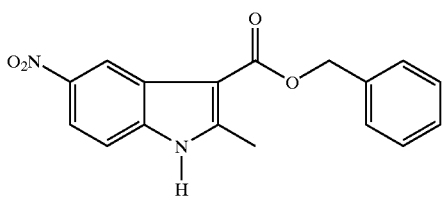

2-Methyl-5-nitro-1H-indole-3-carboxylic acid benzyl ester

NaH (60% in oil) (1.75 g, 43.80 mmol, 2 eq) was washed with dry hexanes under nitrogen in the normal way to remove oil. The NaH and hexanes dispersion was stirred for 2 minutes. NaH was allowed to settle, and the supernatant liquid was removed with syringe. Repeated the washing operation with additional 20 mL hexanes. DMF (10 mL) was added to the reaction flask, covered the gray solid. benzyl acetoacetate (6.56 mL, 32.80 mmol, 1.5 eq) was added dropwise with syringe, at the same time, hydrogen was released. After several minutes, when the evolution of hydrogen was stopped, CuI (6.25 g, 32.80 mmol, 1.5 eq) was added to the yellow solution. The color of the solution changed to orange and then to brown. 2-Iodo-4-nitro-phenylamine (5.19 g, 21.9 mmol, 1.0 eq) was added to the brown solution, and the mixture was heated to 120° C.–130° C. in the heating control oil bath. The color of the reaction mixture further darkened as the temperature increased. The mixture was stirred for 16 hours, cooled to room temperature, poured into 1N HCl solution (100 mL), the aqueous solution was extracted with ethyl acetate (3×200 mL). Some precipitate went into the organic phase. The combined organic solution was dried over $MgSO_4$, filtered and concentrated in vacuo to gave a dark brown oil which was purified by flash chromatography ($SiO_2$, 60:40 hexanes-ethyl acetate) to yield the mixture of the desired indole and 4-nitroaniline (1.22 g) as a dark brown solid. The mixture was carried over to the next step.

Step C

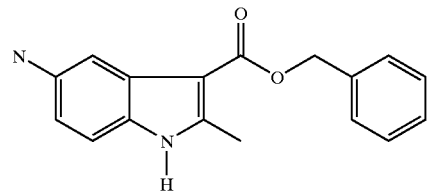

5-Amino-2-methyl-1H-indole-3-carboxylic acid benzyl ester

The mixture obtained in the previous step (1.10 g) and $SnCl_2$ (6.07 g, 32 mmol) was placed in a 100-mL round bottom flask, and 45 mL ethanol was added. The reaction mixture was heated to reflux for 12 hours (followed by TLC, 50:50 hexanes-ethyl acetate). After ethanol was removed in vacuo, the residue was dissolved in 100 mL 10% NaOH and 150 mL ethyl acetate solution. The separated organic phase was washed with water (3×150 mL), then dried over $MgSO_4$, filtered and concentrated in vacuo to give a dark color oil which was further purified by flash chromatography ($SiO_2$, 50:50–20:80 hexanes-ethyl acetate) to yield 420 mg the desired 5-amino-indole as a pale yellow solid (yield over the two steps: 7%).

Step D

To a 50-mL round bottom flask was added sequentially anhydrous DMF (2 mL), the 5-amino-2-methyl-1H-indole-3-carboxylic acid benzyl ester from previous step (100 mg, 0.36 mmol, 1.0 eq), KI (84 mg, 0.18 mmol, 0.5 eq), anhydrous $K_2CO_3$ (54.7 mg, 0.396 mmol, 1.1 eq) and 1-(2-chloroethyl) pyrrolidine (48 mg, 0.36 mmol, 1.0 eq). The reaction mixture was stirred at 50° C. under nitrogen overnight. After DMF was removed in vacuo, the residue was purified by gravity chromatography ($SiO_2$, 90: 10:1 methanol-dichloromethane-$NH_4OH$) to give 32 mg of the desired indole amine as a gel-like product. (24% yield). Elemental Analysis: $C_{23}H_{27}N_3O_2.2HCl.1.2H_2O$ Calcd: C: 58.52; H: 6.70; N: 8.90. Found: C:58.51; H: 6.66; N: 8.57. ESI-MS: m/z 378.61 $(M+H)^+$.

Example 21

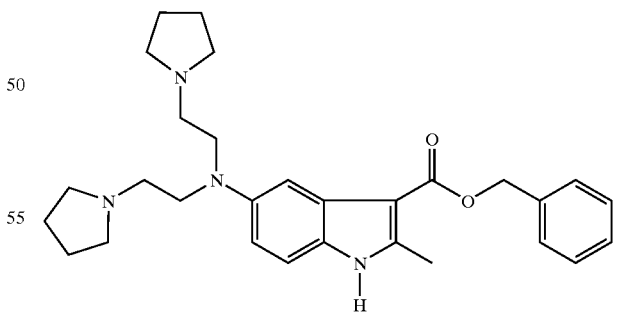

5-[Bis-(2-pyrrolidine-1-yl-ethyl)-amino]-2-methyl-1H-indole-3-carboxylic acid benzyl ester To a 50-mL round bottom flask was added sequentially anhydrous DMF (4 mL), the 5-amino-2-methyl-1H-indole-3-carboxylic acid benzyl ester (450 mg, 1.60 mmol, 1.2 eq), KI (112 mg, 0.67 mmol, 0.5 eq), anhydrous $K_2CO_3$ (204 mg, 1.47 mmol, 1.1 eq) and 1-(2-chloroethyl) pyrrolidine (178 mg, 1.34 mmol, 1.0 eq). The reaction mixture was stirred at 50° C. under nitrogen overnight. After DMF was removed by spin-oven in vacuo, the residue was purified by flash chromatography and gravity chromatography sequentially (SiO$_2$.90:10:1 methanol-dichloromethane-NH$_4$OH) to give 27 mg of the crude di-amine indole, which was further purified by preparative HPLC to yield 2.0 mg of the pure desired product. ESI-MS: m/z 475.88 (M+H)$^+$.

Example 22

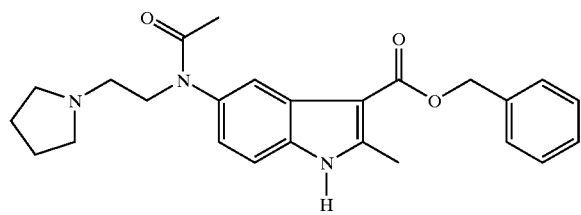

5-[Acetyl-(2-pyrrolidine-1-yl-ethyl)-amino)-2-methyl-1H-indole-3-carboxylic acid benzyl ester To a stirred solution of the 2-methyl-5-(2-pyrrolidine-1-yl-ethylamino)-1H-indole-3-carboxylic acid benzyl ester (147 mg, 0.39 mmol, 1.0 eq) and triethylamine (47.6 mg, 0.47 mmol, 1.2 eq) in acetonitrile in an ice-water bath was added dropwise a solution of acetyl chloride in acetonitrile. After the ice-water bath was removed, the reaction mixture was heated to reflux for overnight. After the mixture was concentrated, the residue was purified by preparative HPLC (reverse-phase, 10–100 CH$_3$CN:H$_2$O, 0.1% TFA) to yield the desire indole amine in 33.0% yield. Elemental Analysis: C$_{25}$H$_{29}$N$_3$O$_3$.2HCl.0.3H$_2$O Calcd: C: 60.31; H: 6.40; N: 8.44. Found: C: 60.63; H: 6.40; N: 8.04. ESI-MS: m/z 420.78 (M+H)+.

Example 23

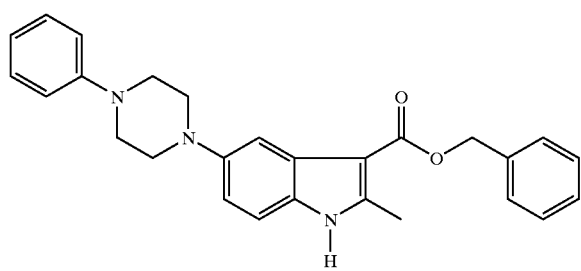

2-methyl-5-(4-phenyl-piperazin-1-yl)-1H-indole-3-carboxylic acid benzyl ester

To a flame-dried 100-mL round bottomed flask with condenser charged with argon was added, 5-Amino-2-methyl-1H-indole-3-carboxylic acid benzyl ester (0.399 g, 1.42 mmol, 1.0 eq), N,N-bis(2-chloroethyl)aniline (0.388 g, 1.78 mmol, 1.25 eq), dimethylformamide (10 mLs), and catalytic KI. The reaction was stirred for 24 hours at 50° C., 84 hours at 80° C. and monitored by TLC (EtOAc). The mixture was concentrated under reduced pressure at 40° C. and subjected to flash chromatography on silica gel (4×13.5 cm) eluting with EtOAc. The product was further purified by trituration with methanol, yielding 0.037 g (6%) of benzyl-(2-methyl-5-(4-phenyl)-piperazine)indole-3-carboxylate.

TLC (SiO$_2$, EtOAc) R$_f$=0.73. ESI-MS: M+1=426.6. Elemental Analysis (C$_{27}$H$_{27}$N$_3$O$_2$.0.25% H$_2$O). Theory C:75.41; H:6.45; N:9.77. Found C:75.36; H:6.38; N:9.56.

Example 24

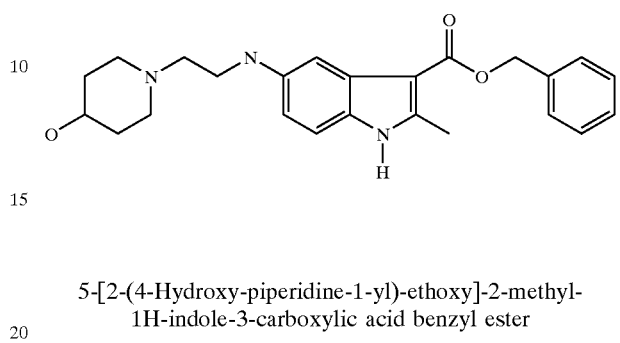

5-[2-(4-Hydroxy-piperidine-1-yl)-ethoxy]-2-methyl-1H-indole-3-carboxylic acid benzyl ester 5-(2-Chloro-ethoxy)-2-methyl-1H-indole-3-carboxylic acid benzyl ester (0.200 g, 0.58 mmol, 1.0 eq, Example 1, Step A) was dissolved in freshly distilled THF (100 mL), followed by 4-hydroxypiperidine (0.150 g, 1.48 mmol, 2.55 eq). Potassium carbonate (0.328 g, 2.37 mmol, 4.09 eq) was also added followed by potassium iodide (catalytic amount). The reaction mixture was refluxed for 7 days. The reaction mixture was washed with brine and extracted with ethyl acetate (3×100 ML) and dried over sodium sulfate. The product was chromatographed in an ethyl acetate/methanol/triethylamine system 87:10:3. 0.027 g of the product was obtained (11% yield) and converted to the HCl salt. LC/MS (ESI+) 408(M+1) (+42) as the acetonitrile adduct. Anal. (C$_{24}$H$_{28}$N$_2$O$_4$.HCl.1.5H$_2$O.0.2CHCl$_3$) C,H,N.

Example 25

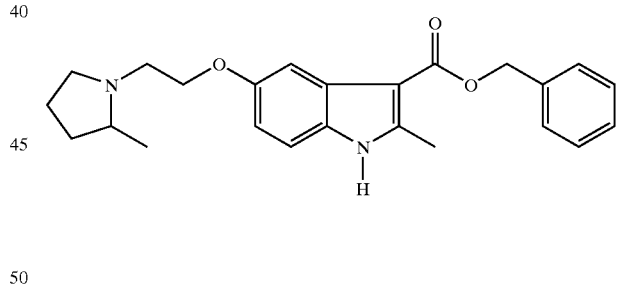

2-Methyl-5-[2-(2-methyl-pyrrolidin-1-yl)-ethoxy]-1H-indole-3-carboxylic acid benzyl ester 5-(2-Chloro-ethoxy)-2-methyl-1H-indole-3-carboxylic acid benzyl ester (0.200 g, 0.58 mmol, 1.0 eq, Example 1, Step A) was dissolved in acetonitrile (30 mL), followed by 2-methylpyrrolidine (0.247 g, 2.9 mmol, 5.0 eq). Potassium carbonate (0.4 g, 2.9 mmol, 5.0 eq) was also added followed by potassium iodide (catalytic amount). The reaction mixture was refluxed for 24 hours. The reaction mixture was washed with brine and extracted with ethyl acetate (3×100 mL) and dried over sodium sulfate. The product was chromatographed in an ethyl acetate/methanol/triethylamine system 87:10:3. 0.258 g of the product was obtained (100% yield) and converted to the HCl salt. LC/MS (ESI+) 392.5 (M+1). Anal. (C$_{24}$H$_{28}$N$_2$O$_3$.HCl.1H$_2$O) C,H,N.

Example 26

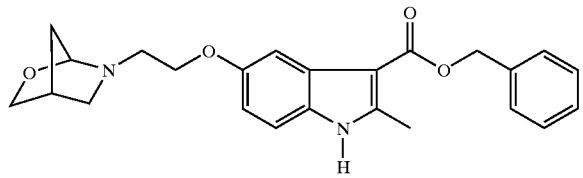

2-Methyl-5-[2-(2-oxa-6-aza-bicyclo[2.2.1]hept-6-yl)-ethoxy]-1H-indole-3-carboxylic acid benzyl ester 5-(2-Chloro-ethoxy)-2-methyl-1H-indole-3-carboxylic acid benzyl ester (0.200 g, 0.58 mmol, 1.0 eq, Example 1, Step A) was dissolved in acetonitrile (30 mL), followed by (1S,4S)-(+)-2-azaoxabicyclo[2.2.1]heptane.HCl salt (0.393 g, 2.9 mmol, 5.0 eq). Potassium carbonate (0.802 g, 5.8 mmol, 10 eq) was also added followed by potassium iodide (catalytic amount). The reaction mixture was refluxed for 24 hours. The reaction mixture was washed with brine and extracted with ethyl acetate (3×100 mL) and dried over sodium sulfate. The product was chromatographed in an ethyl acetate/methanol/triethylamine system 87:10:3. 0.230 g of the product was obtained (98% yield) and converted to the HCl salt. LC/MS (ESI+)406.5(M+1). Anal. ($C_{24}H_{26}N_2O_4$.HCl.1H$_2$O.0.2 dioxane) C,H,N.

Example 27

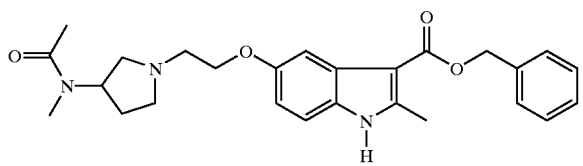

5-{2-[3-(Acetyl-methyl-amino)-pyrrolidin-1-yl)-ethoxy}-2-methyl-1H-indole-3-carboxylic acid benzyl ester 5-(2-Chloro-ethoxy)-2-methyl-1H-indole-3-carboxylic acid benzyl ester (0.200 g, 0.58 mmol, 1.0 eq, Example 1, Step A) was dissolved in 30 mL of acetonitrile, followed by (N-acetyl)-(N-methylamino)-pyrrolidine (0.412 g, 2.9 mmol, 5.0 eq). Potassium carbonate (0.400 g, 2.9 mmol, 5.0 eq) was also added followed by potassium iodide (catalytic amount). The reaction mixture was refluxed for 24 hours. The reaction mixture was washed with brine and extracted with ethyl acetate (3×100 mL) and dried over sodium sulfate. The product was chromatographed in an ethyl acetate/methanol/triethylamine system 87:10:3. 0.309 g of the product was obtained (100% yield) and converted to the HCl salt. LC/MS (ESI+) 449.56 (M+1). Anal. ($C_{26}H_{31}N_3O_4$.HCl.2H$_2$O) C,H,N.

Example 28

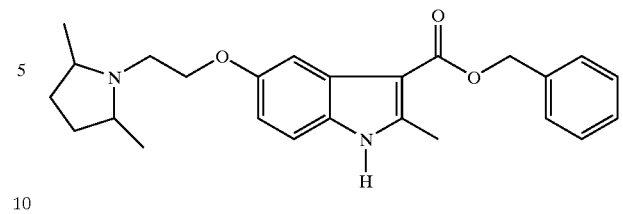

5-[2-(2,5-Dimethyl-pyrrolidin-1-yl)-ethoxy]-2-methyl-1H-indole-3-carboxylic acid benzyl ester 5-(2-Chloro-ethoxy)-2-methyl-1H-indole-3-carboxylic acid benzyl ester (0.200 g, 0.58 mmol, 1.0 eq, Example 1, Step A) was dissolved in 30 mL of acetonitrile, followed by (2,5-dimethyl)-pyrrolidine (0.500 g, 5.04 mmol, 8.7 eq). Potassium carbonate (0.697 g, 5.04 mmol, 8.7 eq) was also added followed by potassium iodide (catalytic amount). The reaction mixture was refluxed for 24 hours. The reaction mixture was washed with brine and extracted with ethyl acetate (3×100 mL) and dried over sodium sulfate. The product was chromatographed in an ethyl acetate/methanol/triethylamine system 87:10:3. 0.063 g of the product was obtained, 27% yield and converted to the HCl salt. LC/MS (ESI+)406.53 (M+1). Anal. ($C_{25}H_{30}N_2O_3$.HCl.1.3H$_2$O.0.7 dioxane-0.22CHCl$_3$) C,H,N.

Example 29

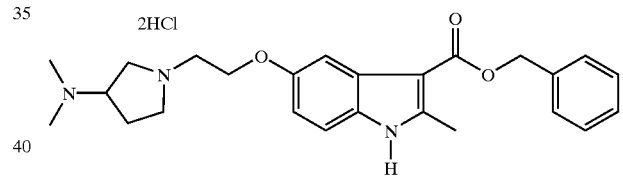

5-[2-(3-Dimethylamino-pyrrolidin-1-yl)-ethoxy]-2-methyl-1H-indole-3-carboxylic acid benzyl ester, dihydrochloride 5-(2-Chloro-ethoxy)-2-methyl-1H-indole-3-carboxylic acid benzyl ester (0.400 g, 1.163 mmol, 1 eq, Example 1, Step A) was suspended in dry acetonitrile (50 mL) under Ar. K$_2$CO$_3$ (0.320 g, 2.32 mmol, 2 eq) and KI (0.020 g, 0.116 mmol, 0.1 eq) were added followed by the addition of 3-(dimethylamino)pyrrolidine (0.198 g, 1.740 mmol, 1.5 eq). The reaction mixture was stirred and heated to reflux for 3 days. Then the reaction was quenched with saturated sodium bicarbonate and extracted with ethyl acetate (3×). The combined organic phases were washed with brine and dried over Na$_2$SO$_4$. After removing the solvent, the residue was loaded on silica gel and chromatographed, eluting with ethyl acetate/methanol/triethyl amine (100/10/1). 0.270 g (55%) of the indole-pyrrolidine was obtained as a white solid. This was converted to the .2HCl salt. LC/MS (ESI+) 422 (M+1); Anal. Calcd for $C_{25}H_{31}N_3O_3$.2HCl.2H$_2$O.0.25AcOEt: C, 56.52; H, 7.11; N, 7.61; Found: C, 56.50; H,. 6.73; N, 7.23.

Example 30

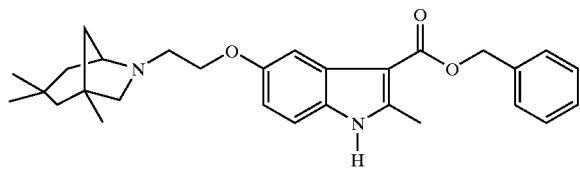

2-Methyl-5-[2-(1,3,3-trimethyl-6-aza-bicyclo[3.2.1] oct-6-yl)-ethoxy]-1H-indole-3-carboxylic acid benzyl ester 5-(2-Chloro-ethoxy)-2-methyl-1H-indole-3-carboxylic acid benzyl ester (0.500 g, 1.450 mmol, 1 eq, Example 1, Step A) was suspended in dry acetonitrile (30 mL) under Ar. $K_2CO_3$ (0.400 g, 2.900 mmol, 2 eq) and KI (0.025 g, 0.145 mmol, 0.1 eq) were added followed by the addition of 1,3,3-trimethyl-6-azabicyclo-[3,2,1]octane (0.334 g, 2.180 mmol, 1.5 eq). The reaction mixture was stirred and heated to reflux for 24 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.100 g (15%) of the indole-amine was obtained as a white solid. This was converted to the .HCl salt. LC/MS (ESI+) 461 (M+1); Anal. Calcd for $C_{29}H_{36}N_2O_3.1$ HCl.0.75$H_2O$: C, 68.22; H, 7.60; N, 5.49; Found: C, 68.25; H, 7.41; N, 5.56.

Example 31

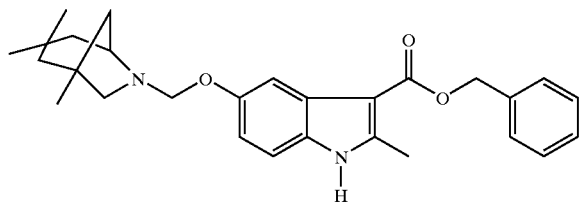

2-Methyl-5-[2-(1,3,3-trimethyl-6-aza-bicyclo[3.2.1] oct-6-yl)-ethyl]-1H-indole-3-carboxylic acid benzyl ester 5-(2-Methanesulfonyloxy-ethyl)-2-methyl-1H-indole-3-carboxylic acid benzyl ester (0.200 g, 0.510 mmol, 1 eq, Example 56, Step D) was suspended in dioxane (30 mL) under Ar. 1,3,3-trimethyl-6-azabicyclo-[3,2,1]octane (0.235 g, 1.540 mmol, 3 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.123 g (54%) of the indole-amine was obtained as a white solid. This was converted to the .HCl salt. LC/MS (ESI+) 446 (M+1); Anal. Calcd for $C_{29}H_{36}N_2O_2.1HCl.1.25H_2O$: C, 68.55; H, 7.93; N, 5.51; Found: C, 68.66; H, 7.54; N, 5.41.

Example 32

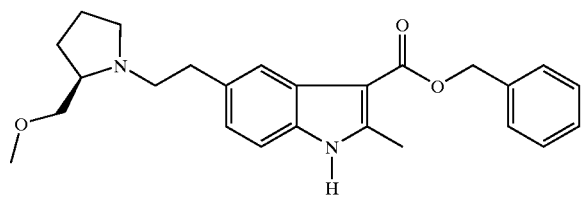

5-[2-((R)-2-methoxymethyl-pyrrolidin-1-yl)-ethyl]-2-methyl-1H-indole-3-carboxylic acid benzyl ester 5-(2-Methanesulfonyloxy-ethyl)-2-methyl-1H-indole-3-carboxylic acid benzyl ester (0.350 g, 0.900 mmol, 1 eq, Example 56, Step D) was suspended in dioxane (20 mL) under Ar. (R)-2-(Methoxymethyl)-pyrrolidine (0.207 g, 1.800 mmol, 2 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.300 g (82%) of the indole-amine was obtained as a white solid. This was converted to the .HCl salt. LC/MS (ESI+) 407 (M+1); Anal. Calcd for $C_{25}H_{30}N_2O_3.1$ HCl.1$H_2O$: C, 65.14; H, 7.22; N, 6.08; Found: C, 65.07; H, 7.08; N, 6.19.

Example 33

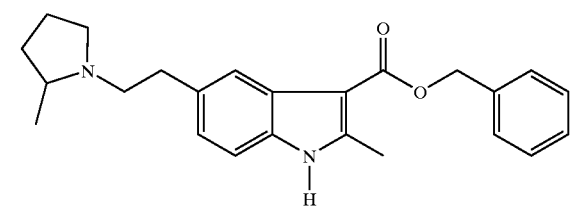

2-Methyl-5-[2-(2-methyl-pyrrolidin-1-yl)-ethyl]-1H-indole-3-carboxylic acid benzyl ester 5-(2-Methanesulfonyloxy-ethyl)-2-methyl-1H-indole-3-carboxylic acid benzyl ester (0.350 g, 0.900 mmol, 1 eq, Example 56, Step D) was suspended in dioxane (20 mL) under Ar. 2-Methyl-pyrrolidine (0.207 g, 1.800 mmol, 2 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.300 g (88%) of the indole-amine was obtained as a white solid. This was converted to the HCl. salt. LC/MS (ESI+) 377 (M+1); Anal. Calcd for $C_{24}H_{28}N_2O_2.1HCl.0.75H_2O$: C, 67.59; H, 7.21; N, 6.57; Found: C, 67.79; H, 7.16; N, 6.50.

Example 34

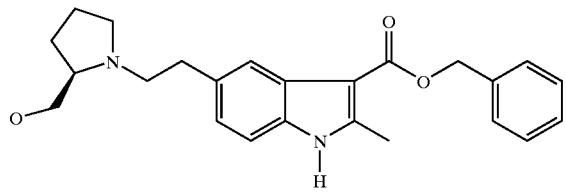

5-[2-((R)-2-Hydroxymethyl-pyrrolidin-1-yl)-ethyl]-
2-methyl-1H-indole-3-carboxylic acid benzyl ester 5-(2-Methanesulfonyloxy-ethyl)-2-methyl-1H-indole-3-carboxylic acid benzyl ester (0.350 g, 0.900 mmol, 1 eq, Example 56, Step D) was suspended in dioxane (20 mL) under Ar. (R)-2-Pyrrolidine methanol (0.272 g, 2.700 mmol, 3 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.200 g (57%) of the indole-amine was obtained as a white solid. This was converted to the .HCl salt. LC/MS (ESI+) 393 (M+1); Anal. Calcd for $C_{24}H_{28}N_2O_3 \cdot 1HCl \cdot 1.25H_2O$: C, 63.85; H, 7.03; N, 6.20; Found: C, 63.68; H, 6.81; N, 6.20.

Example 35

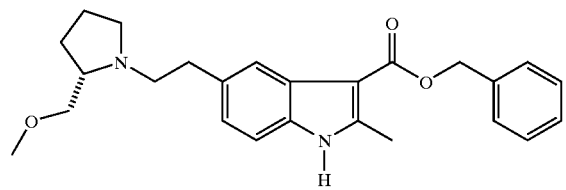

5-[2-((S)-2-methoxymethyl-pyrrolidin-1-yl)-ethyl]-
2-methyl-1H-indole-3-carboxylic acid benzyl ester 5-(2-Methanesulfonyloxy-ethyl)-2-methyl-1H-indole-3-carboxylic acid benzyl ester (0.350 g, 0.900 mmol, 1 eq, Example 56, Step D) was suspended in dioxane (20 mL) under Ar. (S)-2-(Methoxymethyl)-pyrrolidine (0.207 g, 1.800 mmol, 2 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.200 g (55%) of the indole-amine was obtained as a white solid. This was converted to the HCl salt. LC/MS (ESI+) 407 (M+1); Anal. Calcd for $C_{25}H_{30}N_2O_3 \cdot 1HCl \cdot 1H_2O$: C, 65.14; H, 7.22; N, 6.08; Found: C, 65.48; H, 7.14; N, 6.04.

Example 36

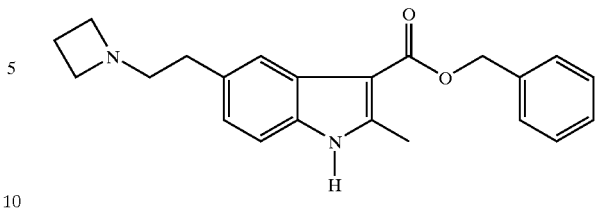

5-(2-azetidin-1-yl-ethyl]-2-methyl-1H-indole-3-
carboxylic acid benzyl ester 5-(2-Methanesulfonyloxy-ethyl)-2-methyl-1H-indole-3-carboxylic acid benzyl ester (0.300 g, 0.770 mmol, 1 eq, Example 56, Step D) was suspended in dioxane (20 mL) under Ar. $K_2CO_3$ (0.320 g, 2.320 mmol, 3 eq) was added followed by the addition of azetidine hydrochloride (0.217 g, 2.320 mmol, 3 eq). The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.030 g (11%) of the indole-amine was obtained as a white solid. This was converted to the .HCl salt. LC/MS (ESI+) 349 (M+1); Anal. Calcd for $C_{22}H_{24}N_2O_2 \cdot 1HCl \cdot 0.75H_2O$: C, 73.00; H, 7.10; N, 7.74; Found: C, 73.06; H, 6.95; N, 7.51.

Example 37

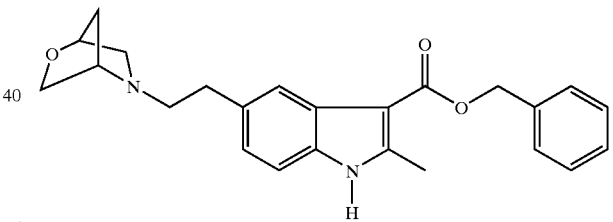

2-Methyl-5-[2-(2-oxa-5-aza-bicyclo[2.2.1]hept-5-
yl)-ethyl]-1H-indole-3-carboxylic acid benzyl ester 5-(2-Methanesulfonyloxy-ethyl)-2-methyl-1H-indole-3-carboxylic acid benzyl ester (0.300 g, 0.770 mmol, 1 eq, Example 56, Step D) was suspended in DMF (5 mL) under Ar. $K_2CO_3$ (0.425 g, 3.080 mmol, 4 eq) was added followed by the addition of (1S,4S)-(+)-1-Aza-5-oxabicycle[2,2,1]-heptane hydrochloride (0.314 g, 2.320 mmol, 3 eq). The reaction mixture was stirred at 80° C. for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.150 g (50%) of the indole-amine was obtained as a white solid. This was converted to the .HCl salt. LC/MS (ESI+) 391 (M+1); Anal. Calcd for $C_{24}H_{26}N_2O_3 \cdot 1HCl \cdot 0.90H_2O$: C, 65.05; H, 6.55; N, 6.32; Found: C, 65.05; H, 6.60; N, 6.13.

Example 38

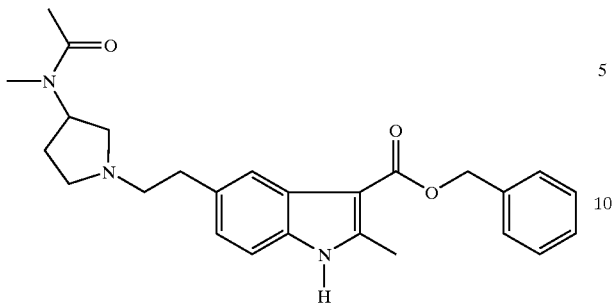

5-{2-[3-(Acetyl-methyl-amino)-pyrrolidin-1-yl)-ethyl}-2-methyl-1H-indole-3-carboxylic acid benzyl ester 5-(2-Methanesulfonyloxy-ethyl)-2-methyl-1H-indole-3-carboxylic acid benzyl ester (0.300 g, 0.770 mmol, 1 eq, Example 56, Step D) was suspended in Dioxane (20 mL) under Ar. 3-(N-Acetyl-N-methylamino)-pyrrolidine (0.330 g, 2.320 mmol, 3 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.200 g (60%) of the indole-amine was obtained as a white solid. This was converted to the .HCl salt. LC/MS (ESI+) 434 (M+1); Anal. Calcd for $C_{26}H_{31}N_3O_3 \cdot 1HCl \cdot 1.25H_2O$: C, 63.40; H, 7.06; N, 8.53; Found: C, 63.51; H, 6.95; N, 8.30.

Example 39

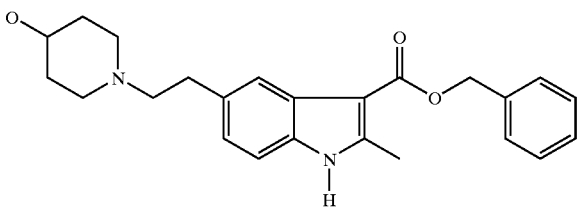

5-[2-(4-Hydroxy-piperidine-1-yl)-ethyl]-2-methyl-1H-indole-3-carboxylic acid benzyl ester 5-(2-Methanesulfonyloxy-ethyl)-2-methyl-1H-indole-3-carboxylic acid benzyl ester (0.300 g, 0.770 mmol, 1 eq, Example 56, Step D) was suspended in Dioxane (20 mL) under Ar. 4-Hydroxypiperidine (0.234 g, 2.320 mmol, 3 eq) was added. The reaction mixture was stirred and heated to reflux for 18 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.200 g (66%) of the indole-amine was obtained as a white solid. This was converted to the .HCl salt. LC/MS (ESI+) 393 (M+1); Anal. Calcd for $C_{24}H_{28}N_2O_3 \cdot 1HCl \cdot 0.4H_2O$: C, 66.09; H, 6.89; N, 6.42; Found: C, 66.18; H, 6.77; N, 6.30.

Example 40

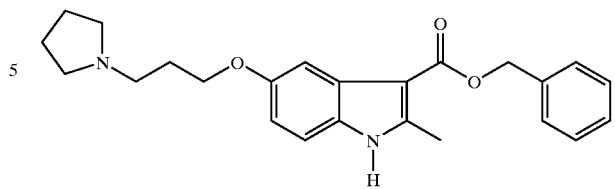

2-Methyl-5-(3-pyrrolidin-1-yl-propoxy)-1H-indole-3-carboxylic acid benzyl ester

Step A

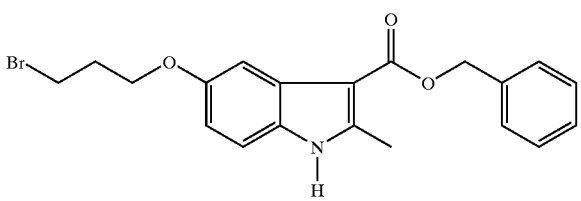

5-(3-Bromo-propoxy)-2-methyl-1H-indole-3-carboxylic acid benzyl ester

2-Methyl-3-benzyloxycarbonyl-5-hydroxyindole (0.558 g, 1.980 mmol, 1 eq) was suspended in acetonitrile (10 mL) under Ar. $Cs_2CO_3$ (0.645 g, 1.980 mmol, 1 eq) and KI (0.328 g, 1.980 mmol, 1 eq) were added followed by 1,3-dibromopropane (0.523 g, 2.590 mmol, 1.3 eq). The reaction mixture was stirred and heated to reflux for 20 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/hexane (1/5). 0.244 g (31%) of the indole-bromide was obtained as a colorless oil.

Step B 5-(3-Bromo-propoxy)-2-methyl-1H-indole-3-carboxylic acid benzyl ester (0.244 g, 0.605 mmol, 1 eq) was suspended in dry acetonitrile (10 mL) under Ar. Pyrrolidine (0.100 mL, 1.210 mmol, 2 eq) was added. The reaction mixture was stirred and heated to reflux for 24 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.100 g (42%) of the indole-pyrrolidine was obtained as a white solid. This was converted to the .HCl salt. LC/MS (ESI+) 393 (M+1); Anal. Calcd for $C_{24}H_{28}N_2O_3 \cdot HCl \cdot H_2O$: C, 64.49; H, 6.99; N, 6.27; Found: C, 64.36; H, 6.93; N, 6.15.

Example 41

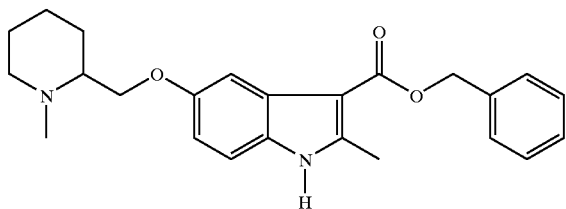

2-Methyl-5-(1-methyl-piperidin-2-yl-methoxy)-1H-indole-3-carboxylic acid benzyl ester 1-Methyl-2-piperidinemethanol (0.459 g, 3.580 mmol, 1 eq) was suspended in dry $CH_2Cl_2$ (5 mL). p-Toluenesulfonyl chloride (0.684 g, 3.580 mmol, 1 eq) and triethyl amine (1.00 mL, 7.160 mmol, 2 eq) were added. The reaction mixture was stirred at room temperature for 8 hours. Then the reaction was quenched with saturated sodium bicarbonate and extracted with ethyl acetate (3×). The combined organic phases were washed with brine and dried over $Na_2SO_4$. After removing the solvent, the residue was dissolved in dry acetonitrile (20 mL). 2-Methyl-3-benzyloxycarbonyl-5-hydroxyindole (1.005 g, 3.580 mmol, 1 eq) and $Cs_2CO_3$ (1.159 g, 3.580 mmol, 1 eq) were added. The reaction mixture was stirred and heated to reflux for 16 hours. Then the reaction was quenched with saturated sodium bicarbonate and extracted with ethyl acetate (3×). The combined organic phases were washed with brine and dried over $Na_2SO_4$. After removing the solvent, the residue was loaded on silica gel and chromatographed, eluting with ethyl acetate/methanol/triethyl amine (100/10/1). 0.200 g (15%) of the indole-piperidine ether was obtained as a brown solid. This was converted to the .HCl salt. LC/MS (ESI+) 393 (M+1); Anal. Calcd for $C_{24}H_{28}N_2O_3 \cdot HCl \cdot 0.8H_2O$: C, 65.02; H, 6.96; N, 6.32; Found: C, 65.36; H, 7.02; N, 5.96.

Example 42

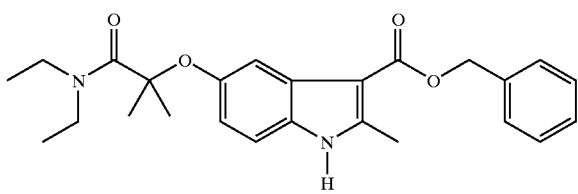

5-(1-Diethylcarbamoyl-1-methyl-ethoxy)-2-methyl-1H-indole-3-carboxylic acid benzyl ester

Step A

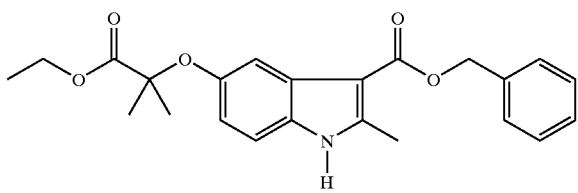

5-(1-Ethoxycarbonyl-1-methyl-ethoxy)-2-methyl-1H-indole-3-carboxylic acid benzyl ester 2-Methyl-3-benzyloxycarbonyl-5-hydroxyindole (10.0 g, 35.54 mmol, 1.0 eq) was dissolved in acetonitrile (250 mL), followed by ethyl-2-bromo-isobutyrate (7.63 g, 39.10 mmol, 2.0 eq). Potassium carbonate (9.82 g, 71.08 mmol, 8.7 eq) was also added followed by potassium iodide (catalytic amount). The reaction mixture was refluxed for 24 hours. The reaction mixture was washed with brine and extracted with ethyl acetate (3×100 mL) and dried over sodium sulfate. The product was chromatographed in a hexane to hexane/ethyl acetate 7:3. 6.88 g of the product was obtained, 48% yield.

Step B

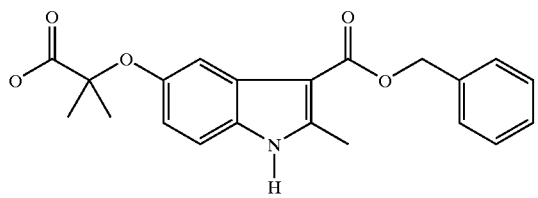

5-(1-Carboxy-1-methyl-ethoxy)-2-methyl-1H-indole-3-carboxylic acid benzyl ester 5-(1-Ethoxycarbonyl-1-methyl-ethoxy)-2-methyl-1H-indole-3-carboxylic acid benzyl ester (6.88 g, 16.5 mmol, 1.0 eq) was dissolved in THF (16 mL), followed by LiOH (0.395 g, 16.5 mmol, 1.0 eq) in $H_2O$ (16 mL). The reaction mixture was refluxed for 24 hours. Another equivalent of LiOH was added, and reflux was continued for another 24 hours. The reaction was then judged complete by TLC in hexane ethyl acetate 1:1. 5.0 g of the product was obtained, 84% yield (crude).

Step C 5-(1-Carboxy-1-methyl-ethoxy)-2-methyl-1H-indole-3-carboxylic acid benzyl ester (1.0 g, 2.76 mmol, 1.0 eq) was dissolved in ethylacetate (100 mL), and treated with diethylamine (0.241 g, 3.3 mmol, 1.2 eq) followed by HBTU (0.446 g, 3.3 mmol, 1.2 eq). The reaction mixture was stirred at room temperature for 24 hours and was followed by TLC (hexane/ethyl acetate 1/1). The reaction was quenched with aqueous sodium bicarbonate, extracted with ethyl acetate, and the organic layers dried over sodium sulfate, evaporated, and loaded on silica gel, followed by flash chromatography (hexane/ethyl acetate 1/1). 0.109 g of the product was obtained, 12% yield. LC/MS (ESI+) 422.52 (M+1) $(C_{25}H_{30}N_2O_4)$.

Example 43

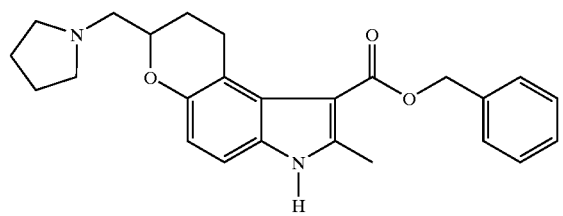

2-Methyl-7-pyrrolidin-1-ylmethyl-3,7,8,9-tetrahydro-pyrano[3,2-e]indole-1-carboxylic acid benzyl ester Step A

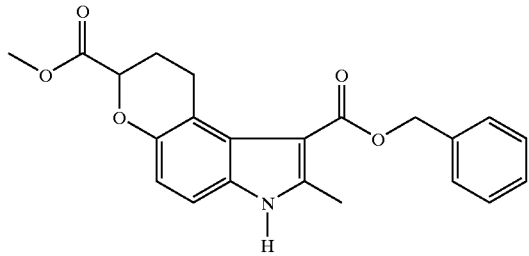

2-Methyl-3,7,8,9-tetrahydro-pyrano[3,2-e]indole-1,7-dicarboxylic acid 1-benzyl ester 7-methyl ester 2-Methyl-3-benzyloxycarbonyl-4-dimethylaminomethyl-5-hydroxyindole (1.04 g, 3.08 mmol, 1 eq) was suspended in methyl acrylate (30 mL). The reaction mixture was stirred at 120° C. in a sealed tube. After 21 hours, the crude reaction mixture was loaded on silica gel and chromatographed eluting with methanol/CH$_2$Cl$_2$, 95/5. 0.545 g (47% yield) of the indole-ester was obtained as an off-white solid.

Step B

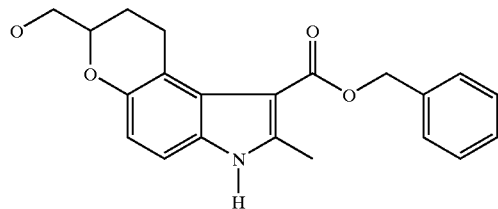

7-Hydroxymethyl-2-methyl-3,7,8,9-tetrahydro-pyrano[3,2-e]indole-1-carboxylic acid benzyl ester 2-Methyl-3,7,8,9-tetrahydro-pyrano[3,2-e]indole-1,7-dicarboxylic acid 1-benzyl ester 7-methyl ester (0.536 g, 1.41 mmol, 1 eq) was suspended in dry THF (10 mL) under Ar. Methanol (0.203 mL, 5.0 mmol, 3.5 eq) was added followed by cooling to 4° C. and the addition of lithium borohydride (2.5 mL of 2 M, 5.0 mmol, 3.5 eq). The reaction mixture was stirred and allowed to warm to room temperature, then heated to reflux. The reaction was followed by TLC (CH$_2$Cl$_2$/MeOH 9/1). After 1 hour, the reaction was quenched with brine and extracted with ethyl acetate (3×). The combined organic extracts were washed with brine and dried over Na$_2$SO$_4$. After removing the solvent, the residue was loaded on silica gel and chromatographed, eluting with CH$_2$Cl$_2$/MeOH 9/1. 0.430 g (87% yield) of the indole-alcohol was obtained as a white solid Step C

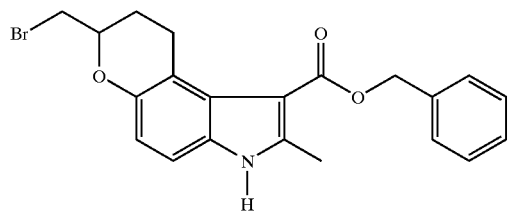

7-Bromomethyl-2-methyl-3,7,8,9-tetrahydro-pyrano[3,2-e]indole-1-carboxylic acid benzyl ester 7-Hydroxymethyl-2-methyl-3,7,8,9-tetrahydro-pyrano[3,2-e]indole-1-carboxylic acid benzyl ester (0.410 g, 1.16 mmol, 1 eq) was suspended in dry CH$_2$Cl$_2$ (20 mL) under Ar. Carbon tetrabromide (0.615 g, 1.86 mmol, 1.6 eq) was added followed by the addition of triphenylphosphine (0.441 g, 1.5 mmol, 1.3 eq). The reaction mixture was stirred at room temperature. The reaction was followed by TLC (CH$_2$Cl$_2$/MeOH 9/1). After 3 hours, the reaction mixture was loaded on silica gel and chromatographed, eluting with CH$_2$Cl$_2$/MeOH 9/1. 0.191 g (40% yield) of the indole-bromide was obtained as an unstable brown oil.

Step D

7-Bromomethyl-2-methyl-3,7,8,9-tetrahydro-pyrano[3,2-e]indole-1-carboxylic acid benzyl ester (0.160 g, 0.390 mmol, 1 eq) was suspended in dry acetonitrile (10 mL) under Ar. Potassium iodide (catalytic) was added followed by the addition of pyrrolidine (0.125 mL, 1.50 mmol, 3.75 eq). The reaction mixture was stirred and heated to reflux. The reaction was followed by TLC (ethyl acetate/methanol/triethylamine 87/10/3). After 18 hours, the reaction was quenched with aqueous sodium bicarbonate and extracted with ethyl acetate (3×). The combined organic extracts were washed with brine and dried over Na$_2$SO$_4$. After removing the solvent, the residue was loaded on silica gel and chromatographed, eluting with ethyl acetate /methanol/triethylamine 87/10/3. 0.063 g (40% yield) of the indole-pyrrolidine was obtained as a white solid. This was converted to the .HCl salt, LC/MS (ESI+) 405 (M+1), Anal. (C$_{25}$H$_{28}$N$_2$O$_3$.HCl.0.2 DMF) C, H, N.

Example 44

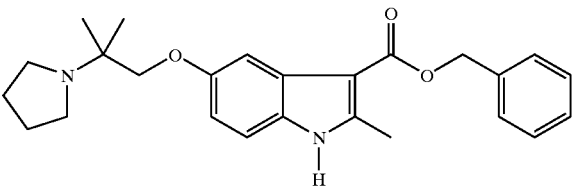

2-Methyl-5-(2-methyl-2-pyrrolidin-1-yl-propoxy)-1H-indole-3-carboxylic acid benzyl ester

Step A

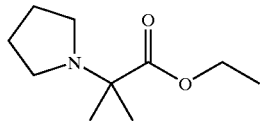

2-Methyl-2-pyrrolidin-1-yl-propionic acid ethyl ester

2-Bromo-2-methyl-propionic acid ethyl ester (2.0 mL, 13.6 mmol, 1 eq) was dissolved in dry acetonitrile (50 mL) under Ar. Potassium iodide (catalytic) was added followed by the addition of potassium carbonate (3.5 g, 26 mmol, 2.0 eq) and pyrrolidine (1.67 mL, 20 mmol, 1.5 eq). The reaction mixture was stirred and heated to reflux. The reaction was followed by TLC ($CH_2Cl_2$/MeOH 9/1). After 18 hours, the reaction was quenched with aqueous sodium bicarbonate and extracted with ethyl acetate (3×). The combined organic extracts were washed with brine, dried over $Na_2SO_4$, and evaporated. 2.05 g (82% yield) of the ester-pyrrolidine was obtained as a brown oil.

Step B

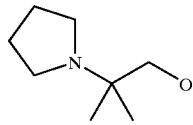

2-Methyl-2-pyrrolidin-1-yl-propan-1-ol

2-Methyl-2-pyrrolidin-1-yl-propionic acid ethyl ester (2.00 g, 10.8 mmol, 1 eq) was suspended in dry THF (20 mL) under Ar. Methanol (2.0 mL, 50 mmol, 5.0 eq) was added followed by cooling to 4° C. and the addition of lithium borohydride (25 mL of 2M, 50 mmol, 5.0 eq). The reaction mixture was stirred and allowed to warm to room temperature. After 18 hours, the reaction was quenched with methanol, then aqueous NaOH, and extracted with $CH_2Cl_2$ (3×). The combined organic extracts were washed with brine and dried over $Na_2SO_4$. After removing the solvent, the crude residue was used in the next step.

Step C

Crude 2-methyl-2-pyrrolidin-1-yl-propan-1-ol (0.849 g, 5.94 mmol, 1 eq) was suspended in dry acetonitrile (30 mL) under Ar. Triethylamine (1.4 mL, 10 mmol, 1.7 eq) was added followed by the addition of toluenesulfonyl chloride (1.05 g, 5.50 mmol, 1.0 eq). The reaction mixture was stirred at room temperature for 1 hour. After 4 hours, the reaction was treated with 2-methyl-3-benzyloxycarbonyl-5-hydroxyindole (1.5 g; 5.5 mmol, 1 eq) and potassium carbonate (1.38 g, 10 mmol, 1.7 eq.). The reaction was heated to reflux and followed by TLC (ethyl acetate/methanol/triethylamine 87/10/3). After 23 hours, the reaction was loaded directly on silica gel and chromatographed (ethyl acetate/methanol/triethylamine 87/10/3). Impure product was further purified by reverse-phase prep-HPLC 10–100% Acetonitrile/water, 0.1% TFA. 0.040 g (5% yield) of the indole-amine was obtained as a brown semisolid: LC/MS (ESI+) 407 (M+1), Anal. ($C_{24}H_{30}N_2O_2$.TFA.1.0$H_2O$) C, H, N.

Example 45

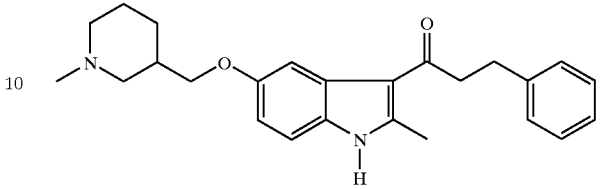

2-Methyl-5-(1-methyl-piperidin-3-ylmethoxy)-1H-indole-3-carboxylic acid benzyl ester

Step A

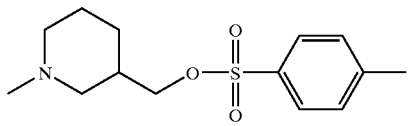

Toluene-4-sulfonic acid 1-methyl-piperidin-3-ylmethyl ester (1-Methyl-piperidin-3-yl)-methanol (1.0 mL, 7.75 mmol, 1 eq) was suspended in dry $CH_2Cl_2$ (20 mL) under Ar. Triethylamine (1.9 mL, 14 mmol, 2.0 eq) was added followed by the addition of toluenesulfonyl chloride (1.49 g, 7.8 mmol, 1.0 eq.). The reaction mixture was stirred at room temperature for 18 hours, and then quenched with aqueous sodium bicarbonate. The aqueous layers were extracted several times with $CH_2Cl_2$, and the combined organic layers were dried over $Na_2SO_4$. After removing the solvent, the residue was loaded on silica gel and chromatographed (ethyl acetate/methanol/triethylamine 87/10/3). 1.85 g (85% yield) of the amine tosylate was obtained as a yellow oil.

Step B

Toluene-4-sulfonic acid 1-methyl-piperidin-3-ylmethyl ester (0.753 g, 2.66 mmol, 1.0 eq) was dissolved in dry acetonitrile (30 mL), and treated with 2-methyl-3-benzyloxycarbonyl-5-hydroxyindole (0.759 g, 2.70 mmol, 1 eq) and potassium carbonate (0.690 g, 5 mmol, 2.0 eq.). The reaction was heated to reflux and followed by TLC (ethyl acetate/methanol/triethylamine 87/10/3). After 96 hours, the reaction was loaded directly on silica gel and chromatographed (ethyl acetate/methanol/triethylamine 87/10/3) to afford a white solid: 0.237 g (24% yield). This was converted to the corresponding hydrochloride salt: LC/MS (ESI+) 393 (M+1), Anal. ($C_{24}H_{28}N_2O_3$.HCl.0.6$H_2O$) C, H, N.

Example 46

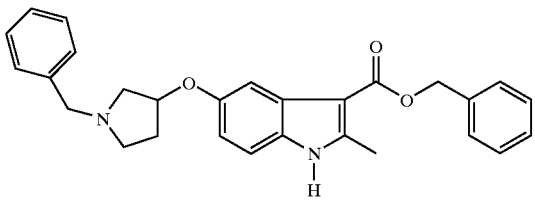

5-(1-benzyl-pyrrolidin-3-yloxy)-2-methyl-1H-indole-3-carboxylic acid benzyl ester 1-benzyl-3-toluenesulfonyloxypyrrolidine (0.662 g, 2.00 mmol, 1.0 eq, see *Bio. Org. & Med. Chem. Lett.*, 1999;9:1379) was dissolved in dry acetonitrile (20 mL) and DMF (1 mL), and treated with 2-methyl-3-benzyloxycarbonyl-5-hydroxyindole (0.562 g, 2.00 mmol, 1 eq) and potassium carbonate (0.276 g, 2.0 mmol, 1.0 eq.). The reaction was heated to reflux and followed by TLC (hexane/ethyl acetate 1/1). After 24 hours, the reaction was loaded directly on silica gel and chromatographed (hexane/ethyl acetate 1/1) to afford a yellow oil: 0.162 g (18% yield). This was converted to the corresponding hydrochloride salt: LC/MS (ESI+) 441 (M+1), Anal. ($C_{28}H_{28}N_2O_3 \cdot HCl \cdot 1.6H_2O$) C, H, N.

Example 47

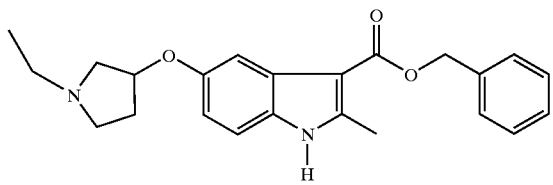

5-(1-Ethyl-pyrrolidin-3-yloxy)-2-methyl-1H-indole-3-carboxylic acid benzyl ester

Step A

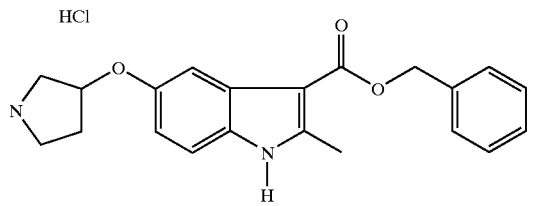

2-Methyl-5-(pyrrolidin-3-yloxy)-1H-indole-3-carboxylic acid benzyl ester, hydrochloride 5-(1-benzyl-pyrrolidin-3-yloxy)-2-methyl-1H-indole-3-carboxylic acid benzyl ester (0.118 g, 0.268 mmol, 1.0 eq.) was dissolved in dry 1,2-dichloroethane (5 mL) and treated with α-chloroethyl chloroformate (0.035 mL, 0.32 mmol, 1.2 eq.). The reaction was heated to reflux and followed by TLC (hexane/ethyl acetate 1/1). After 2 hours, the reaction was concentrated in vacuo, redissolved in methanol (5 mL), and heated to reflux. After 4 hours, the crude hydrochloride salt was precipitated from methanol/ethyl acetate/hexane to afford a brown solid, which was carried directly to the next step.

Step B

Crude 2-methyl-5-(pyrrolidin-3-yloxy)-1H-indole-3-carboxylic acid benzyl ester, hydrochloride (0.075 g, 0.194 mmol, 1 eq) was suspended in methanol (5 mL). Acetaldehyde (0.028 mL, 0.5 mmol, 2.6 eq) was added followed by the addition of sodium cyanoborohydride (0.032 g, 0.5 mmol, 2.6 eq). The reaction mixture was kept at pH 6 and stirred at room temperature. After 24 hours, the reaction was quenched with aqueous sodium bicarbonate, extracted several times with $CH_2Cl_2$. The combined organic layers were dried over sodium sulfate, loaded on silica gel and chromatographed (ethyl acetate/methanol/triethylamine 87/10/3). Impure product was further purified by reverse-phase prep-HPLC 10–100% Acetonitrile/water, 0.1% TFA. 0.008 g (10% yield) of the indole-amine was obtained as a brown semisolid: LC/MS (ESI+) 379 (M+1), Anal. ($C_{23}H_{26}N_2O_3 \cdot TFA \cdot 1.0H_2O$) C, H, N.

Example 48

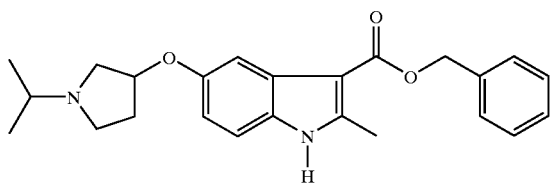

5-(1-Isopropyl-pyrrolidin-3-yloxy)-2-methyl-1H-indole-3-carboxylic acid benzyl ester Crude 2-methyl-5-(pyrrolidin-3-yloxy)-1H-indole-3-carboxylic acid benzyl ester, hydrochloride (0.040 g, 0.100 mmol, 1 eq, Example 47, Step A) was suspended in methanol (5 mL). Acetone (0.100 mL) was added followed by the addition of sodium cyanoborohydride (0.013 g, 0.2 mmol, 2.0 eq). The reaction mixture was kept at pH 6 and stirred at room temperature. After 24 hours, the reaction was quenched with aqueous sodium bicarbonate, extracted several times with $CH_2Cl_2$. The combined organic layers were dried over sodium sulfate, loaded on silica gel and chromatographed (ethyl acetate/methanol/triethylamine 87/10/3. 0.025 g (64% yield) of the indole-amine was obtained as a brown semisolid, and converted to the corresponding HCl salt: LC/MS (ESI+) 393 (M+1), Anal. ($C_{24}H_{28}N_2O_3 \cdot HCl$) C, H, N.

Example 49

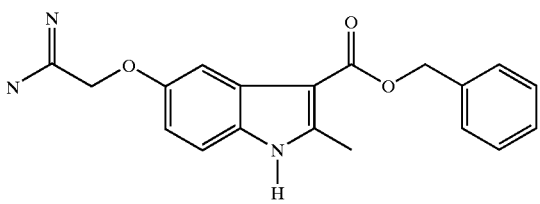

5-Carbamimidoylmethoxy-2-methyl-1H-indole-3-carboxylic acid benzyl ester

Step A

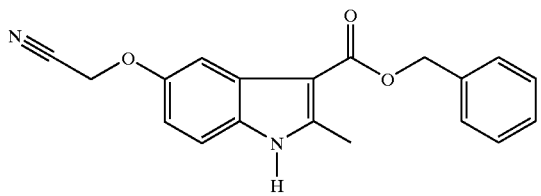

5-Cyanomethoxy-2-methyl-1H-indole-3-carboxylic acid benzyl ester

α-Bromoacetonitrile (0.209 mL, 3.00 mmol, 1.0 eq.) was dissolved in dry acetonitrile (30 mL) and treated with 2-methyl-3-benzyloxycarbonyl-5-hydroxyindole (0.972 g, 3.46 mmol, 1.2 eq.) and potassium carbonate (0.690 g, 5.0 mmol, 1.7 eq.). The reaction was heated to reflux and followed by TLC (hexane/ethyl acetate 3/2). After 6 hours, the reaction was quenched with water and extracted with ethyl acetate. The resulting organic layers were concentrated, taken up in methylene chloride, and filtered. The filtrate was evaporated to afford a brown solid: 0.490 g (51% yield).

Step B

5-Cyanomethoxy-2-methyl-1H-indole-3-carboxylic acid benzyl ester (0.185 g, 0.578 mmol, 1 eq) was suspended in ethanol (15 mL). The solution was acidified by bubbling a stream of anhydrous HCl at room temperature for 10 minutes, capped, and stirred at room temperature. After 18 hours, the reaction was concentrated in vacuo, taken up in more dry ethanol, and anhydrous ammonia was bubbled through for 10 minutes. The reaction was capped and stirred at room temperature. After 18 hours, the reaction was chromatographed (acetonitrile/water/acetic acid 10/2/1). Impure product was further purified by reverse-phase prep-HPLC 10–100% Acetonitrile/water, 0.1% TFA. 0.009 g (4% yield) of the indole-amidine was obtained as a brown semisolid: LC/MS (ESI+) 338 (M+1), Anal. ($C_{19}H_{19}N_3O_3$.TFA.1.3$H_2O$.1.0 MeOH) C, H, N.

Example 50

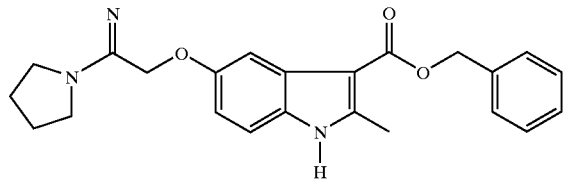

5-(2-Imino-2-pyrrolidin-1-yl-ethoxy)-2-methyl-1H-indole-3-carboxylic acid benzyl ester 5-Cyanomethoxy-2-methyl-1H-indole-3-carboxylic acid benzyl ester (0.189 g, 0.590 mmol, 1 eq, Example 49, Step A) was suspended in chloroform (10 mL) and treated with dry ethanol (0.046 mg, 1.0 mmol, 1.8 eq.). The solution was acidified by bubbling a stream of anhydrous HCl at room temperature for 10 minutes, capped, and stirred at room temperature. After 18 hours, the reaction was concentrated in vacuo, taken up in dry acetonitrile, and treated with pyrrolidine (0.125 mL, 1.50 mmol, 3 eq). The reaction was capped and stirred at room temperature. After 18 hours, the reaction was chromatographed (acetonitrile/water/acetic acid 10/2/1). Impure product was further purified by reverse-phase prep-HPLC 10–100% Acetonitrile/water, 0.1% TFA. 0.024 g (10% yield) of the indole-amidine was obtained as a brown semisolid: LC/MS (ESI+) 392 (M+1), Anal. ($C_{23}H_{25}N_3O_3$.TFA.1.5$H_2O$) C, H, N.

Example 51

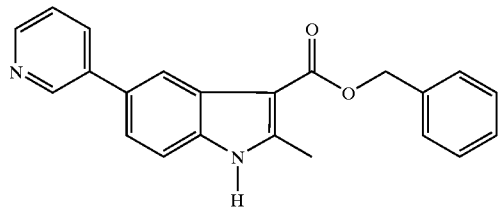

2-Methyl-5-pyridin-3-yl-1H-indole-3-carboxylic acid benzyl ester

Step A

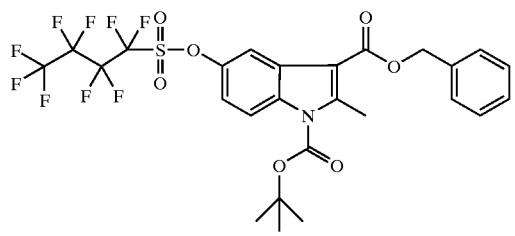

2-Methyl-5-(nonafluorobutane-1-sulfonyloxy)-indole-1,3-dicarboxylic acid 3-benzyl ester 1-tert-butyl ester 2-Methyl-3-benzyloxycarbonyl-5-hydroxyindole (2.89 g, 10.2 mmol, 1 eq) was suspended in dry $CH_2Cl_2$ (50 mL) and dry DMF (2 mL) under Ar. Triethylamine (4.2 mL, 30 mmol, 3 eq) was added followed by the addition of perfluorobutanesulfonyl fluoride (1.88 mL, 10.5 mmol, 1.0 eq). The reaction mixture was stirred at room temperature and followed by TLC ($CH_2Cl_2$/MeOH 98/2). After 18 hours, the reaction was treated with di-tert-butyl dicarbonate (2.3 g, 10.5 mmol, 1 eq.) and diazabicycloundecane (3 mL, 20 mmol, 2 eq.). After an additional 24 hours, the reaction was quenched with aqueous citric acid. The organic phase was washed with water (2×) and the combined aqueous phases extracted with $CH_2Cl_2$. The combined organic extracts were washed with brine and dried over $Na_2SO_4$. After removing the solvent, the residue was loaded on silica gel and chromatographed eluting with hexane/ethyl acetate (9/1). 4.90 g (72% yield) of the indole-BOC-nonaflate was obtained as a white solid.

Step B

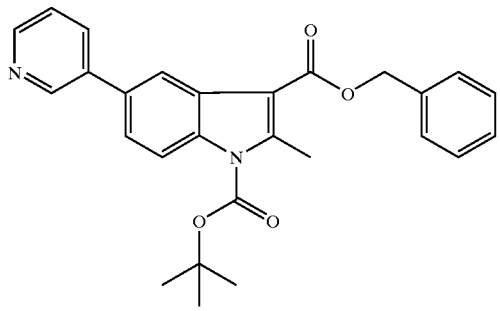

2-Methyl-5-pyridin-3-yl-indole-1,3-dicarboxylic acid 3-benzyl ester 1-tert-butyl ester 2-Methyl-5-(nonafluorobutane-1-sulfonyloxy)-indole-1,3-dicarboxylic acid 3-benzyl ester 1-tert-butyl ester (0.100 g, 0.151 mmol, 1 eq) was dissolved in toluene (2 mL) and aqueous sodium carbonate (0.5 mL, saturated) under Ar. 3-Pyridylboronic acid-ethyleneglycol ester (0.049 g, 0.3 mmol, 3 eq.) was added followed by the addition of dichloropalladium (II) bis-diphenylphosphinoferrocene (0.016 g, 0.02 mmol, 15 mol %). The reaction mixture was stirred at reflux and followed by TLC (hexane/ethyl acetate 2/3). After 18 hours, the crude reaction was loaded on silica gel and chromatographed (hexane/ethyl acetate 2/3). 0.027 g (40% yield) of the BOC-indole-pyridine was obtained as a white solid.

Step C

2-Methyl-5-pyridin-3-yl-indole-1,3-dicarboxylic acid 3-benzyl ester 1-tert-butyl ester (0.027 g, 0.061 mmol, 1 eq) was suspended in dry $CH_2Cl_2$ (5 mL) under Ar. Trifluoroacetic acid (1.0 mL) was added, and the reaction mixture was stirred at room temperature. After 4 hours, the solvent was removed in vacuo, leaving 0.028 g (40% yield) of the indole-pyridine, a brown solid: LC/MS (ESI+) 343 (M+1), Anal.

($C_{22}H_{18}N_2O_2$.TFA.1.0$H_2O$.0.5 $CH_2Cl_2$) C, H, N.

Example 52

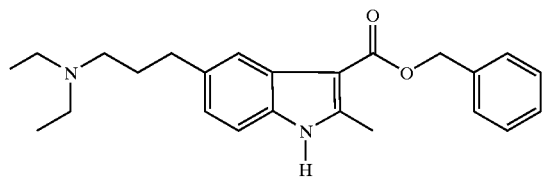

5-(3-Diethylamino-propyl)-2-methyl-1H-indole-3-carboxylic acid benzyl ester

Step A

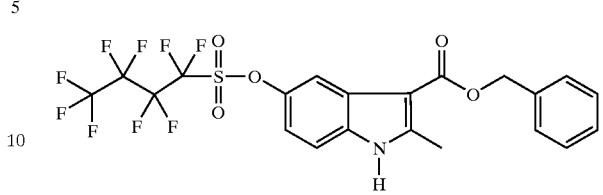

2-Methyl-5-(nonafluorobutane-1-sulfonyloxy)-1H-indole-3-carboxylic acid benzyl ester 2-Methyl-3-benzyloxycarbonyl-5-hydroxyindole (5.90 g, 21.0 mmol, 1 eq) was suspended in dry $CH_2Cl_2$ (100 mL) and dry DMF (2 mL) under Ar. Triethylamine (8.77 mL, 63 mmol, 3 eq) was added followed by the addition of perfluorobutanesulfonyl fluoride (4.2 mL, 23.4 mmol, 1.1 eq). The reaction mixture was stirred at room temperature and followed by TLC ($CH_2Cl_2$/MeOH 98/2). After 18 hours, the reaction was quenched with aqueous hydrochloric acid. The organic phase was washed with water (2×) and the combined aqueous phases extracted with $CH_2Cl_2$. The combined organic extracts were washed with brine and dried over $Na_2SO_4$. After removing the solvent, the residue was loaded on silica gel and chromatographed eluting with methanol/$CH_2Cl_2$(98/2). 10.17 g (86% yield) of the indole-nonaflate was obtained as a white solid.

Step B

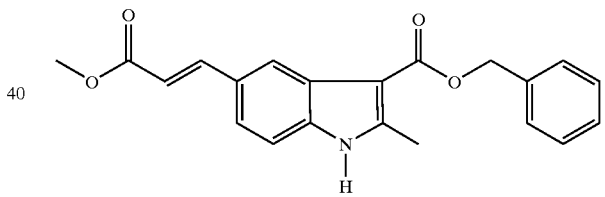

5-((E)Methoxcarbonyl-vinyl)-2-methyl-1H-indole-3-carboxylic acid benzyl ester

2-Methyl-5-(nonafluorobutane-1-sulfonyloxy)-1H-indole-3-carboxylic acid benzyl ester (1.22 g, 2.16 mmol, 1 eq) was suspended in dry DMF (5 mL) under Ar. Triethylamine (0.7 mL, 5.0 mmol, 2.2 eq) was added followed by the addition of methyl acrylate (0.45 mL, 5.0 mmol, 2.2 eq), palladium (II) acetate (0.022 g, 0.10 mmol, 5 mol %), and diphenylphosphinopropane (0.071 g, 0.17 mmol, 8 mol %). The reaction mixture was stirred at 80° C. and followed by TLC (hexane/ethyl acetate 3:2). After 18 hours, the reaction was quenched with aqueous hydrochloric acid and extracted with ethyl acetate (3×). The organic phase was washed with water (2×) and the combined aqueous phases extracted with ethyl acetate. The combined organic extracts were washed with brine and dried over $Na_2SO_4$. After removing the solvent, the residue was loaded on silica gel and chromatographed, eluting with hexane/ethyl acetate (3/2). 0.602 g (80% yield) of the indole-acrylate was obtained as a white solid.

Step C

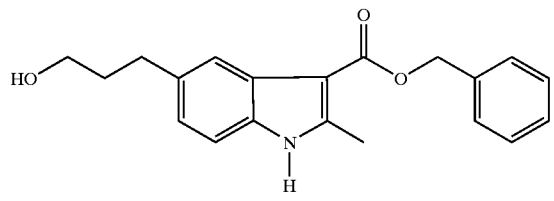

5-(3-Hydroxy-propyl)-2-methyl-1H-indole-3-carboxylic acid benzyl ester 5-((E)-2-Methoxycarbonyl-vinyl)-2-methyl-1H-indole-3-carboxylic acid benzyl ester (0.200 g, 0.573 mmol, 1 eq) was suspended in dry THF (10 mL) under Ar. Methanol (0.116 mL, 2.87 mmol, 5.0 eq) was added followed by cooling to 4° C. and the addition of lithium borohydride (1.40 mL of 2 M, 2.87 mmol, 5.0 eq). The reaction mixture was stirred and allowed to warm to room temperature, then heated to reflux. The reaction was followed by TLC ($CH_2Cl_2$/MeOH 9/1). After 24 hours, the reaction was quenched with brine and extracted with ethyl acetate (3x). The combined organic extracts were washed with brine and dried over $Na_2SO_4$. After removing the solvent, the residue was loaded on silica gel and chromatographed, eluting with $CH_2Cl_2$/MeOH 9/1. 0.149 g (81% yield) of the indole-propanol was obtained as a white solid, with some contamination by the E-allylic alcohol (20%–30%).

Step D 5-((E)-2-Methoxycarbonyl-vinyl)-2-methyl-1H-indole-3-carboxylic acid benzyl ester (0.200 g, 0.573 mmol, 1 eq) was suspended in dry THF (10 mL) under Ar. Methanol (0.116 mL, 2.87 mmol, 5.0 eq) was added followed by cooling to 4° C. and the addition of lithium borohydride (1.40 mL of 2 M, 2.87 mmol, 5.0 eq). The reaction mixture was stirred and allowed to warm to room temperature, then heated to reflux. The reaction was followed by TLC ($CH_2Cl_2$/MeOH 9/1). After 24 hours, the reaction was quenched with brine and extracted with ethyl acetate (3x). The combined organic extracts were washed with brine and dried over $Na_2SO_4$. After removing the solvent, the residue was loaded on silica gel and chromatographed, eluting with $CH_2Cl_2$/MeOH 9/1. 0.149 g (81% yield) of the indole-propanol was obtained as a white solid, with some contamination by the E-allylic alcohol (20%–30%).

The crude mesylate ester (0.168 g, 0.430 mmol, 1 eq) was suspended in dry acetonitrile (5 mL) under Ar. Potassium carbonate (0.110 g, 0.8 mmol, 2.0 eq) was added followed by the addition of diethylamine (0.083 mL, 0.8 mmol, 2.0 eq) and catalytic potassium iodide. The reaction mixture was stirred and heated to reflux. The reaction was followed by TLC (ethyl acetate/methanol/triethylamine 87/10/3). After 18 hours, the reaction was quenched with aqueous sodium bicarbonate and extracted with ethyl acetate (3x). The combined organic extracts were washed with brine and dried over $Na_2SO_4$. After removing the solvent, the residue was loaded on silica gel and chromatographed, eluting with ethyl acetate/methanol/triethylamine 87/10/3. 0.040 g (40% yield) of the indole-propylamine was obtained as a white solid, and converted to the .HCl salt: LC/MS (ESI+) 380 (M+1), Anal. ($C_{24}H_{30}N_2O_2 \cdot HCl \cdot 0.7H_2O$) C, H, N.

Example 53

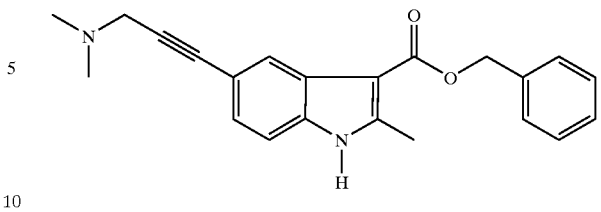

5-(3-Dimethylamino-prop-1-ynyl)-2-methyl-1H-indole-3-carboxylic acid benzyl ester 2-Methyl-5-(nonafluorobutane-1-sulfonyloxy)-1H-indole-3-carboxylic acid benzyl ester (0.480 g, 0.85 mmol, 1 eq, Example 52, Step A) was dissolved in dry THF (10 mL) under Ar. Triethylamine (0.223 mL, 1.6 mmol, 2.0 eq) was added followed by the addition of copper (1) iodide (0.008 g, 0.04 mmol, 5 mol %), dichloropalladium (II) bis-diphenylphosphinoferrocene (0.016 g, 0.02 mmol, 2 mol %), and N,N-dimethylpropargylamine (0.184 mL, 1.6 mmol, 2 eq). The reaction mixture was stirred at 80° C. and followed by TLC (ethyl acetate/methanol/triethylamine 87/10/3). After 48 hours, the reaction was loaded on silica gel and chromatographed, (ethyl acetate/methanol/triethylamine 87/10/3). The resulting product was contaminated with bis-alkyne side product, and was further purified using reverse-phase prep-HPLC 10%–1 00% Acetonitrile/water, 0.1% TFA. 0.070 g (18% yield) of the indole-amine was obtained as a brown semisolid: LC/MS (ESI+) 347 (M+1).

Example 54

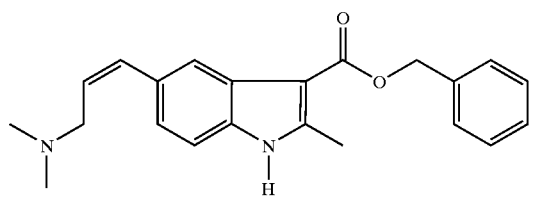

5-((Z)-3-Dimethylamino-propenyl)-2-methyl-1H-indole-3-carboxylic acid benzyl ester 5-(3-Dimethylamino-prop-1-ynyl)-2-methyl-1H-indole-3-carboxylic acid benzyl ester (0.160 g, 0.428 mmol, 1 eq, Example 53) was dissolved in ethanol (30 mL). Lindlar's catalyst (0.05 mg) was added, and the reaction was hydrogenated at room temperature under a hydrogen atmosphere, 35 PSI. The reaction mixture was shaken at room temperature and followed by LC-MS. After one week, the reaction was loaded on silica gel and chromatographed, (ethyl acetate/methanol/triethylamine 87/10/3). The resulting indole-alkene product (0.019 g, 12%) was converted to the —HCl salt, obtained as a brown semisolid: LC/MS (ESI+) 377 (M+1), Anal. ($C_{24}H_{28}N_2O_2 \cdot HCl \cdot 1.0H_2O$) C, H, N.

Example 55

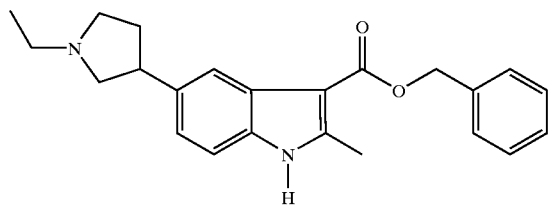

5-(1-Ethyl-pyrrolidin-3-yl)-2-methyl-1H-indole-3-carboxylic acid benzyl ester

Step A

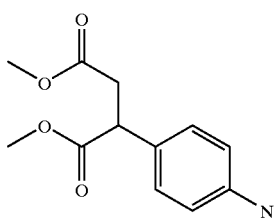

2-(4-amino-phenyl)-succinic acid dimethyl ester 2-(4-aminophenyl)-succinic acid (2.30 g, 11.0 mmol, 1 eq) was dissolved in methanol (30 mL). Thionyl chloride (2.4 mL, 33 mmol, 3 eq) was added, and the reaction was stirred at room temperature. The reaction mixture was followed by TLC ($CH_2Cl_2$/MeOH 9/1). After 7 hours, the reaction was quenched with aqueous sodium bicarbonate and extracted several times with ethyl acetate. The combined organic layers were dried over sodium sulfate, loaded on silica gel and chromatographed, ($CH_2Cl_2$/MeOH 9/1). 2.6 g (93% yield) of the resulting bis-methyl ester product was obtained as a red solid.

Step B

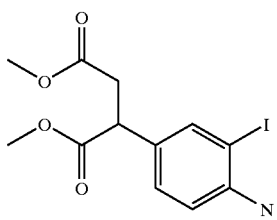

2-(4-Amino-3-iodo-phenyl)-succinic acid dimethyl ester 2-(4-amino-phenyl)-succinic acid dimethyl ester (2.40 g, 10.0 mmol, 1 eq) was dissolved in ethanol (50 mL). Iodine (2.54 g, 10 mmol, 1 eq) was added, followed by silver sulfate (3.12 g, 10 mmol, 1 eq). The reaction was stirred at room temperature and followed by TLC (hexane/ethyl acetate 3/2). After 1.5 hours, the reaction was loaded on silica gel and chromatographed, (hexane/ethyl acetate 3/2). 2.0 g (55% yield) of the resulting bis-methyl ester iodide product was obtained as a red oil.

Step C

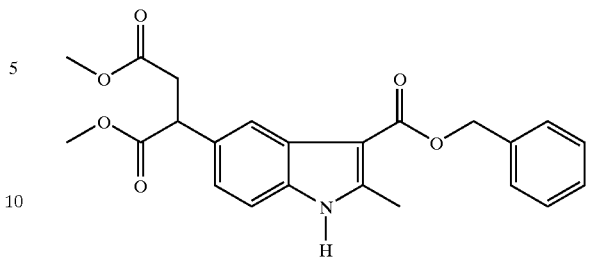

2-(3-benzyloxycarbonyl-2-methyl-1-indol-5-yl)-succinic acid dimethyl ester 2-(4-Amino-3-iodo-phenyl)-succinic acid dimethyl ester (2.00 g, 5.00 mmol, 1 eq) was dissolved in dry benzene (50 mL). benzyl acetoacetate (0.952 mL, 5.5 mmol, 1 eq) was added, followed by toluenesulfonic acid monohydrate (0.048 g, 0.25 mmol, 5 mol %). The reaction was heated to reflux with removal of water by a Dean-Stark apparatus. After 16 hours, the reaction was concentrated in vacuo. The resulting amino-crotonate, a red oil, was carried on to the next step.

The crude aminocrotonate (5.00 mmol theoretical, 1 eq) was dissolved in dry DMF (5 mL) under Ar. Tri-n-propylamine (1.25 mL, 6.6 mmol, 1.2 eq) was added followed by the addition of palladium (II) acetate (0.112 g, 0.5 mmol, 10 mol %). The reaction mixture was stirred at 80° C. and followed by TLC (hexane/ethyl acetate 2/3). After 2 hours, the reaction was quenched with aqueous brine and extracted several times with ethyl acetate. The combined organic layers were dried over sodium sulfate, loaded on silica gel and chromatographed, (hexane/ethyl acetate 2/3). 1.01 g (48% yield) of the resulting bis-methyl ester indole product was obtained as a brown oil.

Step D

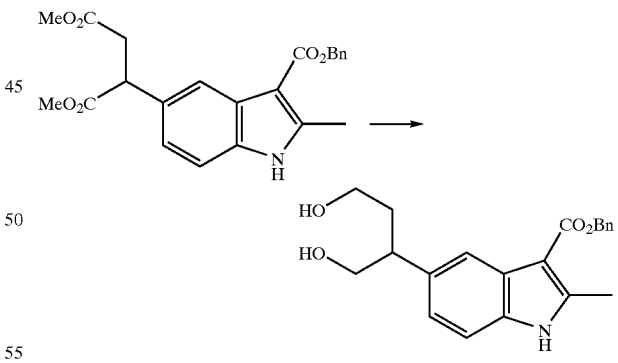

5-(3-Hydroxy-1-hydroxymethyl-propyl)-2-methyl-1H-indole-3-carboxylic acid benzyl ester 2-(3-Benzyloxycarbonyl-2-methyl-1-indol-5-yl)-succinic acid dimethyl ester (0.300 g, 0.779 mmol, 1 eq) was suspended in dry THF (20 mL) under Ar. Methanol (0.316 mL, 7.8 mmol, 10.0 eq) was added followed by cooling to 4° C. and the addition of lithium borohydride (3.9 mL of 2 M, 7.8 mmol, 10.0 eq). The reaction mixture was stirred and allowed to warm to room temperature, then heated to reflux.

The reaction was followed by TLC (CH$_2$Cl$_2$/MeOH 9/1). After 24 hours, the reaction was quenched with brine and extracted with ethyl acetate (3×). The combined organic extracts were washed with brine and dried over Na$_2$SO$_4$. After removing the solvent, the residue was loaded on silica gel and chromatographed, eluting with CH$_2$Cl$_2$/MeOH 9/1. 0.185 g (72% yield) of the indole-diol was obtained as a colorless oil.

Step E 5-(3-Hydroxy-1-hydroxymethyl-propyl)-2-methyl-1H-indole-3-carboxylic acid benzyl ester (0.180 g, 0.547 mmol, 1 eq) was suspended in dry THF (5 mL) under Ar. Triethylamine (0.307 mL, 2.2 mmol, 4 eq) was added followed by the addition of methanesulfonyl chloride (0.088 mL, 0.1.09 mmol, 2.0 eq). The reaction mixture was stirred at room temperature. The reaction was followed by TLC (CH$_2$Cl$_2$/MeOH 9/1). After 4 hours, the reaction was quenched with brine and extracted with ethyl acetate (3×). The combined organic extracts were washed with brine and dried over Na$_2$SO$_4$. After removing the solvent, the crude residue was collected. 0.272 g of the indole-bis-mesylate was obtained as a colorless oil. This was carried on crude to the next step.

The crude bis-mesylate (0.272 g, 0.547 mmol, 1 eq) was suspended in dry acetonitrile (20 mL). Potassium carbonate (0.138 g, 1.0 mmol, 2 eq) was added followed by the addition of ethylamine (0.100 mL, 2.0 mmol, 4.0 eq) and catalytic potassium iodide. The reaction mixture was stirred and heated to 80° C. in a sealed tube. The reaction was followed by TLC (ethyl acetate/methanol/triethylamine 87/10/3). After 24 hours, the reaction was quenched with aqueous sodium bicarbonate and extracted with ethyl acetate (3×). The combined organic extracts were washed with brine and dried over Na$_2$SO$_4$. After removing the solvent, the residue was loaded on silica gel and chromatographed, eluting with ethyl acetate/methanol/triethylamine 87/10/3. 0.132 g (69% yield) of the indole-pyrrolidine was obtained as a white solid, and converted to the .HCl salt: LC/MS (ESI+) 363 (M+1), Anal. (C$_{24}$H$_{30}$N$_2$O$_2$.HCl.0.5H$_2$O) C, H, N.

Example 56

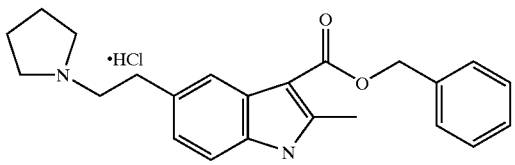

2-Methyl-5-(2-pyrrolidin-1-yl-ethyl)-1H-indole-3-carboxylic acid benzyl ester hydrochloride Step A

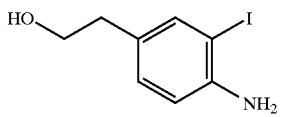

2-(4-amino-3-iodo-phenyl)-ethanol

To a mixture of 4-aminophenethyl alcohol (20 g, 145.8 mmol) and calcium carbonate (18.2 g, 145.8 mmol) in methanol (200 mL) was added iodine (37 g, 182.3 mmol) in portions. The mixture was heated at reflux overnight and then concentrated in vacuo to give a dark brown residue, which was partitioned between ethyl acetate and saturated sodium bisulfite solution. The organic phase was washed with water and brine, dried over Na$_2$SO$_4$ and filtered. The filtrate was concentrated in vacuo to give 14.1 g (37%) of desired product as a light brown syrup. MS(APCI$^+$): m/z 264.1 (MH$^+$). The compound was taken to Step B without further purification.

Step B

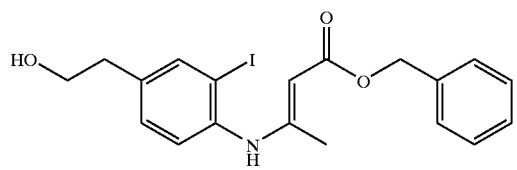

(E)-3-[4-(2-Hydroxy-ethyl)-2-iodo-phenylamino]-but-2-enoic acid benzyl ester

To a solution of 4-amino-3-iodophenethyl alcohol from Step A (10 g, 38 mmol) and benzyl acetoacetate (7.3 g, 38 mmol) in benzene (150 mL) was added p-toluenesulfonic acid (361 mg, 1.9 mmol). The mixture was heated at reflux overnight using a Dean Stark condenser. The mixture was washed with water and brine, dried over Na$_2$SO$_4$ and filtered. The filtrate was concentrated in vacuo to give 16.6 g (99%) of the crude desired product as a light brown oil: MS(APCI$^+$): m/z 438.1 (MH$^+$). The compound was taken to Step C without further purification.

Step C

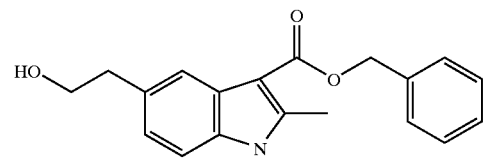

5-(2-Hydroxy-ethyl)-2-methyl-1H-indole-3-carboxylic acid benzyl ester

To a mixture of (E)-3-[4-(2-hydroxy-ethyl)-2-iodo-phenylamino}-but-2-enoic acid benzyl ester (16.6 g, 38 mmol) and tripropylamine (7.2 mL, 38 mmol) in DMF (30 mL) was added palladium acetate (170 mg, 0.76 mmol). The mixture was stirred at 120° C. for 1 hour and then partitioned between ethyl acetate and water. The organic phase was washed with water and brine, dried over Na$_2$SO$_4$ and filtered. The filtrate was concentrated in vacuo to give a residue, which was purified by chromatography (10%–30% ethyl acetate in hexanes) to give 3.0 g (26%) of the desired product as a white solid: mp 170–172° C.; MS(APCI$^+$): m/z 310.4 (MH$^+$); Anal. Calcd for C$_{19}$H$_{19}$N$_1$O$_3$.0.1H$_2$O: C, 73.34; H, 6.22; N, 4.50. Found: C, 73.32; H, 6.37; N, 4.39.

Step D

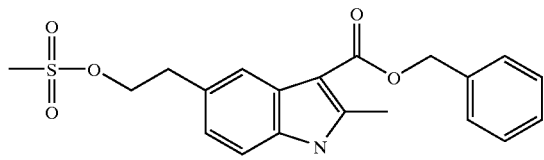

5-(2-Methanesulfonyloxy-ethyl)-2-methyl-1H-indole-3-carboxylic acid benzyl ester To a mixture of 5-(2-hydroxy-ethyl)-2-methyl-1H-indole-3-carboxylic acid benzyl ester (1.02 g, 3.3 mmol) and triethylamine (0.92 mL, 6.6 mmol) in dry THF (10 mL) was added methanesulfonyl chloride (0.26 mL, 3.3 mmol) under nitrogen atmosphere at room temperature. The mixture was stirred at room temperature for 3 hours and then partitioned between ethyl acetate and water. The organic phase was washed with water and brine, dried over $Na_2SO_4$ and filtered. The filtrate was concentrated in vacuo to give 1.27 g (99%) of the desired product as a white solid: mp 122–124° C.; MS(APCI$^-$): m/z 386.0 (M−H); Anal. Calcd for $C_{20}H_{21}N_1O_5S_1$: C, 62.00; H, 5.46; N, 3.62; S, 8.28. Found: C, 61.95; H, 5.61; N, 3.54; S, 8.32.

Step E

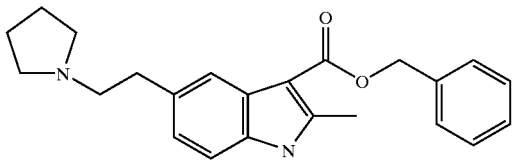

2-Methyl-5-(2-pyrrolidin-1-yl-ethyl)-1H-indole-3-carboxylic acid benzyl ester

To a solution of 5-(2-methanesulfonyloxy-ethyl)-2-methyl-1H-indole-3-carboxylic acid benzyl ester (100 mg, 0.26 mmol) in dioxane (5 mL) was added pyrrolidine (0.2 mL, 2.6 mmol). The mixture was stirred at 70° C. for 1 hour and then was concentrated in vacuo to give a residue, which was purified by chromatography (5%–15% methanol in methylene chloride) to give 85 mg (91%) of the desired product as a thick oil: MS(APCI$^+$): m/z 363.2 (MH$^+$).

Step F

To a solution of 2-methyl-5-(2-pyrrolidin-1-yl-ethyl)-1H-indole-3-carboxylic acid benzyl ester (70 mg, 0.19 mmol) in methylene chloride (1 mL) was added hydrogen chloride in diethyl ether. The resulting mixture was concentrated in vacuo and triturated with diethyl ether to give 61 mg (79%) of titled compound as a white foam: mp 76–78° C.; Anal. Calcd for $C_{23}H_{27}Cl_1N_2O_2 \cdot 2.9H_2O$: C, 61.23; H, 7.33; N, 6.21. Found: C, 60.83; H, 6.93; N, 5.92.

Example 57

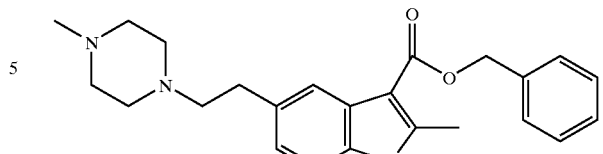

2-Methyl-5-[2-(4-methyl-piperazin-1-yl)-ethyl]-1H-indole-3-carboxylic acid benzyl ester To a solution of 5-(2-methanesulfonyloxy-ethyl)-2-methyl-1H-indole-3-carboxylic acid benzyl ester (424 mg, 1.1 mmol, Example 56, Step D) in dioxane (10 mL) was added 1-methylpiperazine (0.6 mL, 5.5 mmol). The mixture was stirred at 70° C. overnight and then partitioned between methylene chloride and water. The organic phase was washed with water and brine, dried over $Na_2SO_4$ and filtered. The filtrate was concentrated in vacuo to give a solid residue, which was recrystallized from ethyl acetate to give 191 mg (45%) of the desired product as a white solid: mp 167–168° C.; MS(APCI$^+$): m/z 392.3 (MH$^+$); Anal. Calcd for $C_{24}H_{29}N_3O_2 \cdot 0.5H_2O$: C, 71.97; H, 7.55; N, 10.49. Found: C, 72.35; H, 7.54; N, 10.12.

Example 58

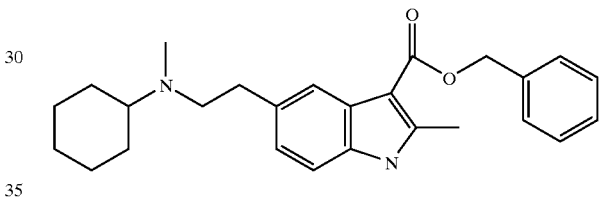

5-[2-(Cyclohexyl-methyl-amino)-ethyl]-2-methyl-1H-indole-3-carboxylic acid benzyl ester To a solution of 5-(2-methanesulfonyloxy-ethyl)-2-methyl-1H-indole-3-carboxylic acid benzyl ester (400 mg, 1.03 mmol, Example 56, Step D) in dioxane (10 mL) was added N-methylcyclohexylamine (1.3 mL, 10.3 mmol). The mixture was stirred at 80° C. overnight and then partitioned between methylene chloride and water. The organic phase was washed with water and brine, dried over $Na_2SO_4$ and filtered. The filtrate was concentrated in vacuo to give a solid residue, which was purified by chromatography (5%–15% methanol in methylene chloride) to give 250 mg (60%) of the desired product as a white solid: mp 122–124° C.; MS(APCI$^+$): m/z 405.2 (MH$^+$); Anal. Calcd for $C_{26}H_{32}N_2O_2 \cdot 0.5H_2O$: C, 75.51; H, 8.04; N, 6.77. Found: C, 75.25; H, 8.04; N, 6.78.

Example 59

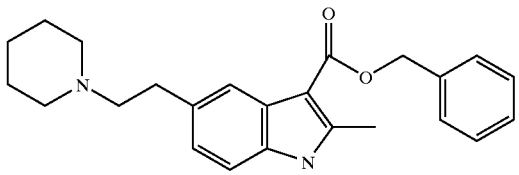

2-Methyl-5-(2-piperidin-1-yl-ethyl)-1H-indole-3-carboxylic acid benzyl ester

To a solution of 5-(2-methanesulfonyloxy-ethyl)-2-methyl-1H-indole-3-carboxylic acid benzyl ester (450 mg, 1.16 mmol, Example 56, Step D) in dioxane (10 mL) was added piperidine (1.1 mL, 11.6 mmol). The mixture was stirred at 80° C. for 2 hours and then partitioned between methylene chloride and water. The organic phase was washed with water and brine, dried over $Na_2SO_4$ and filtered. The filtrate was concentrated in vacuo to give a solid residue, which was recrystallized from ethyl acetate and diethyl ether to give 275 mg (63%) of the desired product as a white solid: mp 159–161° C.; MS(APCI$^+$): m/z 377.1 (MH$^+$); Anal. Calcd for $C_{24}H_{28}N_2O_2 \cdot 1.04H_2O$: C, 72.93; H, 7.67; N, 7.09. Found: C, 72.54; H, 7.31; N, 7.04.

Example 60

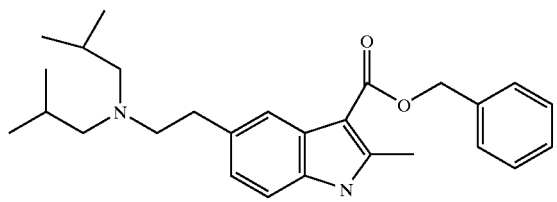

5-(2-Diisobutylamino-ethyl)-2-methyl-1H-indole-3-carboxylic acid benzyl ester

To a solution of 5-(2-methanesulfonyloxy-ethyl)-2-methyl-1H-indole-3-carboxylic acid benzyl ester (360 mg, 0.93 mmol, Example 56, Step D) in dioxane (10 mL) was added diisobutylamine (1.62 mL, 9.3 mmol). The mixture was stirred at 100° C. overnight and then partitioned between methylene chloride and water. The organic phase was washed with water and brine, dried over $Na_2SO_4$ and filtered. The filtrate was concentrated in vacuo to give a solid residue, which was purified by chromatography (20% ethyl acetate in hexanes) to give 303 mg (77%) of the desired product as a white solid: mp 134–135° C.; MS(APCI$^+$): m/z 421.3 (MH$^+$); Anal. Calcd for $C_{27}H_{36}N_2O_2$: C, 77.10; H, 8.63; N, 6.66. Found: C, 76.94; H, 8.75; N, 6.55.

Example 61

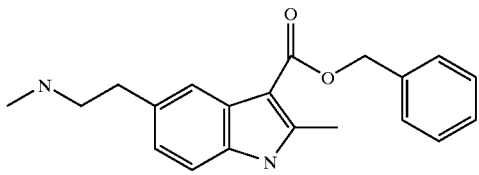

2-Methyl-5-(2-methylamino-ethyl)-1H-indole-3-carboxylic acid benzyl ester

A mixture of 5-(2-methanesulfonyloxy-ethyl)-2-methyl-1H-indole-3-carboxylic acid benzyl ester (500 mg, 1.29 mmol, Example 56, Step D) in 29% methylamine in ethanol solution (6 mL) was stirred at room temperature overnight and then partitioned between methylene chloride and water. The organic phase was washed with water and brine, dried over $Na_2SO_4$ and filtered. The filtrate was concentrated in vacuo to give a residue, which was triturated with diethyl ether to give 410 mg (99%) of the desired product as a white foam: mp 65–68° C.; MS(APCI$^+$): m/z 323.1 (MH$^+$); Anal. Calcd for $C_{20}H_{22}N_2O_2 \cdot 0.5H_2O$: C, 72.48; H, 7.00; N, 8.45. Found: C, 72.21; H, 6.85; N, 8.34.

Example 62

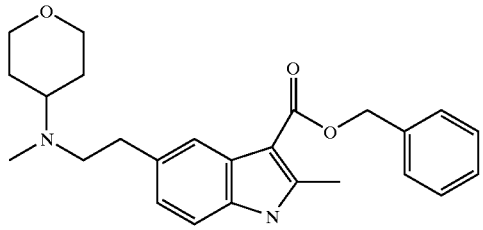

2-Methyl-5-{2-[methyl-(tetrahydro-pyran-4-yl)-amino]-ethyl}-1H-indole-3-carboxylic acid benzyl ester To a mixture of 2-methyl-5-(2-methylamino-ethyl)-1H-indole-3-carboxylic acid benzyl ester (403 mg, 1.25 mmol) and tetrahydro-4H-pyran-4-one (0.115 ML, 1.25 mmol) in dichloroethane (10 mL) was added sodium triacetoxyboro hydride (371 mg, 1.75 mmol) followed by acetic acid (0.071 mL, 1.25 mmol). The mixture was stirred at room temperature under nitrogen atmosphere for 3 hours and then partitioned between ethyl acetate and water. The organic phase was washed with saturated sodium bicarbonate solution and brine, dried over $Na_2SO_4$ and filtered. The filtrate was concentrated in vacuo to give a solid residue, which was purified by chromatography (5% methanol in methylene chloride) to give 270 mg (53%) of the desired product as a white foam: mp 109–11 1° C.; MS(APCI$^+$): m/z 407.2 (MH$^+$); Anal. Calcd for $C_{25}H_{30}N_2O_3 \cdot 0.25H_2O$: C, 73.05; H, 7.48; N, 6.82. Found: C, 72.86; H, 7.59; N, 6.78.

Example 63

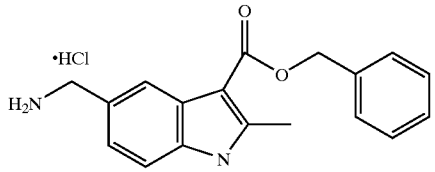

5-Aminomethyl-2-methyl-1H-indole-3-carboxylic acid benzyl ester, hydrochloride

Step A

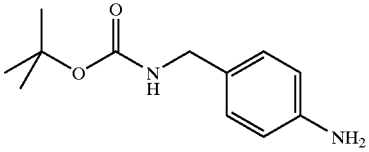

(4-Amino-benzyl)-carbamic acid tert-butyl ester

To a mixture of 4-aminobenzylamine (5 g, 41 mmol) in methanol (200 mL) was added di-tert-butyl dicarbonate (6.3 g, 28.7 mmol) in portions. The mixture was stirred for 0.5 hour and then concentrated in vacuo to give a residue, which was partitioned between ethyl acetate and water. The organic layer was washed with water and brine, dried over $Na_2SO_4$ and filtered. The filtrate was concentrated in vacuo to give 5.3 g (83%) of the desired product as a syrup. MS(APCI$^+$):

m/z 223.1 (MH⁺). The compound was taken to Step B without further purification.

Step B

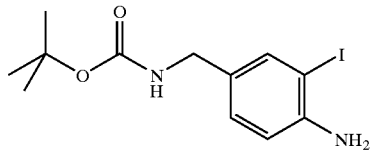

(4-Amino-3-iodo-benzyl)-carbamic acid tert-butyl ester

To a mixture of (4-amino-benzyl)-carbamic acid tert-butyl ester (4.8 g, 21.6 mmol) and calcium carbonate (2.7 g, 27 mmol) in methanol (60 mL) was added iodine (5.5 g, 21.6 mmol) in portions. The mixture was heated at reflux overnight and then concentrated in vacuo to give a dark brown residue, which was partitioned between ethyl acetate and saturated sodium bisulfite solution. The organic phase was washed with water and brine, dried over $Na_2SO_4$ and filtered. The filtrate was concentrated in vacuo to give a residue, which was purified by chromatography (5%–20% ethyl acetate in hexanes) to give 3.5 g (47%) of the desired product as a brown semi-solid. MS(APCI⁺): m/z 349.1 (MH⁺).

Step C

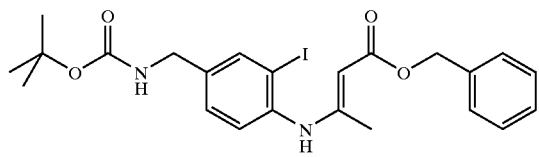

(E)-3-[4-(tert-Butoxycarbonylamino-methyl)-2-iodo-phenylamino]-but-2-enoic acid benzyl ester To a solution of (4-amino-3-iodo-benzyl)-carbamic acid tert-butyl ester (3.5 g, 10 mmol) and benzyl acetoacetate (1.92 g, 10 mmol) in benzene (80 mL) was added p-toluenesulfonic acid (95 mg, 0.5 mmol). The mixture was heated at reflux overnight using a Dean Stark condenser. The mixture was washed with water and brine, dried over $Na_2SO_4$ and filtered. The filtrate was concentrated in vacuo to give 5.25 g (99%) of crude desired product as a light brown oil: MS(APCI⁺): m/z 523.1 (MH⁺). The compound was taken to Step D without further purification.

Step D

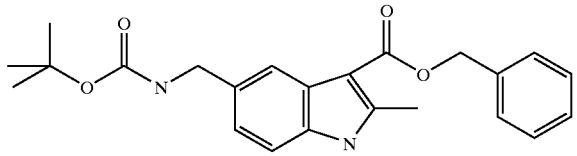

5-(tert-Butoxycarbonylamino-methyl)-2-methyl-1H-indole-3-carboxylic acid benzyl ester To a mixture of (E)-3-[4-(tert-butoxycarbonylamino-methyl)-2-iodo-phenylamino]-but-2-enoic acid benzyl ester (5.25 g, 10 mmol) and tripropylamine (1.9 mL, 10 mmol) in DMF (10 mL) was added palladium acetate (112 mg, 0.5 mmol). The mixture was stirred at 120° C. for 1 hour and then partitioned between ethyl acetate and water. The organic phase was washed with water and brine, dried over $Na_2SO_4$ and filtered. The filtrate was concentrated in vacuo to give a residue, which was recrystallized from ethyl acetate and hexanes to give 1.9 g (48%) of the desired product as a yellowish solid: MS(APCI⁻): m/z 393.1.4 (M–H).

Step E

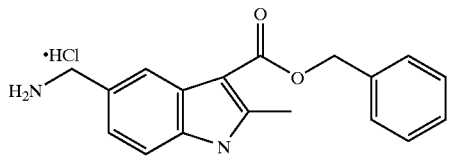

5-Aminomethyl-2-methyl-1H-indole-3-carboxylic acid benzyl ester, hydrochloride

To a solution of 5-(tert-butoxycarbonylamino-methyl)-2-methyl-1H-indole-3-carboxylic acid benzyl ester (1.8 g, 4.6 mmol) in methylene chloride (10 μL) was added 4 M hydrogen chloride in dioxane (1.2 mL, 4.8 mmol). The mixture was stirred at room temperature for 1 hour and the formed solid was then filtered. The product was further purified by recrystallization (ethanol and methylene chloride) to give 950 mg (63%) of titled product as a beige solid: mp 260–261° C.; MS(APCI⁻): m/z 293.1 (M–H); Anal. Calcd for $C_{18}H_{18}N_2O_2 \cdot 1.06HCl$: C, 64.92; H, 5.77; N, 8.41; Cl, 11.29. Found: C, 64.58; H, 5.79; N, 8.31; Cl, 11.38.

Example 64

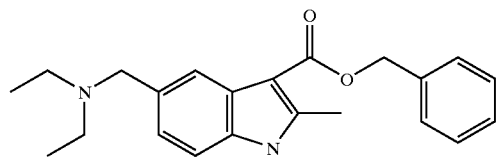

5-Diethylaminomethyl-2-methyl-1H-indole-3-carboxylic acid benzyl ester

To a mixture of 5-aminomethyl-2-methyl-1H-indole-3-carboxylic acid benzyl ester, hydrochloride (300 mg, 0.91 mmol, Example 63, Step E) and in dichloroethane (40 mL) was added acetaldehyde (0.1 mL, 1.82 mmol). The mixture was stirred for 0.5 hour and then sodium triacetoxyborohydride (289 mg, 1.37 mmol) was added. The mixture was stirred at room temperature overnight and then partitioned between methylene chloride and water. The organic phase was washed with saturated sodium bicarbonate solution and brine, dried over $Na_2SO_4$, and filtered. The filtrate was concentrated in vacuo to give a solid residue, which was purified by chromatography (5%–15% methanol in methylene chloride) to give 107 mg (34%) of the desired product as a white solid: mp 106–108° C.; MS(APCI⁺): m/z 351.1 (MH⁺); Anal. Calcd for $C_{22}H_{26}N_2O_2 \cdot 0.25H_2O$: C, 74.44; H, 7.52; N, 7.89. Found: C, 74.30; H, 7.51; N, 7.79.

Example 65

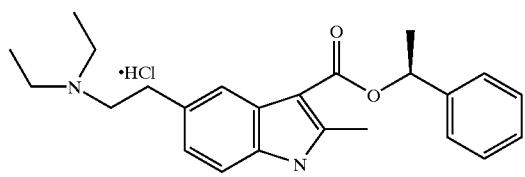

5-(2-Diethylamino-ethyl)-2-methyl-1H-indole-3-carboxylic acid (S)-1-phenyl-ethyl ester, hydrochloride

Step A

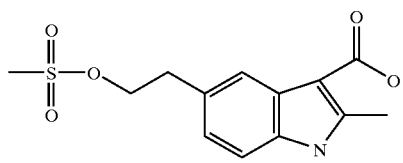

5-(2-Methanesulfonyloxy-ethyl)-2-methyl-1H-indole-3-caboxylic acid

To a solution of 5-(2-methanesulfonyloxy-ethyl)-2-methyl-1H-indole-3-carboxylic acid benzyl ester (1.22 g, 3.15 mmol, Example 56, Step D) in dry THF (10 mL) was added 20% palladium on carbon (1 g). The mixture was stirred under hydrogen atmosphere at room temperature overnight. The TLC showed the reaction was complete. The mixture was filtered and the filtrate was concentrated in vacuo to give a residue, which was purified by chromatography (50%–100% ethyl acetate in hexanes) to give 450 mg (48%) of the desired product as a white solid: mp 157–158° C.; MS(APCI⁻): m/z 296.0 (M–H).

Step B

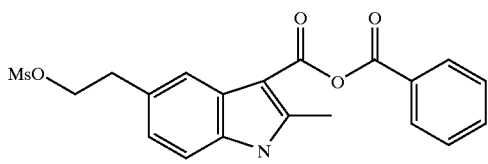

To a mixture of 5-(2-methanesulfonyloxy-ethyl)-2-methyl-1H-indole-3-caboxylic acid (285 mg, 0.96 mmol) and triethylamine (0.134 mL, 0.96 mmol) in dry THF (10 mL) was added benzoyl chloride (0.11 mL, 0.96 mmol). The mixture was stirred under nitrogen atmosphere at room temperature for 3 hours. The mixture was filtered and the filtrate was concentrated in vacuo to give a residue, which was triturated with diethyl ether to give 310 mg (81%) of the desired product as a off-white foam: MS(APCI⁻): m/z 400.0 (M–H).

Step C

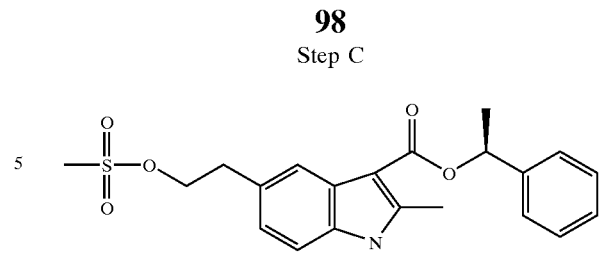

5-(2-Methanesulfonyloxy-ethyl)-2-methyl-1H-indole-3-carboxylic acid (S)-1-phenyl-ethyl ester A mixture of the mixed anhydride from Step B (290 mg, 0.72 mmol) and S(–)-1-phenylethanol (0.33 mL, 2.88 mmol) was heated at 150° C. for 2 minutes. The mixture was partitioned between ethyl acetate and water. The organic phase was washed with saturated sodium bicarbonate solution and brine, dried over Na₂SO₄, and filtered. The filtrate was concentrated in vacuo to give a solid residue, which was purified by chromatography (20%–50% ethyl acetate in hexanes) to give 140 mg (48%) of the desired product as a off-white foam: MS(APCI⁻): m/z 400.0 (M–H).

Step D

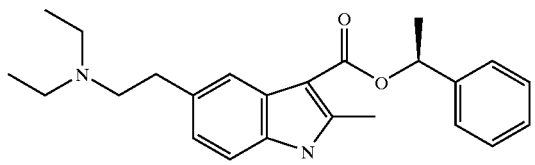

5-(2-Diethylamino-ethyl)-2-methyl-1H-indole-3-carboxylic acid (S)-1-phenyl-ethyl ester A solution of 67072×116 from Step C (118 mg, 0.29 mmol) and diethylamine (0.3 mL, 2.9 mmol) in dioxane (5 mL) was stirred at 60° C. for 2 days. The mixture was partitioned between ethyl acetate and water. The organic phase was washed with saturated sodium bicarbonate solution and brine, dried over Na₂SO₄, and filtered. The filtrate was concentrated in vacuo to give a residue, which was purified by chromatography (10%–25% methanol in methylene chloride) to give 78 mg (70%) of the desired product as a syrup: MS(APCI⁺): m/z 379.1 (MH⁺).

Step E

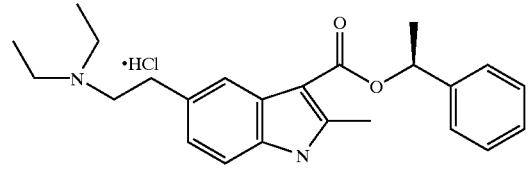

To a solution of 67072×117 from Step D (65 mg, 0.17 mmol) in diethyl ether (2 mL) was added 4 M hydrogen chloride in dioxane (0.1 mL, 0.4 mmol). The resulting mixture was concentrated in vacuo and triturated with diethyl ether to give 68 mg (96%) of titled compound as a white foam: mp 95–97° C.; Anal. Calcd for $C_{24}H_{31}Cl_1N_2O_2 \cdot 0.6H_2O$: C, 67.70; H, 7.62; N, 6.58; Cl, 8.33. Found: C, 67.58; H, 7.77; N, 6.41; Cl, 8.38.

Example 66

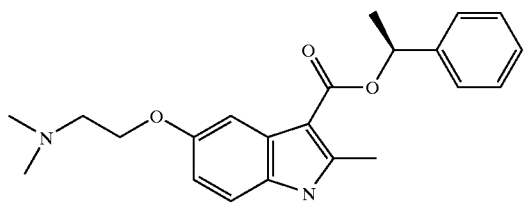

5-(2-Dimethylamino-ethoxy)-2-methyl-1H-indole-3-carboxylic acid (S)-1-phenyl-ethyl ester

Step A

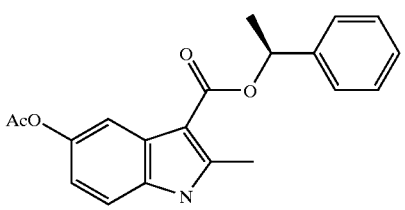

5-Acetoxy-2-methyl-1H-indole-3-carboxylic acid (S)-1-phenyl-ethyl ester Compound 66291X52 (23.1 mmol, 7.80 g) was mixed with (S)-1-phenyl-ethanol (69.4 mmol, 8.48 g) and stirred for approximately 10 minutes at 150° C. The mixture was then cooled to rt and ethyl acetate (125 mL) was added. The resulting solution was then washed with NaHCO₃ and brine. The organic layer was then dried on Na₂SO₄ and concentrated in vacuo to give an oil which was purified on SiO₂ (30% EtOAc/hexane) to give 4.58 g (58.7%) of a white solid. 5-acetoxy-2-methyl-1H-indole-3-carboxylic acid (S)-1-phenyl-ethyl ester. ¹HNMR (400 MHz, DMSO-d₆): δ 1.56 (d, J=6.40 Hz, 3H,CH₃), 2.23 (s, 3H, CH₃CO), 2.63 (s, 3H, Ar—CH₃), 6.00 (q, J=7.20 Hz, 1H), 6.84 (dd, J=8.80 Hz, J=2.45 Hz, 1H), 7.26 (d, J=7.60 Hz, 1H), 7.36 (m, 5H), 7.58 (d, 1H, J=2.20 Hz), 11.93 (s, 1H, N—H); MS (APCI—) m/z 336.1 (M−1). Anal. Calcd for $C_{20}H_{19}NO_4 \cdot 0.20 C_4H_8O_2$: C, 70.37; H, 5.85; N, 3.95. Found: C, 70.86: H, 5.62: N, 3.97. IR(KBr): 3322, 1755, 1692, 1669, 1483, 1457, 1216, 1200, 1152 cm⁻¹.

Step B

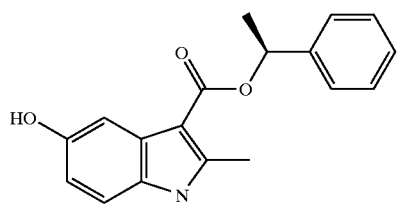

5-Hydroxy-2-methyl-1H-indole-3-carboxylic acid (S)-1-phenyl-ethyl ester

5-Acetoxy-2-methyl-1H-indole-3-carboxylic acid (S)-1-phenyl-ethyl ester (13.2 mmol, 4.46 g) was added to a solution of sodium methoxide in methanol (52.9 mmol, 2.85 g) and stirred at room temperature. After 90 minutes the reaction was stopped by acidification to pH=1 by the dropwise addition of 1.4 M HCl (40 mL). The resulting solution was extracted with ethyl acetate (2×200 mL). The combined organic layers were washed with deionized water, 5% NaHCO₃ and brine, then dried on sodium sulfate to give 4.7 g of an oil which was purified on SiO₂ (hexane/EtOAc) to afford 5-hydroxy-2-methyl-1H-indole-3-carboxylic acid (S)-1-phenyl-ethyl ester (3.06 g, 78.3%). ¹HNMR (400 MHz, DMSO-d₆): δ 1.56 (d, J=6.35 Hz, 3H, CH₃), 2.56 (s, 3H, Ar—CH₃), 3.98 (m, 1H), 6.00 (q, J=6.35 Hz, 1H), 6.57 (d, J=8.50 Hz, 1H), 7.10 (d, J=8.55 Hz, 1H), 7.23–7.42 (m, 5H), 8.85 (s, 1H), 11.54 (s, 1H, N—H);MS(APCI⁻)m/z294 (M−1);IR(KBr):3313, 1646,1460, 1218, 1201, 1164 cm⁻¹.

Step C

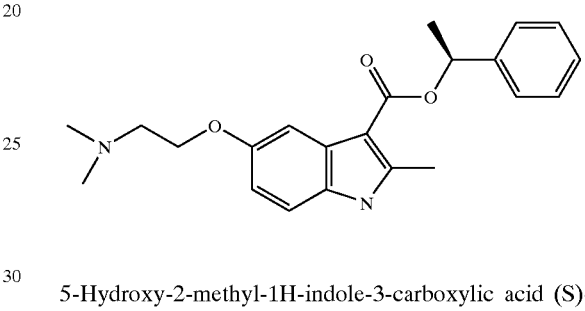

5-Hydroxy-2-methyl-1H-indole-3-carboxylic acid (S)-1-phenyl-ethyl ester (0.50 g, 1.69 mmol), K₂CO₃ (0.58 g, 4.23 mmol), KI 0.028 g, 0.169 mmol) and N,N'-dimethylchloroethylamine hydrochloride were mixed together in MEK (50 mL) and refluxed (73° C.) for 24 hours. The reaction was then permitted to cool whereupon the mixture was diluted with EtOAc. The solution was then washed with deionized water and brine, dried on anhydrous Na₂SO₄, and filtered. The solution was concentrated to dryness and the chromatographed (10% MeOH, CH₂Cl₂) to give 0.260 g (42%) of PD 0224371-0000 mp 135–140° C. ¹HNMR (400 MHz, DMSO-d₆): δ 1.58 (d, J=6.59 Hz, 3H,CH₃), 2.20 (s, 6H), 2.59–2.62 (m, 5H), 3.95 (m, 2H, OCH₂), 6.00 (q, J=6.35 Hz, 1H), 6.57 (dd, J=9.35 Hz, J=3.00 Hz, 1H), 7.19 (d, J=8.65 Hz, 1H), 7.24–7.45 (m, 6H, ArH), 11.69 (s, 1H, N—H); MS (APCI⁻)m/z 365.1 (M−1). Anal. Calcd for $C_{22}H_{26}N_2O_3 \cdot 0.1$ MeOH: C, 71.81; H, 7.20; N, 7.58. Found: C, 71.42: H, 7.26: N, 7.57. IR (KBr): 2976, 2951, 2772, 1678, 1455, 1170, 1079 cm⁻¹.

Example 67

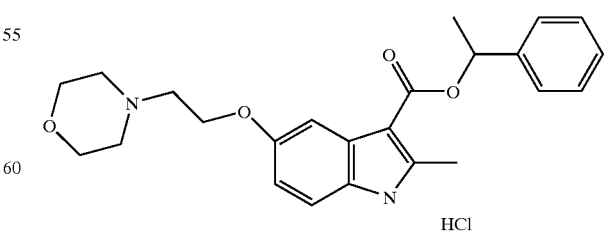

2-Methyl-5-(2-morpholin-4-yl-ethoxy)-1H-indole-3-carboxylic acid 1-phenyl ethyl ester hydrochloride

Step A

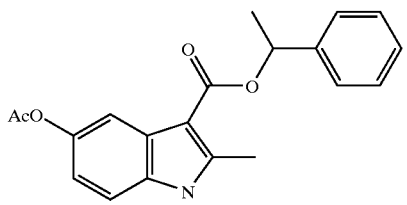

5-Acetoxy-2-methyl-1H-indole-3-carboxylic acid-1-phenyl ethyl ester

The mixed anhydride (10 g, 29.6 mmol) was mixed with α-methylphenylmethanol (14.4 g, 0.118 mmol) and stirred at 150° C. for 10 minutes. Then resulting mixture was then permitted to cool and was then diluted with ethyl acetate and washed with NaHCO$_3$ and brine. The organic layer was then concentrated in vacuo and the crude material was chromatographed (30% EtOAc/hexanes) to afford 5.5 g (62%) of 5-acetoxy-2-methyl-1H-indole-3-carboxylic acid-1-phenyl ethyl ester. $^1$HNMR(400 MHz, DMSO): δ 1.56 (d, J=6.59 Hz, 3H,CH$_3$),2.23 (s, 3H, COCH$_3$), 2.63 (s, 3H, ArCH$_3$), 6.00 (q, J=6.59 Hz, 1H), 6.83 (dd, J=8.55 Hz, J=2.20 Hz, 1H), 7.23–7.46 (m, 7H, ArH), 7.58 (d, J=2.20 Hz, H),11.93 (s, 1H, N—H); MS(APCI$^-$) m/z 336.1(M−1).

Step B

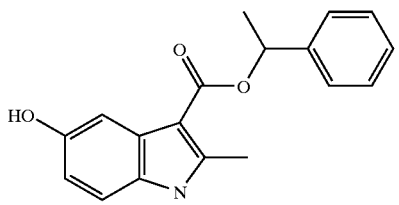

5-Hydroxy-2-methyl-1H-indole-3-carboxylic acid 1-phenyl ethyl ester

5-Acetoxy-2-methyl-1H-indole-3-carboxylic acid-1-phenyl ethyl ester (16.3 mmol, 5.49 g) was added into sodium methoxide in methanol (65.1 mmol, 3.52 g) and stirred at room temperature for 1 hour. The reaction was monitored by TLC (30% EtOAc/hexanes). The mixture was then acidified to pH=1 by the slow, dropwise addition of 1.4 M HCl (40 mL). The resulting solution was extracted with ethyl acetate (2×200 mL) and the combined organic layers washed with deionized water, 5% NaHCO$_3$ and brine and dried on sodium sulfate. Purification on SiO$_2$ gave 4.7 g (97%) of 5-hydroxy-2-methyl-1H-indole-3-carboxxylic acid 1-phenyl ethyl ester. $^1$HNMR(400 MHz, DMSO): δ 1.56 (d, J=6.59 Hz, 3H,CH$_3$), 2.55 (s, 3H, ArCH$_3$), 6.00 (q, J=6.35 Hz, 1H), 6.56 (d, J=8.55 Hz, 1H), 7.09 (d, J=8.31 Hz,1H), 7.22–7.42 (m, 5H, ArH), 8.84 (s, H),11.69 (s, 1H, N—H); MS(APCI$^+$) m/z 294.1 (M−1)

Step C

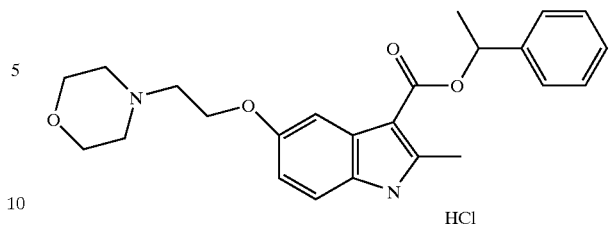

2-methyl-5-(2-morpholine-4-yl-ethoxy)-1H-indole-3-carboxylic acid 1-phenyl ethyl ester hydrochloride 5-Hydroxy-2-methyl-1H-indole-3-carboxylic acid 1-phenyl ethyl ester (0.40 g, 1.35 mmol), K$_2$CO$_3$ (0.46 g, 3.39 mmol), KI (0.023 g, 0.135 mmol), and N(chloroethyl) morpholine hydrochloride were mixed together in MEK (50 mL) and refluxed at 80° C. for 24 hours. The reaction was then cooled and diluted with ethyl acetate. Then the solution was washed with deionized water and brine, dried over anhydrous Na$_2$SO$_4$, and filtered under vacuum. The solution was concentrated to dryness and chromatographed (30% CH$_3$COCH$_3$/CH$_2$Cl$_2$) to give 0.315 g, (63%) of 2-methyl-5-(2-morpholine-4-yl-ethoxy)-1H-indole-3-carboxylic acid 1-phenyl ethyl ester as a viscous oil. Anal. Calcd for C$_{24}$H$_{28}$N$_2$O$_4$: C, 68.86; H, 6.77; N, 6.65. Found: C, 68.48: H, 7.02: N, 6.69; MS(APCI$^-$) m/z 407.2(M−1) $^1$HNMR(400 MHz, DMSO): δ 1.57 (d, J=6.59 Hz, 3H,CH$_3$), 2.48 (m, 2H), 2.30(s,3H), 2.65 (m, 2H), 3.50–3.55 (m, 2H), 3.93–4.07 (m, 2H), 6.00 (q, J=6.59 Hz, 1H), 6.70 (dd, J=8.79 Hz, J=2.20 Hz, 1H), 7.19 (d, J=8.55 Hz,1H), 7.25–7.45 (m, 6H, ArH), 11.69 (s, 1H, N—H). The oil was dissolved in ether and triturated with ethereal HCl and filtered to afford 0.360 g (100%) of a white solid. mp 45–55° C. 2-methyl-5-(2-morpholine-4-yl-ethoxy)-1H-indole-3-carboxylic acid 1-phenyl ethyl ester hydrochloride. $^1$HNMR(400 MHz, DMSO): δ 1.57 (d, J=6.59 Hz, 3H, CH$_3$), 2.48 (m, 2H), 2.30 (s,3H), 2.65 (m, 2H), 3.52 (m, 2H), 3.99 (m, 2H), 6.00 (q, J=6.59 Hz, 1H), 6.94 (dd, J=8.79 Hz, J=2.20 Hz, 1H), 7.19 (d, J=8.55 Hz,1H), 7.34 (m, 6H, ArH), 11.81 (s, 1H, N—H). MS(APCI$^+$) m/z 409.1 (MH$^+$). Anal. Calcd for C$_{24}$H$_{28}$N$_2$O$_4$.1.0HCl.1.59H$_2$O: C, 60.87;H, 6.85; N, 5.92. Found: C, 60.48: H, 6.92: N, 5.81.1R(KBr): 1677, 1452, 1174, 1084 cm$^{-1}$.

Example 68

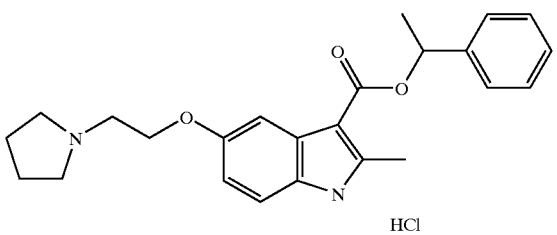

2-Methyl-5-(2-pyrrolidin-1-yl-ethoxy)-1H-indole-3-carboxylic acid-1-phenyl ethyl ester hydrochloride 5-Hydroxy-2-methyl-1H-indole-3-carboxylic acid 1-phenyl ethyl ester (0.40 g, 1.35 mmol), K$_2$CO$_3$ (0.46 g, 3.37 mmol), KI (0.023 g, 0.135 mmol) and N(chloroethyl)

cyclopentyl hydrochloride(0.344 g, 2.03 mmol) were mixed together in MEK (50 mL) and refluxed at 80° C. for 24 hours. The reaction was then permitted to cool diluted with ethyl acetate. The solution was then washed with deionized water and brine, dried over anhydrous Na₂SO₄, and filtered under vacuum. The filtrate was then concentrated under reduced pressure and chromatographed (10% MeOH/CH₂Cl₂) to give 0.200 g (37%) 2-methyl-5-(2-pyrrolidin-1-yl-ethoxy)-1H-indole-3-carboxylic acid-1-phenyl ethyl ester as a viscous oil. ¹HNMR (400 MHz, DMSO): δ 1.57 (d, J=6.60 Hz, 3H,CH₃), 1.63 (b, 4H), 2.46 (b, 4H), 2.59 (s, 3H, Ar—CH₃), 2.76 (t, J=5.62 Hz, 2H), 3.95–4.01 (m, 2H), 5.98 (q, J=6.35 Hz, 1H), 6.70 (dd, J=8.54 Hz, J=2.44 Hz, 1H), 7.19 (d, J=8.80 Hz, 1H), 7.26–7.46 (m, 6H, ArH),11.69 (s, 1H, N—H); MS(APCI⁻) m/z 393.2 (M−1). Anal. Calcd for C₂₄H₂₈N₂O₃.0.39CH₂Cl₂: C,68.83;H, 6.82; N, 6.58. Found: C, 68.48: H, 7.02: N, 6.69 IR(KBr): 3299, 2971, 2934, 1689, 1666, 1455, 1174, 1064 cm⁻¹.

Then oil was then dissolved in ether, triturated with ethereal HCl and filtered to afford 0.200 g (100%) of the hydrochloride salt. mp 75–80° C.). ¹HNMR (400 MHz, DMSO): δ 1.58 (d, J=6.59 Hz, 3H,CH₃), 2.04–2.61 (b, 4H), 2.60 (s, 3H, Ar—CH₃), 3.10 (b, 2H), 3.55 (b, 4H), 4.28 (m, 2H), 5.98 (q, J=6.59 Hz, 1H), 6.80 (dd, J=10.54 Hz, J=2.44 Hz, 1H), 7.25–7.47 (m, 7H, ArH), 11.83 (s, 1H, N—H). MS(APCI⁻) m/z 391.1(M−1). Anal. Calcd for C₂₄H₂₈N₂O₄.1.0HCl.0.20C₄H₁₀..O.33 CH₂Cl₂: C, 64.11; H, 6.56; N, 5.95. Found: C, 63.89: H, 6.96: N, 5.75; IR(KBr): 2980, 1681, 1454, 1173, 747 cm⁻¹.

Example 69

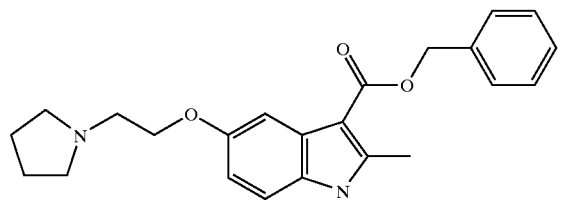

2-Methyl-5-(pyrrolidin-1-yl-ethoxy)-1H-indole-3-carboxylic acid benzyl ester

5-Hydroxy-2-methyl-1H-indole-3-carboxylic acid benzyl ester (5.0 g, 17.8 mmol), K₂CO₃ (6.14 g, 44.4 mmol), KI (0.029 g, 1.78 mmol) and N(chloroethyl)cyclopentyl hydrochloride (3.02 g, 17.8 mmol) were mixed together in MEK (100 mL) and refluxed at 80° C. for 72 hours. The reaction was then permitted to cool and diluted with ethyl acetate. Then solution was washed with deionized water and brine, dried on Na₂SO₄, filtered and concentrated under reduced pressure. The resulting crude mixture was then chromatographed (10% MeOH/CH₂Cl₂) to give 1.20 g (26.8%) of the desired ester as a white solid, mp 110–116° C. ¹HNMR (400 MHz, DMSO): δ 1.64 (b,4H), 2.45 (b, 4H), 2.59 (s, 3H, ArCH₃), 4.00 (m, 2H), 5.27 (s, 2H), 6.70 (dd, J=8.54 Hz, J=2.44 Hz, 1H), 7.15 (d, J=8.79 Hz, 1H), 7.28–7.47 (m, 5H), 11.71 (s, NH); MS(APCI⁺) m/z 379.1(MH⁺). Anal. Calcd for C₂₃H₂₆N₂O₃.0.42H₂O: C, 71.56;H, 7.01; N, 7.26. Found: C, 71.36: H, 6.93: N, 7.04; IR(KBr): 3371, 2909, 1665, 1481, 1448, 1178, 1087 cm⁻¹.

Example 70

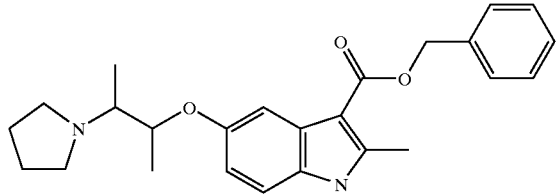

2-Methyl-5-(1-methyl-2-pyrrolidin-1-yl-propoxy)-1H-indole-3-carboxylic acid benzyl ester Step A

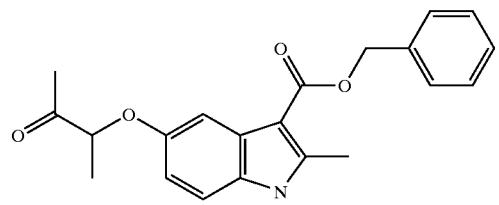

2-Methyl-5-(1-methyl-2-oxo-propoxy)-1H-indole-3-carboxylic acid benzyl ester

5-Hydroxy-2-methyl-1H-indole-3-carboxylic acid benzyl ester (1.0 g, 3.56 mmol), 2-bromobut-2-one (0.806 g, 5.33 mmol) and K₂CO₃ (1.47 g, 10.7 mmol) were mixed together in acetone (30 mL) and stirred at room temperature for 4 hours. The mixture was then filtered, concentrated under reduced pressure and redissolved in ethyl acetate. The resulting solution was washed with deionized water twice and dried over anhydrous Na₂SO₄. The crude was chromatographed (5% EtOAc/CH₂Cl₂) to give 0.97 g (77%) of 2-methyl-5-(1-methyl-2-oxo-propoxy)-1H-indole-3-carboxylic acid as a viscous oil. ¹HNMR (400 MHz, DMSO): δ 1.36 (d, J=6.75 Hz, 3H), 2.06 (s, 3H, CH₃CO), 2.59 (s, ArCH₃), 4.67 (q, J=6.75 Hz, 1H), 5.28 (s, 2H), 6.73 (d, J=8.44 Hz, 1H), 7.23 (d, J=8.64 Hz, 1H), 7.29–7.46 (m, 6H), 11.76 (s, 1H, NH). MS (APCI⁺). Anal. Calcd for C₂₁H₂₁N₁O₄: C, 71.78; H, 6.02; N, 3.99. Found: C, 71.46: H, 6.04: N, 3.76. IR (KBr): 3276, 1715, 1659, 1458, 1168, 1078 cm⁻¹.

Step B

2-Methyl-5-(1-methyl-2-oxo-propoxy)-1H-indole-3-carboxylic acid benzyl ester (0.248 g, 0.707 mmol) and pyrrolidine (0.05 g, 0.706 mmol) were mixed together in dichloroethane and stirred under N₂ at room temperature for 1 hour. The reaction was then cooled to 0° C. whereupon sodium triacetoxyborohydride (0.209 g, 0.988 mmol) was added. After 30 minutes, the reaction was then permitted to warm to rt and stirred for a further 2 hours. It was then stopped by the addition of 1N NaOH (10 mL). The mixture was then extracted with EtOAc and the combined organic layers washed with brine and dried over anhydrous Na₂SO₄ Purification on SiO₂ (10% MeOH/CH₂Cl₂) gave 0.110 g (38%) of the desired compound, mp 94–98° C. ¹HNMR (400 MHz, DMSO): 1.58 (d, J=6.10 Hz, 3H), 1.60 (b, 4H), 2.40 (b, 4H), 2.59 (s, 3H, ArCH₃),3.35 (b, 1H), 4.43 (m, 1H), 5.26 (s, 2H), 6.69 (d, J=8.44 Hz, 1H), 7.19 (d, J=8.64 Hz, 1H), 7.28–7.44 (m, 6H), 11.72 (s, H, H). MS APCI⁺) m/z 407.2(MH⁺). Anal. Calcd for C₂₅H₃₀N₂O₃.0.20H₂O: C, 3.21;H,7.47; N, 6.83. Found: C, 72.84: H, 7.57: N, 6.56 I (KBr): 3294, 2973, 1691, 1665, 1454, 1167, 1073 cm$^{-1}$.

Example 71

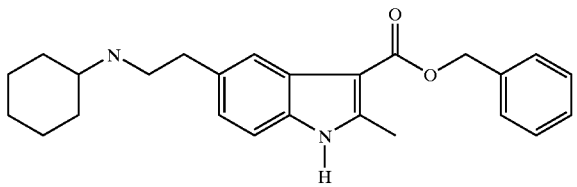

5-(2-Cyclohexylamino-ethyl)-2-methyl-1H-indole-3-carboxylic acid benzyl ester

Step A

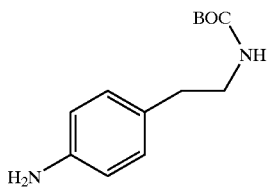

[2-(4-Amino-phenyl)-ethyl]-carbamic acid tert-butyl ester

To a solution of 2-(4-amino-phenyl)-ethylamine (6.92 g, 50.8 mmol) in methanol at 0° C. was added di-tert-butyl dicarbonate (7.47 g, 34.4 mmol) over a period of 2 hours. The reaction was then concentrated under reduced pressure, redissolved in EtOAc and filtered. The filtrate was washed with 0.5 M KH$_2$PO$_4$, dried over anhydrous Na$_2$SO$_4$, concentrated and purified on SiO$_2$ (40% EtOAc/hexane) to give 6.1 g (51%) of [2-(4-amino-phenyl)-ethyl]-carbamic acid tert-butyl ester as a white solid, mp 71–73° C. $^1$HNMR (400 MHz, DMSO): δ 1.33 (s, 9H), 2.45 (m, 2H), 2.97 (m, 2H), 4.80 (s, 2H, NH2), 6.43 (d, J=8.30 Hz, 2H), 6.77 (d, J=8.30 Hz, 2H). MS(APCI$^+$) m/z 236.2(MH$^+$). Anal. Calcd for C$_{13}$H$_{20}$N$_2$O$_2$: C, 66.07; H, 8.53; N, 11.85. Found: C, 66.15: H, 8.61: N, 11.79. IR (KBr): 3360, 2980, 1692, 1515, 1165 cm$^{-1}$.

Step B

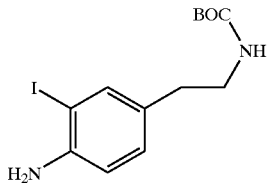

[2-(4-Amino-3-iodo-phenyl)-ethyl]-carbamic acid tert-butyl ester

[2-(4-Amino-phenyl)-ethyl]-carbamic acid tert-butyl ester (6.44 g, 27.3 mmol), I2 (6.93 g, 27.3 mmol), CaCO$_3$ (3.41 g) were refluxed in methanol (125 mL) at70° C. for 6 hours. The reaction was then cooled stopped by the addition of saturated sodium bisulfite (100 mL). The mixture was extracted with EtOAc (3×100 mL) and concentrated under reduced pressure, dried on Na$_2$SO$_4$. Purification on SiO$_2$ (20% EtOAc/C$_6$H$_{14}$) gave 6.5 g (65%) of [2-(4-amino-phenyl)-ethyl]-carbamic acid tert-butyl ester as a white solid, mp 61–64° C.). $^1$HNMR (400 MHz, DMSO): δ 1.33 (s, 9H), 2.45 (m, 2H), 2.97 (m, 2H), 4.97 (s, 2H, NH$_2$), 6.68–6.78 (m, 3H, ArH), 7.32 (d, J=1.71 Hz, NH); MS(APCI$^+$) m/z 363.0 (MH$^+$). Anal. Calcd for C$_{13}$H$_{19}$N$_2$O$_2$I1: C, 43.11;H, 5.29; N, 7.73. Found: C, 42.73: H, 5.31: N, 7.51; MS (APCI$^+$) m/z 360.0 (MH$^+$); IR(KBr): 3348, 2977, 1698, 1500, 1171 cm$^{-1}$.

Step C

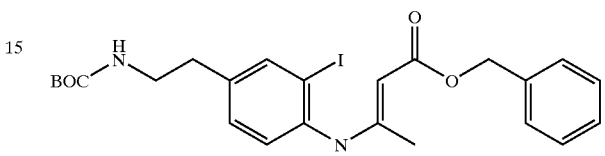

(E)-3-[4-(2-tert-Butoxycarbonylamino-ethyl)-2-methyl-phenylamino]-but-2-enoic acid benzyl ester

[2-(4-Amino-phenyl)-ethyl]-carbamic acid tert-butyl ester (1.0 g, 2.76 mmol), benzyl acetoacetate (0.796 g, 4.14 mmol) and toluenesulfonic acid (0.026 g, 0.138 mmol) were refluxed in toluene at 125° C. 3 hours. The reaction was then cooled, evaporated to dryness, the crude redissolved in EtOAc and dried over anhydrous Na$_2$SO$_4$. Filtration under vacuum followed by purification on SiO$_2$ (30% EtOAc/hexane) gave 1.055 g (71%) of the desired (E)-3-[4-(2-tert-butoxycarbonylamino-ethyl)-2-methyl-phenylamino]-but-2-enoicacid benzyl ester. $^1$HNMR (400 MHz, DMSO): δ 1.32 (s, 9H), 1.81 (s, 3H, olefineCH$_3$),2.63 (t, J=2.96 Hz, 2H), 3.12 (q, J=6.03 Hz, 2H), 4.77 (s, 1H, olefineH), 5.07 (s, 2H), 6.83 (b, ArH), 7.20–7.35 (m, 6H, ArH), 7.70 (s, 1H, ArH), 10.05 (s, ArNH). MS(APCI$^-$) m/z 535.2(M−1).

Step D

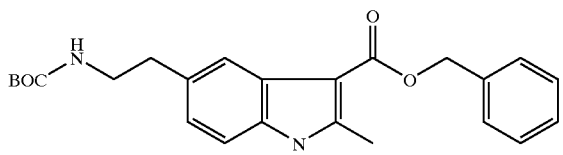

5-(2-tert-butoxycarbonylamino ethyl)-2-methyl-1H-indole-3-carboxylic acid benzyl ester (E)-3-[4-(2-tert-Butoxycarbonylamino-ethyl)-2-methyl-phenylamino]-but-2-enoic acid benzyl ester (0.251 g, 0.469 mmol), palladium acetate (2.63 mg, 0.012 mmol), triethylamine (0.107 g, 0.563 mmol) and DMF (0.18 mL) were mixed together and refluxed at 120° C. for 5 hours. The reaction was then cooled and concentrated. The mixture was then partitioned between EtOAc and water (20 mL) and the organic layer then filtered through celite. The filtrate was washed with water, dried over anhydrous Na$_2$SO$_4$, and concentrated under reduced pressure to give 0.43 g of a viscous oil which was chromatographed (30% EtOAc/C$_6$H$_{14}$) to give 0.083 g (43%) of 5-(2-tert-butoxycarbonylamino ethyl)-2-methyl-1H-indole-3-carboxylic acid benzyl ester. $^1$HNMR (400 MHz, DMSO): δ 1.34 (s, 9H), 2.60 (s, 3H, ArCH$_3$), 2.69 (t, J=7.35 Hz, 2H), 3.10 (b, 2H), 5.31 (s, 2H), 6.93 (d, J=7.96 Hz, ArH), 7.23 (d, J=8.20 Hz, 1H), 7.29–7.46 (m, 5H, ArH), 7.73 (s, 1H, ArH), 11.75 (s, ArNH); MS(APCI⁻) m/z 407.2 (M–H).

Step E

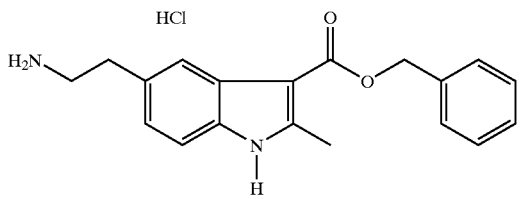

5-(2-Amino-ethyl)-2-methyl-1H-indole-3-carboxylic acid benzyl ester hydrochloride To a solution of 5-(2-tert-butoxycarbonylamino ethyl)-2-methyl-1H-indole-3-carboxylic acid benzyl ester (1.972 g, 4.827 mmol) in dioxane (25 mL) at room temperature was added aqueous HCl (3.0 mL, 37%). The resulting mixture was then stirred at ambient temperature for 22 hours. After this duration, the mixture was concentrated in vacuo. Trituration with acetone gave 1.48 g (89%) of the desired product as a white solid, mp 282–283° C.; MS (APCI⁺): m/z 309.0 (M+1).

Step F 5-(2-Amino-ethyl)-2-methyl-1H-indole-3-carboxylic acid benzyl ester hydrochloride (0.331 g, 0.961 mmol) and cyclopentanone (99.6 µL, 0.961 mmol) were mixed together in dichloroethane and stirred at room temperature under $N_2$ for 30 minutes. The mixture was then cooled to 0° C., whereupon sodium triacetoxyborohydride (0.209 g, 0.988 mmol) was added and stirred without warming for a further 30 minutes). The reaction was then permitted to warm to rt and stirred for 20 hours. 1N NaOH (10 ML) was then added and extracted with EtOAc. The combined organic layers was washed with brine, dried on $Na_2SO_4$ and chromatographed (10% MeOH/$CH_2Cl_2$) to give 0.200 g, (53%), of the desired product, mp 97–100° C. pure product. ¹HNMR (400 MHz, DMSO): δ 0.86–1.73 (m, 10H), 2.31 (m, 1H), 2.59 (s, 3H, ArCH₃), 2.69 (m, 4H), 5.29 (s, 2H), 6.93 (d, J=8.06 Hz, J=1.64 Hz, ArH), 7.21 (d, J=8.06 Hz, 1H), 7.28–7.45 (m, 5H, ArH), 7.70 (s, 1H, ArH), 11.74 (s, ArNH). MS (APCI⁺) m/z 391.2(MH⁺). Anal. Calcd for $C_{25}H_{30}N_2O_2 \cdot 0.20H_2O$: C, 76.19; H, 7.77; N, 7.11. Found: C, 75.84: H, 8.09: N, 6.73. IR (KBr): 3309, 2927, 2854,1662, 1450, 1076 cm⁻¹.

Example 72

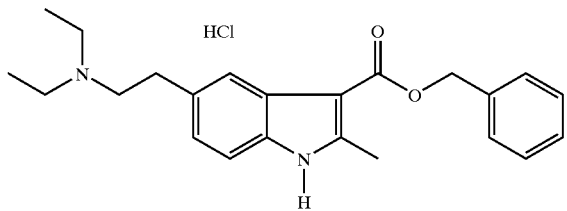

5-(2-Diethylamino-ethyl)-2-methyl-1H-indole-3-carboxylic acid benzyl ester hydrochloride To a solution of 5-(2-amino-ethyl)-2-methyl-1H-indole-3-carboxylic acid benzyl ester hydrochloride (283.7 mg, 0.8227 mmol) in $CH_2Cl_2$ was added acetaldehyde (72.50 mg, 1.6 mmol) and stirred at room temperature for 30 minutes before NaBH (OAc)₃ (261.5 mg, 1.234 mmol) was added. After 14 hours at ambient temperature, the reaction was stopped by the addition of saturated NaHCO₃ (100 mL) and the mixture extracted with $CH_2Cl_2$ (60 mL). The organic layers were dried on $Na_2SO_4$ and concentrated in vacuo. Purification on $SiO_2$ (20% MeOH, 0.5% Et₃N in HCCl₃) gave a viscous oil. Treatment of the free amine with ethereal HCl gave 172 mg (52%) of the desired product as a white solid,. mp 130–134° C.; MS (APCI⁺): m/z 365.2 (M+1).

Example 73

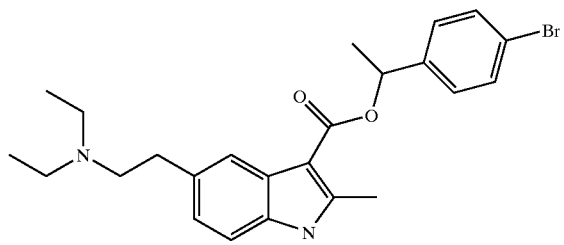

5-(2-Diethylamino-ethyl)-2-methyl-1H-indole-3-carboxylic acid-1-(4-bromophenyl)-ethyl ester The procedure for Example 65 was followed, substituting 1-(4-bromophenyl)-ethanol for (S)-phenylethanol. ESI+MS m/z 458 (M+1).

Example 74

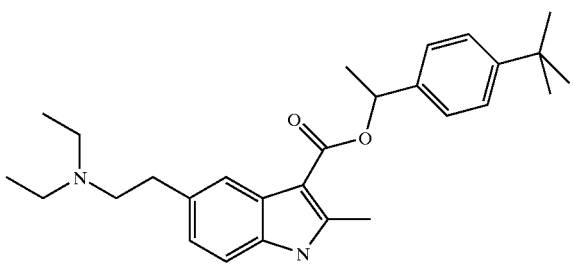

5-(2-Diethylamino-ethyl)-2-methyl-1H-indole-3-carboxylic acid-1-(4-t-butylphenyl)-ethyl ester The procedure for Example 65 was followed, substituting 1-(4-(2-methyl-2-propyl)-phenyl)-ethanol for (S)-phenylethanol. ESI+MS m/z 435 (M+1).

Example 75

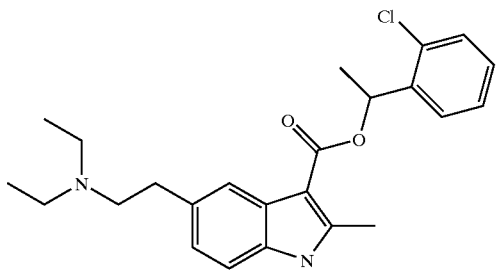

5-(2-Diethylamino-ethyl)-2-methyl-1H-indole-3-carboxylic acid-1-(2-chlorophenyl)-ethyl ester The procedure for Example 65 was followed, substituting 1-(2-chlorophenyl)-ethanol for (S)-phenylethanol. ESI+MS m/z 413 (M+1).

Example 76

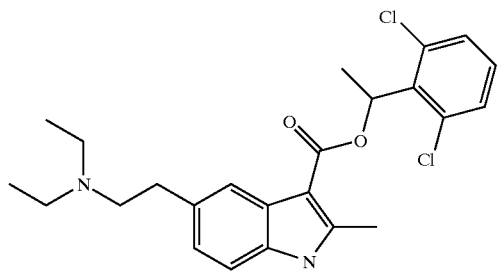

5-(2-Diethylamino-ethyl)-2-methyl-1H-indole-3-carboxylic acid-1-(2,6-dichlorophenyl)-ethyl ester The procedure for Example 65 was followed, substituting 1-(2,6-dichlorophenyl)-ethanol for (S)-phenylethanol. ESI+ MS m/z 447 (M+1).

Example 77

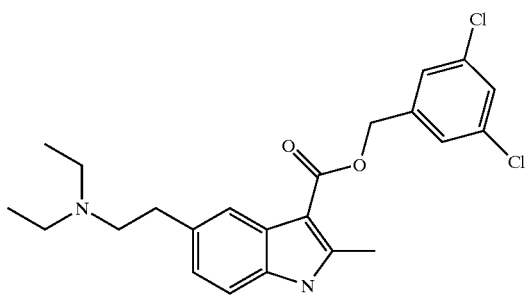

5-(2-Diethylamino-ethyl)-2-methyl-1H-indole-3-carboxylic acid 3,5-dichloro-benzyl ester The procedure for Example 65 was followed, substituting 3,5-dichlorobenzyl alcohol for (S)-phenylethanol. ESI+MS m/z 433 (M+1).

Example 78

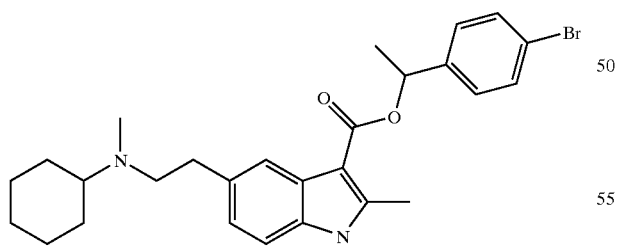

5-(2-N-Cyclohexyl-N-methyl-amino-ethyl)-2-methyl-1H-indole-3-carboxylic acid-1-(4-bromophenyl)-ethyl ester The procedure for Example 65 was followed, substituting 1-(4-bromophenyl)-ethanol for (S)-phenylethanol, and substituting N-cyclohexyl-N-methylamine for diethylamine. ESI+MS m/z 497 (M+1).

Example 79

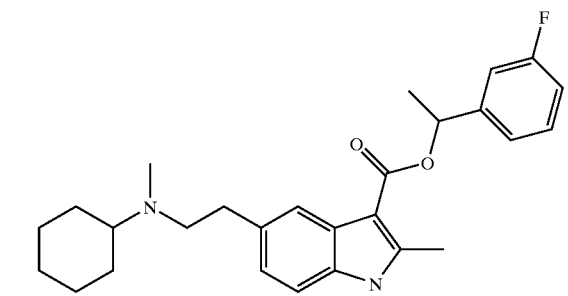

5-(2-N-Cyclohexyl-N-methyl-amino-ethyl)-2-methyl-H-indole-3-carboxylic acid-1-(3-fluorophenyl)-ethyl ester The procedure for Example 65 was followed, substituting 1-(3-fluorophenyl)-ethanol for (S)-phenylethanol, and substituting N-cyclohexyl-N-methylamine for diethylamine. ESI+MS m/z 437 (M+1).

Example 80

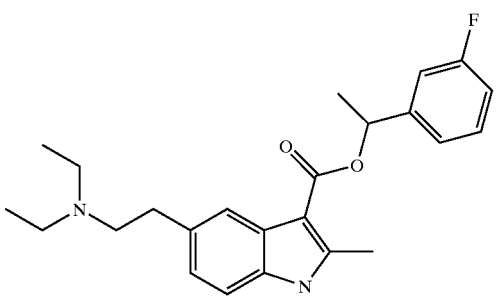

5-(2-Diethylamino-ethyl)-2-methyl-1H-indole-3-carboxylic acid-1-(3-fluorophenyl)-ethyl ester The procedure for Example 65 was followed, substituting 1-(3-fluorophenyl)-ethanol for (S)-phenylethanol. ESI+MS m/z 397 (M+1).

Example 81

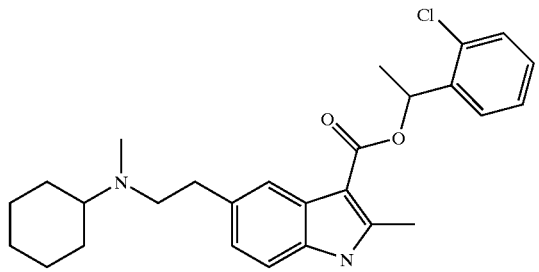

5-(2-N-Cyclohexyl-N-methyl-amino-ethyl)-2-methyl-1H-indole-3-carboxylic acid-1-(2-chlorophenyl)-ethyl ester The procedure for Example 65 was followed, substituting 1-(2-chlorophenyl)-ethanol for (S)-phenylethanol, and substituting N-cyclohexyl-N-methylamine for diethylamine. ESI+MS m/z 453 (M+1).

Example 82

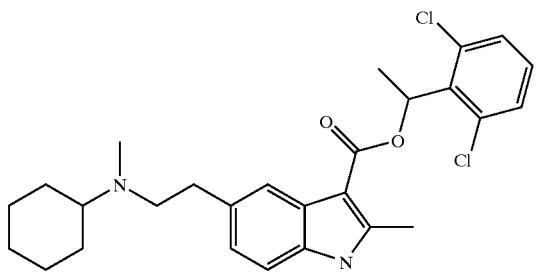

5-(2-N-Cyclohexyl-N-methyl-amino-ethyl)-2-methyl-1H-indole-3-carboxylic acid-1-(2,6-dichlorophenyl)-ethyl ester The procedure for Example 65 was followed, substituting 1-(2,6-dichlorophenyl)-ethanol for (S)-phenylethanol, and substituting N-cyclohexyl-N-methylamine for diethylamine. ESI+MS m/z 487 (M+1).

Example 83

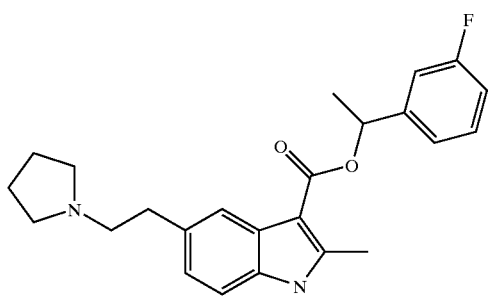

5-(2-Pyrrolidino-ethyl)-2-methyl-1H-indole-3-carboxylic acid-1-(3-fluorophenyl)-ethyl ester The procedure for Example 65 was followed, substituting 1-(3-fluorophenyl)-ethanol for (S)-phenylethanol, and substituting pyrrolidine for diethylamine. ESI+MS m/z 395 (M+1).

Example 84

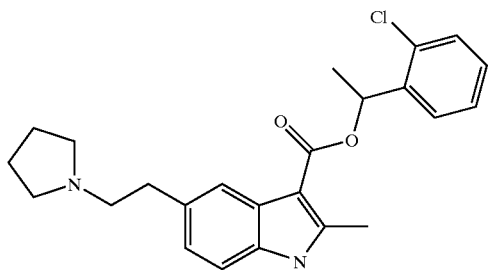

5-(2-Pyrrolidino-ethyl)-2-methyl-1H-indole-3-carboxylic acid-1-(2-chlorophenyl)-ethyl ester The procedure for Example 65 was followed, substituting 1-(2-chlorophenyl)-ethanol for (S)-phenylethanol, and substituting pyrrolidine for diethylamine. ESI+MS m/z 411 (M+1).

Example 85

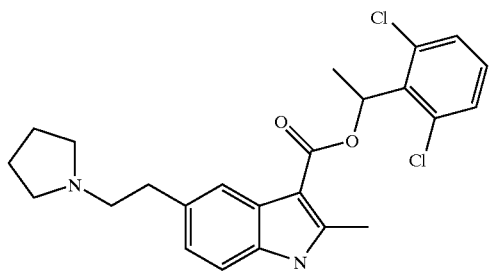

5-(2-Pyrrolidino-ethyl)-2-methyl-1H-indole-3-carboxylic acid-1-(2,6-dichlorophenyl)-ethyl ester The procedure for Example 65 was followed, substituting 1-(2,6-dichlorophenyl)-ethanol for (S)-phenylethanol, and substituting pyrrolidine for diethylamine. ESI+MS m/z 445 (M+1).

Example 86

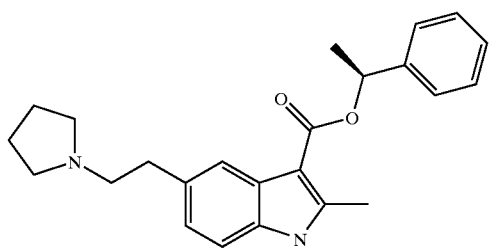

5-(2-Pyrrolidino-ethyl)-2-methyl-1H-indole-3-carboxylic acid-(S)-1-phenyl-ethyl ester The procedure for Example 65 was followed, substituting pyrrolidine for diethylamine. ESI+MS m/z 377 (M+1).

Example 87

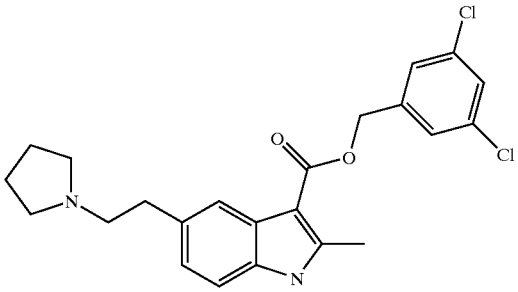

5-(2-Pyrrolidino-ethyl)-2-methyl-1H-indole-3-carboxylic acid 3,5-dichloro-benzyl ester The procedure for Example 65 was followed, substituting 3,5-dichlorobenzyl alcohol for (S)-phenylethanol, and substituting pyrrolidine for diethylamine. ESI+MS m/z 431 (M+1).

Example 88

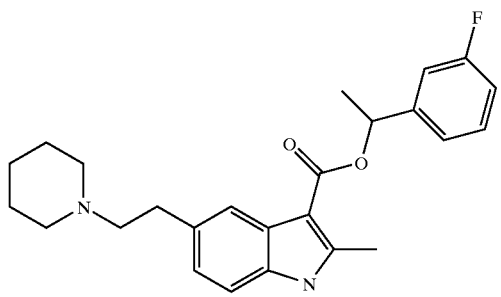

5-(2-Piperidino-ethyl)-2-methyl-1H-indole-3-carboxylic acid-1-(3-fluorophenyl)-ethyl ester The procedure for Example 65 was followed, substituting 1-(3-fluorophenyl)-ethanol for (S)-phenylethanol, and substituting piperidine for diethylamine. ESI+MS m/z 409 (M+1).

Example 89

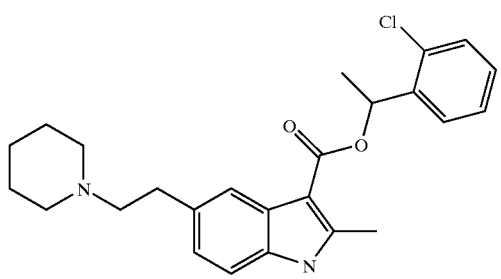

5-(2-Piperidino-ethyl)-2-methyl-1H-indole-3-carboxylic acid-1-(2-chlorophenyl)-ethyl ester The procedure for Example 65 was followed, substituting 1-(2-chlorophenyl)-ethanol for (S)-phenylethanol, and substituting piperidine for diethylamine. ESI+MS m/z 425 (M+1).

Example 90

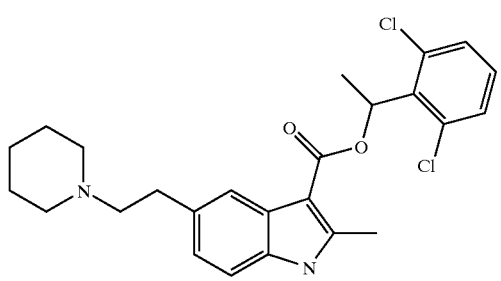

5-(2-Piperidino-ethyl)-2-methyl-1H-indole-3-carboxylic acid-1-(2,6-dichlorophenyl)-ethyl ester The procedure for Example 65 was followed, substituting 1-(2,6-dichlorophenyl)-ethanol for (S)-phenylethanol, and substituting piperidine for diethylamine. ESI+MS m/z 459 (M+1).

Example 91

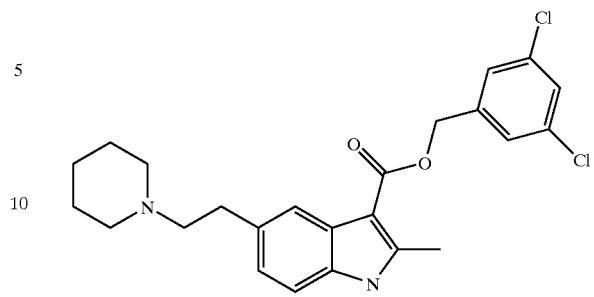

5-(2-Piperidino-ethyl)-2-methyl-1H-indole-3-carboxylic acid 3,5-dichloro-benzyl ester The procedure for Example 65 was followed, substituting 3,5-dichlorobenzyl alcohol for (S)-phenylethanol, and substituting piperidine for diethylamine. ESI+MS m/z 445 (M+1).

Example 92

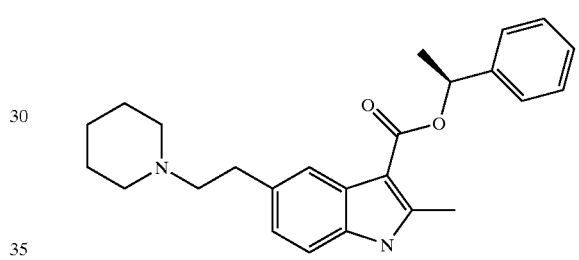

5-(2-Piperidino-ethyl)-2-methyl-1H-indole-3-carboxylic acid-(S)-1-phenyl-ethyl ester The procedure for Example 65 was followed, substituting piperidine for diethylamine. ESI+MS m/z 391 (M+1).

Example 93

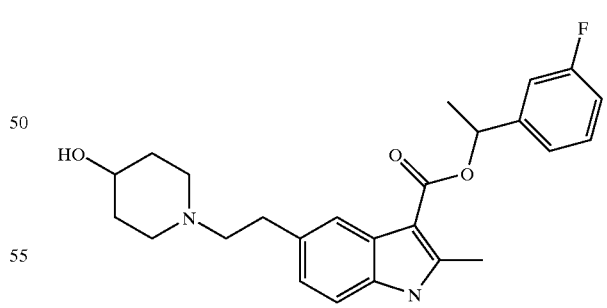

5-(2-(4-Hydroxy-piperidino)-ethyl)-2-methyl-1H-indole-3-carboxylic acid-1-(3-fluorophenyl)-ethyl ester The procedure for Example 65 was followed, substituting 1-(3-fluorophenyl)-ethanol for (S)-phenylethanol, and substituting 4-hydroxypiperidine for diethylamine. ESI+MS m/z 425 (M+1).

Example 94

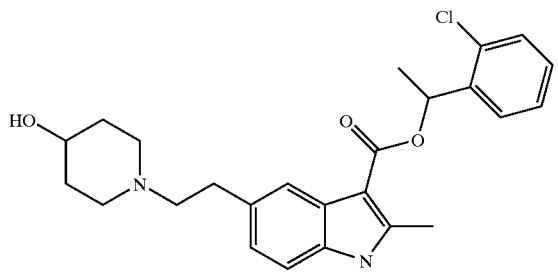

5-(2-(4-Hydroxy-piperidino)-ethyl)-2-methyl-1H-indole-3-carboxylic acid-1-(2-chlorophenyl)-ethyl ester The procedure for Example 65 was followed, substituting 1-(2-chlorophenyl)-ethanol for (S)-phenylethanol, and substituting 4-hydroxypiperidine for diethylamine. ESI+MS m/z 441 (M+1).

Example 95

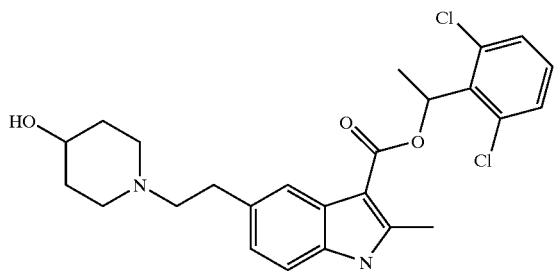

5-(2-(4-Hydroxy-piperidino)-ethyl)-2-methyl-1H-indole-3-carboxylic acid-1-(2,6-dichlorophenyl)-ethyl ester The procedure for Example 65 was followed, substituting 1-(2,6-dichlorophenyl)-ethanol for (S)-phenylethanol, and substituting 4-hydroxypiperidine for diethylamine. ESI+MS m/z 475 (M+1).

Example 96

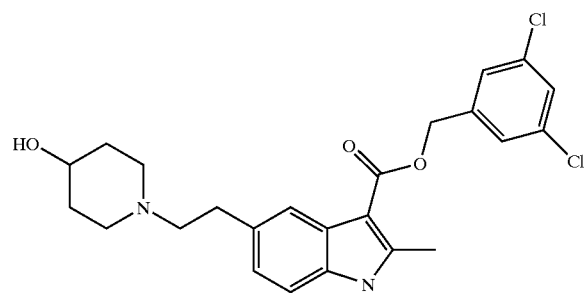

5-(2-(4-Hydroxy-piperidino)-ethyl)-2-methyl-1H-indole-3-carboxylic acid 3,5-dichlorobenzyl ester The procedure for example 65 was followed, substituting 3,5-dichlorobenzyl alcohol for (S)-phenylethanol, and substituting 4-hydroxypiperidine for diethylamine. ESI+MS m/z 461 (M+1).

Example 97

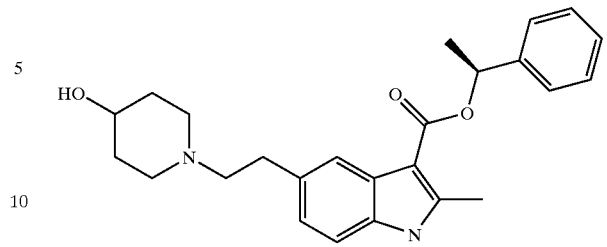

5-(2-(4-Hydroxy-piperidino)-ethyl)-2-methyl-1H-indole-3-carboxylic acid-(S)-1-phenyl-ethyl ester The procedure for Example 65 was followed, substituting 4-hydroxypiperidine for diethylamine. ESI+MS m/z 407 (M+1).

Example 98

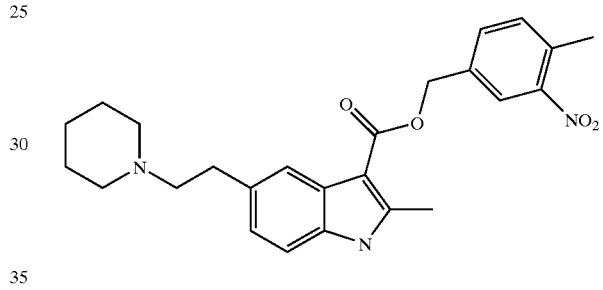

5-(2-Piperidino-ethyl)-2-methyl-1H-indole-3-carboxylic acid 3-nitro-4-methyl-benzyl ester The procedure for Example 65 was followed, substituting 3-nitro-4-methyl-benzyl alcohol for (S)-phenylethanol, and substituting piperidine for diethylamine. ESI+MS m/z 436 (M+1).

Example 99

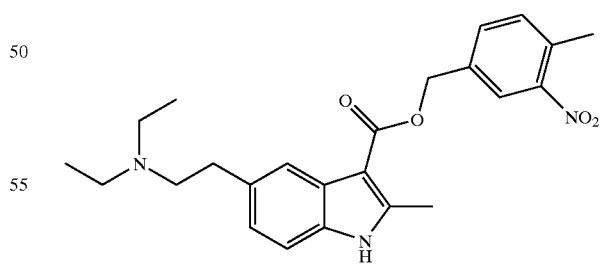

5-(2-Diethylamino-ethyl)-2-methyl-1H-indole-3-carboxylic acid 3-nitro-4-methyl-benzyl ester The procedure for Example 65 was followed, substituting 3-nitro-4-methyl-benzyl alcohol for (S)-phenylethanol. ESI+MS m/z 424 (M+1).

Example 100

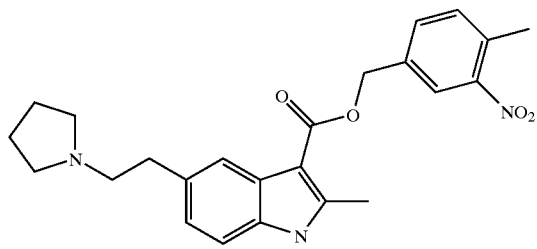

5-(2-Pyrrolidino-ethyl)-2-methyl-1H-indole-3-carboxylic acid 3-nitro-4-methyl-benzyl ester The procedure for Example 65 was followed, substituting 3-nitro-4-methyl-benzyl alcohol for (S)-phenylethanol, and substituting pyrrolidine for diethylarmine. ESI+MS m/z 422 (M+1).

Example 101

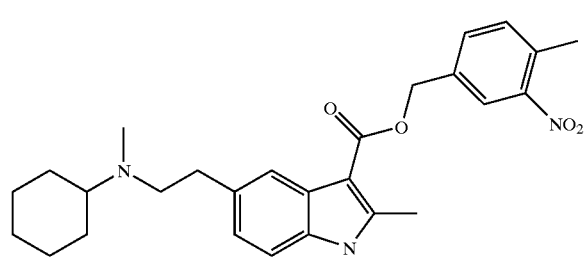

5-(2-N-Cyclohexyl-N-methyl-amino-ethyl)-2-methyl-1H-indole-3-carboxylic acid 3-nitro-4-methyl-benzyl ester The procedure for Example 65 was followed, substituting 3-nitro-4-methyl-benzyl alcohol for (S)-phenylethanol, and substituting N-cyclohexyl-N-methylamine for diethylamine. ESI+MS m/z 436 (M+1).

Example 102

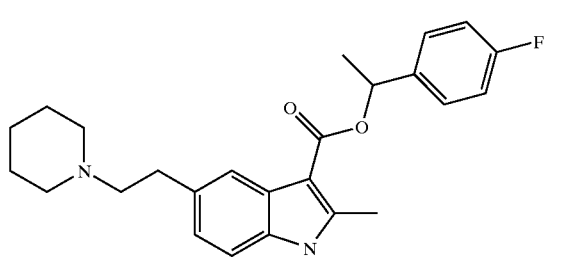

5-(2-Piperidino-ethyl)-2-methyl-1H-indole-3-carboxylic acid-1-(4-fluorophenyl)-ethyl ester The procedure for Example 65 was followed, substituting 1-(4-fluorophenyl)-ethanol for (S)-phenylethanol, and substituting piperidine for diethylamine. ESI+MS m/z 409 (M+1).

Example 103

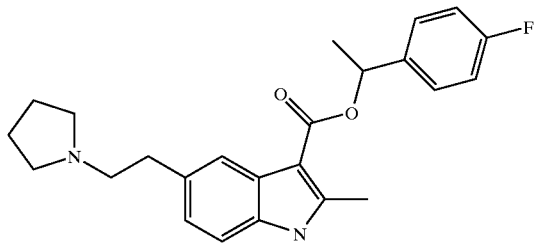

5-(2-Pyrrolidino-ethyl)-2-methyl-1H-indole-3-carboxylic acid-1-(4-fluorophenyl)-ethyl ester The procedure for Example 65 was followed, substituting 1-(4-fluorophenyl)-ethanol for (S)-phenylethanol, and substituting pyrrolidine for diethylamine. ESI+MS m/z 395 (M+1).

Example 104

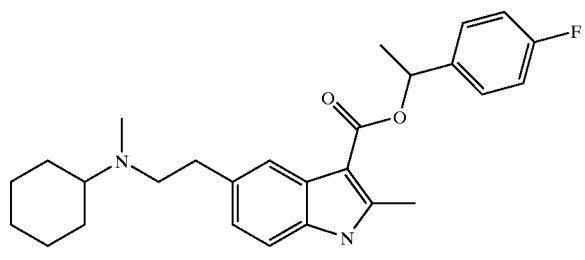

5-(2-N-Cyclohexyl-N-methyl-amino-ethyl)-2-methyl-1H-indole-3-carboxylic acid-1-(4-fluorophenyl)-ethyl ester The procedure for Example 65 was followed, substituting 1-(4-fluorophenyl)-ethanol for (S)-phenylethanol, and substituting N-cyclohexyl-N-methylamine for diethylamine. ESI+MS m/z 437 (M+1).

Example 105

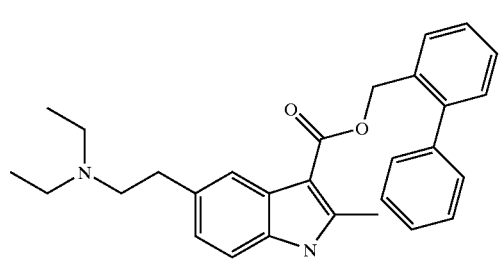

5-(2-Diethylamino-ethyl)-2-methyl-1H-indole-3-carboxylic acid 2-biphenyl methyl ester The procedure for Example 65 was followed, substituting 2-biphenylmethyl alcohol for (S)-phenylethanol. ESI+MS m/z 441 (M+1).

Example 106

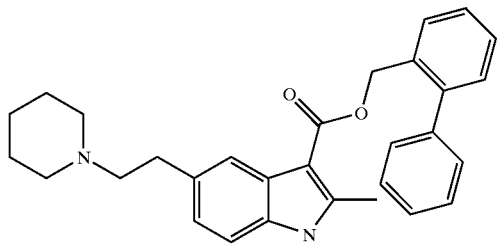

5-(2-Piperidino-ethyl)-2-methyl-1H-indole-3-carboxylic acid 2-biphenyl Methyl ester The procedure for Example 65 was followed, substituting 2-biphenylmethyl alcohol for (S)-phenylethanol, and substituting piperidine for diethylamine. ESI+MS m/z 453 (M+1).

Example 107

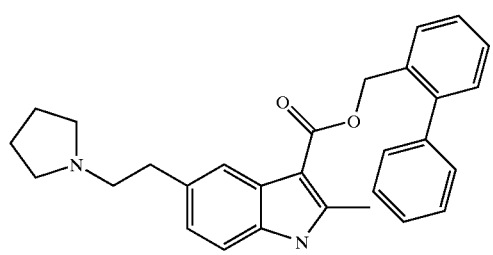

5-(2-Pyrrolidino-ethyl)-2-methyl-1H-indole-3-carboxylic acid 2-biphenyl methyl ester The procedure for Example 65 was followed, substituting 2-biphenylmethyl alcohol for (S)-phenylethanol, and substituting pyrrolidine for diethylamine. ESI+MS m/z 439 (M+1).

Example 108

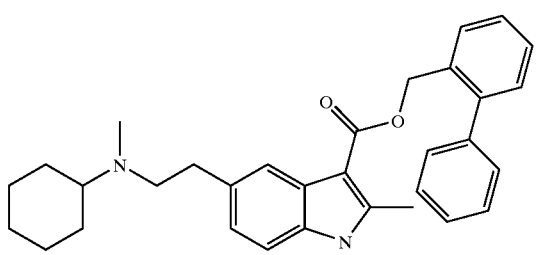

5-(2-N-Cyclohexyl-N-methyl-amino-ethyl)-2-methyl-1H-indole-3-carboxylic acid 2-biphenyl methyl ester The procedure for Example 65 was followed, substituting 2-biphenylmethyl alcohol for (S)-phenylethanol, and substituting N-cyclohexyl-N-methylamine for diethylamine. ESI+MS m/z 481 (M+1).

Example 109

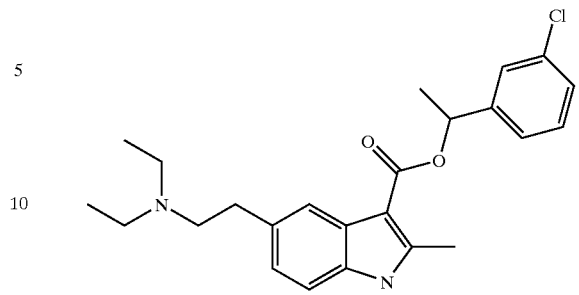

5-(2-Diethylamino-ethyl)-2-methyl-1H-indole-3-carboxylic acid-1-(3-chlorophenyl)-ethyl ester The procedure for Example 65 was followed, substituting 1-(3-chlorophenyl)-ethanol for (S)-phenylethanol. ESI+MS m/z 413 (M+1).

Example 110

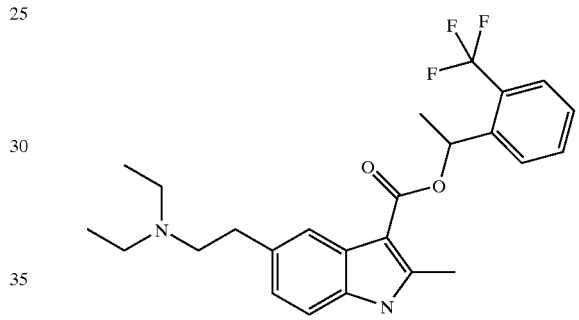

5-(2-Diethylamino-ethyl)-2-methyl-1H-indole-3-carboxylic acid-1-(2-trifluoromethylphenyl)-ethyl ester The procedure for Example 65 was followed, substituting 1-(2-trifluoromethylphenyl)-ethanol for (S)-phenylethanol. ESI+MS m/z 447 (M+1).

Example 111

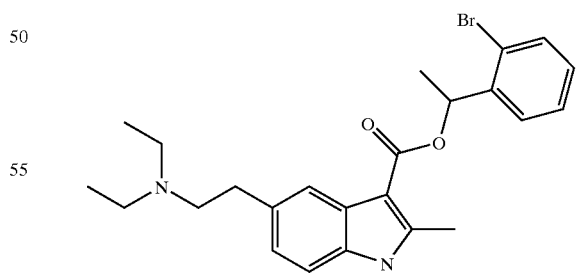

5-(2-Diethylamino-ethyl)-2-methyl-1H-indole-3-carboxylic acid-1-(2-bromophenyl)-ethyl ester The procedure for Example 65 was followed, substituting 1-(2-bromophenyl)-ethanol for (S)-phenylethanol. ESI+MS m/z 457 (M+1).

Example 112

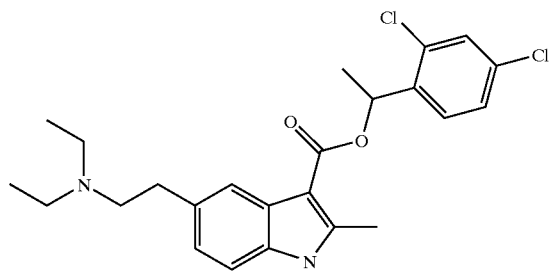

5-(2-Diethylamino-ethyl)-2-methyl-1H-indole-3-carboxylic acid-1-(2,4-dichlorophenyl)-ethyl ester The procedure for Example 65 was followed, substituting 1-(2,4-dichlorophenyl)-ethanol for (S)-phenylethanol. ESI+ MS m/z 447 (M+1).

Example 113

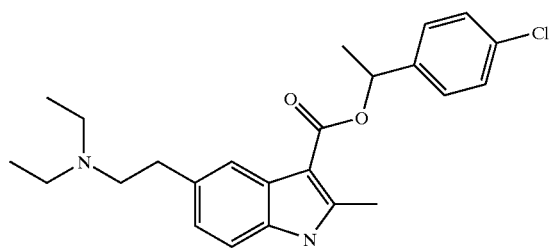

5-(2-Diethylamino-ethyl)-2-methyl-1H-indole-3-carboxylic acid-1-(4-chlorophenyl)-ethyl ester The procedure for Example 65 was followed, substituting 1-(4-chlorophenyl)-ethanol for (S)-phenylethanol. ESI+MS m/z 413 (M+1).

Example 114

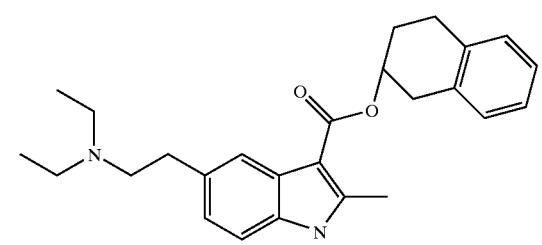

5-(2-Diethylamino-ethyl)-2-methyl-1H-indole-3-carboxylic acid 5,6,7,8-tetrahydronaphth-5-yl ester The procedure for Example 65 was followed, 5-hydroxy-5,6,7,8-tetrahydronaphthalene for (S)-phenylethanol. ESI+ MS m/z 405 (M+1).

Example 115

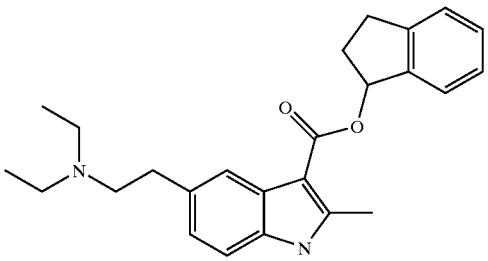

5-(2-Diethylamino-ethyl)-2-methyl-1H-indole-3-carboxylic acid indan-1-yl ester

The procedure for Example 65 was followed, 1-hydroxy-indane for (S)-phenylethanol. ESI+MS m/z 391 (M+1).

Example 116

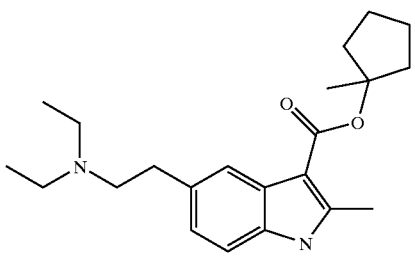

5-(2-Diethylamino-ethyl)-2-methyl-1H-indole-3-carboxylic acid 1-methyl-1-cyclopentyl ester The procedure for Example 65 was followed, substituting 1-methyl-1-cyclopentanol for (S)-phenylethanol. ESI+MS m/z 357 (M+1).

Example 117

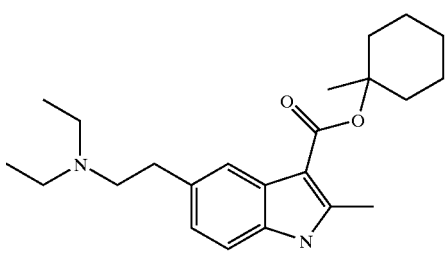

5-(2-Diethylamino-ethyl)-2-methyl-1H-indole-3-carboxylic acid 1-methyl-1-cyclohexyl ester The procedure for Example 65 was followed, substituting 1-methyl-1-cyclohexanol for (S)-phenylethanol. ESI+MS m/z 371 (M+1).

Example 118

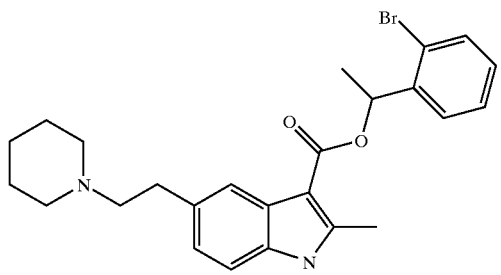

5-(2-Piperidino-ethyl)-2-methyl-1H-indole-3-carboxylic acid-1-(2-bromophenyl)-ethyl ester The procedure for Example 65 was followed, substituting 1-(2-bromophenyl)-ethanol for (S)-phenylethanol, and substituting piperidine for diethylamine. ESI+MS m/z 469 (M+1).

Example 119

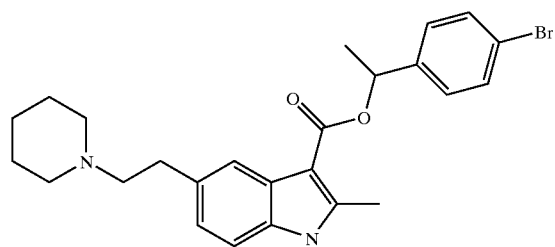

5-(2-Piperidino-ethyl)-2-methyl-1H-indole-3-carboxylic acid-1-(4-bromophenyl)-ethyl ester The procedure for Example 65 was followed, substituting 1-(4-bromophenyl)-ethanol for (S)-phenylethanol, and substituting piperidine for diethylamine. ESI+MS m/z 469 (M+1).

Example 120

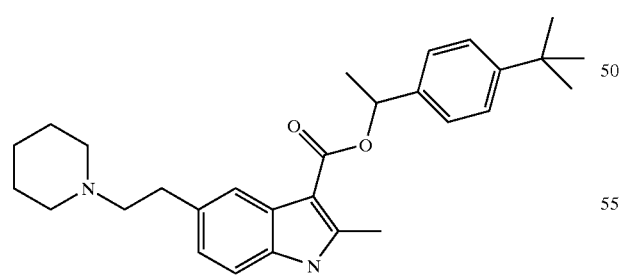

5-(2-Piperidino-ethyl)-2-methyl-1H-indole-3-carboxylic acid-1-(4-t-butylphenyl)-ethyl ester The procedure for Example 65 was followed, substituting 1-(4-(2-methyl-2-propyl)-phenyl)-ethanol for (S)-phenylethanol, and substituting piperidine for diethylamine. ESI+MS m/z 447 (M+1).

Example 121

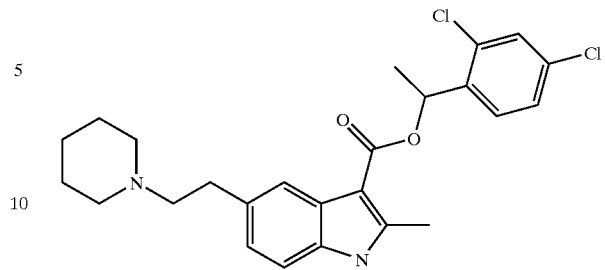

5-(2-Piperidino-ethyl)-2-methyl-1H-indole-3-carboxylic acid-1-(2,4-dichlorophenyl)-ethyl ester The procedure for Example 65 was followed, substituting 1-(2,4-dichlorophenyl)ethanol for (S)-phenylethanol, and substituting piperidine for diethylamine. ESI+MS m/z 459 (M+1).

Example 122

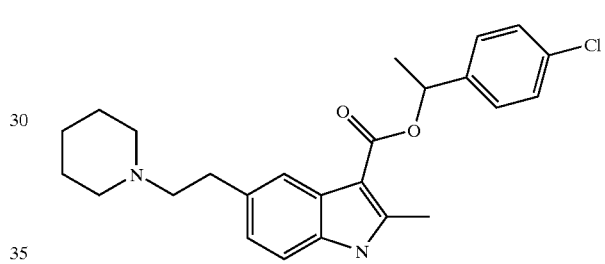

5-(2-Piperidino-ethyl)-2-methyl-1H-indole-3-carboxylic acid-1-(4-chlorophenyl)-ethyl ester The procedure for Example 65 was followed, substituting 1-(4-chlorophenyl)ethanol for (S)-phenylethanol, and substituting piperidine for diethylamine. ESI+MS m/z 425 (M+1).

Example 123

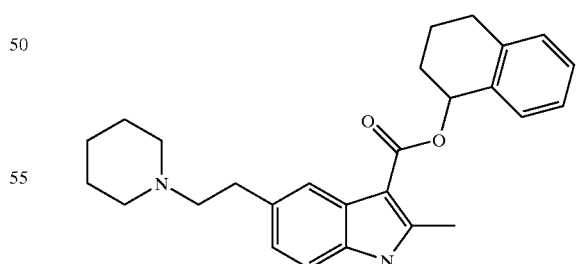

5-(2-Piperidino-ethyl)-2-methyl-1H-indole-3-carboxylic acid 1,2,3,4-tetrahydronaphth-1-yl ester The procedure for Example 65 was followed, 1,2,3,4-tetrahydronaphthalan-1-ol for (S)-phenylethanol and substituting piperidine for diethylamine. ESI+MS m/z 417 (M+1).

Example 124

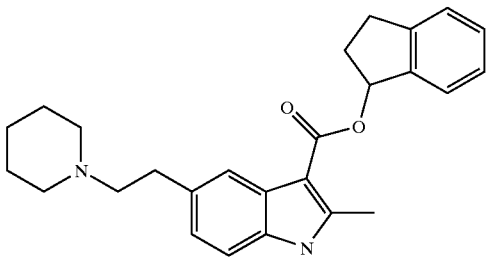

5-(2-Piperidino-ethyl)-2-methyl-1H-indole-3-carboxylic Indan-1-yl ester

The procedure for Example 65 was followed, indan-1-ol for (S)-phenylethanol and substituting piperidine for diethylamine. ESI+MS m/z 403 (M+1).

Example 125

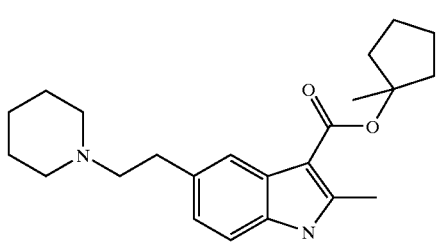

5-(2-Piperidino-ethyl)-2-methyl-1H-indole-3-carboxylic acid 1-methyl-1-cyclopentyl ester The procedure for Example 65 was followed, substituting 1-methyl-1-cyclopentanol for (S)-phenylethanol and substituting piperidine for diethylamine. ESI+MS m/z 369 (M+1).

Example 126

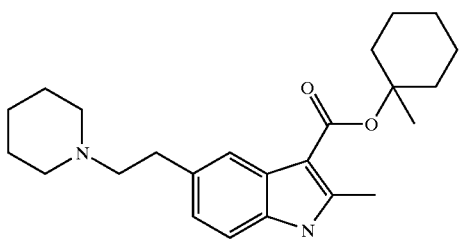

5-(2-Piperidino-ethyl)-2-methyl-1H-indole-3-carboxylic acid 1-methyl-1-cyclohexyl ester The procedure for Example 65 was followed, substituting 1-methyl-1-cyclohexanol for (S)-phenylethanol and substituting piperidine for diethylamine. ESI+MS m/z 383 (M+1).

Example 127

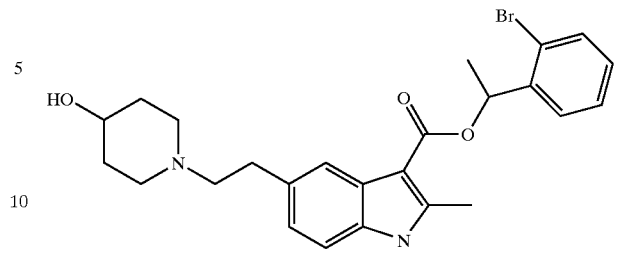

5-(2-(4-Hydroxy-piperidino)-ethyl)-2-methyl-1H-indole-3-carboxylic acid-1-(2-bromophenyl)-ethyl ester The procedure for Example 65 was followed, substituting 1-(2-bromophenyl)-ethanol for (S)-phenylethanol, and substituting 4-hydroxypiperidine for diethylamine. ESI+MS m/z 485 (M+1).

Example 128

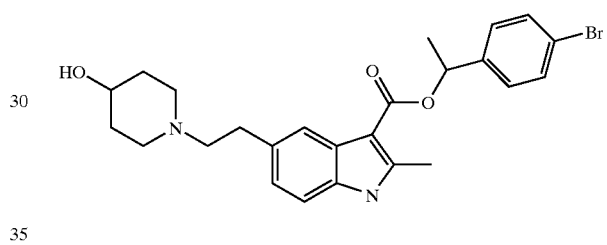

5-(2-(4-Hydroxy-piperidino)-ethyl)-2-methyl-1H-indole-3-carboxylic acid-1-(4-bromophenyl)-ethyl ester The procedure for Example 65 was followed, substituting 1-(4-bromophenyl)-ethanol for (S)-phenylethanol, and substituting 4-hydroxypiperidine for diethylamine. ESI+MS m/z 485 (M+1).

Example 129

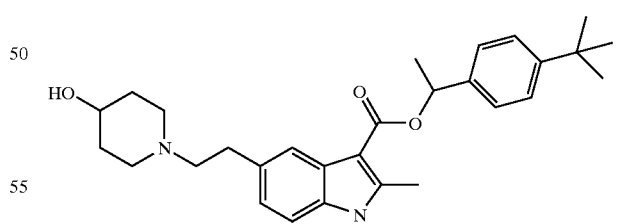

5-(2-(4-Hydroxy-piperidino)-ethyl)-2-methyl-1H-indole-3-carboxylic acid-1-(4-t-butylphenyl)-ethyl ester The procedure for Example 65 was followed, substituting 1-(4-(2-methyl-2-propyl)-phenyl)-ethanol for (S)-phenylethanol, and substituting 4-hydroxypiperidine for diethylamine. ESI+MS m/z 463 (M+1).

Example 130

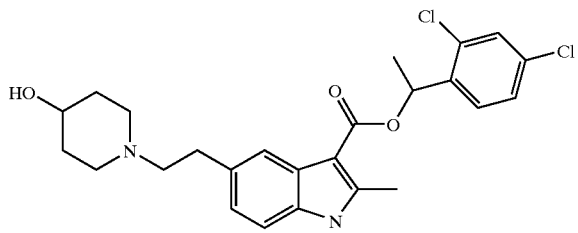

5-(2-(4-Hydroxy-piperidino)-ethyl)-2-methyl-1H-indole-3-carboxylic acid-1-(2,4-dichlorophenyl)-ethyl ester The procedure for Example 65 was followed, substituting 1-(2,4-dichlorophenyl)-ethanol for (S)-phenylethanol, and substituting 4-hydroxypiperidine for diethylamine. ESI+MS m/z 475 (M+1).

Example 131

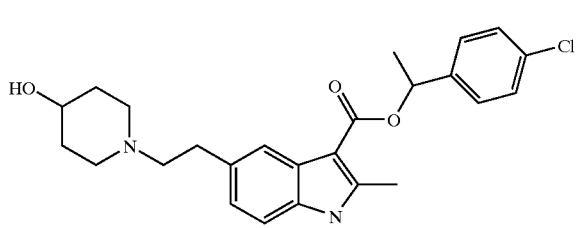

5-(2-(4-Hydroxy-piperidino)-ethyl)-2-methyl-1H-indole-3-carboxylic acid-1-(4-chlorophenyl)-ethyl ester The procedure for Example 65 was followed, substituting 1-(4-chlorophenyl)-ethanol for (S)-phenylethanol, and substituting 4-hydroxypiperidine for diethylamine. ESI+MS m/z 485 (M+1).

Example 132

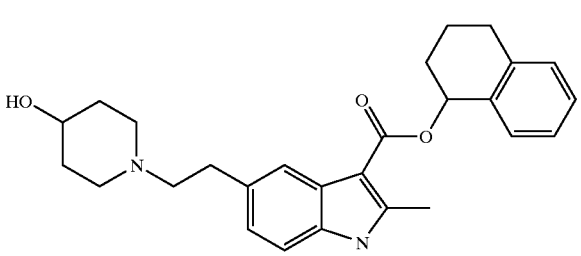

5-(2-(4-Hydroxy-piperidino)-ethyl)-2-methyl-1H-indole-3-carboxylic acid (1,2,3,4-tetrahydronaphthyl-1-yl) ester The procedure for Example 65 was followed, substituting 1,2,3,4-tetrahydro-1-naphthol for (S)-phenylethanol, and substituting 4-hydroxypiperidine for diethylamine. ESI+MS m/z 434 (M+1).

Example 133

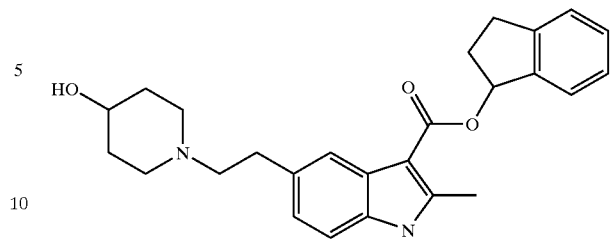

5-(2-(4-Hydroxy-piperidino)-ethyl)-2-methyl-1H-indole-3-carboxylic acid (1-indanyl) ester The procedure for Example 65 was followed, substituting 1-indanol for (S)-phenylethanol, and substituting 4-hydroxypiperidine for diethylamine. ESI+MS m/z 420 (M+1).

Example 134

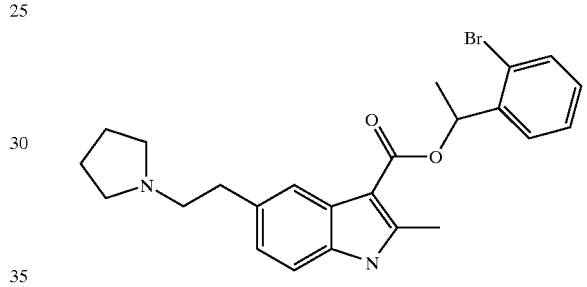

5-(2-Pyrrolidino-ethyl)-2-methyl-1H-indole-3-carboxylic acid 1-(2-bromophenyl)-ethyl ester The procedure for Example 65 was followed, substituting 1-(2-bromophenyl)-ethanol for (S)-phenylethanol, and substituting pyrrolidine for diethylamine. ESI+MS m/z 454 (M+1).

Example 135

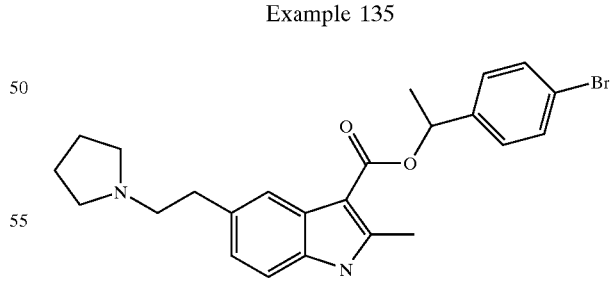

5-(2-Pyrrolidino-ethyl)-2-methyl-1H-indole-3-carboxylic acid 1-(4-bromophenyl)-ethyl ester The procedure for Example 65 was followed, substituting 1-(4-bromophenyl)-ethanol for (S)-phenylethanol, and substituting pyrrolidine for diethylamine. ESI+MS m/z 454 (M+1).

Example 136

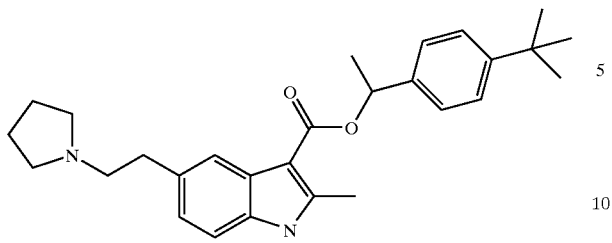

5-(2-Pyrrolidino-ethyl)-2-methyl-1H-indole-3-carboxylic acid 1-(4-t-butylphenyl)-ethyl ester The procedure for Example 65 was followed, substituting 1-(4-t-butylphenyl)-ethanol for (S)-phenylethanol, and substituting pyrrolidine for diethylamine. ESI+MS m/z 434 (M+1).

Example 137

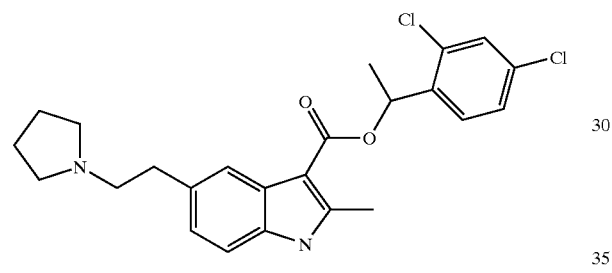

5-(2-Pyrrolidino-ethyl)-2-methyl-1H-indole-3-carboxylic acid 1-(2,4-dichlorophenyl)-ethyl ester The procedure for Example 65 was followed, substituting 1-(2,4-dichlorophenyl)-ethanol for (S)-phenylethanol, and substituting pyrrolidine for diethylamine. ESI+MS m/z 445 (M+1).

Example 138

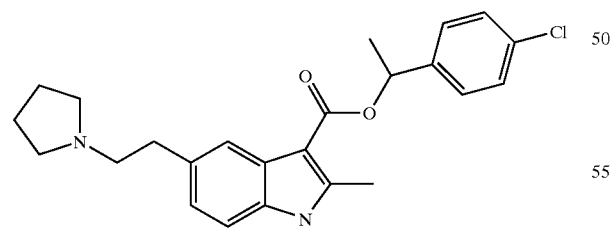

5-(2-Pyrrolidino-ethyl)-2-methyl-1H-indole-3-carboxylic acid 1-(4-chlorophenyl)-ethyl ester The procedure for Example 65 was followed, substituting 1-(4-chlorophenyl)-ethanol for (S)-phenylethanol, and substituting pyrrolidine for diethylamine. ESI+MS m/z 411 (M+1).

Example 139

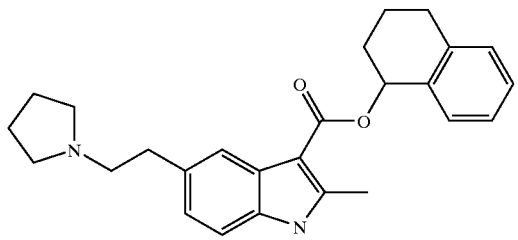

5-(2-(2-Pyrrolidino-ethyl)-2-methyl-1H-indole-3-carboxylic acid (1,2,3,4-tetrahydronaphthyl-1-yl) ester The procedure for Example 65 was followed, substituting 1,2,3,4-tetrahydro-1-naphthol for (S)-phenylethanol, and substituting pyrrolidine for diethylamine. ESI+MS m/z 404 (M+1).

Example 140

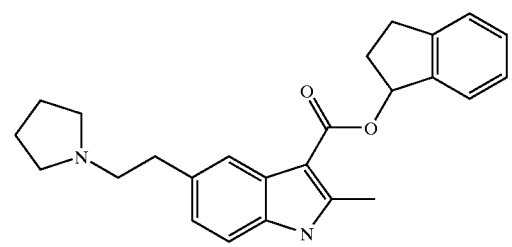

5-(2-(2-Pyrrolidino-ethyl)-2-methyl-1H-indole-3-carboxylic acid (1-indanyl) ester The procedure for Example 65 was followed, substituting 1-indanol for (S)-phenylethanol, and substituting pyrrolidine for diethylamine. ESI+MS m/z 390 (M+1).

Example 141

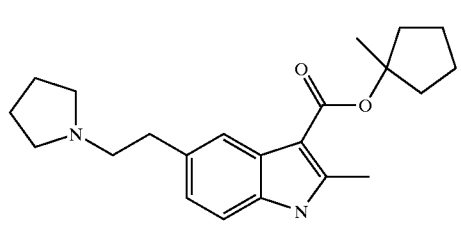

5-(2-(2-Pyrrolidino-ethyl)-2-methyl-1H-indole-3-carboxylic acid (1-methylcyclopetan-1-yl) ester The procedure for Example 65 was followed, substituting 1-methylcyclopentan-1-ol for (S)-phenylethanol, and substituting pyrrolidine for diethylamine. ESI+MS m/z 356 (M+1).

Example 142

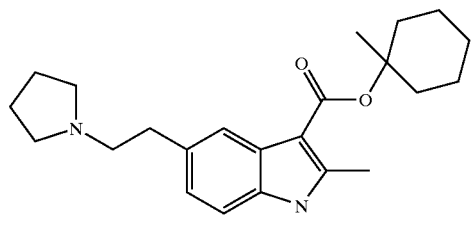

5-(2-(2-Pyrrolidino-ethyl)-2-methyl-1H-indole-3-carboxylic acid (1-methylcyclohex-1-yl) ester The procedure for Example 65 was followed, substituting 1 methylcyclohexan-1-ol for (S)-phenylethanol, and substituting pyrrolidine for diethylamine. ESI+MS m/z 370 (M+1).

Example 143

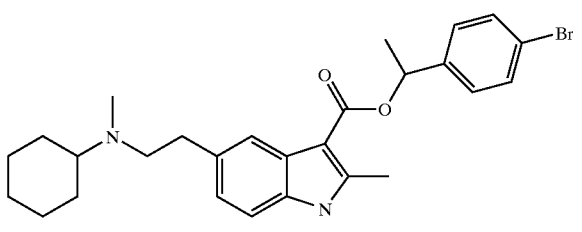

5-(2-N-Cyclohexyl-N-methyl-amino-ethyl)-2-methyl-1H-indole-3-carboxylic acid 1-(4-bromophenyl)-ethyl ester The procedure for Example 65 was followed, substituting 1-(4-bromophenyl)-ethanol for (S)-phenylethanol, and substituting N-cyclohexyl-N-methylamine for diethylamine. ESI+MS m/z 497 (M+1).

Example 144

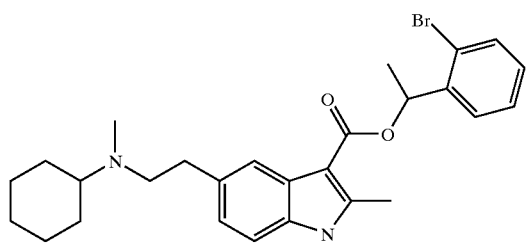

5-(2-N-Cyclohexyl-N-methyl-amino-ethyl)-2-methyl-1H-indole-3-carboxylic acid 1-(2-bromophenyl)-ethyl ester The procedure for Example 65 was followed, substituting 1-(2-bromophenyl)-ethanol for (S)-phenylethanol, and substituting N-cyclohexyl-N-methylamine for diethylamine. ESI+MS m/z 497 (M+1).

Example 145

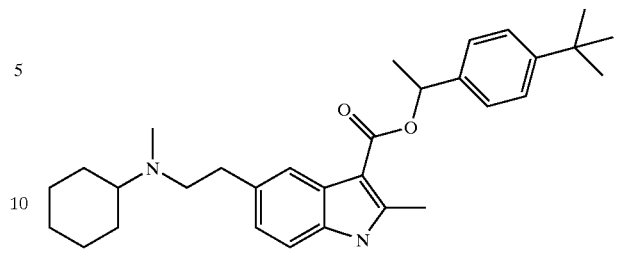

5-(2-N-Cyclohexyl-N-methyl-amino-ethyl)-2-methyl-1H-indole-3-carboxylic acid 1-(4-t-butylphenyl)-ethyl ester The procedure for Example 65 was followed, substituting 1-(4-t-butylphenyl)-ethanol for (S)-phenylethanol, and substituting N-cyclohexyl-N-methylamine for diethylamine. ESI+MS m/z 476 (M+1).

Example 146

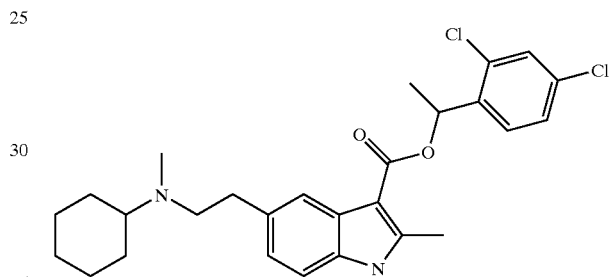

5-(2-N-Cyclohexyl-N-methyl-amino-ethyl)-2-methyl-1H-indole-3-carboxylic acid 1-(2,4-dichlorophenyl)-ethyl ester The procedure for Example 65 was followed, substituting 1-(2,4-dichlorophenyl)-ethanol for (S)-phenylethanol, and substituting N-cyclohexyl-N-methylamine for diethylamine. ESI+MS m/z 487 (M+1).

Example 147

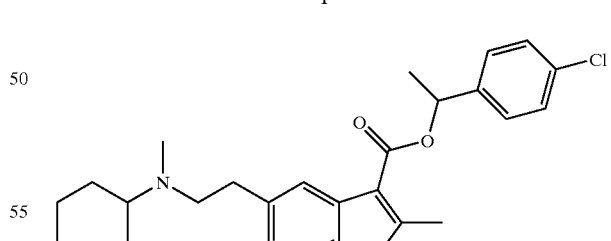

5-(2-N-Cyclohexyl-N-methyl-amino-ethyl)-2-methyl-1H-indole-3-carboxylic acid 1-(4-chlorophenyl)-ethyl ester The procedure for Example 65 was followed, substituting 1-(2-chloroophenyl)-ethanol for (S)-phenylethanol, and substituting N-cyclohexyl-N-methylamine for diethylamine. ESI+MS m/z 451 (M+1).

Example 148

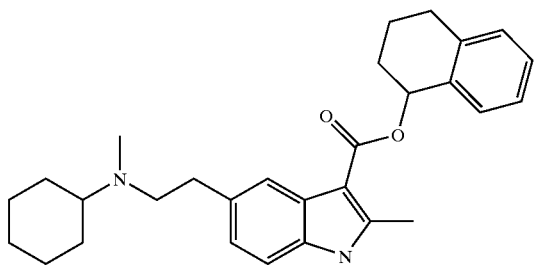

5-(2-N-Cyclohexyl-N-methyl-amino-ethyl)-2-methyl-1H-indole-3-carboxylic acid (1,2,3,4-tetrahydronaphthyl-1-yl) ester The procedure for Example 65 was followed, substituting 1,2,3,4-tetrahydronaphthan-1-ol for (S)-phenylethanol, and substituting N-cyclohexyl-N-methylamine for diethylamine. ESI+MS m/z 446 (M+1).

Example 149

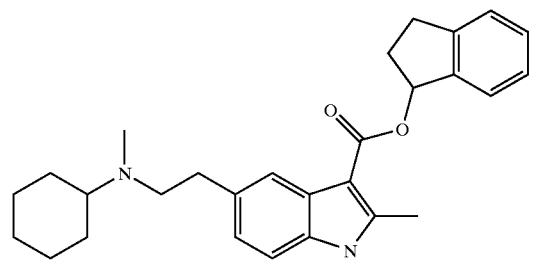

5-(2-N-Cyclohexyl-N-methyl-amino-ethyl)-2-methyl-1H-indole-3-carboxylic acid (1-indanyl)ester The procedure for Example 65 was followed, substituting indan-1-ol for (S)-phenylethanol, and substituting N-cyclohexyl-N-methylamine for diethylamine. ESI+MS m/z 432 (M+1).

Example 150

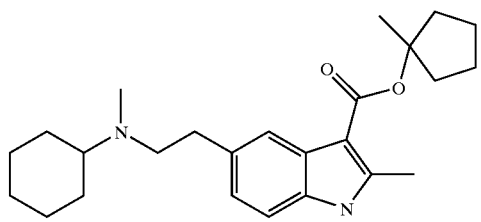

5-(2-N-Cyclohexyl-N-methyl-amino-ethyl)-2-methyl-1H-indole-3-carboxylic acid (1-methylcyclopetan-1-yl) ester The procedure for Example 65 was followed, substituting 1-methylcyclopetan-1-ol for (S)-phenylethanol, and substituting N-cyclohexyl-N-methylamine for diethylamine. ESI+MS m/z 398 (M+1).

Example 151

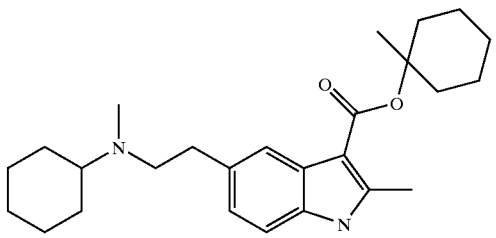

5-(2-N-Cyclohexyl-N-methyl-amino-ethyl)-2-methyl-1H-indole-3-carboxylic acid (1-methylcyclohex-1-yl) ester The procedure for Example 65 was followed, substituting 1-methylcyclohexan-1-ol for (S)-phenylethanol, and substituting N-cyclohexyl-N-methylamine for diethylamine. ESI+MS m/z 412 (M+1).

Example 152

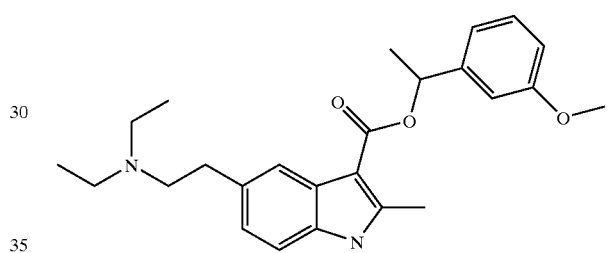

5-(2-Diethylamino-ethyl)-2-methyl-1H-indole-3-carboxylic acid 1-(3-methoxyphenyl)-ethyl ester The procedure for Example 65 was followed, substituting 1-(3-methoxyphenyl)-ethanol for (S)-phenylethanol. ESI+MS m/z 410 (M+1).

Example 153

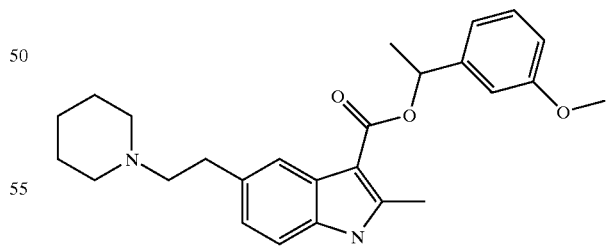

5-(2-Piperidino-ethyl)-2-methyl-1H-indole-3-carboxylic acid 1-(3-methoxyphenyl)-ethyl ester The procedure for Example 65 was followed, substituting 1-(3-methoxyphenyl)-ethanol for (S)-phenylethanol and substituting piperidine for diethylamine. ESI+MS m/z 422 (M+1).

Example 154

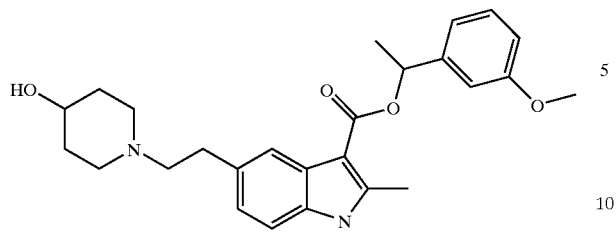

5-(2-(4-Hydroxy-piperidino)-ethyl)-2-methyl-1H-indole-3-carboxylic acid 1-(3-methoxyphenyl)-ethyl ester The procedure for Example 65 was followed, substituting 1-(3-methoxyphenyl)-ethanol for (S)-phenylethanol, and substituting 4-hydroxypiperidine for diethylamine. ESI+MS m/z 438 (M+1).

Example 155

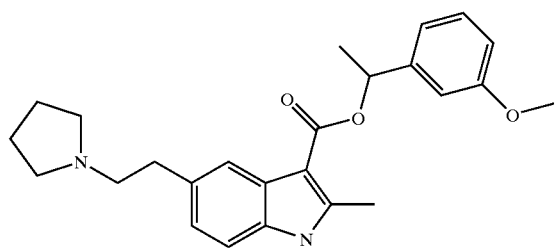

5-(2-Pyrrolidino-ethyl)-2-methyl-1H-indole-3-carboxylic acid 1-(3-methoxyphenyl)-ethyl ester The procedure for Example 65 was followed, substituting 1-(3-methoxyphenyl)-ethanol for (S)-phenylethanol, and substituting pyrrolidine for diethylamine. ESI+MS m/z 408 (M+1).

Example 156

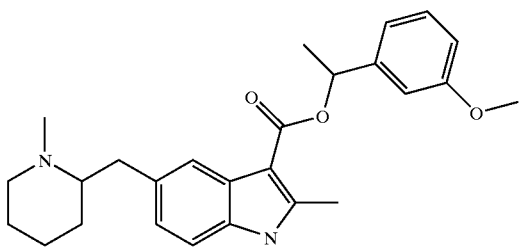

5-(2-N-Cyclohexyl-N-methyl-amino-ethyl)-2-methyl-1H-indole-3-carboxylic acid 1-(3-methoxyphenyl)-ethyl ester The procedure for Example 65 was followed, substituting 1-(3-methoxyphenyl)-ethanol for (S)-phenylethanol, and substituting N-cyclohexyl-N-methylamine for diethylamine. ESI+MS m/z 450 (M+1).

Example 157

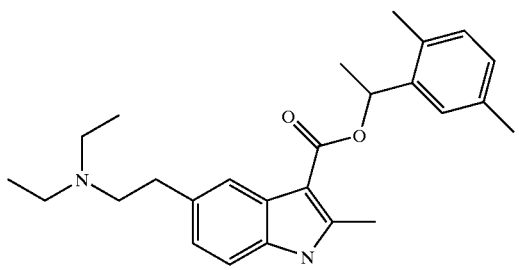

5-(2-Diethylamino-ethyl)-2-methyl-1H-indole-3-carboxylic acid 1-(2,5-dimethylphenyl)-ethyl ester The procedure for Example 65 was followed, (2,5-dimethylphenyl)-ethan-1-ol for (S)-phenylethanol. ESI+MS m/z 408 (M+1).

Example 158

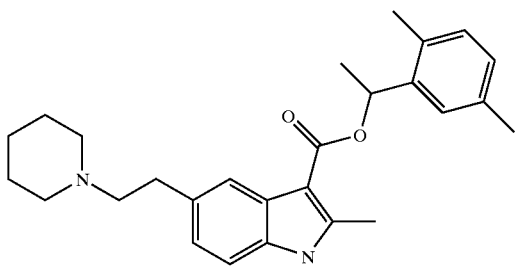

5-(2-Piperidinyl-ethyl)-2-methyl-1H-indole-3-carboxylic 1-(2,5-dimethylphenyl)-ethyl ester The procedure for Example 65 was followed, substituting (2,5-dimethylphenyl)-ethan-1-ol for (S)-phenylethanol, and substituting piperidine for diethylamine. ESI+MS m/z 420 (M+1).

Example 159

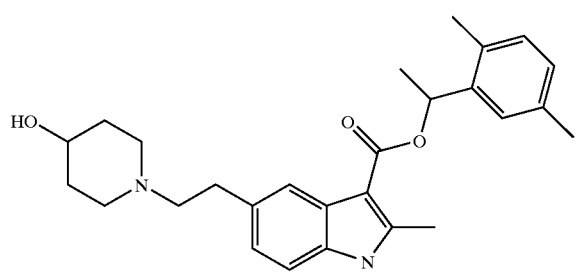

5-(2-(4-Hydroxy-piperidino)-ethyl)-2-methyl-1H-indole-3-carboxylic acid 1-(2,5-dimethylphenyl)-ethyl ester The procedure for Example 65 was followed, substituting (2,5-dimethylphenyl)-ethan-1-ol for (S)-phenylethanol, and substituting 4-hydroxypiperidine for diethylamine. ESI+MS m/z 436 (M+1).

Example 160

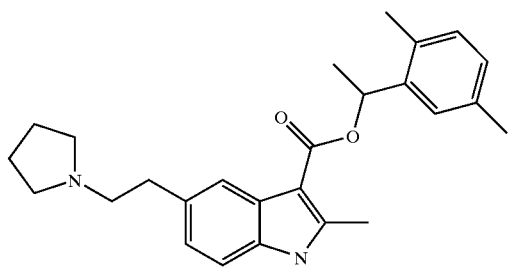

5-(2-Pyrrolidino-ethyl)-2-methyl-1H-indole-3-carboxylic acid 1-(2,5-dimethylphenyl)-ethyl ester The procedure for Example 65 was followed, substituting (2,5-dimethylphenyl)-ethan-1-ol for (S)-phenylethanol, and substituting pyrrolidine for diethylamine. ESI+MS m/z 406 (M+1).

Example 161

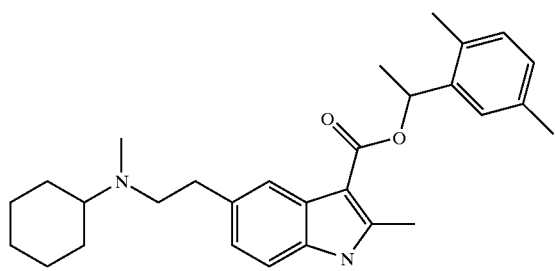

5-(2-N-Cyclohexyl-N-methyl-amino-ethyl)-2-methyl-1H-indole-3-carboxylic acid 1-(2,5-dimethylphenyl)-ethyl ester The procedure for Example 65 was followed, substituting (2,5-dimethylphenyl)-ethan-1-ol for (S)-phenylethanol, and substituting N-cyclohexyl-N-methylamine for diethylamine. ESI+MS m/z 448 (M+1).

Example 162

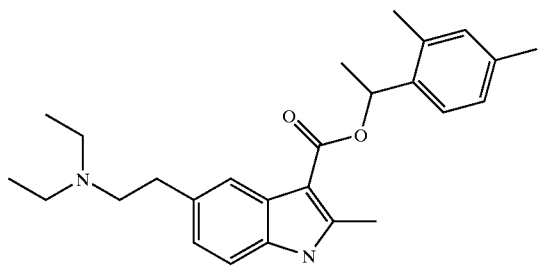

5-(2-Diethylamino-ethyl)-2-methyl-1H-indole-3-carboxylic acid 1-(2,4-dimethylphenyl)-ethyl ester The procedure for Example 65 was followed, (2,4-dimethylphenyl)-ethan-1-ol for (S)-phenylethanol. ESI+MS m/z 408 (M+1).

Example 163

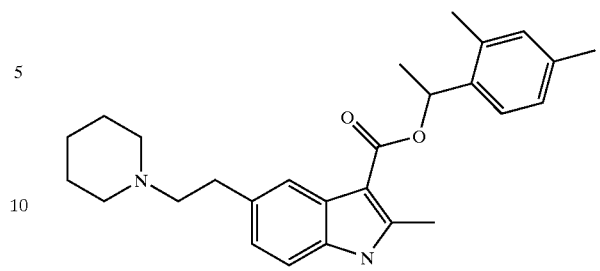

5-(2-Piperidinyl-ethyl)-2-methyl-1H-indole-3-carboxylic 1-(2,4-dimethylphenyl)-ethyl ester The procedure for Example 65 was followed, substituting (2,4-dimethylphenyl)-ethan-1-ol for (S)-phenylethanol, and substituting piperidine for diethylamine. ESI+MS m/z 420 (M+1).

Example 164

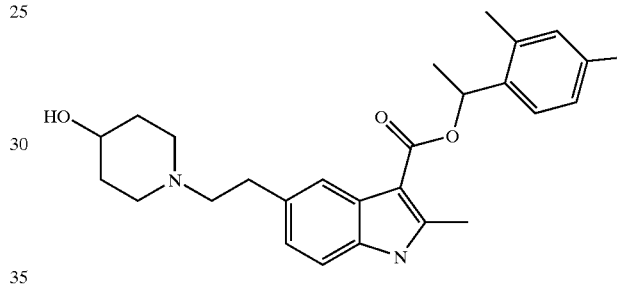

5-(2-(4-Hydroxy-piperidino)-ethyl)-2-methyl-1H-indole-3-carboxylic acid 1-(2,4-dimethylphenyl)-ethyl ester The procedure for Example 65 was followed, substituting (2,4-dimethylphenyl)-ethan-1-ol for (S)-phenylethanol, and substituting 4-hydroxypiperidine for diethylamine. ESI+MS m/z 436 (M+1).

Example 165

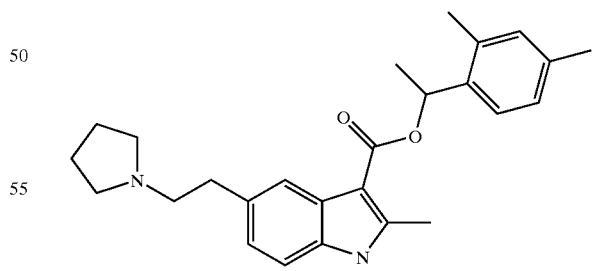

5-(2-Pyrrolidino-ethyl)-2-methyl-1H-indole-3-carboxylic acid 1-(2,4-dimethylphenyl)-ethyl ester The procedure for example 65 was followed, substituting (2,4-dimethylphenyl)-ethan-1-ol for (S)-phenylethanol, and substituting pyrrolidine for diethylamine. ESI+MS m/z 406 (M+1).

Example 166

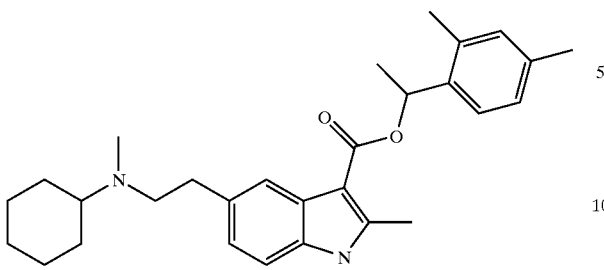

5-(2-N-Cyclohexyl-N-methyl-amino-ethyl)-2-methyl-1H-indole-3-carboxylic acid 1-(2,4-dimethylphenyl)-ethyl ester The procedure for Example 65 was followed, substituting (2,4-dimethylphenyl)-ethan-1-ol for (S)-phenylethanol, and substituting N-cyclohexyl-N-methylamine for diethylamine. ESI+MS m/z 448 (M+1).

Example 167

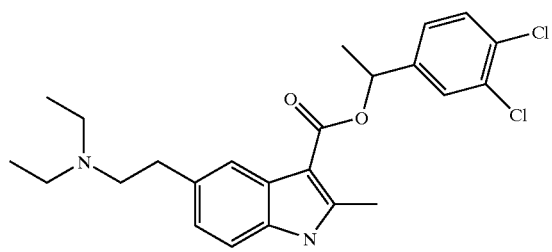

5-(2-Diethylamino-ethyl)-2-methyl-1H-indole-3-carboxylic acid 1-(3,4-dichlorophenyl)-ethyl ester The procedure for Example 65 was followed, (3,4-dichlorophenyl)-ethan-1-ol for (S)-phenylethanol. ESI+MS m/z 447 (M+1).

Example 168

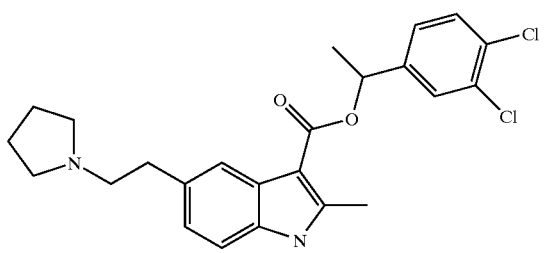

5-(2-Pyrrolidino-ethyl)-2-methyl-1H-indole-3-carboxylic acid 1-(3,4-dichlorophenyl)-ethyl ester The procedure for Example 65 was followed, substituting (3,4-dichlorophenyl)-ethan-1-ol for (S)-phenylethanol, and substituting pyrrolidine for diethylamine. ESI+MS m/z 445 (M+1).

Example 169

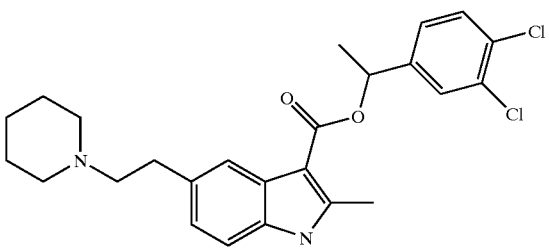

5-(2-Piperidinyl-ethyl)-2-methyl-1H-indole-3-carboxylic 1-(3,4-dichlorophenyl)-ethyl ester The procedure for Example 65 was followed, substituting (3,4-dichlorophenyl)-ethan-1-ol for (S)-phenylethanol, and substituting piperidine for diethylamine. ESI+MS m/z 459 (M+1).

Example 170

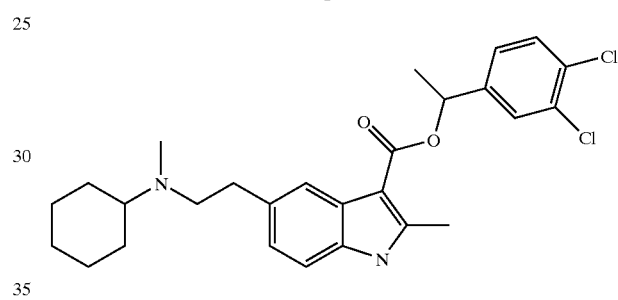

5-(2-N-Cyclohexyl-N-methyl-amino-ethyl)-2-methyl-1H-indole-3-carboxylic acid 1-(3,4-dichlorophenyl)-ethyl ester The procedure for Example 65 was followed, substituting (3,4-dichlorophenyl)-ethan-1-ol for (S)-phenylethanol, and substituting N-cyclohexyl-N-methylamine for diethylamine. ESI+MS m/z 487 (M+1).

Example 171

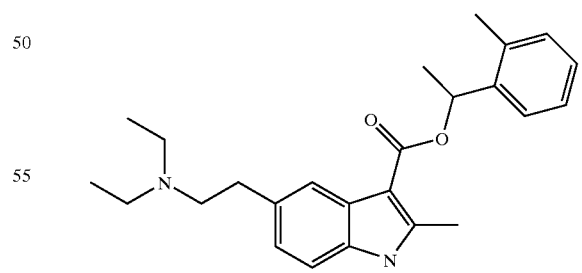

5-(2-Diethylamino-ethyl)-2-methyl-1H-indole-3-carboxylic acid 1-(2-methylphenyl)-ethyl ester The procedure for Example 65 was followed, (2-methylphenyl)-ethan-1-ol for (S)-phenylethanol. ESI+MS m/z 394 (M+1).

Example 172

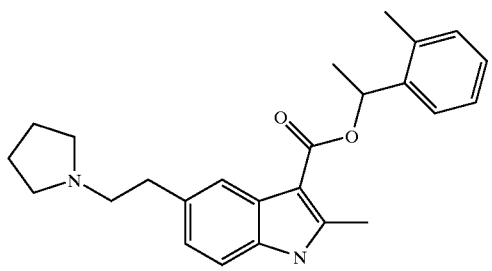

5-(2-Pyrrolidino-ethyl)-2-methyl-1H-indole-3-carboxylic acid 1-(2-methylphenyl)-ethyl ester The procedure for Example 65 was followed, substituting (2-methylphenyl)-ethan-1-ol for (S)-phenylethanol, and substituting pyrrolidine for diethylamine. ESI+MS m/z 392 (M+1).

Example 173

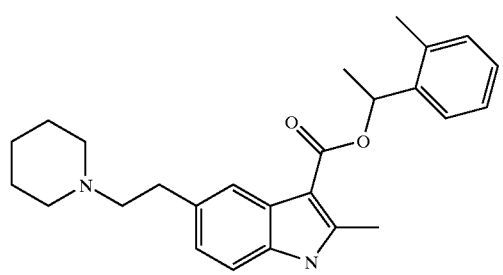

5-(2-Piperidinyl-ethyl)-2-methyl-1H-indole-3-carboxylic 1-(2-methylphenyl)-ethyl ester The procedure for Example 65 was followed, substituting (2-methylphenyl)-ethan-1-ol for (S)-phenylethanol, and substituting piperidine for diethylamine. ESI+MS m/z 406 (M+1).

Example 174

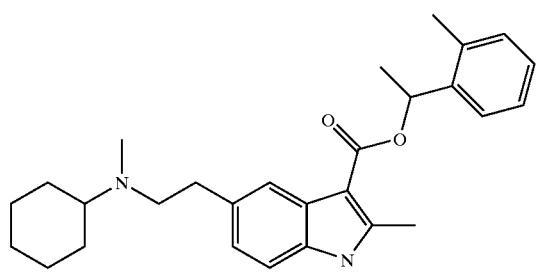

5-(2-N-Cyclohexyl-N-methyl-amino-ethyl)-2-methyl-1H-indole-3-carboxylic acid 1-(2-methylphenyl)-ethyl ester The procedure for Example 65 was followed, substituting (2-methylphenyl)-ethan-1-ol for (S)-phenylethanol, and substituting N-cyclohexyl-N-methylamine for diethylamine. ESI+MS m/z 434 (M+1).

Example 175

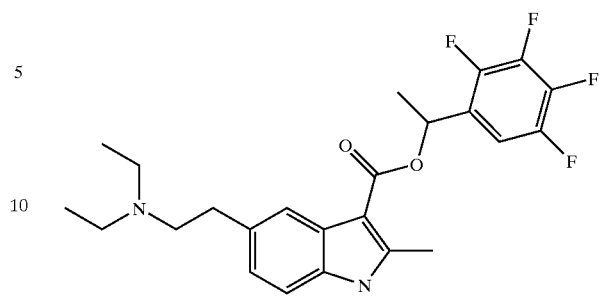

5-(2-Diethylamino-ethyl)-2-methyl-1H-indole-3-carboxylic acid 1-(2,3,4,5-tetrafluorophenyl)-ethyl ester The procedure for Example 65 was followed, (2,3,4,5-tetrafluorophenyl)-ethan-1-ol for (S)-phenylethanol. ESI+MS m/z 451 (M+1).

Example 176

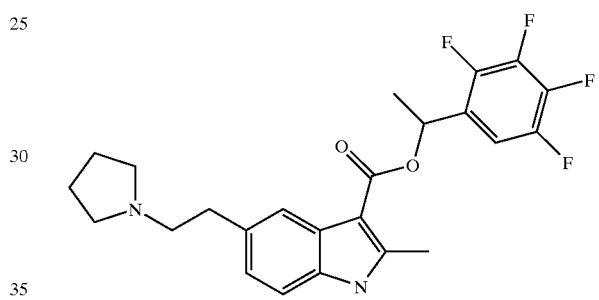

5-(2-Pyrrolidino-ethyl)-2-methyl-1H-indole-3-carboxylic acid 1-(2,3,4,5-tetrafluorophenyl)-ethyl ester The procedure for Example 65 was followed, substituting (2,3,4,5-tetrafluorophenyl)-ethan-1-ol for (S)-phenylethanol, and substituting pyrrolidine for diethylamine. ESI+MS m/z 449 (M+1).

Example 177

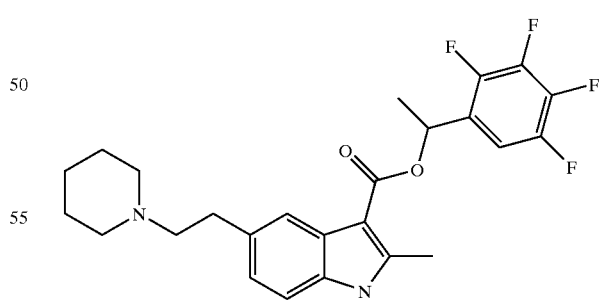

5-(2-Piperidinyl-ethyl)-2-methyl-1H-indole-3-carboxylic acid 1-(2,3,4,5-tetrafluorophenyl)-ethyl ester The procedure for Example 65 was followed, substituting (2,3,4,5-tetrafluorophenyl)-ethan-1-ol for (s)-phenylethanol, and substituting piperidine for diethylamine. ESI+MS m/z 463 (M+1).

Example 178

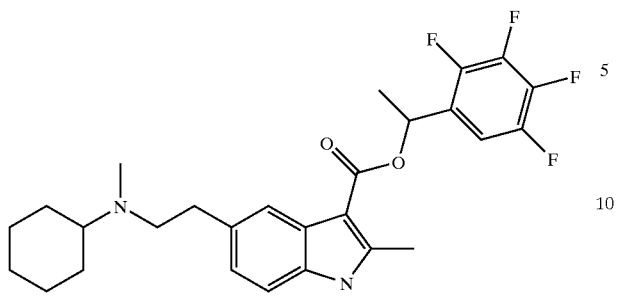

5-(2-N-Cyclohexyl-N-methyl-amino-ethyl)-2-methyl-1H-indole-3-carboxylic acid 1-(2,3,4,5-tetrafluorophenyl)-ethyl ester The procedure for Example 65 was followed, substituting (2,3,4,5-tetrafluorophenyl)-ethan-1-ol for (S)-phenylethanol, and substituting N-cyclohexyl-N-methylamine for diethylamine. ESI+MS m/z 492 (M+1).

Example 179

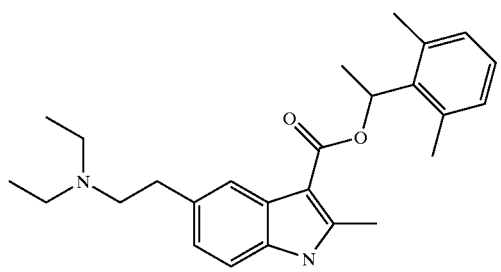

5-(2-Diethylamino-ethyl)-2-methyl-1H-indole-3-carboxylic acid 1-(2,6-dimethylphenyl)-ethyl ester The procedure for Example 65 was followed, (2,6-dimethylphenyl)-ethan-1-ol for (S)-phenylethanol. ESI+MS m/z 408 (M+1).

Example 180

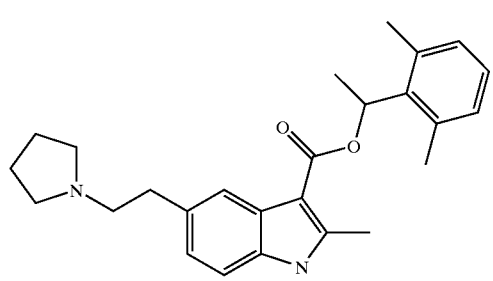

5-(2-Pyrrolidino-ethyl)-2-methyl-1H-indole-3-carboxylic acid 1-(2,6-dimethylphenyl)-ethyl ester The procedure for Example 65 was followed, substituting (2,6-dimethylphenyl)-ethan-1-ol for (S)-phenylethanol, and substituting pyrtolidine for diethylamine. ESI+MS m/z 406 (M+1).

Example 181

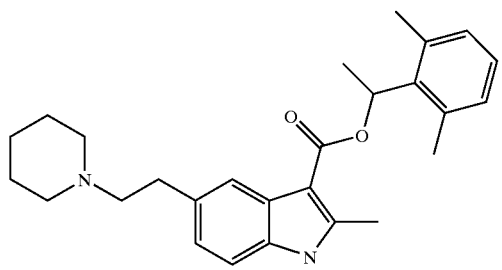

5-(2-Piperidinyl-ethyl)-2-methyl-1H-indole-3-carboxylic 1-(2,6-dimethylphenyl)-ethyl ester The procedure for Example 65 was followed, substituting (2,6-dimethylphenyl)-ethan-1-ol for (S)-phenylethanol, and substituting piperidine for diethylamine. ESI+MS m/z 420 (M+1).

Example 182

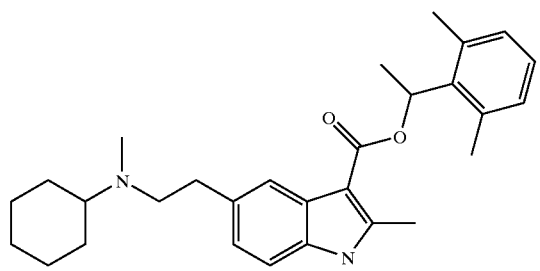

5-(2-N-Cyclohexyl-N-methyl-amino-ethyl)-2-methyl-1H-indole-3-carboxylic acid 1-(2,6-dimethylphenyl)-ethyl ester The procedure for Example 65 was followed, substituting (2,6-dimethylphenyl)-ethan-1-ol for (S)-phenylethanol, and substituting N-cyclohexyl-N-methylamine for diethylamine. ESI+MS m/z 448 (M+1).

Example 183

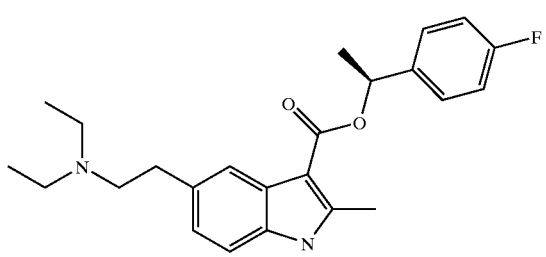

5-(2-Diethylamino-ethyl)-2-methyl-1H-indole-3-carboxylic acid 1-(S)-(4-fluorophenyl)-ethyl ester The procedure for Example 65 was followed, (S)-(4-flourophenyl)ethanol for (S)-phenylethanol. ESI+MS m/z 398 (M+1).

Example 184

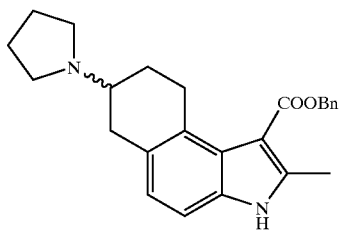

2-Methyl-6-pyrrolidino-4,5,6,7-tetrahydrobenzo[g]-
1H-indole-3-carboxylic acid benzyl ester

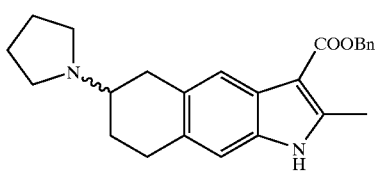

2-Methyl-6-pyrrolidino-5,6,7,8-tetrahydrobenzo[h]-
1H-indole-3-carboxylic acid benzyl ester

Step A

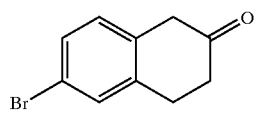

To a solution of 4-bromophenylacetic acid (10.00 g, 46.50 mmol, 1.0 eq) and thionyl chloride (11.06 g, 93.00 mmol, 2.0 eq) in anhydrous dichloromethane (50 mL) was added three drops of DMF. The reaction mixture was refluxed for 16 hours. Then the mixture was cooled to room temperature, evaporated in vacuo to yield the acid chloride, which was redissolved in anhydrous dichloromethane (200 mL) and cooled to 0° C. To the resulting acid chloride solution was slowly added aluminum trichloride (17.17 g, 128.78 mmol, 2.7 eq). The mixture was stirred at 0° C. for 10 minutes, then a gentle stream of ethene was bubbled into the reaction mixture for 5 hours. The resulting mixture was cautiously poured into ice and concentrated hydrochloric acid (5 mL) was added. The layers were separated. The organic phase was washed with saturated sodium carbonate, dried over $Na_2SO_4$, and filtered. After removing the solvent, the crude brown product was loaded on silica gel and chromatographed, eluting with ethyl acetate/hexane (1:4) 9.30 g (89%) of 6-bromo-2-tetralone was obtained as a white solid.

Step B

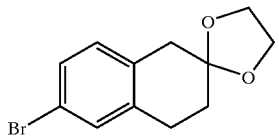

To a solution of 6-bromo-2-tetralone (5.50 g, 24.44 mmol, 1.0 eq) in anhydrous benzene (150 mL) was added ethylene glycol (1.81 g, 29.33 mmol, 1.2 eq) and p-toluenesulfonic acid monohydrate (0.46 g, 2.44 mmol, 0.1 eq). The reaction mixture was refluxed under Dean-Stark trap for 18 hours. Then the mixture was cooled to room temperature and washed with saturated sodium bicarbonate and brine. The organic phase was dried over $Na_2SO_4$. After removing the solvent, the residue was loaded on silica gel and chromatographed, eluting with ethyl acetate/hexane (1:4). 6.22 g (95%) of 1,3-dioxolane was obtained as a pale yellow oil.

Step C

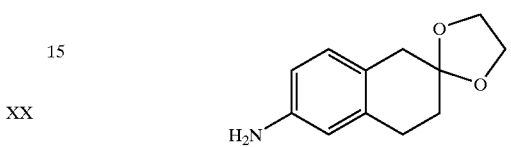

Benzophenone imine (2.52 g, 13.94 mmol, 1.5 eq), tris (dibenzylideneacetone) dipalladium (0.51 g, 0.56 mmol, 0.06 eq), (S)-(−)BINAP (0.23 g, 0.37 mmol, 0.04 eq), and sodium tert-butoxide (1.25 g, 13.00 mmol, 1.4 eq) were added to a solution of 1,3-dioxolane (2.50 g, 9.29 mmol, 1.0 eq) in anhydrous toluene (50 mL) under Ar. The reaction mixture was stirred and heated to reflux for 5 to 18 hours. The mixture was cooled to room temperature, diluted with ether (10× volume of toluene), filtered, and concentrated to obtain a black residue.

To a solution of the imine in MeOH (90 mL, 0.1 M) at room temperature was added sodium acetate (1.83 g, 22.29 mmol, 2.4 eq) and hydroxylamine hydrochloride (1.16 g, 16.70 mmol, 1.8 eq). The reaction mixture was stirred at room temperature until the starting material had been consumed. The mixture was concentrated to obtain a black tar. The black tar was redissolved in ethyl acetate (40 mL) and washed with 0.1N NaOH solution. The organic phase was dried over $Na_2SO_4$. After removing the solvent, the residue was loaded on silica gel and chromatographed, eluting with ethyl acetate/hexane (1:3). 1.70 g (89%) of aniline was obtained as a pale brown solid.

Step D

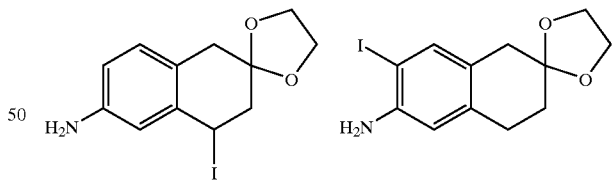

To a solution of ketal-aniline (10.23 g, 49.90 mmol) and 2,6-lutidine (5.80 mL, 49.90 mmol) in EtOH was added iodine (12.67 g, 49.90 mmol) and $Ag_2SO_4$ (15.53 g, 49.90 mmol). The reaction mixture was stirred at room temperature for 4 hours. The mixture was concentrated and redissolved in EtOAc (100 mL). The resulting solution was washed with saturated $Na_2CO_3$ solution and diluted $Na_2S_2O_3$ solution. The organic phase was dried over $MgSO_4$. After removing the solvent, the residue was loaded on silica gel and chromatographed, eluting with ethyl acetate/hexane (1:3). 9.21 g (55%) of 2-Iodole-aniline and 8-iodole-aniline was obtained in a ratio of 2.2:1 as a pale brown solid.

Step E

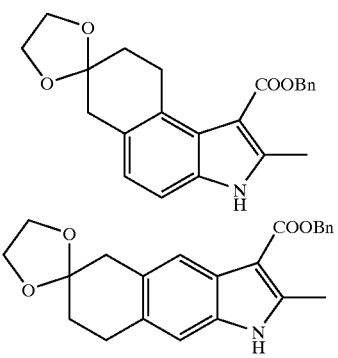

A solution of iodo-aniline (9.21 g, 27.82 mmol), benzylacetoacetate (4.80 mL, 27.82 mmol) and toluenesulfonic acid (2.54 g, 2.78 mmol) in anhydrous benzene was heated at reflux under a Dean-stark condenser for 1.5 hours. After cooling, the reaction solution was concentrated to provide crude amino crotonate. This crude material was redissolved in dry DMF (10 mL). To this solution was added tris(dibenzylideneacetone) dipalladium (2.547 g, 2.78 mmol) and tri-n-propyl amine (8.0 mL, 41.73 mmol). The mixture was heated at 80° C. under Ar for 3 hours. The reaction was quenched with water and extracted with EtOAc. The organic phases were dried over MgSO$_4$. After removing the solvent, the residue was loaded on silica gel and chromatographed, eluting with ethyl acetate/hexane (1:3). 2.3 g (22%) of Bent and linear indole ketal was obtained in a ratio of 1:1 as a brown solid.

Step F

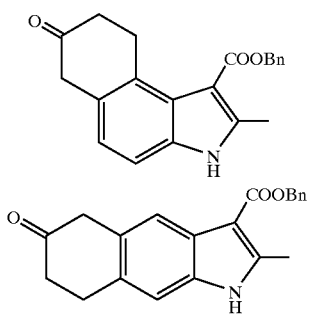

The mixture of bent and linear indole ketal (280 mg, 0.74 mmol) was dissolved in Acetone (15 mL) and H$_2$O (5 mL). PPTS (372 mg, 1.48 mmol) was added. The reaction mixture was heated at reflux for overnight. The mixture was concentrated and redissolved in EtOAc. The resulting solution was washed with saturated sodium bicarbonate and dried over Na$_2$SO$_4$. After removing the solvent, the residue was loaded on silica gel and chromatographed, eluting with ethyl acetate/hexane (1:5). 182 mg (73%) of bent and linear indole ketone was obtained as a brown solid. These two isomers could be separated by chromatography.

Step G

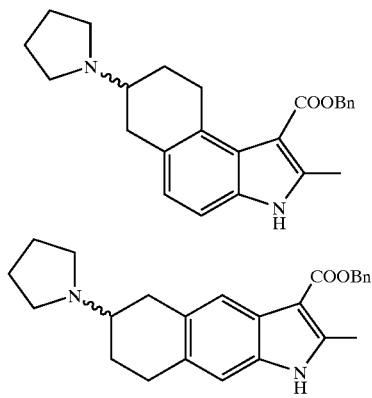

To a solution of bent indole ketone (80 mg, 0.24 mg) in dichloroethane (3 mL), was added pyrrolidine (25 µL, 0.28 mmol), sodium triacetoxyborohydride (81 mg, 0.38 mmol), and acetic acid (14 mg, 0.24 mmol). The reaction mixture was stirred at room temperature for overnight. The mixture was diluted with dichloromethane and washed with saturated sodium bicarbonate. The organic phases were dried over Na$_2$SO$_4$. After removing the solvent, the residue was loaded on silica gel and chromatographed, eluting with ethyl acetate/methanol/triethyl amine (10:1:0.1). 40 mg (46%) of bent indole amine was obtained as a light brown solid. This amine was converted into a hydrochloride salt: LC/MS (ESI+) 389 (M+1); Anal. (C$_{25}$H$_{28}$O$_2$N$_2$.HCl.0.4H$_2$O): C, N, H.

Following the above procedure, linear indole amine was generated in 100% yield: LC/MS (ESI+) 389 (M+1); Anal. (C$_{25}$H$_{28}$O$_2$N$_2$.HCl): C, N, H.

Example 185

8h

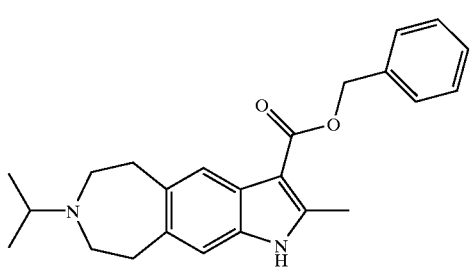

2-Methyl-7-(2-propyl)-1H-azepino[5,6-h]indole-3-carboxylic acid benzyl ester

Figure 8:
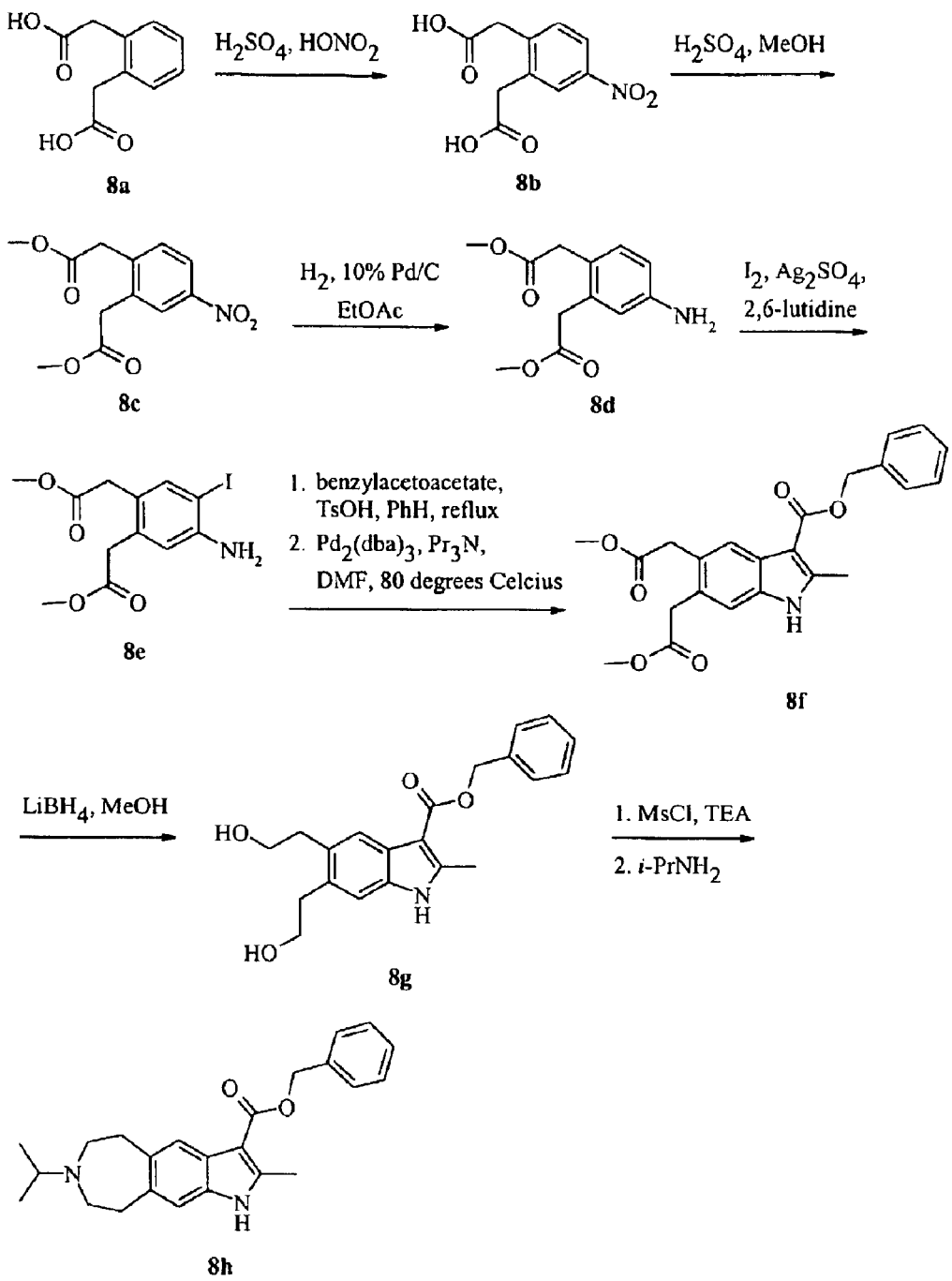
FIG. 8 is a schematic diagram showing the preparation of Example 185.

A diagram of the synthesis of Example 185 is presented in FIG. 8.

Step A

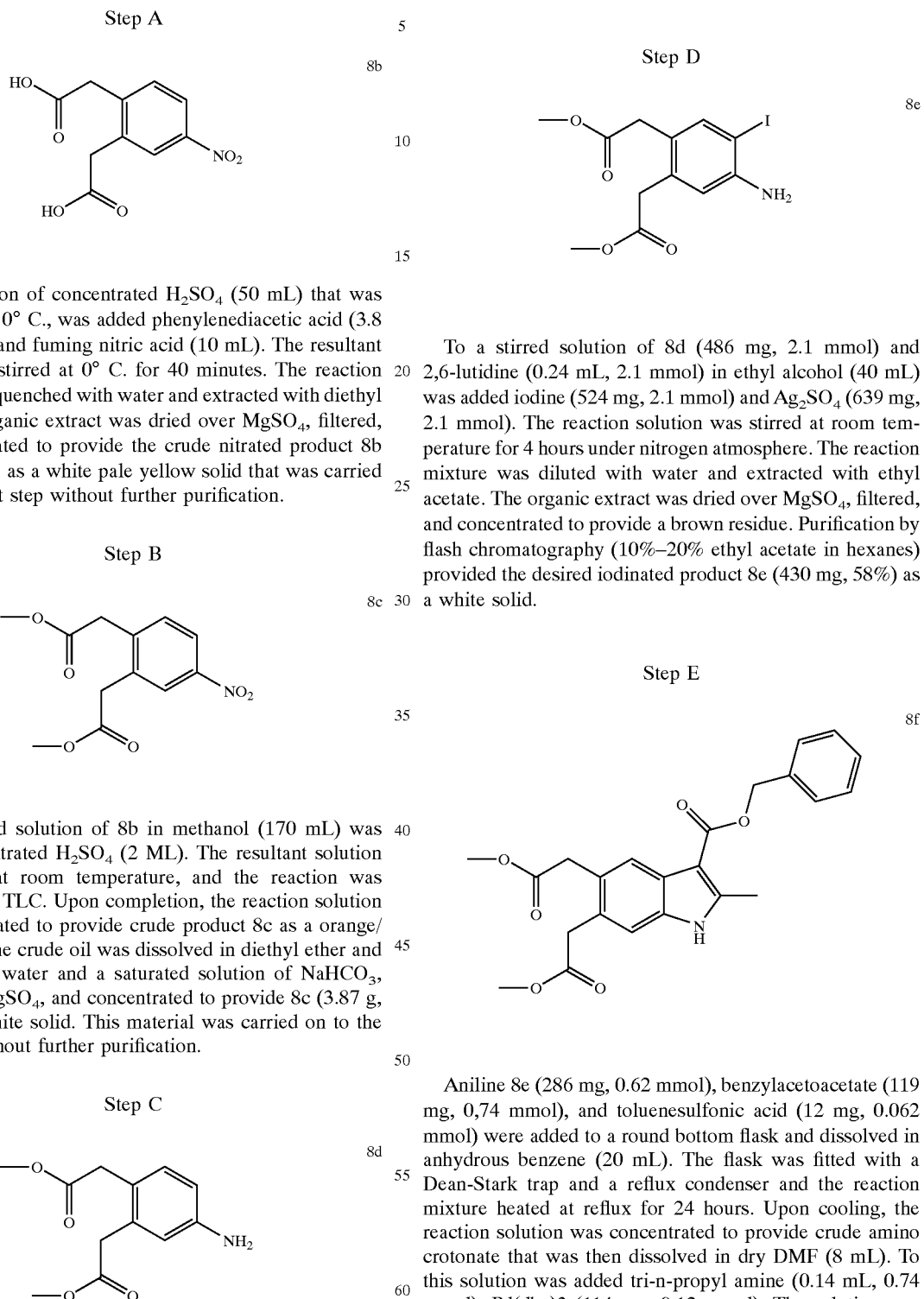

To a solution of concentrated H₂SO₄ (50 mL) that was pre-cooled to 0° C., was added phenylenediacetic acid (3.8 g, 20 mmol) and fuming nitric acid (10 mL). The resultant mixture was stirred at 0° C. for 40 minutes. The reaction solution was quenched with water and extracted with diethyl ether. The organic extract was dried over MgSO₄, filtered, and concentrated to provide the crude nitrated product 8b (4.35 g, 90%) as a white pale yellow solid that was carried on to the next step without further purification.

Step B

To a stirred solution of 8b in methanol (170 mL) was added concentrated H₂SO₄ (2 ML). The resultant solution was stirred at room temperature, and the reaction was monitored by TLC. Upon completion, the reaction solution was concentrated to provide crude product 8c as a orange/yellow oil. The crude oil was dissolved in diethyl ether and washed with water and a saturated solution of NaHCO₃, dried over MgSO₄, and concentrated to provide 8c (3.87 g, 81%) as a white solid. This material was carried on to the next step without further purification.

Step C

To a solution of 8c (3.87 g, 14.5 mmol) in ethyl acetate was added 10% Pd/C (1.0 g, Degussa type E101, 13 wt. %), and the resultant solution was stirred under an atmospheric pressure of hydrogen gas for 5 hours. The reaction mixture was filtered through a pad of celite and concentrated to afford the crude product 8d (3.25 g, 95%) as a yellow oil. This material was used without further purification.

Step D

To a stirred solution of 8d (486 mg, 2.1 mmol) and 2,6-lutidine (0.24 mL, 2.1 mmol) in ethyl alcohol (40 mL) was added iodine (524 mg, 2.1 mmol) and Ag₂SO₄ (639 mg, 2.1 mmol). The reaction solution was stirred at room temperature for 4 hours under nitrogen atmosphere. The reaction mixture was diluted with water and extracted with ethyl acetate. The organic extract was dried over MgSO₄, filtered, and concentrated to provide a brown residue. Purification by flash chromatography (10%–20% ethyl acetate in hexanes) provided the desired iodinated product 8e (430 mg, 58%) as a white solid.

Step E

Aniline 8e (286 mg, 0.62 mmol), benzylacetoacetate (119 mg, 0,74 mmol), and toluenesulfonic acid (12 mg, 0.062 mmol) were added to a round bottom flask and dissolved in anhydrous benzene (20 mL). The flask was fitted with a Dean-Stark trap and a reflux condenser and the reaction mixture heated at reflux for 24 hours. Upon cooling, the reaction solution was concentrated to provide crude amino crotonate that was then dissolved in dry DMF (8 mL). To this solution was added tri-n-propyl amine (0.14 mL, 0.74 mmol), Pd(dba)3 (114 mg, 0.12 mmol). The solution was degassed, then heated at 80° C. for 4 hours. The reaction mixture was quenched with water and extracted with diethyl ether. The organic extracts were dried over MgSO₄, filtered, and concentrated to provide the crude product as a yellow oil. Purification by flash chromatography (30% ethyl acetate in hexanes) provided the indole product 8f as a clear oil.

Step F

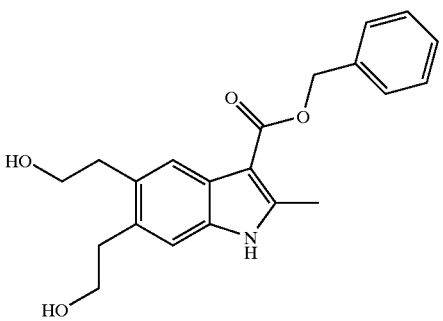

8g

A solution of 8f (409 mg, 1 mmol) in THFMeOH (5:1, 20 mL) is cooled to 0° C. and treated with lithium borohydride(5 mL of 2 M, 10 mmol). The resulting mixture is allowed to warm to room temperature, then is heated at reflux. Upon completion, the reaction is quenched with brine and extracted with ethyl acetate. The organic extracts are dried over MgSO$_4$, filtered, and concentrated to provide the crude product. Purification by flash chromatography (9:1 CH$_2$Cl$_2$: MeOH) provides the desired product 8 g.

Step G

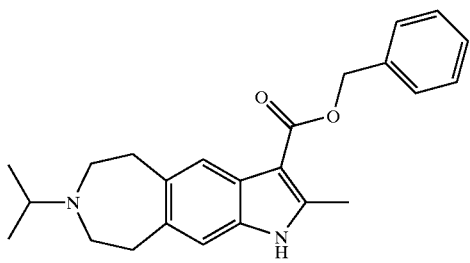

8h

To a solution of 8 g (354 mg, 1 mmol) in dry THF (10 mL) is added triethylamine (202 mg, 2 mmol) followed by methanesulfonyl chloride (229 mg, 2 mmol). The reaction mixture is stirred at room temperature and reaction progress monitored by TLC. Upon completion, the reaction solution is quenched with water and extracted with ethyl acetate. The organic extract is dried over MgSO$_4$, filtered, and concentrated to provide the crude product mesylated product that is used directly in the next reaction without further purification. The crude mesylate product is dissolved in dry acetonitrile (10 mL). To this solution is added potassium carbonate (138 mg, 1 mmol), isopropyl amine (60 mg, 1 mmol), and a catalytic amount of potassium iodide. The reaction mixture is heated at 80° C. in a sealed tube. Upon completion, the reaction is quenched with water and extracted with ethyl acetate. The organic extract is washed with aqueous NaHCO$_3$ solution then dried over MgSO$_4$, filtered, and concentrated to provide the crude product 8h. Purification by flash chromatography (87:10:3 ethyl acetate:MeOH:TEA) provides the pure product as a solid.

Example 186

Figure 22:
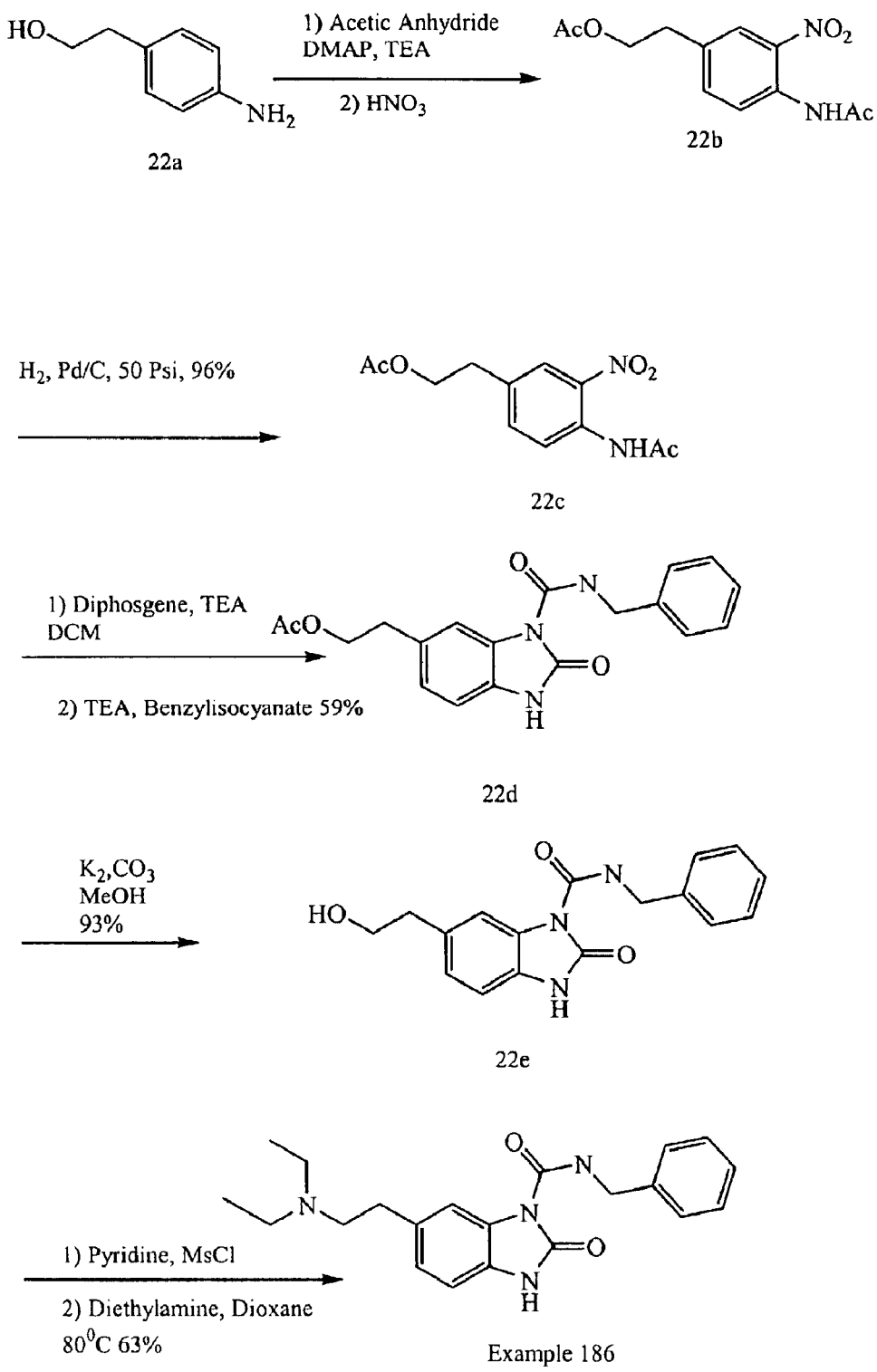
FIG. 22 is a schematic diagram showing the preparation of Example 186.

6-(2-Diethylamino-ethyl)-2-oxo-dihydro-benzoimidazole-1-carboxylic acid benzylamide;

FIG. 22 is a schematic diagram showing the synthesis of Example 186.

Compound 22b. To a solution of 4-amino phenethyl alcohol (10 g, 73 mmol) in THF (200 mL) under Argon at room temperature, was added acetic anhydride (14.4 mL, 153 mmol), followed by TEA (21.3 mL, 153 mmol), and DMAP (0.890 g, 7.3 mmol). The reaction was stirred for 24 hours and then concentrated in vacuo. The residue was dissolved in ethyl acetate (200 mL), washed 2× 1N HCl, dried with MgSO$_4$, filtered, concentrated in vacuo, and dried on high vacuum overnight. The crude material was used directly in the next reaction. To a solution of fuming HNO$_3$ (16.9 mL) at 0° C. was added the above material in 4 portions over 15 minutes. The reaction was stirred at 0° C. for 2 at which time TLC indicated the reaction was complete. The reaction was poured into H$_2$O and extracted 3×15 mL dichloromethane. The organics were combined, dried with NaSO$_4$, filtered, and concentrated in vacuo. The residue was filtered through silica (50:50 ethyl acetate/hexane) and then recrystallized from ethyl acetate/hexane to give 13.7 g (70%, 2 steps) of 22b as a yellow solid.

Compound 22c. Compound 22b (13.7 g, 52 mmol) and Pd/C (0.8 g) in ethanol (250 mL) were shaken in a Parr shaker under 35 psi of H2 for 4 hours. The reaction was then filtered through celite and concentrated in vacuo to give 11.8 g (96%) of compound 22c. Compound 22d. To a solution of diphosgene (1.51 mL, 12.5 mmol) in CH$_2$Cl$_2$ (75 mL) in a MeOH/ice bath under Argon, was added dropwise over 1 hour a second solution of consisting of 22c (2.46 g, 10.4 mmol) and TEA (1.74 mL, 12.5 mmol) in CH$_2$Cl$_2$ (25 mL). The reaction was stirred for an additional 2 hours at 0° C. and quenched by the addition of saturated NH$_4$Cl. The phases were separated and the aqueous phase was extracted 2×50 mL CH$_2$Cl$_2$. The organics were combined, dried with NaSO$_4$, filtered, and concentrated in vacuo to give 2.96 g a white solid. After drying overnight on high-vacuum, the white solid was dissolved in CH$_2$Cl$_2$ (67 mL) and cooled to 0° C. under Argon. TEA (1.73 mL, 12.4 mmol) was added dropwise, followed by benzylisocyanate (1.55 mL, 12.4 mmol). The reaction was stirred for 2 hours and quenched with saturated NH$_4$Cl. The organic phase organic was washed 1× H$_2$O, dried with MgSO$_4$, filtered, and concentrated in vacuo to give a yellow oil which was purified by silica gel chromatography (20% ethyl acetate/hexane) to yield 2.42 g (59%, 2 steps) of 22d as a yellow oil which crystallized upon standing.

Compound 4. To a slurry of 22d (1.02 g, 2.58 mmol) in MeOH (17 mL) at 0° C. under Argon, was added K$_2$CO$_3$ in one portion. The reaction was stirred at −20° C. overnight and then acidified with 1N HCl. The resulting white solid was filtered, air dried until dry, and then placed on the high-vacuum yielding 0.745 g (92%) of 22e as a white solid.

Example 186. To a solution of 22e (0.438 g, 1.4 mmol) in pyridine (5 mL) at 0° C. under Argon, was added methanesulfonyl chloride (0.119 mL, 1.54 mmol) dropwise. The reaction was stirred at 0 for 2 hours and then quenched with 1N HCl. The solution was extracted 2×ethyl acetate and 1×CH$_2$Cl$_2$. The organics were combined, dried with NaSO$_4$, filtered, and concentrated in vacuo to give 0.450 g of a white solid. A slurry of 0.162 g of the white solid and diethylamine in dioxane was heated at 80° C. for 24 hours. The reaction was concentrated in vacuo, purified by ion-exchange chromatography (Dowex 50WX2-200) and eluted with 2 M NH₃ in MeOH to give 0.102 g (63%, 2 steps) of Example 186 as yellow solid. EI-MS (M+H+=367)

Example 187

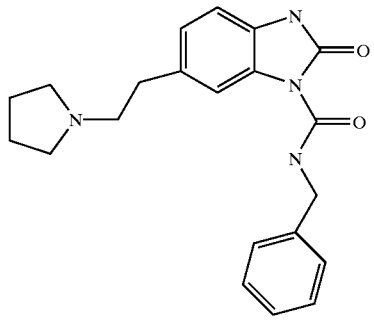

2-Oxo-6-(2-pyrrolidin-1-yl-ethyl)-2,3-dihydro-benzoimidazole-1-carboxylic acid benzylamide Compound 187 was prepared following the procedure for compound 186 but substituting pyrrolidine for diethylamine. LC-MS (ESI+) 365 (M+1).

Example 188

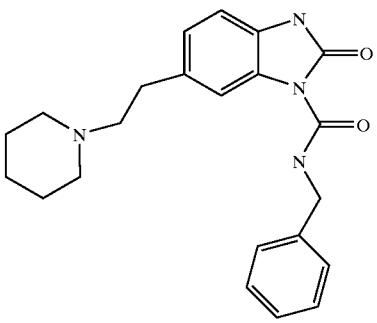

2-Oxo-6-(2-piperidin-1-yl-ethyl)-2,3-dihydro-benzoimidazole-1-carboxylic acid benzylamide Compound 188 was prepared following the procedure for compound 186 but substituting piperidineylamine. LC-MS (ESI+) 379 (M+1).

Example 189

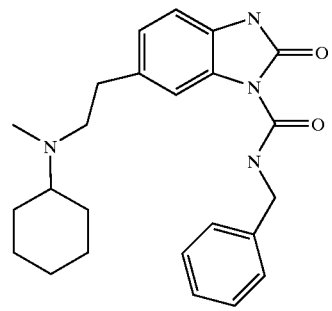

6-[2-(Cyclohexyl-methyl-amino)-ethyl]-2-oxo-2,3-dihydro-benzoimidazole-1-carboxylic acid benzylamide Compound 189 was prepared following the procedure for compound 186 but substituting N-methyl-N-cyclohexyl amine for diaethyl amine. LC-MS (ESI+) 365 (M+1).

Example 190

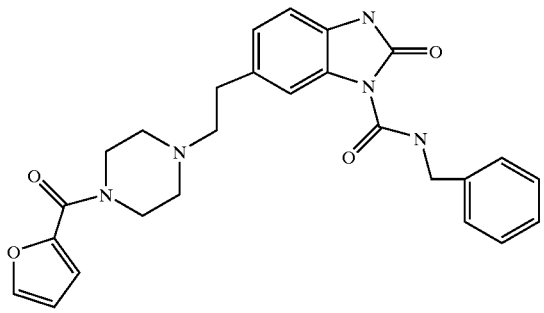

6-{2-[4-(Furan-2-carbonyl)-piperazin-1-yl]-ethyl}-2-oxo-2,3-dihydro-benzoimidazole-1-carboxylic acid benzylamide Compound 190 was prepared following the procedure for compound 186 but substituting 1-(2-furoyl)-piperazine for diethylamine. LC-MS (ESI+) 474 (M+1).

Example 191

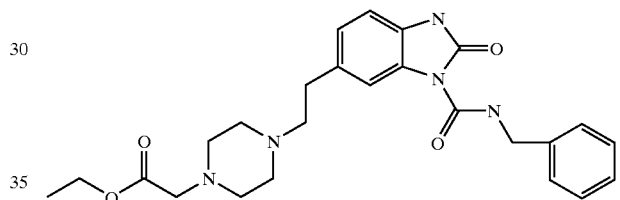

{4-[2-(3-benzylcarbamoyl-2-oxo-2,3-dihydro-1H-benzoimidazol-5-yl)-ethyl]-piperazin-1-yl}-acetic acid ethyl ester Compound 191 was prepared following the procedure for compound 186 but substituting N-(carboethoxymethyl)-piperazine for diethylamine. LC-MS (ESI+) 474 (M+1).

Example 192

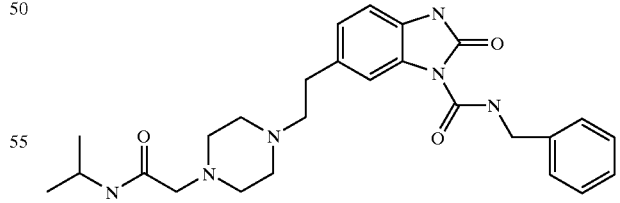

6-{2-[4-(Isopropylcarbamoyl-methyl)-piperazin-1-yl]ethyl}-2-oxo-2,3-dihydro-benzoimidazole-1-carboxylic acid benzylamide Compound 192 was prepared following the procedure for compound 186 but substituting N-isopropyl-1-piperazine acetamine for diethylamine. LC-MS (ESI+) 474 (M+1).

Example 193

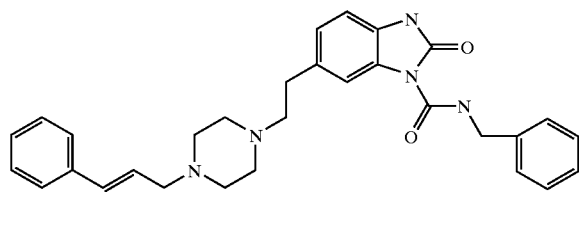

2-Oxo-6-{2-[4-(3-phenyl-allyl)-piperazin-1-yl]-ethyl}-2,3-dihydro-benzoimidazole-1-carboxylic acid benzylamide Compound 193 was prepared following the procedure for compound 186 but substituting 1-trans-1-cinnamylpiperazine for diethylamine. LC-MS (ESI+) 496 (M+1).

Example 194

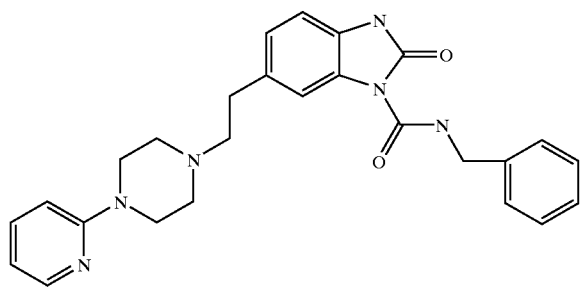

2-Oxo-6-[2-(4-pyridin-2-yl-piperazin-1-yl)-ethyl]-2,3-dihydro-benzoimidazole-1-carboxylic acid benzylamide Compound 194 was prepared following the procedure for compound 186 but substituting 1(2-pyridyl)piperazine for diethylamine. LC-MS (ESI+) 474 (M+1).

Example 195

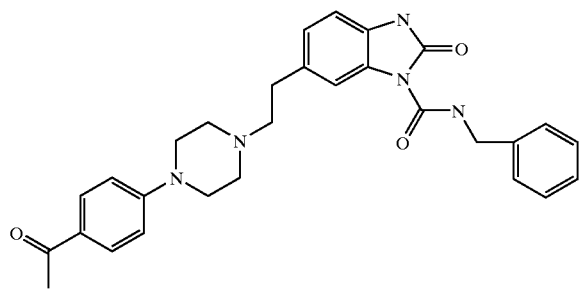

6-{2-[4-(4-Acetyl-phenyl)-piperazin-1-yl]-ethyl}-2-oxo-2,3-dihydro-benzoimidazole-1-carboxylic acid benzylamide Compound 195 was prepared following the procedure for compound 186 but substituting 4-piperazinoacetophone for diethylamine. LC-MS (ESI+) 498 (M+1).

Example 196

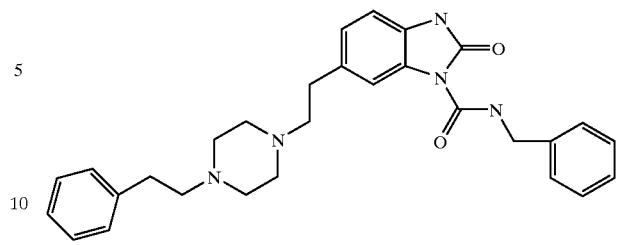

2-Oxo-6-[2-(4-phenethyl-piperazin-1-yl)-ethyl]-2,3-dihydro-benzoimidazole-1-carboxylic acid benzylamide Compound 196 was prepared following the procedure for compound 186 but substituting 1-(phenyl-ethyl)piperazine for diethylamine. LC-MS (ESI+) 484 (M+1).

Example 197

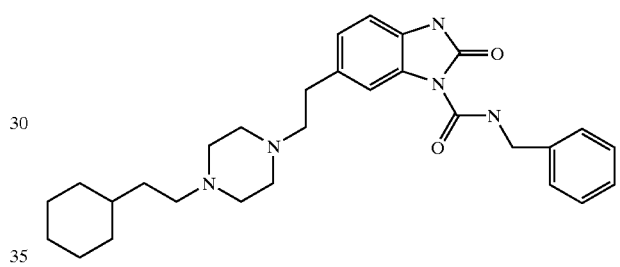

6-{2-[4-(2-Cyclohexyl-ethyl)-piperazin-1-yl]-ethyl}-2-oxo-2,3-dihydro-benzoimidazole-1-carboxylic acid benzylamide Compound 197 was prepared following the procedure for compound 186 but substituting 1-(cycloheylethyl)piperazine for diethylamine. LC-MS (ESI+) 490 (M+1).

Example 198

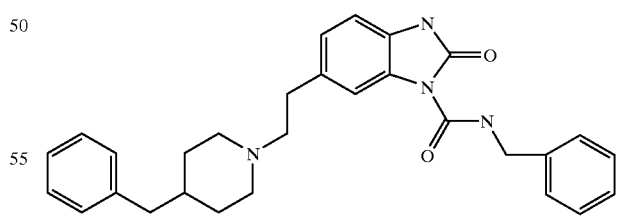

6-[2-(4-benzyl-piperidin-1-yl)-ethyl]-2-oxo-2,3-dihydro-benzoirmidazole-1-carboxylic acid benzylamide Compound 198 was prepared following the procedure for compound 186 but substituting benzylpiperidine for diethylamine. LC-MS (ESI+) 469 (M+1).

Example 199

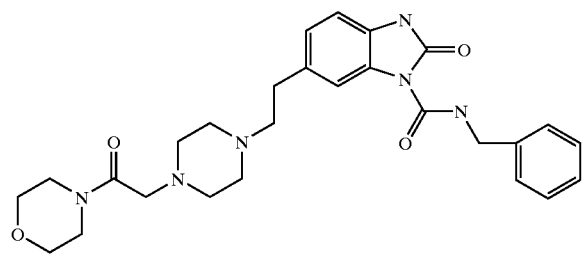

6-{2-[4-(2-Morpholin-4-yl-2-oxo-ethyl)-piperazin-1-yl]-ethyl}-2-oxo-2,3-dihydro-benzoimidazole-1-carboxylic acid benzylamide Compound 199 was prepared following the procedure for compound 186 but substituting 4-morpholino-1-piperazine acetamine for diethylamine. LC-MS (ESI+) 501 (M+1).

Example 200

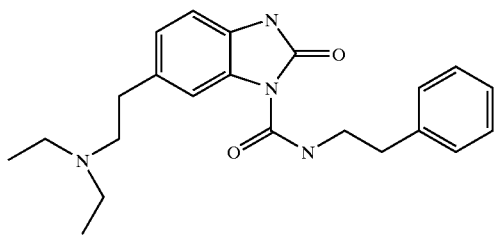

6-(2-Diethylamino-ethyl)-2-oxo-2,3-dihydro-benzoimidazole-1-carboxylic acid phenethylamide A diagram of the synthesis of Example 200 is presented in FIG. 10. Compound 10b. To a solution of 4-(nitrophenyl) ethyl bromide (23.4 g, 101.7 mmol) in DMF under argon at room temperature was added diethylamine (15.8 mL, 152.6 mmol). The reaction was stirred at room temperature for 16 hours and then concentrated in vacuo. The residue was dissolved in ethyl acetate, washed twice in 1N HCl, dried with MgSO$_4$, filtered, concentrated in vacuo and then dried on high vacuum overnight to give 13.5 g (60%0) of compound 10b as an orange oil.

Compound 10c. Compound 10b(13.5 g, 62.1 mmol) and 10% Pd/C (1.0 g) in ethanol (200 mL) were shaken in a Parr shaker under 45 psi of H$_2$ for 4 hours. The reaction was then filtered through Celite and concentrated in vacuo to give 11.5 g (98%) of compound 10c.

Compound 10d. To a solution of compound 10c (1 1.5 g, 59.8 mmol) in DCM (120 mL) under argon at room temperature, was added acetic anhydride (6.21 mL, 65.8 mmol) followed by TEA (9.2 mL, 65 mmol) and DMAP (0.731 g, 5.98 mmol). The reaction was stirred at room temperature for 24 hours, then diluted with DCM and washed twice with water. The organic layer was dried with MgSO$_4$, filtered, then concentrated and dried on high vacuum overnight to give 12.2 (87%) of compound 10d as a pale orange solid.

Compound 10e. To a solution of fuming HNO$_3$ (16.7 mL, 416.5 mmol) at 0° C. was added compound 10d (12.2 g, 52.0 mmol) in four portions over 15 minutes. The reaction was stirred at 0° C. for 2 hours and then room temperature for 16 hours. The reaction was then poured into water then extracted with DCM (3×150 mL). The organics were combined, dried with MgSO$_4$, filtered and concentrated in vacuo and dried on high vacuum overnight to give 11.2 (77%) of compound 10e as a yellow oil which was used directly in the next reaction.

Compound 10f Compound 10e (11.2 g, 40.0 mmol) and 10% Pd/C (0.800 mg) in ethanol (150 mL) were shaken in a Parr shaker under 45 psi of H$_2$ for 4 hours. The reaction was then filtered through Celite and concentrated in vacuo to give 9.84 g (98%) of compound 10f as an orange oil.

Compound 10g. To a solution of compound 10f (9.84 g, 39.5 mmol) and TEA (5.5 mL, 39.5 mmol) in DCM (250 mL) and THF (150 mL) under argon at −70° C. was added a solution of diphosgene (2.38 mL, 19.7 mmol) in DCM (150 mL) dropwise over 90 minutes. The reaction was stirred an additional 30 minutes at −70° C. and then quenched by the addition of saturated NaHCO$_3$. The solution was then diluted with DCM, and allowed to warm to room temperature. The layers were separated and the aqueous phase was extracted with DCM (3 times). The organics were combined, dried with MgSO$_4$, filtered and concentrated in vacuo, then dried under high vacuum overnight to give 6.3 g (58%) of compound 10g as a pale yellow solid.

Compound 200. To a solution of compound 10g (0.138 g, 0.501 mmol) in DCM (4.5 mL) at 0° C. was added TEA (0.070 mL, 0.501 mmol), followed by phenethyl isocyanate (0.070 mL, 0.501 mmol). The reaction was stirred at 0° C. for 4 hours, then MeOH (5 mL) was added and the reaction was allowed to warm to room temperature. The solution was stirred at room temperature for 16 hours. the solvent was evaporated in vacuo, and then the crude material was crystalized from acetonitrile to give 0.100 g (50%) of compound 200 as a pale yellow solid. LC/ms (ESI+) 381 (M+1)

Example 201

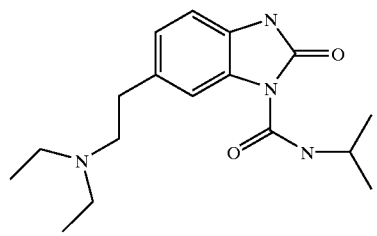

6-(2-Diethylamino-ethyl)-2-oxo-2,3-dihydro-benzoimidazole-1-carboxylic acid isopropylamide Compound 201 was prepared following the procedure for compound 200 but substituting isopropyl isocyanate for phenethyl isocyanate. LC-MS (ESI+) 234 (M+1).

Example 202

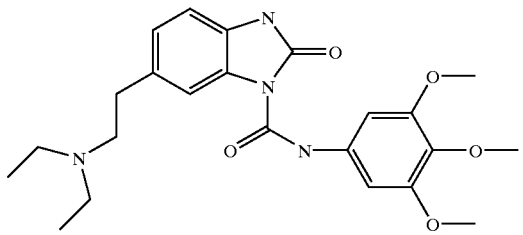

6-(2-Diethylamino-ethyl)-2-oxo-2,3-dihydro-benzoimidazole-1-carboxylic acid (3,4,5-trimethoxy-phenyl)-amide Compound 202 was prepared following the procedure for compound 200 but substituting 3,4,5-trimethoxy isocyanate for phenethyl isocyanate. LC-MS (ESI+) 393 (M+1).

Example 203

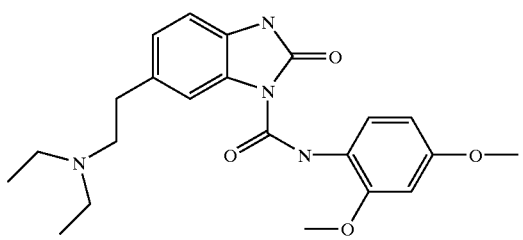

6-(2-Diethylamino-ethyl)-2-oxo-2,3-dihydro-benzoimidazole-1-carboxylic acid (2,4-dimethoxy-phenyl)-amide Compound 203 was prepared following the procedure for compound 200 but substituting 2,4-dimethoxy isocyanate for phenethyl isocyanate. LC-MS (ESI+) 413 (M+1).

Example 204

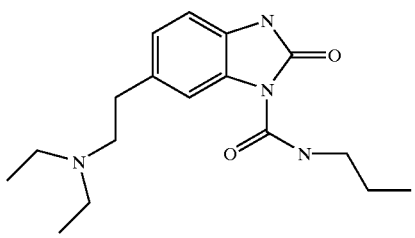

6-(2-Diethylamino-ethyl)-2-oxo-2,3-dihydro-benzoimidazole-1-carboxylic acid propylamide Compound 204 was prepared following the procedure for compound 200 but substituting propyl isocyanate for phenctliyl isocyanate. LC-MS (ESI+) 217 (M+1).

Example 205

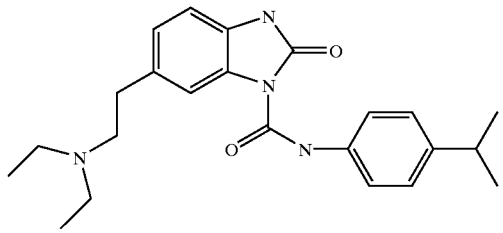

6-(2-Diethylamino-ethyl)-2-oxo-2,3-dihydro-benzoimidazole-1-carboxylic acid (4-isopropylphenyl)-amide Compound 205 was prepared following the procedure for compound 200 but substituting 4-isopropylphenyl isocyanate for phenethyl isocyanate. LC-MS (ESI+) 395 (M+1).

Example 206

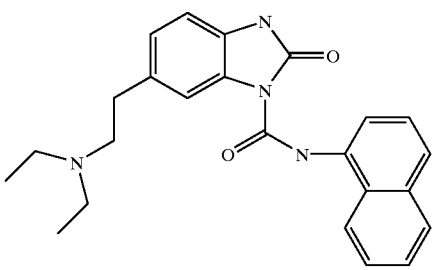

6-(2-Diethylamino-ethyl)-2-oxo-2,3-dihydro-benzoimidazole-1-carboxylic acid naphthalen-1-ylamide Compound 206 was prepared following the procedure for compound 200 but substituting 1-napthyl isocyanate for phenethyl isocyanate. LC-MS (ESI+) 403 (M+1).

Example 207

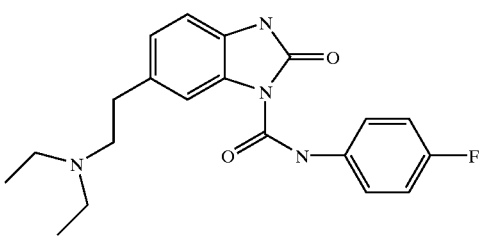

6-(2-Diethylamino-ethyl)-2-oxo-2,3-dihydro-benzoimidazole-1-carboxylic acid (4-fluoro-phenyl)-amide Compound 207 was prepared following the procedure for compound 200 but substituting 4-fluorphenyl isocyanate for phenethyl isocyanate. LC-MS (ESI+) 369 (M+1).

Example 208

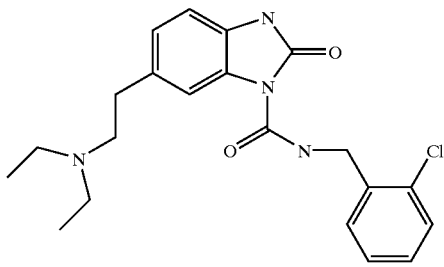

6-(2-Diethylamino-ethyl)-2-oxo-2,3-dihydro-
benzoimidazole-1-carboxylic acid 2-
chlorobenzylamide Compound 208 was prepared following the procedure for compound 200 but substituting 2-chlorophenyl isocyanate for phenethyl isocyanate. LC-MS (ESI+) 401 (M+1).

Example 209

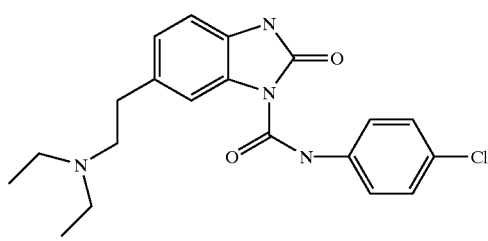

6-(2-Diethylamino-ethyl)-2-oxo-2,3-dihydro-
benzoimidazole-1-carboxylic acid (4-chloro-
phenyl)-amide Compound 209 was prepared following the procedure for compound 200 but substituting 4-chlorophenyl isocyanate for phenethyl isocyanate. LC-MS (ESI+) 385 (M+1).

Example 210

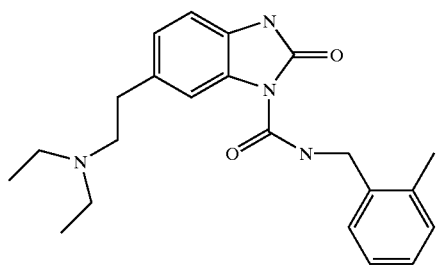

6-(2-Diethylamino-ethyl)-2-oxo-2,3-dihydro-
benzoimidazole-1-carboxylic acid 2-
methylbenzylamide Compound 210 was prepared following the procedure for compound 200 but substituting 2-methylbenzyl isocyanate for phenethyl isocyanate. LC-MS (ESI+) 381 (M+1).

Example 211

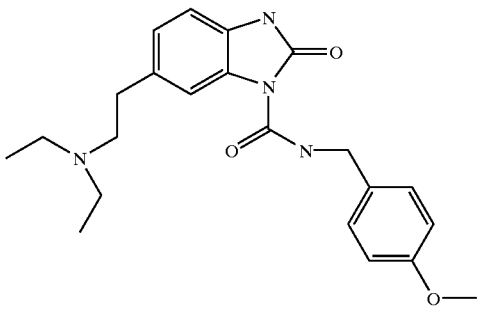

6-(2-Diethylamino-ethyl)-2-oxo-2,3-dihydro-
benzoimidazole-1-carboxylic acid 4-
methoxybenzylamide Compound 211 was prepared following the procedure for compound 200 but substituting 4-methoxybenzyl isocyanate for phenethyl isocyanate. LC-MS (ESI+) 397 (M+1).

Example 212

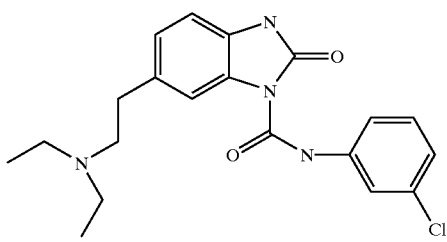

6-(2-Diethylamino-ethyl)-2-oxo-2,3-dihydro-
benzoimidazole-1-carboxylic acid (3-chloro-
phenyl)-amide Compound 212 was prepared following the procedure for compound 200 but substituting 3-chlorophenyl isocyanate for phenethyl isocyanate. LC-MS (ESI+) 385 (M+1).

Example 213

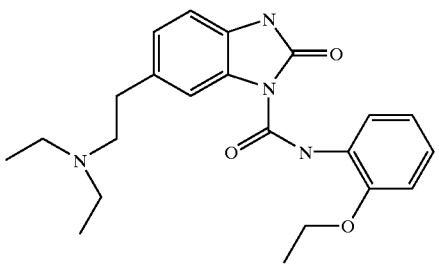

6-(2-Diethylamino-ethyl)-2-oxo-2,3-dihydro-
benzoimidazole-1-carboxylic acid (2-ethoxy-
phenyl)-amide Compound 213 was prepared following the procedure for compound 200 but substituting 2-ethoxyphenyl isocyanate for phenethyl isocyanate. LC-MS (ESI+) 397 (M+1).

Example 214

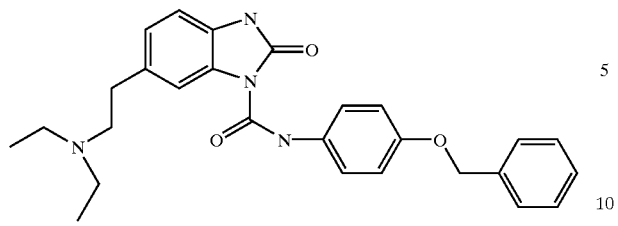

6-(2-Diethylamino-ethyl)-2-oxo-2,3-dihydro-benzoimidazole-1-carboxylic acid (4-benzyloxy-phenyl)-amide Compound 214 was prepared following the procedure for compound 200 but substituting 4-benzyloxyphenyl isocyanate for phenethyl isocyanate. LC-MS (ESI+) 495 (M+1).

Example 215

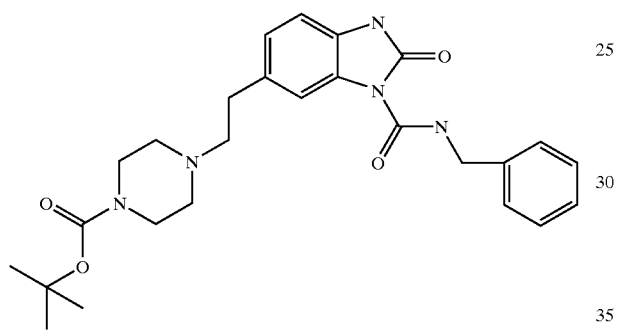

4-[2-(3-benzylcarbamoyl-2-oxo-2,3-dihydro-1H-benzoimidazol-5-yl)-ethyl]-piperazine-1-carboxylic acid tert-butyl ester Compound 215 was prepared following the procedure for compound 186 but substituting tert-butyl-1-piperazine carboxylate for diethyl amine. LC-MS (ESI+) 480 (M+1).

Example 216

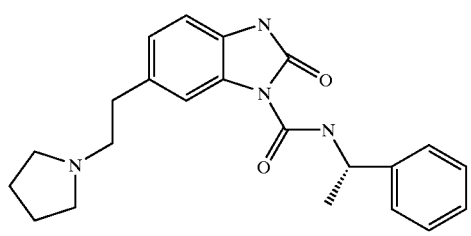

2-Oxo-6-(2-pyrrolidin 1-yl-ethyl)-2,3-dihydro-benzoimidazole-1-carboxylic acid (1-phenyl-ethyl) amide Compound 216 was prepared following the procedure for compound 186 but substituting pyrolidine for diethyl amine and (s)-1-phenyl-1-isocyanate-ethane for benzylisocyanate. LC-MS (ESI+) 379 (M+1).

Example 217

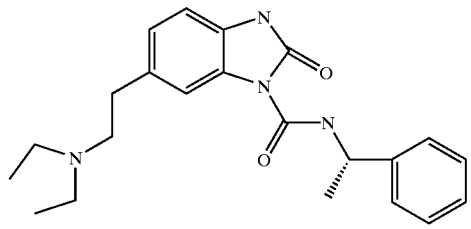

6-(2-Diethylamino-ethyl)-2-oxo-2,3-dihydro-benzoimidazole-1-carboxylic acid (1S-phenylethyl)-amide Compound 217 was prepared following the procedure for compound 186 but substituting (s)-1-phenyl-1-isocyanate-ethane for benzylisocyanate. LC-MS (ESI+) 381 (M+1).

Example 218

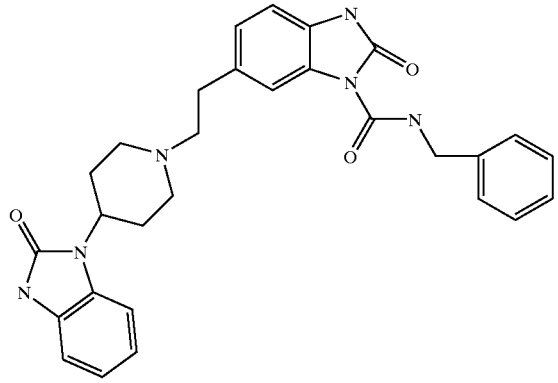

2-Oxo-6-{2-[4-(2-oxo-2,3-dihydro-benzoimidazole-1-yl)-piperidin-1-yl]-ethyl}-2,3-dihydrobenzoimidazole-1-carboxylic acid benzylamide Compound 218 was prepared following the procedure for compound 186 but substituting 4-(2-keto-1-benzimidazolinyl)piperadine for diethyl amine. LC-MS (ESI+) 511 (M+1).

Example 219

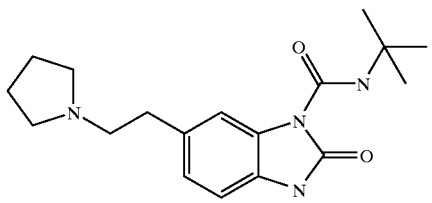

2-Oxo-6-(2-pyrrolidin-1-yl-ethyl)-2,3-dihydro-benzoimidazole-1-carboxylic acid tert-butylamide Compound 1. To a solution of 4-aminophenethyl alcohol (10.0 g, 73 mmol) in tetrohydrofuran (200 mL) was added acetic anhydride (15 mL, 160 mmol), followed by diisopropyl ethylamine (28 mL, 160 mmol)) then 4-dimethylaminopyridine (0.89 g, 7.3 mmol). The solution was stirred at room temperature for 3 hours. The mixture was evaporated in vacuum and the residue was dissolved in EtOAc (200 mL), washed with aqueous HCl (1%, 2×200 mL), water (2×200 mL) and brine (100 mL). The organic layer was dried over $Na_2SO_4$ and filtered. the filtrate was evaporated in vacuum to give a solid (13.35 g, yield 83%). LC-MS: m/z=222 (M+H+).

Compound 2. To a solution of compound 1 (10.0 g, 45 mmol) in acetic anhydride (60 mL) at 0° C. was added aqueous $HNO_3$ (70%, 4.36 mL) dropwise. The solution was stirred at room temperature for one hour and poured into ice-water (200 mL). The mixture was extracted with dichloromethane (2×100 mL). The organic layer was evaporated in vacuum and the residue was dissolved in EtOAc (200 mL), washed with saturated $NaHCO_3$ (5×100 mL) in an open separation funnel, then washed with water (2×100 mL) and brine (100 mL). the organic layer was dried over $Na_2SO_4$ and filtered. the filtrate was concentrated in vacuum with addition of hexane. The resulting yellow solid was collected by filtration and washed with EtOAc/hexane (1/9) and dried in a high vacuum to yield 11.52 g of product (96%). LC-MS: m/z=267 (M+H+).

Compound 3. To a mixture of compound 2 (11.52 g, 43.3 mmol) and Pd/C (10%, 0.8 g) under nitrogen flow was added ethanol (250 mL). The mixture was shaken under hydrogen atmosphere (50 psi) for 14 hours, filtered through Celite, concentrated in vacuum to give a solid (8.5 g, yield 83%). LC-MS: m/z=237 (M+H+).

Compound 4. To a solution of compound 3 (2.27 g, 9.62 mmol) in dichloromethane (60 mL) at −10° C. was added diisopropyl ethylamine (6 mL), followed by dropwise addition of diphosgene (4.0 g, 20 mmol) at 0° C. to room temperature. Butyl amine (9.62 mmol) was then added, the resulting mixture was refluxed for 3 hours, cooled to room temperature and diluted with dichloromethane (100 mL), washed with aqueous citric acid solution (10%), 50 mL and 1%, 50 mL), water (2×50 mL) and brine. The organic solution was dried over $Na_2SO_4$ and filtered. The filtrate was subject to flash-chromatography purification (EtOAc/hexane=1/9 to 1/6) to give the product as a solid (0.74 g, yield 21%)., LC-MS: m/z=362 (M+H+).

Compound 5. Ta a suspension of compound 4 (772 mg, 2 mmol) in methanol (30 mL) at −5° C. was added $K_2CO_3$ (414 mg, 3 mmol) and the mixture was stirred at 0° C. to room temperature overnight. The mixture was then evaporated in vacuum and the residue was dissolved in EtOAc (100 mL), washed with 1N aqueous HCl (10 mL), water (2×50 mL) and brine (30 mL), and dried over $NA_2SO_4$ and filtered. The filtrate was evaporated in vacuum to give a white solid (0.51 g, yield 92%). LC-MS: m/z=278 (M+H+) and 276 (M−H+).

Compound 6. To a solution of compound 5 (510 mg, 1.84 mmol) in pyridine (3 μL) at 0° C. was dropewise added methansulfonyl chloride (156 μL, 2.0 mmol). The mixture was stirred at 0° C. for 14 hours, poured into an aqueous citric acid solution (10%, 100 mL), extracted with EtOAc (3×50 mL). The combined EtOAc solution was dried over $Na_2SO_4$ and filtered. The filtrate was evaporated in vacuum to give a foaming white solid (650 mg, yield 100%). LC-MS: m/z=356 (M+H+) and 354 (M−H+).

Compound 219. Compound 6 (300 mg, 0.85 mmol) was refluxed with pyrrolidine (0.5 mL) overnight, then the mixture was evaporated in vacuum. The residue was purified by chromatography using a strong acid resin (DOWEX 50wx2-200) eluted with 2M $NH_3$/methanol solution to give a white solid (150 mg, yield 54%). LC-MS: m/z=331 (M+H+) and 329 (M−H+).

Example 220

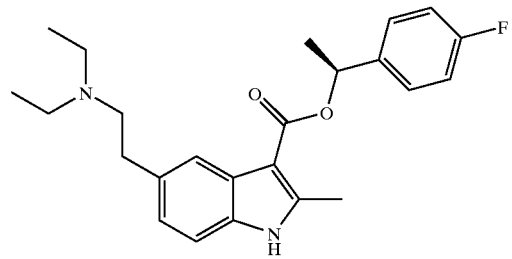

5-(2-Diethylamino-ethyl)-2-methyl-1H-indole-3-carboxylic acid 1-(4-fluoro-phenyl)-ethyl ester Step A

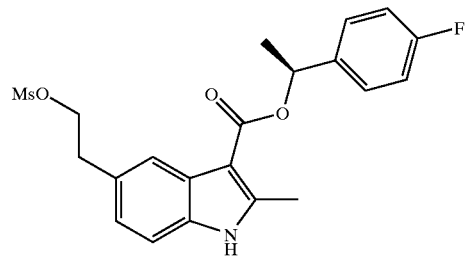

5-(2-Methanesulfonyloxy-ethyl)-2-methyl-1H-indole-3-carboxylic acid 1-(4-fluoro-phenyl)-ethyl ester Mixed anhydrid of Example 5, step B (100 mg, 0.25 mmol) and (S)-1-(4-fluorophenyl)-ethanol (105 mg, 0.75 mmol) were combined in a test tube equipped with a stir bar and heated at 135° C. for 35 seconds. The crude product was purified by flash chromatography (30–50% Ethyl Acetate in Hexanes) to provide 58 mg of the desired product as a clear oil.

Step B

To a solution of the product of Step A (58 mg, 0.14 mmol) in dioxane (1 mL) was added diethyl amine (0.14 mL, 1.4 mmol) and the resultant solution was heated at 70° C. overnight. The reaction solution was concentrated in vacuo and the crude product purified by flash chromatography (9:1 Ethyl Acetate:Methanol w/0.5% triethylamine) to provide the compound (44 mg, 80%) as a yellow oil. LC/MS (ESL+) 397 (M+1).

Example 221

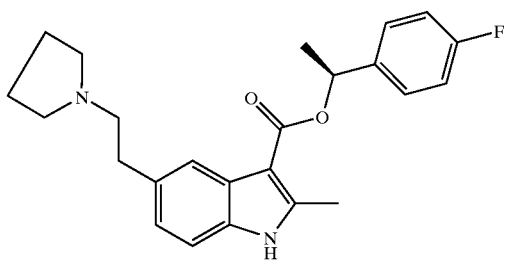

2-methyl-5-(2-pyrrolidin-1-yl-ethyl)-1H-indole-3-carboxylic acid 1-(4-fluoro-phenyl)-ethyl ester

Step A

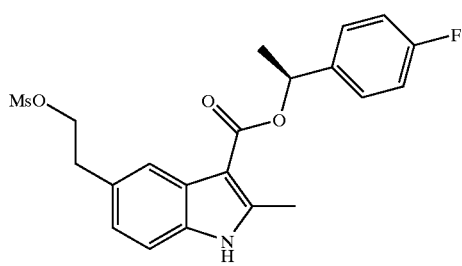

5-(2-Methanesulfonyloxy-ethyl)-2-methyl-1H-indole-3-carboxylic acid 1-(4-fluoro-phenyl)-ethyl ester Mixed anhydrid of Example 5, step B (100 mg, 0.25 mmol) and (S)-1-(4-fluorophenyl)-ethanol (105 mg, 0.75 mmol) were combined in a test tube equipped with a stir bar and heated at 135° C. for 35 seconds. The crude product was purified by flash chromatography (30–50% Ethyl Acetate in Hexanes) to provide 58 mg of the desired product as a clear oil. LC/MS (ESI+) 395 (M+1).

Step B

To a solution of the product of Step A (58 mg, 0.14 mmol) in dioxane (1 mL) was added pyrrolidine (0.14 mL, 1.4 mmol) and the resultant solution was heated at 70° C. overnight. The reaction solution was concentrated in vacuo and the crude product purified by flash chromatography (9:1 Ethyl Acetate:Methanol w/0.5% triethylamine) to provide the compound (44 mg, 80%) as a yellow oil.

Example 222

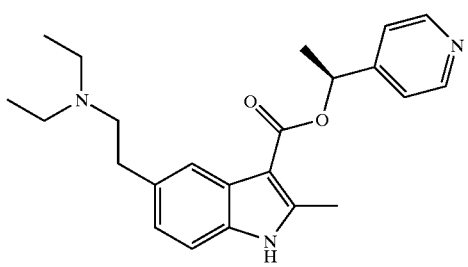

5-(2-Diethylamino-ethyl)-2-methyl-1H-indole-3-carboxylic acid 1-pyridin-4-yl-ethyl ester

Step A

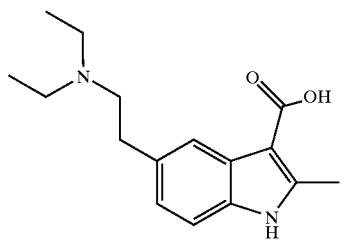

5-(2-Diethylamino-ethyl)-2-methyl-1H-indole-3-carboxylic acid

To a solution of 5-(2-Diethylamino-ethyl)-2-methyl-1H-indole-3-carboxylic acid benzyl ester (364. mg, 1 mmol) in methanol was added 10% palladium on carbon (72 mg). The resultant suspension was agitated under an 50 atmosphere of hydrogen gas overnight. The reaction mixture was filtered through celite and the filtrate concentrated in vacuo to produce the amine acid as an off-white solid (274 mg, 100%).

Step B

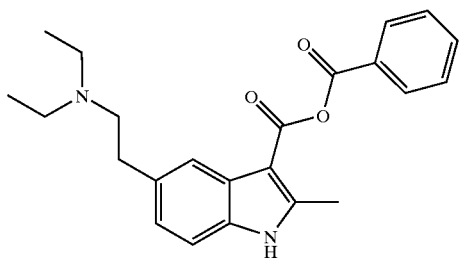

To a mixture of the product of Step A (274 mg, 1 mmol) and triethylamine (101 mg, 1 mmol) in dry THF (5 mL) was added benzoyl chloride (140 mg, 1 mmol). the resulting suspension was stirred at room temperature overnight. Upon completion, the reaction solution was filtered and the filtrate concentrated to provide the crude product (378 mg) which was used without further purification.

Step C

A mixture of the product of step B (378 mg, 1 mmol) and (s)-1-(4-pyridyl)-1-ethanol (369 mg, 3 mmol) was heated at 150° C. for 2 minutes. the crude product was purified by flash chromatography (9:1 Ethyl Acetate:Methanol w/0.5% triethyl amine) to provide the desired product (140 mg, 37%). LC-MS (ESI+) 380 (M+1).

All publications cited above are incorporated herein by reference in their entirety, for all purposes, to the same extent as if each individual publication or patent were specifically and individually indicated to be so incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the formula

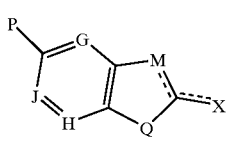

(I)

or a physiologically acceptable salt thereof, wherein:

G is $CR_1$;

J is $CR_2$;

H is $CR_3$;

M is C—Y or CH—Y;

Q is $NR_4$;

X is $C_1$–$C_8$ alkyl, substituted $C_1$–$C_8$ alkyl, $C_2$–$C_5$ alkenyl, substituted $C_2$–$C_8$ alkenyl, $C_2$–$C_8$ alkynyl, substituted $C_2$–$C_8$ alkynyl;

Y is

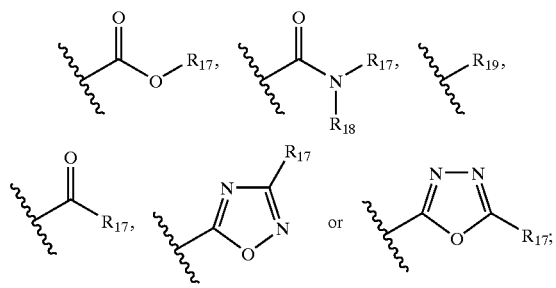

P is —A—L—nitrogen-containing heteroaryl, —A—L—substituted nitrogen-containing heteroaryl,

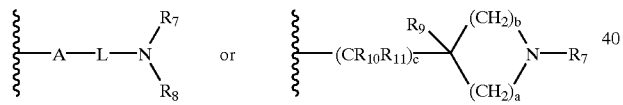

wherein a, b and c are each, independently, an integer from 0 to 4, with the proviso that when a is 0, c is not 1 and when b is 0, c is not 1;

A is O, N(—$R_{12}$), a bond or is absent;

L is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, a bond, or

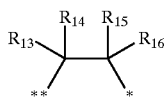

wherein * is the point of attachment to A; and

** is the point of attachment to N;

$R_1$, $R_2$, $R_3$, $R_{11}$, $R_{13}$, $R_{14}$, $R_{15}$, $R_{16}$ and $R_{19}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, halogen, $C_1$–$C_8$ alkoxy,

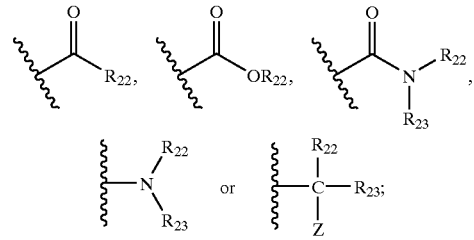

Z is aryl, substituted aryl, heteroaryl or substituted heteroaryl;

$R_{22}$ and $R_{23}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl; or $R_{22}$ and $R_{23}$ taken together with the atoms to which they are bonded form a three to eight membered cyclic ring which contains zero to three heteroatoms selected from the group consisting of oxygen, nitrogen and sulfur;

$R_4$, $R_7$, $R_8$, $R_9$, $R_{12}$, $R_{17}$ and $R_{18}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, $R_{20}$ and $R_{21}$ are independently hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl or alkylheteroaryl; or $R_{20}$ and $R_{21}$ taken together with the atoms to which they are bonded form a three to eight membered cyclic ring which contains zero to three heteroatoms selected from the group consisting of oxygen, nitrogen and sulfur;

Z' is aryl, substituted aryl, heteroaryl or substituted heteroaryl; or $R_1$ taken together with any one of $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

$R_2$ taken together with any one of $R_3$, $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

P taken together with either $R_1$ or $R_2$ and the atoms to which they are bonded form a five to eight membered substituted nonaromatic ring that contains a heteroatom selected from the group consisting of oxygen, nitrogen and sulfur;

any two of $R_7$, $R_8$, $R_9$, $R_{10}$, $R_{11}$, $R_{12}$, $R_{13}$, $R_{14}$, $R_{15}$, $R_{16}$ and $R_{17}$, taken together with the atoms to which they are bonded form a substituted or unsubstituted three to eight membered cyclic ring which contains zero to three heteroatoms selected from the group consisting of oxygen, nitrogen and sulfur; and wherein said substituted alkyl, substituted alkenyl and substituted alkynyl comprise one to three substituents, and said substituted aryl and substituted heteroaryl comprises one to five substituents, and said substituents are independently selected from the group consisting of $C_1$–$C_8$ alkyl, $C_2$–$C_8$ alkenyl, $C_2$–$C_8$ alkynyl, heteroalkyl, $C_1$–$C_8$ alkoxy, carboxy, hydroxy, nitro, halogen, cyano, amino, $C_1$–$C_8$ alkyl amino, $C_2$–$C_8$ alkenyl amino, $C_2$–$C_8$ alkynyl amino, aryl amino, $C_1$–$C_8$ dialkyl amino, $C_2$–$C_8$ dialkenyl amino, diaryl amino, aryl, substituted aryl, heteroaryl, substituted heteroaryl, $C_1$–$C_8$ alkyl aryl, aryl $C_1$–$C_8$ alkyl, heteroaryl $C_1$–$C_8$ alkyl, keto (=O), =$NR^{60}$, wherein $R^{60}$ is —H, —OH, —$NH_2$, an aromatic group or a substituted aromatic group, —$SO_3H$, —CHO, —$(CH_2)_n$—$NH_2$, —$(CH_2)_n$—NH—$C_1$–$C_8$ alkyl, —$(CH_2)_n$—N($C_1$–$C_8$ alkyl)$_2$, wherein n is an integer from one to eight;

said heteroaryl is an aromatic ring having from five to fifteen atoms in the ring, wherein one or more of the atoms in the ring is a heteroatom selected from the group consisting of oxygen, nitrogen and sulfur;

said aryl is an aromatic carbocyclic ring having from five to fifteen carbon atoms;

said arylalkyl is —$C_1$–$C_8$ alkyl-aryl;

said heteroarylalkyl is —$C_1$–$C_8$ alkyl-heteroaryl;

said alkylaryl is -aryl-$C_1$–$C_8$ alkyl;

said alkylheteroaryl is -heteroaryl-$C_1$–$C_8$ alkyl;

with the proviso that the compound does not have the formula:

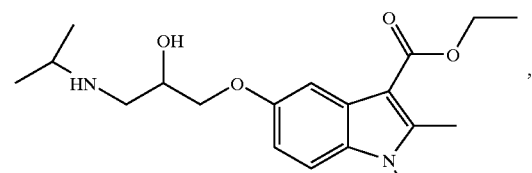

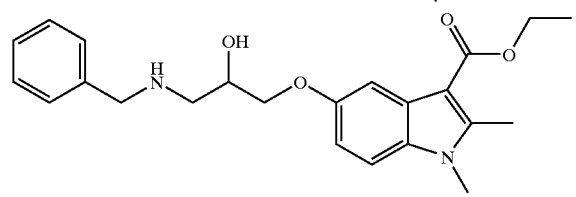

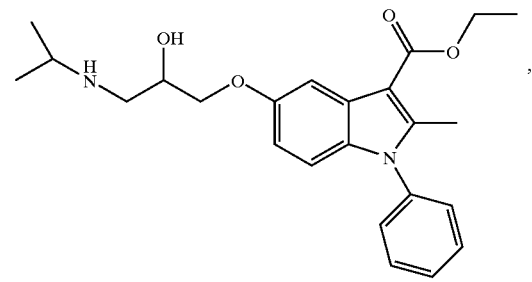

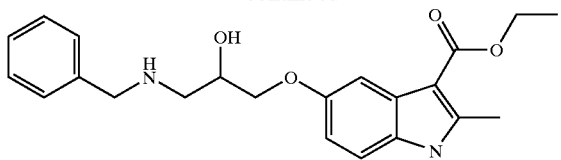

-continued

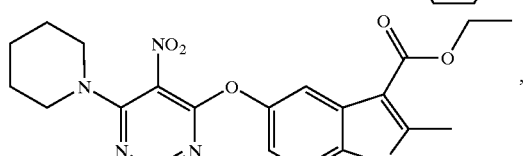

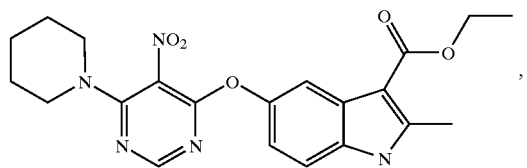

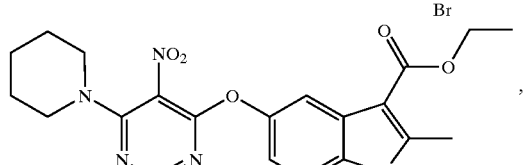

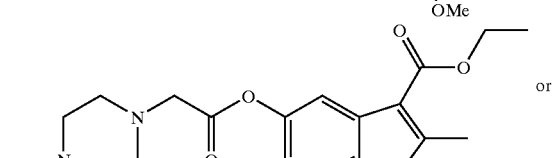

or

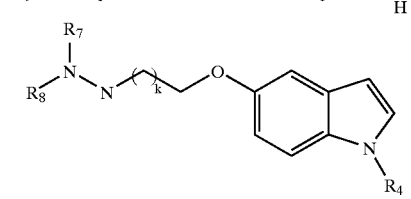

wherein $R_7$ and $R_8$ are independently hydrogen, methyl, ethyl or isopropyl; k is zero or one; and $R_4$ is hydrogen, methyl, ethyl, n-propyl, n-butyl, pentyl, phenyl or substituted phenyl.

2. The compound of claim 1, wherein X is $C_1$–$C_8$ alkyl or substituted $C_1$–$C_8$ alkyl.

3. The compound of claim 2, wherein X is —$CH_3$ or —$CF_3$.

4. The compound of claim 1, wherein $R_4$ is hydrogen.

5. The compound of claim 1, wherein $R_1$ and $R_2$ independently, hydrogen, a halogen, —$CH_3$, —$CF_3$ or —$OCH_3$.

6. The compound of claim 1, wherein Y is

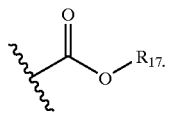

7. The compound of claim 6, wherein $R_{17}$ is $C_1$–$C_8$ alkyl, phenyl, substituted phenyl or pyridyl.

8. The compound of claim 6, wherein $R_{17}$ is phenyl.

9. The compound of claim 1, wherein Y is

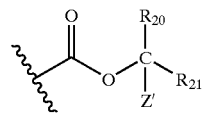

wherein $R_{20}$ and $R_{21}$ are independently hydrogen, $C_1$–$C_8$ alkyl, substituted $C_1$–$C_8$ alkyl; or $R_{20}$ and $R_{21}$ taken together with the carbon atom to which they are bonded form a three to eight membered ring which contains one to three heteroatoms selected from the group consisting of oxygen, nitrogen and sulfur; and Z' is selected from the group consisting of aryl, substituted aryl, heteroaryl and substituted heteroaryl.

10. The compound of claim 9, wherein Y is

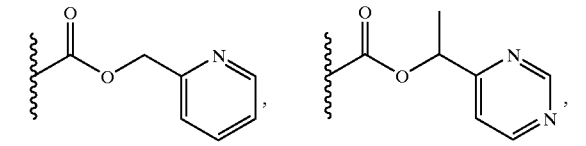
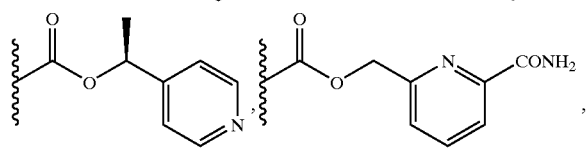
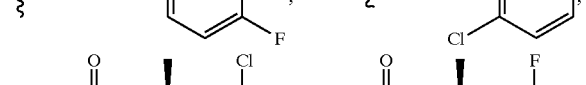
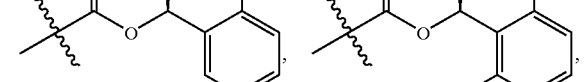
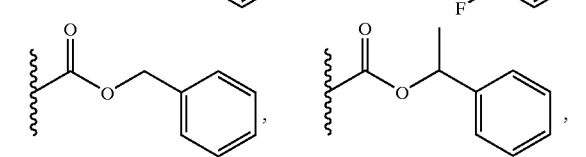

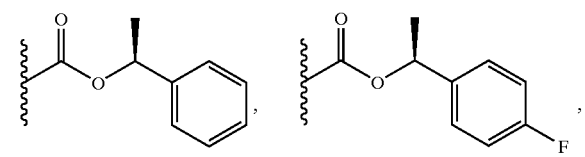
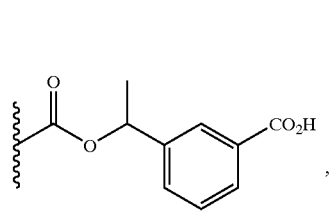
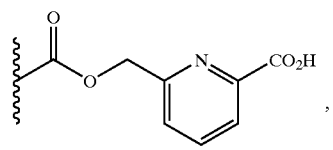
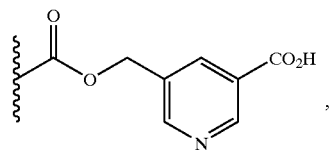
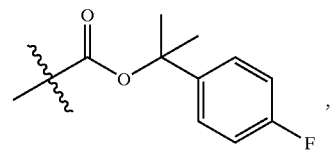
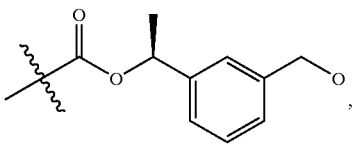
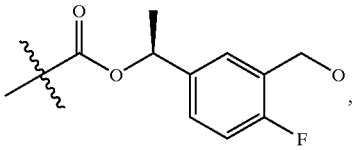
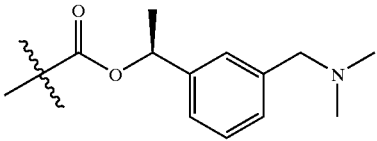
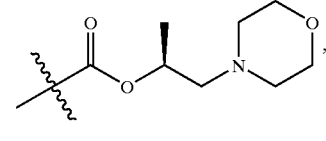
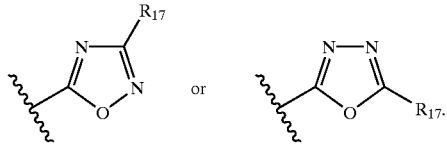

11. The compound of claim 1, wherein Y is

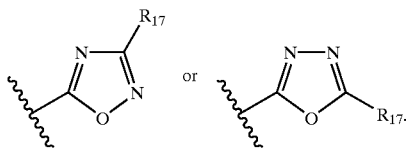

12. The compound of claim 11, wherein $R_{17}$ is $C_1$–$C_8$ alkyl, phenyl, substituted phenyl or pyridyl.

13. The compound of claim 11, wherein $R_{17}$ is phenyl.

14. The compound of claim 1, wherein L is

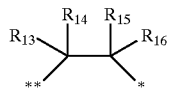

wherein

* is the point of attachment to A;
** is the point of attachment to N; and
A is a bond.

15. The compound of claims 1, wherein P is

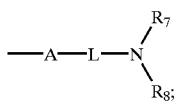

$R_7$ and $R_8$ are ethyl; and
L is

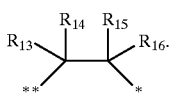

16. The compound of claim 1, wherein P is

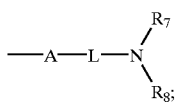

$R_7$ and $R_8$ are ethyl;
L is

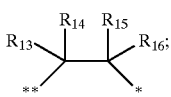

and Y is

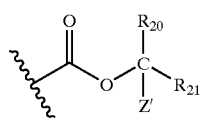

wherein $R_{20}$ and $R_{21}$ are independently hydrogen, $C_1$–$C_6$ alkyl, substituted $C_1$–$C_8$ alkyl, or $R_{20}$ and $R_{21}$ taken together with the carbon atom to which they are bonded form a three to eight membered ring which contains one to three heteroatoms selected from the group consisting of oxygen, nitrogen and sulfur; and Z' is selected from the group consisting of aryl, substituted aryl, heteroaryl and substituted heteroaryl.

17. The compound of claim 1, wherein P is

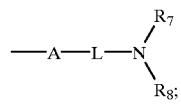

$R_7$ and $R_8$ taken together with the nitrogen atom to which they are bonded form a three to eight membered cyclic ring which contains one or two additional heteroatoms selected from the group consisting of oxygen, nitrogen and sulfur;

L is

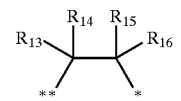

and Y is

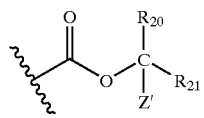

wherein $R_{20}$ and $R_{21}$ are independently hydrogen, $C_1$–$C_8$ alkyl, substituted $C_1$–$C_8$ alkyl, or $R_{20}$ and $R_{21}$ taken together with the carbon atom to which they are bonded form a three to eight membered ring which contains one to three heteroatoms selected from the group consisting of oxygen, nitrogen and sulfur; and Z' is selected from the group consisting of aryl, substituted aryl, heteroaryl and substituted heteroaryl.

18. The compound of claim 1, wherein

X is methyl or trifluoromethyl;

A is a bond;

$R_4$ is hydrogen; and

Y is

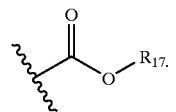

19. The compound of claim 1, wherein said compound has the formula

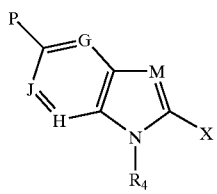

(IV)

wherein

M is C—Y.

20. The compound of claim 19, wherein $R_4$ is hydrogen.

21. The compound of claim 19, wherein X is $C_1$–$C_8$ alkyl, —$CH_3$ or —$CF_3$.

22. The compound of claim 1, wherein said compound is selected from the group consisting of:
- 5-[2-(4-tert-Butoxycarbonyl-piperazin-1-yl)-ethoxy]-2-methyl-1H-indole-3-carboxylic acid benzyl ester;
- 1-[2-(3-Benzyloxycarbonyl-2-methyl-1H-indole-5-yloxy)-ethyl]-piperazin-1-ium; chloride;
- 2-Methyl-5-[2-(4-methyl-piperazin-1-yl)-ethoxy]-1H-indole-3-carboxylic acid benzyl ester;
- 2-Methyl-5-[2-(3-methyl-pyrrolidin-1-yl)-ethoxy]-1H-indole-3-carboxylic acid benzyl ester;
- 1-[2-(3-Benzyloxycarbonyl-2-methyl-1H-indole-5-yloxy)-ethyl]-3-phenyl-pyrrolidinium chloride;
- 5-(2-Diisopropylamino-ethoxy)-2-methyl-1H-indole-3-carboxylic acid benzyl ester;
- 1-Benzyl-5-(2-diethylamino-ethoxy)-2-methyl-1H-indole-3-carboxylic acid benzyl ester;
- 1-Methyl-5-(2-diethylamino-ethoxy)-2-methyl-1H-indole-3-carboxylic acid benzyl ester;
- 5-(1-Diethylcarbamoyl-propoxy)-2-methyl-1H-indole-3-carboxylic acid benzyl ester;
- 2-Methyl-5-(4-pyrrolidin-1-yl-butoxy)-1H-indole-3-carboxylic acid benzyl ester;
- 2-Methyl-5-(2-piperidin-1-yl-ethoxy)-1H-indole-3-carboxylic acid benzyl ester;
- 5-(2-Diethylamino-ethoxy)-2-methyl-1H-indole-3-carboxylic acid benzyl ester;
- 2-Methyl-5-[2-(3,3,4,4-tetramethyl-pyrrolidin-1-yl)-ethoxy]-1H-indole-3-carboxylic acid benzyl ester;
- 2-Methyl-5-[2-(2-phenyl-pyrrolidin-1-yl)-ethoxy]-1H-indole-3-carboxylic acid benzyl ester;
- 5-[2-((R)-3-Hydroxymethyl-pyrrolidin-1-yl)-ethoxy]-2-methyl-1H-indole-3-carboxylic acid benzyl ester;
- 2-Methyl-5-[2-(2-pyridin-3-yl-pyrrolidin-1-yl)-ethoxy]-1H-indole-3-carboxylic acid benzyl ester;
- 5-(2-Dipropylamino-ethoxy)-2-methyl-1H-indole-3-carboxylic acid benzyl ester;
- 5-(2-Diethylamino-ethyl)-2-trifluoromethyl-1H-indole-3-carboxylic acid benzyl ester;
- 2-Methyl-5-(2-pyrrolidine-1-yl-ethylamino)-1H-indole-3-carboxylic acid benzyl ester;
- 5-Amino-2-methyl-1H-indole-3-carboxylic acid benzyl ester;
- 5-[Bis-(2-pyrrolidine-1-yl-ethyl)-amino]-2-methyl-1H-indole-3-carboxylic acid benzyl ester;
- 5-[Acetyl-(2-pyrrolidine-1-yl-ethyl)-amino]-2-methyl-1H-indole-3-carboxylic acid benzyl ester;
- 2-Methyl-5-(4-phenyl-piperazin-1-yl)-1H-indole-3-carboxylic acid benzyl ester.

23. The compound of claim 1, wherein said compound is selected from the group consisting of:
- 5-[2-(4-Hydroxy-piperidine-1-yl)-ethoxy]-2-methyl-1H-indole-3-carboxylic acid benzyl ester;
- 2-Methyl-5-[2-(2-methyl-pyrrolidin-1-yl)-ethoxy]-1H-indole-3-carboxylic acid benzyl ester;
- 2-Methyl-5-[2-(2-oxa-6-aza-bicyclo[2.2.1]hept-6-yl)-ethoxy]-1H-indole-3-carboxylic acid benzyl ester;
- 5-{2-[3-(Acetyl-methyl-amino)-pyrrolidin-1-yl)-ethoxy}-2-methyl-1H-indole-3-carboxylic acid benzyl ester;
- 5-[2-(2,5-Dimethyl-pyrrolidin-1-yl)-ethoxy]-2-methyl-1H-indole-3-carboxylic acid benzyl ester;
- 5-[2-(3-Dimethylamino-pyrrolidin-1-yl)-ethoxy]-2-methyl-1H-indole-3-carboxylic acid benzyl ester, dihydrochloride;
- 2-Methyl-5-[2-(1,3,3-trimethyl-6-aza-bicyclo[3.2.1]oct-6-yl)-ethoxy]-1H-indole-3-carboxylic acid benzyl ester;
- 2-Methyl-5-[2-(1,3,3-trimethyl-6-aza-bicyclo[3.2.1]oct-6-yl)-ethyl]-1H-indole-3-carboxylic acid benzyl ester;
- 5-[2-((R)-2-Methoxymethyl-pyrrolidin-1-yl)-ethyl]-2-methyl-1H-indole-3-carboxylic acid benzyl ester;
- 2-Methyl-5-[2-(2-methyl-pyrrolidin-1-yl)-ethyl]-1H-indole-3-carboxylic acid benzyl ester;
- 5-[2-((R)-2-Hydroxymethyl-pyrrolidin-1-yl)-ethyl]-2-methyl-1H-indole-3-carboxylic acid benzyl ester;
- 5-[2-((S)-2-Methoxymethyl-pyrrolidin-1-yl)-ethyl]-2-methyl-1H-indole-3-carboxylic acid benzyl ester;
- 5-(2-Azetidin-1-yl-ethyl]-2-methyl-1H-indole-3-carboxylic acid benzyl ester;
- 2-Methyl-5-[2-(2-oxa-5-aza-bicyclo[2.2.1]hept-5-yl)-ethyl]-1H-indole-3-carboxylic acid benzyl ester;
- 5-{2-[3-(Acetyl-methyl-amino)-pyrrolidin-1-yl)-ethyl}-2-methyl-1H-indole-3-carboxylic acid benzyl ester;
- 5-[2-(4-Hydroxy-piperidine-1-yl)-ethyl]-2-methyl-1H-indole-3-carboxylic acid benzyl ester;
- 2-Methyl-5-(3-pyrrolidin-1-yl-propoxy)-1H-indole-3-carboxylic acid benzyl ester;
- 2-Methyl-5-(1-methyl-piperidin-2-yl-methoxy)-1H-indole-3-carboxylic acid benzyl ester;
- 5-(1-Diethylcarbamoyl-1-methyl-ethoxy)-2-methyl-1H-indole-3-carboxylic acid benzyl ester;
- 2-Methyl-5-(2-methyl-2-pyrrolidin-1-yl-propoxy)-1H-indole-3-carboxylic acid benzyl ester;
- 2-Methyl-5-(1-methyl-piperidin-3-ylmethoxy)-1H-indole-3-carboxylic acid benzyl ester;
- 5-(1-Benzyl-pyrrolidin-3-yloxy)-2-methyl-1H-indole-3-carboxylic acid benzyl ester;
- 5-(1-Ethyl-pyrrolidin-3-yloxy)-2-methyl-1H-indole-3-carboxylic acid benzyl ester; and
- 2-Methyl-5-(pyrrolidin-3-yloxy)-1H-indole-3-carboxylic acid benzyl ester, hydrochloride.

24. The compound of claim 1, wherein said compound is selected from the group consisting of:
- 5-(1-Isopropyl-pyrrolidin-3-yloxy)-2-methyl-1H-indole-3-carboxylic acid benzyl ester;
- 5-Carbamimidoylmethoxy-2-methyl-1H-indole-3-carboxylic acid benzyl ester;
- 5-(2-Imino-2-pyrrolidin-1-yl-ethoxy)-2-methyl-1H-indole-3-carboxylic acid benzyl ester;

2-Methyl-5-pyridin-3-yl-1H-indole-3-carboxylic acid benzyl ester;

2-Methyl-5-pyridin-3-yl-indole-1,3-dicarboxylic acid 3-benzyl ester 1-tert-butyl ester;

5-(3-Dimethylamino-propyl)-2-methyl-1H-indole-3-carboxylic acid benzyl ester;

5-(3-Dimethylamino-prop-1-ynyl)-2-methyl-1H-indole-3-carboxylic acid benzyl ester;

5-((Z)-3-dimethylamino-propenyl)-2-methyl-1H-indole-3-carboxylic acid benzyl ester;

5-(1-Ethyl-pyrrolidin-3-yl)-2-methyl-1H-indole-3-carboxylic acid benzyl ester;

2-Methyl-5-(2-pyrrolidin-1-yl-ethyl)-1H-indole-3-carboxylic acid benzyl ester hydrochloride;

2-Methyl-5-(2-pyrrolidin-1-yl-ethyl)-1H-indole-3-carboxylic acid benzyl ester;

2-Methyl-5-[2-(4-methyl-piperazin-1-yl)-ethyl]-1H-indole-3-carboxylic acid benzyl ester;

5-[2-(Cyclohexyl-methyl-amino)-ethyl]-2-methyl-1H-indole-3-carboxylic acid benzyl ester;

2-Methyl-5-(2-piperidin-1-yl-ethyl)-1H-indole-3-carboxylic acid benzyl ester;

5-(2-Diisobutylamino-ethyl)-2-methyl-1H-indole-3-carboxylic acid benzyl ester;

2-Methyl-5-(2-methylamino-ethyl)-1H-indole-3-carboxylic acid benzyl ester;

2-Methyl-5-{2-[methyl-(tetrahydro-pyran-4-yl)-amino]-ethyl}-1H-indole-3-carboxylic acid benzyl ester;

5-Aminomethyl-2-methyl-1H-indole-3-carboxylic acid benzyl ester, hydrochloride;

5-(tert-Butoxycarbonylamino-methyl)-2-methyl-1H-indole-3-carboxylic acid benzyl ester;

5-Diethylaminomethyl-2-methyl-1H-indole-3-carboxylic acid benzyl ester;

5-(2-Diethylamino-ethyl)-2-methyl-1H-indole-3-carboxylic acid (S)-1-phenyl-ethyl ester, hydrochloride;

5-(2-Diethylamino-ethyl)-2-methyl-1H-indole-3-carboxylic acid (S)-1-phenyl-ethyl ester;

5-(2-dimethylamino-ethoxy)-2-methyl-1H-indole-3-carboxylic acid (S)-1-phenyl-ethyl ester;

2-Methyl-5-(2-morpholin-4-yl-ethoxy)-1H-indole-3-carboxylic acid 1-phenyl ethyl ester hydrochloride; and 2-Methyl-5-(2-pyrrolidin-1-yl-ethoxy)-1H-indole-3-carboxylic acid-1-phenyl ethyl ester hydrochloride.

25. The compound of claim 1, wherein said compound is selected from the group consisting of:

2-Methyl-5-(pyrrolidin-1-yl-ethoxy)-1H-indole-3-carboxylic acid benzyl ester;

2-Methyl-5-(1-methyl-2-pyrrolidin-1-yl-propoxy)-1H-indole-3-carboxylic acid benzyl ester;

5-(2-Cyclohexylamino-ethyl)-2-methyl-1H-indole-3-carboxylic acid benzyl ester;

5-(2-tert-Butoxycarbonylamino ethyl)-2-methyl-1H-indole-3-carboxylic acid benzyl ester;

5-(2-Diethylamino-ethyl)-2-methyl-1H-indole-3-carboxylic acid-1-(4-bromophenyl)-ethyl ester;

5-(2-Diethylamino-ethyl)-2-methyl-1H-indole-3-carboxylic acid-1-(4-(2-methyl-2-propyl)phenyl)-ethyl ester;

5-(2-Diethylamino-ethyl)-2-methyl-1H-indole-3-carboxylic acid-1-(2-chlorophenyl)-ethyl ester;

5-(2-Diethylamino-ethyl)-2-methyl-1H-indole-3-carboxylic acid-1-(2,6-dichlorophenyl)-ethyl ester;

5-(2-Diethylamino-ethyl)-2-methyl-1H-indole-3-carboxylic acid 3,5-dichloro-benzyl ester;

5-(2-N-Cyclohexyl-N-methyl-amino-ethyl)-2-methyl-1H-indole-3-carboxylic acid-1-(4-bromophenyl)-ethyl ester;

5-(2-N-Cyclohexyl-N-methyl-amino-ethyl)-2-methyl-1H-indole-3-carboxylic acid-1-(3-fluorophenyl)-ethyl ester;

5-(2-Diethylamino-ethyl)-2-methyl-1H-indole-3-carboxylic acid-1-(3-fluorophenyl)-ethyl ester;

5-(2-N-Cyclohexyl-N-methyl-amino-ethyl)-2-methyl-1H-indole-3-carboxylic acid-1-(2-chlorophenyl)-ethyl ester;

5-(2-N-Cyclohexyl-N-methyl-amino-ethyl)-2-methyl-1H-indole-3-carboxylic acid-1-(2,6-dichlorophenyl)-ethyl ester;

5-(2-Pyrrolidino-ethyl)-2-methyl-1H-indole-3-carboxylic acid-1-(3-fluorophenyl)-ethyl ester;

5-(2-Pyrrolidino-ethyl)-2-methyl-1H-indole-3-carboxylic acid-1-(2-chlorophenyl)-ethyl ester;

5-(2-Pyrrolidino-ethyl)-2-methyl-1H-indole-3-carboxylic acid-1-(2,6-dichlorophenyl)-ethyl ester;

5-(2-Pyrrolidino-ethyl)-2-methyl-1H-indole-3-carboxylic acid-(S)-1-phenyl-ethyl ester;

5-(2-Pyrrolidino-ethyl)-2-methyl-1H-indole-3-carboxylic acid 3,5-dichloro-benzyl ester;

5-(2-Piperidino-ethyl)-2-methyl-1H-indole-3-carboxylic acid-1-(3-fluorophenyl)-ethyl ester;

5-(2-Piperidino-ethyl)-2-methyl-1H-indole-3-carboxylic acid-1-(2-chlorophenyl)-ethyl ester;

5-(2-Piperidino-ethyl)-2-methyl-1H-indole-3-carboxylic acid-1-(2,6-dichlorophenyl)-ethyl ester;

5-(2-Piperidino-ethyl)-2-methyl-1H-indole-3-carboxylic acid 3,5-dichloro-benzyl ester;

5-(2-Piperidino-ethyl)-2-methyl-1H-indole-3-carboxylic acid-(S)-1-phenyl-ethyl ester; and 5-(2-(4-Hydroxy-piperidino)-ethyl)-2-methyl-1H-indole-3-carboxylic acid-1-(3-fluorophenyl)-ethyl ester.

26. The compound of claim 1, wherein said compound is selected from the group consisting of:

5-(2-(4-Hydroxy-piperidino)-ethyl)-2-methyl-1H-indole-3-carboxylic acid-1-(2-chlorophenyl)-ethyl ester;

5-(2-(4-Hydroxy-piperidino)-ethyl)-2-methyl-1H-indole-3-carboxylic acid-1-(2,6-dichlorophenyl)-ethyl ester;

5-(2-(4-Hydroxy-piperidino)-ethyl)-2-methyl-1H-indole-3-carboxylic acid 3,5-dichloro-benzyl ester;

5-(2-(4-Hydroxy-piperidino)-ethyl)-2-methyl-1H-indole-3-carboxylic acid-(S)-1-phenyl-ethyl ester;

5-(2-Piperidino-ethyl)-2-methyl-1H-indole-3-carboxylic acid 3-nitro-4-methyl-benzyl ester;

5-(2-Diethylamino-ethyl)-2-methyl-1H-indole-3-carboxylic acid 3-nitro-4-methyl-benzyl ester;

5-(2-Pyrrolidino-ethyl)-2-methyl-1H-indole-3-carboxylic acid 3-nitro-4-methyl-benzyl ester;

5-(2-N-Cyclohexyl-N-methyl-amino-ethyl)-2-methyl-1H-indole-3-carboxylic acid 3-nitro-4-methyl-benzyl ester;

5-(2-Piperidino-ethyl)-2-methyl-1H-indole-3-carboxylic acid-1-(4-fluorophenyl)-ethyl ester;

5-(2-Pyrrolidino-ethyl)-2-methyl-1H-indole-3-carboxylic acid-1-(4-fluorophenyl)-ethyl ester;

5-(2-N-Cyclohexyl-N-methyl-amino-ethyl)-2-methyl-1H-indole-3-carboxylic acid-1-(4-fluorophenyl)-ethyl ester;

5-(2-Diethylamino-ethyl)-2-methyl-1H-indole-3-carboxylic acid 2-biphenyl methyl ester;

5-(2-Piperidino-ethyl)-2-methyl-1H-indole-3-carboxylic acid 2-biphenyl methyl ester;

5-(2-Pyrrolidino-ethyl)-2-methyl-1H-indole-3-carboxylic acid 2-biphenyl methyl ester;

5-(2-N-Cyclohexyl-N-methyl-amino-ethyl)-2-methyl-1H-indole-3-carboxylic acid 2-biphenyl methyl ester;

5-(2-Diethylamino-ethyl)-2-methyl-1H-indole-3-carboxylic acid-1-(3-chlorophenyl)-ethyl ester;

5-(2-Diethylamino-ethyl)-2-methyl-1H-indole-3-carboxylic acid-1-(2-trifluoromethyl-phenyl)-ethyl ester;

5-(2-Diethylamino-ethyl)-2-methyl-1H-indole-3-carboxylic acid-1-(2-bromophenyl)-ethyl ester;

5-(2-Diethylamino-ethyl)-2-methyl-1H-indole-3-carboxylic acid-1-(2,4-dichlorophenyl)-ethyl ester;

5-(2-Diethylamino-ethyl)-2-methyl-1H-indole-3-carboxylic acid-1-(4-chlorophenyl)-ethyl ester;

5-(2-Diethylamino-ethyl)-2-methyl-1H-indole-3-carboxylic acid 5,6,7,8-tetrahydronaphth-5-yl ester;

5-(2-Diethylamino-ethyl)-2-methyl-1H-indole-3-carboxylic acid indan-1-yl ester;

5-(2-Diethylamino-ethyl)-2-methyl-1H-indole-3-carboxylic acid 1-methyl-1-cyclopentyl ester;

5-(2-Diethylamino-ethyl)-2-methyl-1H-indole-3-carboxylic acid 1-methyl-1-cyclohexyl ester;

5-(2-Piperidino-ethyl)-2-methyl-1H-indole-3-carboxylic acid-1-(2-bromophenyl)-ethyl ester.

27. The compound of claim 1, wherein said compound is selected from the group consisting of:

5-(2-Piperidino-ethyl)-2-methyl-1H-indole-3-carboxylic acid-1-(4-bromophenyl)-ethyl ester;

5-(2-Piperidino-ethyl)-2-methyl-1H-indole-3-carboxylic acid-1-(4-(2-methyl-2-propyl)phenyl)-ethyl ester;

5-(2-Piperidino-ethyl)-2-methyl-1H-indole-3-carboxylic acid-1-(2,4-dichlorophenyl)-ethyl ester;

5-(2-Piperidino-ethyl)-2-methyl-1H-indole-3-carboxylic acid-1-(4-chlorophenyl)-ethyl ester;

5-(2-Piperidino-ethyl)-2-methyl-1H-indole-3-carboxylic acid 1,2,3,4-tetrahydronaphth-1-yl ester;

5-(2-Piperidino-ethyl)-2-methyl-1H-indole-3-carboxylic indan-1-yl ester;

5-(2-Piperidino-ethyl)-2-methyl-1H-indole-3-carboxylic acid 1-methyl-1-cyclopentyl ester;

5-(2-Piperidino-ethyl)-2-methyl-1H-indole-3-carboxylic acid 1-methyl-1-cyclohexyl ester;

5-(2-(4-Hydroxy-piperidino)-ethyl)-2-methyl-1H-indole-3-carboxylic acid-1-(2-bromophenyl)-ethyl ester;

5-(2-(4-Hydroxy-piperidino)-ethyl)-2-methyl-1H-indole-3-carboxylic acid-1-(4-bromophenyl)-ethyl ester;

5-(2-(4-Hydroxy-piperidino)-ethyl)-2-methyl-1H-indole-3-carboxylic acid-1-(4-(2-methyl-2-propyl)phenyl)-ethyl ester;

5-(2-(4-Hydroxy-piperidino)-ethyl)-2-methyl-1H-indole-3-carboxylic acid-1-(2,4-dichlorophenyl)-ethyl ester;

5-(2-(4-Hydroxy-piperidino)-ethyl)-2-methyl-1H-indole-3-carboxylic acid-1-(4-chlorophenyl)-ethyl ester;

5-(2-(4-Hydroxy-piperidino)-ethyl)-2-methyl-1H-indole-3-carboxylic acid (1,2,3,4-tetrahydronaphthyl-1-yl) ester;

5-(2-(4-Hydroxy-piperidino)-ethyl)-2-methyl-1H-indole-3-carboxylic acid (1-indanyl) ester;

5-(2-Pyrrolidino-ethyl)-2-methyl-1H-indole-3-carboxylic acid 1-(2-bromophenyl)-ethyl ester;

5-(2-Pyrrolidino-ethyl)-2-methyl-1H-indole-3-carboxylic acid 1-(4-bromophenyl)-ethyl ester;

5-(2-Pyrrolidino-ethyl)-2-methyl-1H-indole-3-carboxylic acid 1-(4-t-butylphenyl)-ethyl ester;

5-(2-Pyrrolidino-ethyl)-2-methyl-1H-indole-3-carboxylic acid 1-(2,4-dichlorophenyl)-ethyl ester;

5-(2-Pyrrolidino-ethyl)-2-methyl-1H-indole-3-carboxylic acid 1-(4-chlorophenyl)-ethyl ester;

5-(2-(2-Pyrrolidino-ethyl)-2-methyl-1H-indole-3-carboxylic acid (1,2,3,4-tetrahydronaphthyl-1-yl) ester;

5-(2-(2-Pyrrolidino-ethyl)-2-methyl-1H-indole-3-carboxylic acid (1-indanyl)ester;

5-(2-(2-Pyrrolidino-ethyl)-2-methyl-1H-indole-3-carboxylic acid (1-methylcyclopetan-1-yl)ester;

5-(2-(2-Pyrrolidino-ethyl)-2-methyl-1H-indole-3-carboxylic acid (1-methylcyclohex-1-yl)ester; and 5-(2-N-Cyclohexyl-N-methyl-amino-ethyl)-2-methyl-1H-indole-3-carboxylic acid 1-(4-bromophenyl)-ethyl ester.

28. The compound of claim 1, wherein said compound is selected from the group consisting of:

5-(2-N-Cyclohexyl-N-methyl-amino-ethyl)-2-methyl-1H-indole-3-carboxylic acid 1-(2-bromophenyl)-ethyl ester;

5-(2-N-Cyclohexyl-N-methyl-amino-ethyl)-2-methyl-1H-indole-3-carboxylic acid 1-(4-t-butylphenyl)-ethyl ester;

5-(2-N-Cyclohexyl-N-methyl-amino-ethyl)-2-methyl-1H-indole-3-carboxylic acid 1-(2,4-dichlorophenyl)-ethyl ester;

5-(2-N-Cyclohexyl-N-methyl-amino-ethyl)-2-methyl-1H-indole-3-carboxylic acid 1-(4-chlorophenyl)-ethyl ester;

5-(2-N-Cyclohexyl-N-methyl-amino-ethyl)-2-methyl-1H-indole-3-carboxylic acid (1,2,3,4-tetrahydronaphthyl-1-yl)ester;

5-(2-N-Cyclohexyl-N-methyl-amino-ethyl)-2-methyl-1H-indole-3-carboxylic acid (1-indanyl)ester;

5-(2-N-Cyclohexyl-N-methyl-amino-ethyl)-2-methyl-1H-indole-3-carboxylic acid (1-methylcyclopetan-1-yl)ester;

5-(2-N-Cyclohexyl-N-methyl-amino-ethyl)-2-methyl-1H-indole-3-carboxylic acid (1-methylcyclohex-1-yl) ester;

5-(2-Diethylamino-ethyl)-2-methyl-1H-indole-3-carboxylic acid 1-(3-methoxyphenyl)-ethyl ester;

5-(2-Piperidino-ethyl)-2-methyl-1H-indole-3-carboxylic acid 1-(3-methoxyphenyl)-ethyl ester;

5-(2-(4-Hydroxy-piperidino)-ethyl)-2-methyl-1H-indole-3-carboxylic acid 1-(3-methoxyphenyl)-ethyl ester;

5-(2-Pyrrolidino-ethyl)-2-methyl-1H-indole-3-carboxylic acid 1-(3-methoxyphenyl)-ethyl ester;

5-(2-N-Cyclohexyl-N-methyl-amino-ethyl)-2-methyl-1H-indole-3-carboxylic acid 1-(3-methoxyphenyl)-ethyl ester;

5-(2-Diethylamino-ethyl)-2-methyl-1H-indole-3-carboxylic acid 1-(2,5-dimethylphenyl)-ethyl ester;

5-(2-Piperidinyl-ethyl)-2-methyl-1H-indole-3-carboxylic 1-(2,5-dimethylphenyl)-ethyl ester;

5-(2-(4-Hydroxy-piperidino)-ethyl)-2-methyl-1H-indole-3-carboxylic acid 1-(2,5-dimethylphenyl)-ethyl ester;

5-(2-Pyrrolidino-ethyl)-2-methyl-1H-indole-3-carboxylic acid 1-(2,5-dimethylphenyl)-ethyl ester;

5-(2-N-Cyclohexyl-N-methyl-amino-ethyl)-2-methyl-1H-indole-3-carboxylic acid 1-(2,5-dimethylphenyl)-ethyl ester;

5-(2-Diethylamino-ethyl)-2-methyl-1H-indole-3-carboxylic acid 1-(2,4-dimethylphenyl)-ethyl ester;

5-(2-Piperidinyl-ethyl)-2-methyl-1H-indole-3-carboxylic 1-(2,4-dimethylphenyl)-ethyl ester;

5-(2-(4-Hydroxy-piperidino)-ethyl)-2-methyl-1H-indole-3-carboxylic acid 1-(2,4-dimethylphenyl)-ethyl ester;

5-(2-Pyrrolidino-ethyl)-2-methyl-1H-indole-3-carboxylic acid 1-(2,4-dimethylphenyl)-ethyl ester;

5-(2-N-Cyclohexyl-N-methyl-amino-ethyl)-2-methyl-1H-indole-3-carboxylic acid 1-(2,4-dimethylphenyl)-ethyl ester;

5-(2-Diethylamino-ethyl)-2-methyl-1H-indole-3-carboxylic acid 1-(3,4-dichlorophenyl)-ethyl ester; and 5-(2-Pyrrolidino-ethyl)-2-methyl-1H-indole-3-carboxylic acid 1-(3,4-dichlorophenyl)-ethyl ester.

29. The compound of claim 1, wherein said compound is selected from the group consisting of:

5-(2-Piperidinyl-ethyl)-2-methyl-1H-indole-3-carboxylic 1-(3,4-dichlorophenyl)-ethyl ester;

5-(2-N-Cyclohexyl-N-methyl-amino-ethyl)-2-methyl-1H-indole-3-carboxylic acid 1-(3,4-dichlorophenyl)-ethyl ester;

5-(2-Diethylamino-ethyl)-2-methyl-1H-indole-3-carboxylic acid 1-(2-methylphenyl)-ethyl ester;

5-(2-Pyrrolidino-ethyl)-2-methyl-1H-indole-3-carboxylic acid 1-(2-methylphenyl)-ethyl ester;

5-(2-Piperidinyl-ethyl)-2-methyl-1H-indole-3-carboxylic 1-(2-methylphenyl)-ethyl ester;

5-(2-N-Cyclohexyl-N-methyl-amino-ethyl)-2-methyl-1H-indole-3-carboxylic acid 1-(2-methylphenyl)-ethyl ester;

5-(2-Diethylamino-ethyl)-2-methyl-1H-indole-3-carboxylic acid 1-(2,3,4,5-tetrafluorophenyl)-ethyl ester;

5-(2-Pyrrolidino-ethyl)-2-methyl-1H-indole-3-carboxylic acid 1-(2,3,4,5-tetrafluorophenyl)-ethyl ester;

5-(2-Piperidinyl-ethyl)-2-methyl-1H-indole-3-carboxylic acid 1-(2,3,4,5-tetrafluorophenyl)-ethyl ester;

5-(2-N-Cyclohexyl-N-methyl-amino-ethyl)-2-methyl-1H-indole-3-carboxylic acid 1-(2,3,4,5-tetrafluorophenyl)-ethyl ester;

5-(2-Diethylamino-ethyl)-2-methyl-1H-indole-3-carboxylic acid 1-(2,6-dimethylphenyl)-ethyl ester;

5-(2-Pyrrolidino-ethyl)-2-methyl-1H-indole-3-carboxylic acid 1-(2,6-dimethylphenyl)-ethyl ester;

5-(2-Piperidinyl-ethyl)-2-methyl-1H-indole-3-carboxylic 1-(2,6-dimethylphenyl)-ethyl ester;

5-(2-N-Cyclohexyl-N-methyl-amino-ethyl)-2-methyl-1H-indole-3-carboxylic acid 1-(2,6-dimethylphenyl)-ethyl ester;

5-(2-Diethylamino-ethyl)-2-methyl-1H-indole-3-carboxylic acid 1-(S)-(4-fluorophenyl)-ethyl ester;

5-(2-Diethylamino-ethyl)-2-methyl-1H-indole-3-carboxylic acid (S)-1-(4-fluoro-phenyl)-ethyl ester;

5-(2-Diethylamino-ethyl)-2-methyl-1H-indole-3-carboxylic acid (S)-1-pyridin-4-yl-ethyl ester; and 2-Methyl-5-(2-pyrrolidin-1-yl-ethyl)-1H-indole-3-carboxylic acid (S)-1-(4-fluoro-phenyl)-ethyl ester.

30. The compound of claim 1, wherein said compound is selected from the group consisting of:

5-(2-Amino-ethyl)-2-methyl-1H-indole-3-carboxylic acid benzyl ester hydrochloride;

5-(2-Diethylamino-ethyl)-2-methyl-1H-indole-3-carboxylic acid benzyl ester hydrochloride;

2-Methyl-5-(2-pyrrolidin-1-yl-ethyl)-1H-indole-3-carboxylic acid (S)-1-pyridin-4-yl-ethyl ester;

2-Methyl-5-(2-piperidin-1-yl-ethyl)-1H-indole-3-carboxylic acid (S)-1-(4-fluoro-phenyl)-ethyl ester;

2-Methyl-5-(2-piperidin-1-yl-ethyl)-1H-indole-3-carboxylic acid (S)-1-pyridin-4-yl-ethyl ester;

5-[2-(4-Hydroxy-piperidin-1-yl)-ethyl]-2-methyl-1H-indole-3-carboxylic acid (S)-1-(4-fluoro-phenyl)-ethyl ester;

5-[2-(4-Hydroxy-piperidin-1-yl)-ethyl]-2-methyl-1H-indole-3-carboxylic acid (S)-1-pyridin-4-yl-ethyl ester;

5-[2-(Cyclohexyl-methyl-amino)-ethyl]-2-methyl-1H-indole-3-carboxylic acid (S)-1-(4-fluoro-phenyl)-ethyl ester;

5-[2-(Cyclohexyl-methyl-amino)-ethyl]-2-methyl-1H-indole-3-carboxylic acid (S)-1-pyridin-4-yl-ethyl ester;

5-(1-Ethyl-piperidin-4-yl)-2-methyl-1H-indole-3-carboxylic acid (S)-1-(4-fluoro-phenyl)-ethyl ester;

5-(1-Ethyl-piperidin-4-yl)-2-methyl-1H-indole-3-carboxylic acid (S)-1-pyridin-4-yl-ethyl ester;

5-[1-(1-Ethyl-piperidin-4-yl)-1-methyl-ethyl]-2-methyl-1H-indole-3-carboxylic acid (S)-1-(4-fluoro-phenyl)-ethyl ester;

5-[1-(1-Ethyl-piperidin-4-yl)-1-methyl-ethyl]-2-methyl-1H-indole-3-carboxylic acid (S)-1-pyridin-4-yl-ethyl ester;

5-(1-Ethyl-4-methyl-piperidin-4-yl)-2-methyl-1H-indole-3-carboxylic acid (S)-1-(4-fluoro-phenyl)-ethyl ester;

5-(1-Ethyl-4-methyl-piperidin-4-yl)-2-methyl-1H-indole-3-carboxylic acid (S)-1-pyridin-4-yl-ethyl ester;

5-(1-Isopropyl-pyrrolidin-3-yl)-2-methyl-1H-indole-3-carboxylic acid (S)-1-(4-fluoro-phenyl)-ethyl ester;

5-(1-Isopropyl-pyrrolidin-3-yl)-2-methyl-1H-indole-3-carboxylic acid (S)-1-pyridin-4-yl-ethyl ester;

5-(1-Ethyl-1-aza-spiro[4.4]non-7-yl)-2-methyl-1H-indole-3-carboxylic acid (S)-1-(4-fluoro-phenyl)-ethyl ester;

5-(1-Ethyl-1-aza-spiro[4.4]non-7-yl)-2-methyl-1H-indole-3-carboxylic acid (S)-1-pyridin-4-yl-ethyl ester;

5-[2-((S)-3-hydroxymethyl-pyrrolidin-1-yl)-ethoxy]-2methyl-1H-indole-3-carboxylic acid benzyl ester;

5-(2-Piperidino-ethyl)-2-methyl-1H-indole-3-carboxylic acid-1-acid-1-(2-chlorophenyl)-ethyl ester; and 5-(2-Piperidino-ethyl)-2-methyl-1H-indole-3-carboxylic acid-1-(2,6-dichlorophenyl)-ethyl ester.

31. A pharmaceutical composition comprising a compound of claim 1 and a physiologically acceptable vehicle, excipient, carrier or adjuvant.

32. A method for modulating the activity of a chemokine receptor in a patient comprising administering to a patient in need thereof an effective amount of a compound having the formula $$\text{(I)}$$

or a physiologically acceptable salt, amide thereof, wherein:

G is $CR_1$;
J is $CR_2$;
H is $CR_3$;
M is C—Y, CH—Y;
Q is $NR_4$;
X is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl;
Y is P is —A—L-nitrogen-containing heteroaryl, —A—L-substituted nitrogen-containing heteroaryl, wherein a, b and c are each, independently, an integer from 0 to about 4, with the proviso that when a is 0, c is not 1 and when b is 0, c is not 1;
A is O, N(—$R_{12}$), a bond or is absent;
L is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, a bond, or wherein * is the point of attachment to A; and
** is the point of attachment to N;
$R_1$, $R_2$, $R_3$, $R_{11}$, $R_{13}$, $R_{14}$, $R_{15}$, $R_{16}$ and $R_{19}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, halogen, $C_1$–$C_8$ alkoxy, Z is aryl, substituted aryl, heteroaryl or substituted heteroaryl;
$R_{22}$ and $R_{23}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl; or
$R_{22}$ and $R_{23}$ taken together with the atoms to which they are bonded can form a three to eight membered cyclic ring which contains zero to three heteroatoms selected from the group consisting of oxygen, nitrogen and sulfur;
$R_4$, $R_7$, $R_8$, $R_9$, $R_{12}$, $R_{17}$ and $R_{18}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, $R_{20}$ and $R_{21}$ are independently hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl or alkylheteroaryl; or
$R_{20}$ and $R_{21}$ taken together with the atoms to which they are bonded form a three to eight membered cyclic ring which contains zero to three heteroatoms selected from the group consisting of oxygen, nitrogen and sulfur;
Z' is aryl, substituted aryl, heteroaryl or substituted heteroaryl; or
$R_1$ taken together with any one of $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to about three heteroatoms selected from the group consisting of oxygen, nitrogen and sulfur;
$R_2$ taken together with any one of $R_5$, $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

P taken together with either $R_1$ or $R_2$ and the atoms to which they are bonded form a five to eight membered substituted nonaromatic ring that contains a heteroatom selected from the group consisting of oxygen, nitrogen and sulfur;

any two of $R_7$, $R_8$, $R_9$, $R_{10}$, $R_{11}$, $R_{12}$, $R_{13}$, $R_{14}$, $R_{15}$, $R_{16}$ and $R_{17}$ taken together with the atoms to which they are bonded form a substituted or unsubstituted three to eight membered cyclic ring which contains zero to three heteroatoms selected from the group consisting of oxygen, nitrogen and sulfur; and wherein said substituted alkyl, substituted alkenyl and substituted alkynyl comprise one to three substituents, and said substituted aryl and substituted heteroaryl comprises one to five substituents, and said substituents are independently selected from the group consisting of $C_1$–$C_8$ alkyl, $C_2$–$C_8$ alkenyl, $C_2$–$C_8$ alkynyl, heteroalkyl, $C_1$–$C_8$ alkoxy, carboxy, hydroxy, nitro, halogen, cyano, amino, $C_1$–$C_8$ alkyl amino, $C_2$–$C_8$ alkenyl amino, $C_2$–$C_8$ alkynyl amino, aryl amino, $C_1$–$C_8$ dialkyl amino, $C_2$–$C_8$ dialkenyl amino, diaryl amino, aryl, substituted aryl, heteroaryl, substituted heteroaryl, $C_1$–$C_8$ alkyl, aryl $C_1$–$C_8$ alkyl, heteroaryl $C_1$–$C_8$ alkyl, keto (=O), =$NR^{60}$, wherein $R^{60}$ is —H, —OH, —$NH_2$, an aromatic group or a substituted aromatic group, —$SO_3H$, —CHO, —$(CH_2)_n$—$NH_2$, —$(CH_2)_n$—NH—$C_1$–$C_8$ alkyl, —$(CH_2)_n$—N($C_1$–$C_8$ alkyl)$_2$, wherein n is an integer from one to eight;

said heteroaryl is an aromatic ring having from five to fifteen atoms in the ring, wherein one or more of the atoms in the ring is a heteroatom selected from the group consisting of oxygen, nitrogen and sulfur;

said aryl is an aromatic carbocyclic ring having from five to fifteen carbon atoms;

said arylalkyl is —$C_1$–$C_8$ alkyl-aryl;

said heteroarylalkyl is —$C_1$–$C_8$ alkyl-heteroaryl;

said alkylaryl is -aryl-$C_1$–$C_8$ alkyl; and said alkylheteroaryl is -heteroaryl-$C_1$–$C_8$ alkyl.

33. The method of claim 27, wherein said chemokine receptor is CCR5.

34. A method for treating a patient having an inflammatory disease comprising administering to said patient an effective amount of a compound having the formula

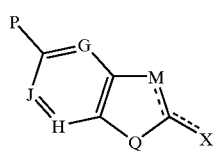

(I)

or a physiologically acceptable salt thereof, wherein:

G is $CR_1$;

J is $CR_2$;

H is $CR_3$;

M is C—Y or CH—Y;

Q is $NR_4$;

X is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl;

Y is

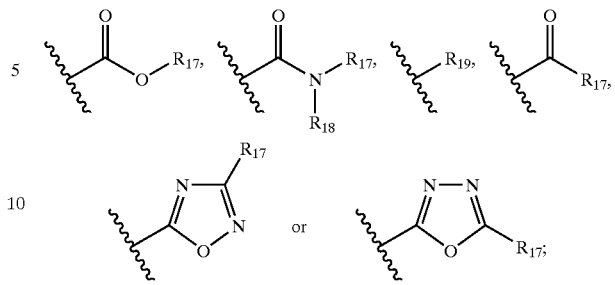

P is —A—L—nitrogen-containing heteroaryl, —A—L—substituted nitrogen-containing heteroaryl,

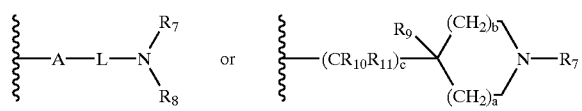

wherein a, b and c are each, independently, an integer from 0 to 4, with the proviso that when a is 0, c is not 1 and when b is 0, c is not 1;

A is O, N(—$R_{12}$), a bond or is absent;

L is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, a bond, or

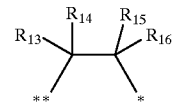

wherein * is the point of attachment to A; and
** is the point of attachment to N;

$R_1$, $R_2$, $R_3$, $R_{11}$, $R_{13}$, $R_{14}$, $R_{15}$, $R_{16}$ and $R_{19}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, halogen, $C_1$–$C_8$ alkoxy,

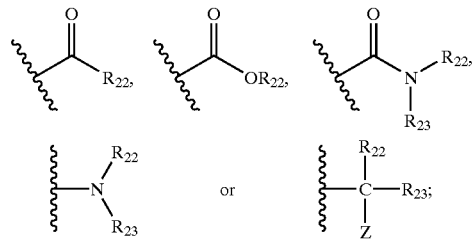

Z is aryl, substituted aryl, heteroaryl or substituted heteroaryl;

$R_{22}$ and $R_{23}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl; or $R_{22}$ and $R_{23}$ taken together with the atoms to which they are bonded can form a three to eight membered cyclic ring which contains zero to three heteroatoms selected from the group consisting of oxygen, nitrogen and sulfur;

$R_4$, $R_7$, $R_8$, $R_9$, $R_{12}$, $R_{17}$ and $R_{18}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl,

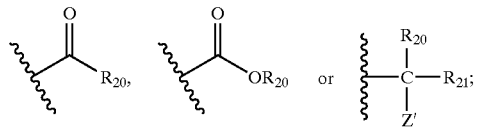

$R_{20}$ and $R_{21}$ are independently hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl or alkylheteroaryl; or $R_{20}$ and $R_{21}$ taken together with the atoms to which they are bonded can form a three to eight membered cyclic ring which can contain zero to three heteroatoms selected from the group consisting of oxygen, nitrogen and sulfur;

Z' is aryl, substituted aryl, heteroaryl or substituted heteroaryl; or $R_1$ taken together with any one of $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

$R_2$ taken together with any one of $R_3$, $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

P taken together with either $R_1$ or $R_2$ and the atoms to which they are bonded form a five to eight membered substituted nonaromatic ring that contains a heteroatom selected from the group consisting of oxygen, nitrogen and sulfur;

any two of $R_7$, $R_8$, $R_9$, $R_{10}$, $R_{11}$, $R_{12}$, $R_{13}$, $R_{14}$, $R_{15}$, $R_{16}$ and $R_{17}$, taken together with the atoms to which they are bonded form a substituted or unsubstituted three to eight membered cyclic ring which contains zero to three heteroatoms selected from the group consisting of oxygen, nitrogen and sulfur; and wherein said substituted alkyl, substituted alkenyl and substituted alkynyl comprises one to three substituents, and said substituted aryl and substituted heteroaryl comprises one to five substituents, and said substituents are independently selected from the group consisting of $C_1$–$C_8$ alkyl, $C_2$–$C_8$ alkenyl, $C_2$–$C_8$ alkynyl, heteroalkyl, $C_1$–$C_8$ alkoxy, carboxy, hydroxy, nitro, halogen, cyano, amino, $C_1$–$C_8$ alkyl amino, $C_2$–$C_8$ alkenyl amino, $C_2$–$C_8$ alkynyl amino, aryl amino, $C_1$–$C_6$ dialkyl amino, $C_2$–$C_8$ dialkenyl amino, diaryl amino, aryl, substituted aryl, heteroaryl, substituted heteroaryl, $C_1$–$C_8$ alkyl aryl, aryl $C_1$–$C_8$ alkyl, heteroaryl $C_1$–$C_8$ alkyl, keto (=O), =$NR^{60}$, wherein $R^{60}$ , is —H, —OH, —$NH_2$, an aromatic group or a substituted aromatic group, —$SO_3H$, —CHO, —$(CH_2)_n$—$NH_2$, —$(CH_2)_{n-NH-C1}$–$C_8$ alkyl, —$(CH_2)_n$—$N(C_1$–$C_8$ alkyl$)_2$, wherein n is an integer from one to eight;

said heteroaryl is an aromatic ring having from five to fifteen atoms in the ring, wherein one or more of the atoms in the ring is a heteroatom selected from the group consisting of oxygen, nitrogen and sulfur;

said aryl is an aromatic carbocyclic ring having from five to fifteen carbon atoms;

said arylalkyl is —$C_1$–$C_8$ alkyl-aryl;

said heteroarylalkyl is —$C_1$–$C_8$ alkyl-heteroaryl;

said alkylaryl is -aryl-$C_1$–$C_8$ alkyl; and said alkylheteroaryl is -heteroaryl-$C_1$–$C_8$ alkyl.

35. A method for treating a patient infected by HIV comprising administering to said patient an effective amount of a compound having the formula

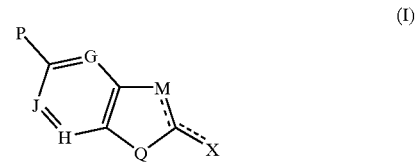

(I)

or a physiologically acceptable salt thereof, wherein:

G is $CR_1$;

J is $CR_2$;

H is $CR_3$;

M is C—Y or CH—Y;

Q is $NR_4$;

X is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl;

Y is

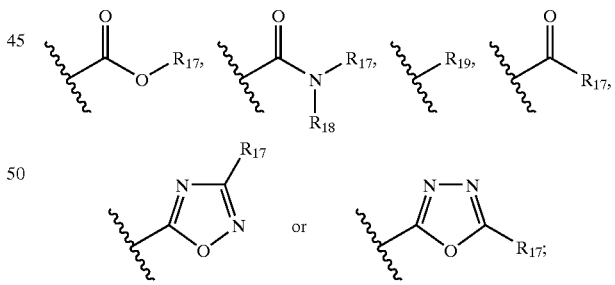

P is —A—L-nitrogen-containing heteroaryl, —A—L-substituted nitrogen-containing heteroaryl,

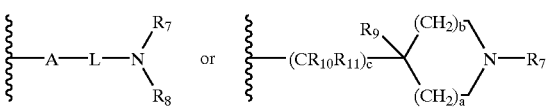

wherein a, b and c are each, independently, an integer from 0 to 4, with the proviso that when a is 0, c is not 1 and when b is 0, c is not 1;

A is O, N(—R$_{12}$), a bond or is absent;

L is C$_1$–C$_8$ alkyl, substituted C$_1$–C$_8$ alkyl, C$_2$–C$_8$ alkenyl, substituted C$_2$–C$_8$ alkenyl, C$_2$–C$_8$ alkynyl, substituted C$_2$–C$_8$ alkynyl, aryl, substituted aryl, heteroaryl, substituted heteroaryl, arylalkyl, alkylaryl, heteroarylalkyl, alkylheteroaryl, a bond, or

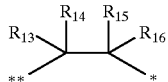

wherein * is the point of attachment to A; and
** is the point of attachment to N;

R$_1$, R$_2$, R$_3$, R$_{11}$, R$_{13}$, R$_{14}$, R$_{15}$, R$_{16}$ and R$_{19}$ are independently, hydrogen, C$_1$–C$_8$ alkyl, substituted C$_1$–C$_8$ alkyl, C$_2$–C$_8$ alkenyl, substituted C$_2$–C$_8$ alkenyl, C$_2$–C$_8$ alkynyl, substituted C$_2$–C$_8$ alkynyl, aryl, substituted aryl, heteroaryl, substituted heteroaryl, arylalkyl, alkylaryl, heteroarylalkyl, alkylheteroaryl, halogen, C$_1$–C$_8$ alkoxy,

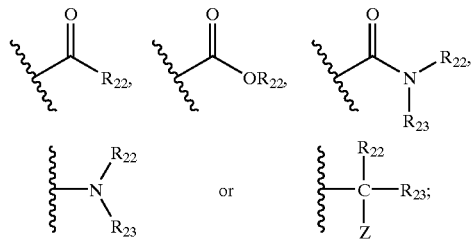

Z is aryl, substituted aryl, heteroaryl or substituted heteroaryl;

R$_{22}$ and R$_{23}$ are independently, hydrogen, C$_1$–C$_8$ alkyl, substituted C$_1$–C$_8$ alkyl, C$_2$–C$_8$ alkenyl, substituted C$_2$–C$_8$ alkenyl, C$_2$–C$_8$ alkynyl, substituted C$_2$–C$_8$ alkynyl, aryl, substituted aryl, heteroaryl, substituted heteroaryl, arylalkyl, alkylaryl, heteroarylalkyl, alkylheteroaryl; or R$_{22}$ and R$_{23}$ taken together with the atoms to which they are bonded can form a three to eight membered cyclic ring which contains zero to three heteroatoms selected from the group consisting of oxygen, nitrogen and sulfur;

R$_4$, R$_7$, R$_8$, R$_9$, R$_{12}$, R$_{17}$ and R$_{18}$ are independently, hydrogen, C$_1$–C$_8$ alkyl, substituted C$_1$–C$_8$ alkyl, C$_2$–C$_8$ alkenyl, substituted C$_2$–C$_8$ alkenyl, C$_2$–C$_8$ alkynyl, substituted C$_2$–C$_8$ alkynyl, aryl, substituted aryl, heteroaryl, substituted heteroaryl, arylalkyl, alkylaryl, heteroarylalkyl, alkylheteroaryl,

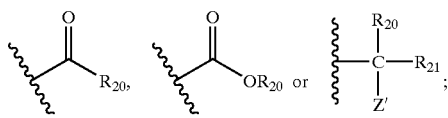

R$_{20}$ and R$_{21}$ are independently hydrogen, C$_1$–C$_8$ alkyl, substituted C$_1$–C$_8$ alkyl, C$_2$–C$_8$ alkenyl, substituted C$_2$–C$_8$ alkenyl, C$_2$–C$_8$ alkynyl, substituted C$_2$–C$_8$ alkynyl, aryl, substituted aryl, heteroaryl, substituted heteroaryl, arylalkyl, alkylaryl, heteroarylalkyl or alkylheteroaryl; or R$_{20}$ and R$_{21}$ taken together with the atoms to which they are bonded form a three to eight membered cyclic ring which contains zero to three heteroatoms selected from the group consisting of oxygen, nitrogen and sulfur;

Z' is aryl, substituted aryl, heteroaryl or substituted heteroaryl; or

R$_1$ taken together with any one of R$_7$, R$_8$, R$_9$, R$_{10}$, R$_{11}$, R$_{12}$, R$_{13}$, R$_{14}$, R$_{15}$ or R$_{16}$ and the atoms to which they are bonded form a substituted or unsubstituted three to eight membered cyclic ring which contains zero to three heteroatoms selected from the group consisting of oxygen, nitrogen and sulfur;

R$_2$ taken together with any one of R$_3$, R$_7$, R$_8$, R$_9$, R$_{10}$, R$_{11}$, R$_{12}$, R$_{13}$, R$_{14}$, R$_{15}$ or R$_{16}$ and the atoms to which they are bonded form a substituted or unsubstituted three to eight membered cyclic ring which contains zero to three heteroatoms selected from the group consisting of oxygen, nitrogen and sulfur;

P taken together with either R$_1$ or R$_2$ and the atoms to which they are bonded form a five to eight membered substituted nonaromatic ring that contains a heteroatom selected from the group consisting of oxygen, nitrogen and sulfur;

any two of R$_7$, R$_8$, R$_9$, R$_{10}$, R$_{11}$, R$_{12}$, R$_{13}$, R$_{14}$, R$_{15}$, R$_{16}$ and R$_{17}$, taken together with the atoms to which they are bonded form a substituted or unsubstituted three to eight membered cyclic ring which contains zero to three heteroatoms selected from the group consisting of oxygen, nitrogen and sulfur; and wherein said substituted alkyl, substituted alkenyl and substituted alkynyl comprise one to three substituents, and said substituted aryl and substituted heteroaryl comprises one to five substituents, and said substituents are independently selected from the group consisting of C$_1$–C$_8$ alkyl, C$_2$–C$_8$ alkenyl, C$_2$–C$_8$ alkynyl, heteroalkyl, C$_1$–C$_8$ alkoxy, carboxy, hydroxy, nitro, halogen, cyano, amino, C$_1$–C$_8$ alkyl amino, C$_2$–C$_8$ alkenyl amino, C$_2$–C$_8$ alkynyl amino, aryl amino, C$_1$–C$_8$ dialkyl amino, C$_2$–C$_8$ dialkenyl amino, diaryl amino, aryl, substituted aryl, heteroaryl, substituted heteroaryl, C$_1$–C$_8$ alkyl aryl, aryl C$_1$–C$_8$ alkyl, heteroaryl C$_1$–C$_8$ alkyl, keto (=O), =NR$^{60}$, wherein R$^{60}$ is —H, —OH, —NH$_2$, an aromatic group or a substituted aromatic group, —SO$_3$H, —CHO, —(CH$_2$)$_n$—NH$_2$, —(CH$_2$)$_{n-NH}$—C$_1$–C$_8$ alkyl, —(CH$_2$)$_n$—N(C$_1$–C$_8$ alkyl)$_2$, wherein n is an integer from one to eight;

said heteroaryl is an aromatic ring having from five to fifteen atoms in the ring, wherein one or more of the atoms in the ring is a heteroatom selected from the group consisting of oxygen, nitrogen and sulfur;

said aryl is an aromatic carbocyclic ring having from five to fifteen carbon atoms;

said arylalkyl is —C$_1$–C$_8$ alkyl-aryl;

said heteroarylalkyl is —C$_1$–C$_8$ alkyl-heteroaryl;

said alkylaryl is -aryl-C$_1$–C$_8$ alkyl; and said alkylheteroaryl is -heteroaryl-C$_1$–C$_8$ alkyl.

36. A method for inhibiting progression to AIDS or ARC in a patient infected with HIV comprising administering to said patient an effective amount of a compound having the formula

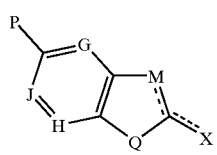

(I)

or a physiologically acceptable salt thereof, wherein:

G is $CR_1$;

J is $CR_2$;

H is $CR_3$;

M is C—Y or CH—Y;

Q is $NR_4$;

X is $C_1$–$C_8$ alkyl, substituted $C_1$–$C_8$ alkyl $C_2$–$C_8$ alkenyl, substituted $C_2$–$C_8$ alkenyl, $C_2$–$C_8$ alkynyl, substituted $C_2$–$C_8$ alkynyl;

Y is

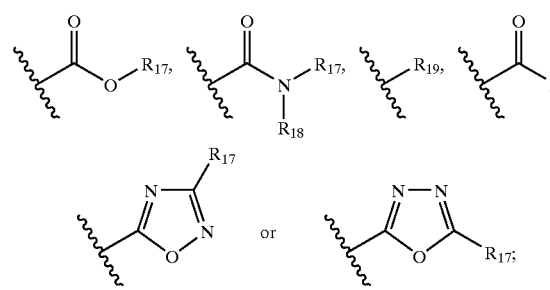

P is —A—L-nitrogen-containing heteroaryl, —A—L-substituted nitrogen-containing heteroaryl,

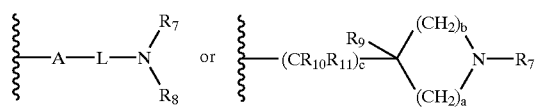

wherein a, b and c are each, independently, an integer from 0 to 4, with the proviso that when a is 0, c is not 1 and when b is 0, c is not 1;

A is O, N(—$R_{12}$), a bond or is absent;

L is $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, a bond, or

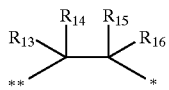

wherein * is the point of attachment to A; and
** is the point of attachment to N;

$R_1$, $R_2$, $R_3$, $R_{11}$, $R_{13}$, $R_{14}$, $R_{15}$, $R_{16}$ and $R_{19}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl, halogen, $C_1$–$C_8$ alkoxy,

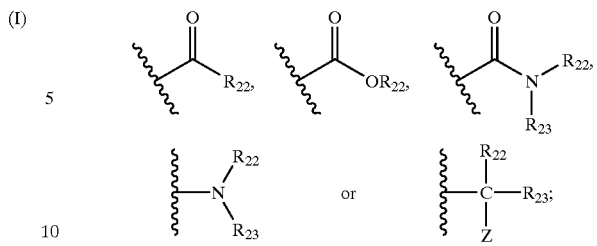

Z is aryl, substituted aryl, heteroaryl or substituted heteroaryl;

$R_{22}$ and $R_{23}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl; or $R_{22}$ and $R_{23}$ taken together with the atoms to which they are bonded form a three to eight membered cyclic ring which contains zero to three heteroatoms selected from the group consisting of oxygen, nitrogen and sulfur;

$R_4$, $R_7$, $R_8$, $R_9$, $R_{12}$, $R_{17}$ and $R_{18}$ are independently, hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl, alkylheteroaryl,

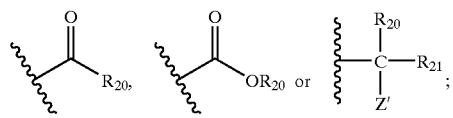

$R_{20}$ and $R_{21}$ are independently hydrogen, $C_1$–$C_8$ alkyl, substituted $C_1$–$C_8$ alkyl, $C_2$–$C_8$ alkenyl, substituted $C_2$–$C_8$ alkenyl, $C_2$–$C_8$ alkynyl, substituted $C_2$–$C_8$ alkynyl, aryl, substituted aryl, heteroaryl, substituted heteroaryl, arylalkyl, alkylaryl, heteroarylalkyl or alkylheteroaryl; or $R_{20}$ and $R_{21}$ taken together with the atoms to which they are bonded form a three to eight membered cyclic ring which contains zero to three heteroatoms selected from the group consisting of oxygen, nitrogen and sulfur;

Z' is aryl, substituted aryl, heteroaryl or substituted heteroaryl; or $R_1$ taken together with any one of $R_7$, $R_8$, $R_9$, $R_{10}$, $R_{11}$, $R_{12}$, $R_{13}$, $R_{14}$, $R_{15}$ or $R_{16}$ and the atoms to which they are bonded form a substituted or unsubstituted three to eight membered cyclic ring which contains zero to three heteroatoms selected from the group consisting of oxygen, nitrogen and sulfur;

$R_2$ taken together with any one of $R_3$, $R_7$, $R_8$, $R_9$, $R_{10}$, $R_{11}$, $R_{12}$, $R_{13}$, $R_{14}$, $R_{15}$, or $R_{16}$ and the atoms to which they are bonded form a substituted or unsubstituted three to eight membered cyclic ring which contains zero to three heteroatoms selected from the group consisting of oxygen, nitrogen and sulfur;

P taken together with either $R_1$ or $R_2$ and the atoms to which they are bonded form a five to eight membered substituted nonaromatic ring that contains a heteroatom selected from the group consisting of oxygen, nitrogen and sulfur;

any two of $R_7$, $R_8$, $R_9$, $R_{10}$, $R_{11}$, $R_{12}$, $R_{13}$, $R_{14}$, $R_{15}$, $R_{16}$ and $R_{17}$, taken together with the atoms to which they are bonded form a substituted or unsubstituted three to eight membered cyclic ring which contains zero to three heteroatoms selected from the group consisting of oxygen, nitrogen and sulfur; and wherein said substituted alkyl, substituted alkenyl and substituted alkynyl comprise one to three substituents, and said substituted aryl and substituted heteroaryl comprises one to five substituents, and said substituents are independently selected from the group consisting of $C_1$–$C_8$ alkyl, $C_2$–$C_8$ alkenyl, $C_2$–$C_8$ alkynyl, heteroalkyl, $C_1$–$C_8$ alkoxy, carboxy, hydroxy, nitro, halogen, cyano, amino, $C_1$–$C_8$ alkyl amino, $C_2$–$C_8$ alkenyl amino, $C_2$–$C_8$ alkynyl amino, aryl amino, $C_1$–$C_8$ dialkyl amino, $C_2$–$C_8$ dialkenyl amino, diaryl amino, aryl, substituted aryl, heteroaryl, substituted heteroaryl, $C_1$–$C_8$ alkyl aryl, aryl $C_1$–$C_8$ alkyl, heteroaryl $C_1$–$C_8$ alkyl, keto (=O), =$NR^{60}$, wherein $R^{60}$ is —H, —OH, —$NH_2$, an aromatic group or a substituted aromatic group, —$SO_3H$, —CHO, —$(CH_2)_n$—$NH_2$, —$(CH_2)_n$—NH—$C_1$–$C_8$ alkyl, —$(CH_2)_n$—N($C_1$–$C_8$ alkyl)$_2$, wherein n is an integer from one to eight;

said heteroaryl is an aromatic ring having from five to fifteen atoms in the ring, wherein one or more of the atoms in the ring is a heteroatom selected from the group consisting of oxygen, nitrogen and sulfur;

said aryl is an aromatic carbocyclic ring having from five to fifteen carbon atoms;

said arylalkyl is —$C_1$–$C_8$ alkyl-aryl;

said heteroarylalkyl is —$C_1$–$C_8$ alkyl-heteroaryl;

said alkylaryl is -aryl-$C_1$–$C_8$ alkyl; and said alkylheteroaryl is -heteroaryl-$C_1$–$C_8$ alkyl.

* * * * *

UNITED STATES PATENT AND TRADEMARK OFFICE
CERTIFICATE OF CORRECTION

PATENT NO. : 6,951,848 B2 Page 1 of 1
DATED : October 4, 2005
INVENTOR(S) : Harriman et al.

It is certified that error appears in the above-identified patent and that said Letters Patent is hereby corrected as shown below:

Column 169,
Line 18, delete "X is $C_1$-$C_8$ alkyl, substituted $C_1$-$C_8$ alkyl, $C_2$-$C_5$ alkenyl," and insert -- X is $C_1$-$C_8$ alkyl, substituted $C_1$-$C_8$ alkyl, $C_2$-$C_8$ alkenyl, --;

Column 176,
Line 1, delete ", "wherein $R_{20}$ and $R_{21}$ are independently hydrogen, $C_1$-$C_6$" and insert -- wherein $R_{20}$ and $R_{21}$ are independently hydrogen, $C_1$-$C_8$ --.

Signed and Sealed this

Fourth Day of April, 2006

JON W. DUDAS
*Director of the United States Patent and Trademark Office*